United States Patent
Beavers et al.

(10) Patent No.: US 7,666,871 B2
(45) Date of Patent: Feb. 23, 2010

(54) OXAZOLE DERIVATIVES AS HISTAMINE H3 RECEPTOR AGENTS, PREPARATION AND THERAPEUTIC USES

(75) Inventors: Lisa Selsam Beavers, Franklin, IN (US); Serge Louis Boulet, Fishers, IN (US); Terry Patrick Finn, Geneva (CH); Robert Alan Gadski, Indianapolis, IN (US); William Joseph Hornback, Fishers, IN (US); Cynthia Darshini Jesudason, Indianapolis, IN (US); Richard Todd Pickard, Noblesville, IN (US); Freddie Craig Stevens, Indianapolis, IN (US); Grant Mathews Vaught, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 11/572,283

(22) PCT Filed: Jul. 14, 2005

(86) PCT No.: PCT/US2005/024883

§ 371 (c)(1), (2), (4) Date: Jan. 18, 2007

(87) PCT Pub. No.: WO2006/019833

PCT Pub. Date: Feb. 23, 2006

(65) Prior Publication Data

US 2007/0197604 A1    Aug. 23, 2007

Related U.S. Application Data

(60) Provisional application No. 60/591,191, filed on Jul. 26, 2004.

(51) Int. Cl.
*A61K 31/501* (2006.01)
*C07D 403/14* (2006.01)

(52) U.S. Cl. .................................. 514/252.05; 544/238

(58) Field of Classification Search ................. 548/215, 548/228, 232, 235; 544/238; 514/252.05
See application file for complete search history.

(56) References Cited

FOREIGN PATENT DOCUMENTS

| DE | 3819037 | * | 1/1979 | ................. 548/200 |
|----|---------|---|--------|--------------------------|
| EP | 03024694.6 | * | 10/2009 | ............... 548/200 |
| WO | WO 95/09159 | * | 4/1995 | ............... 548/200 |
| WO | WO 00/64884 | | 11/2000 | |
| WO | WO 02/076925 | | 10/2002 | |
| WO | WO 03/064411 | | 8/2003 | |
| WO | WO 2004-/054973 | | 7/2004 | |

OTHER PUBLICATIONS

Golub et al. Science (1999), vol. 286 521-537.*
Lala et al. Cancer and Metastasis Reviews (1998), 17(1), 91-106.*
Gripenberg, M, Scand. J. Rheumatology, vol. 10 (2) 1981, 85-91.*
"Epilepsy." Retrieved online [May 28, 2008] via Internet, URL: http://www.nlm.nih.gov/medlineplus/epilepsy.html.*
"Parkinson's Disease." Retrieved online [May 28, 2008] via Internet, URL: http://www.nlm.nih.gov/medlineplus/parkinsonsdisease.html.*
"Anxiety." Retrieved online [May 28, 2008] via Internet, URL: http://www.nlm.nih.gov/medlineplus/anxiety.html#cat3.*
"Dementia." Retrieved online [May 28, 2008] via Internet, URL: http://www.nlm.nih.gov/medlineplus/dementia.html#cat5.*
"Autism." Retrieved online [May 28, 2008] via Internet, URL: http://www.nlm.nih.gov/medlineplus/autism.html.*
"Attention deficit hyperactivity disorder." Retrieved online [May 28, 2008] via Internet, URL: http://www.nlm.nih.gov/medlineplus/attentiondeficithyperactivitydisorder.html#cat3.*
"Cancer." Retrieved online [May 28, 2008] via Internet, URL: http://www.nlm.nih.gov/medlineplus/cancer.html.*
Blum E. et al., "Design and Synthesis of Novel Ligands for the 5-HT3 and the 5-HT4 Receptor" *Bioorganic & Medicinal Chemistry Letters*, vol. 2, No. 5, pp. 461-466, 1992.

* cited by examiner

*Primary Examiner*—Kamal A Saeed
*Assistant Examiner*—Samantha L Shterengarts
(74) *Attorney, Agent, or Firm*—Dan L. Wood

(57) ABSTRACT

The present invention discloses novel aryl oxazole compounds of Formula I (I), or pharmaceutically acceptable salts thereof, which have histamine-H3 receptor antagonist or inverse agonist activity, as well as methods for preparing and using such compounds. In another embodiment, the invention discloses pharmaceutical compositions comprising compounds of Formula I as well as methods of using these compositions to treat obesity, cognitive deficiencies, narcolepsy, and other histamine H3 receptor-related diseases. Formula I (I) or a pharmaceutically acceptable salt thereof, wherein: m is independenlly at each occurrence 1, 2, or 3, Z independently represents carbon (substituted with hydrogen or the optional substituents indicated herein) or nitrogen, provided that when Z is nitrogen then R6 is not attached to Z; R1 and R2 are independently —($C_1$—$C_7$) alkyl (optionally substituted with one to three halogens), or R1 and R2 and the nitrogen to which they are attached form an azetidinyl ring, a pyrrolidinyl ring, or a piperidinyl ring, wherein further the azetidinyl, pyrrolidinyl, or piperidinyl ring so formed may be optionally substituted one to three times with R5; R6 is independently at each occurrence —H, -halogen, or —$CH_3$.

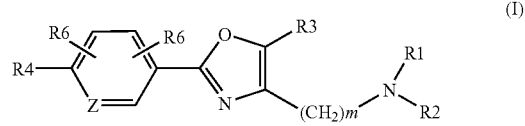

(I)

17 Claims, No Drawings

OXAZOLE DERIVATIVES AS HISTAMINE H3 RECEPTOR AGENTS, PREPARATION AND THERAPEUTIC USES

This patent application claims the benefit of U.S. Provisional Patent Application No. 60/591,191 filed Jul. 26, 2004.

The present invention relates to novel aryl oxazole compounds, and to the use of these compounds as pharmaceutical compositions, to pharmaceutical compositions comprising the compounds, to methods of treatment employing these compounds and compositions, and to intermediates and methods for making these compounds.

The histamine H3 receptor is relatively neuron specific and inhibits the release of a number of monoamines, including histamine. The histamine H3 receptor is a presynaptic autoreceptor and hetero-Receptor located both in the central and the peripheral nervous system. The histamine H3 receptor regulates the release of histamine and other neurotransmitters, such as serotonin and acetylcholine. These are examples of histamine H3 receptor mediated responses. Recent evidence suggests that the H3 receptor shows intrinsic, constitutive activity, in vitro as well as in vivo (i.e. it is active in the absence of an agonist). Compounds acting as inverse agonists can inhibit this activity. A histamine H3 receptor antagonist or inverse agonist would therefore be expected to increase the release of H3 receptor-Regulated neurotransmitters in the brain. A histamine H3 receptor agonist, on the contrary, leads to an inhibition of the biosynthesis of histamine and an inhibition of the release of histamine and also of other neurotransmitters such as serotonin and acetylcholine. These findings suggest that histamine H3 receptor agonists, inverse agonists, and antagonists could be important mediators of neuronal activity, and the activities of other cells that may express this receptor. inverse agonism or selective antagonism of the histamine H3 receptor raises brain levels of histamine, and other monoamines, and inhibits activities such as food consumption while minimizing non-specific peripheral consequences. By this mechanism, H3R inverse agonists or antagonists induce a prolonged wakefulness, improved cognitive function, reduction in food intake and normalization of vestibular reflexes. Accordingly, the histamine H3 receptor is an important target for new therapeutics in Alzheimers disease, mood and attention adjustments, cognitive deficiencies, obesity, dizziness, schizophrenia, epilepsy, sleeping disorders, narcolepsy and motion sickness.

Histamine mediates its activity via four receptor subtypes, H1R, H2R, H3R and a newly identified receptor designated GPRv53 [(Oda T., et al., J. Biol. Chem. 275 (47): 36781-6 (2000)], and alternative names for this receptor are PORT3 or H4R. Although relatively selective ligands have been developed for H1R, H2R and H3R, few specific ligands have been developed that can distinguish H3R from H4R. H4R is a widely distributed receptor found at high levels in human leukocytes. Activation or inhibition of this receptor could result in undesirable side effects when targeting antagonism of the H3R receptor. The identification of the H4R receptor has fundamentally changed histamine biology and must be considered in the development of histamine H3 receptor antagonists.

Some histamine H3 receptor antagonists were created which resembled histamine in possessing an imidazole ring generally substituted in the 4(5) position (Ganellin et al., Ars Pharmaceutica, 1995, 36:3, 455-468). A variety of patents and patent applications directed to antagonists and agonists having such structures include EP 197840, EP 494010, WO 97/29092, WO 96/38141, and WO96/38142. These imidazole-containing compounds have the disadvantage of poor blood-brain barrier penetration, interaction with cytochrome P-450 proteins, and hepatic and ocular toxicities. Recently, other imidazole and non-imidazole ligands of the histamine H3 receptor have been described. The compounds of the present invention differ in structure from the compounds described in the art.

There remains a need for improved treatments using alternative or improved pharmaceutical agents that act as histamine H3 receptor agonists, inverse agonists, or antagonists, to modulate H3 receptor activity, and treat the diseases that could benefit from H3 receptor modulation. The present invention provides such a contribution to the art based on the finding that a novel class of aryl oxazole compounds has a high affinity, selective, and potent activity at the histamine H3 receptor. The subject invention is distinct in the particular structures and their activities.

SUMMARY OF THE INVENTION

The present invention provides a compound structurally represented by Formula I:

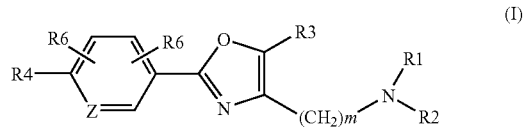

(I)

or a pharmaceutically acceptable salt thereof, wherein:

m is independently at each occurrence 1, 2, or 3,
  wherein optionally one or two of the hydrogens of the —CH$_2$—, —CH$_2$—CH$_2$—, or —CH$_2$—CH$_2$—CH$_2$— so formed may independently be replaced by halogen, or optionally on a carbon not adjacent to nitrogen one of the hydrogens of the —CH$_2$—CH$_2$—, or —CH$_2$—CH$_2$—CH$_2$— so formed may independently be replaced by —OH, —O—(C$_1$-C$_4$) alkyl(optionally substituted with one to three halogens), or —(C$_1$-C$_3$)alkyl(optionally substituted with one to three halogens);

Z independently represents carbon (substituted with hydrogen or the optional substituents indicated herein) or nitrogen, provided that when Z is nitrogen then R6 is not attached to Z;

R1 and R2 are independently
  —(C$_1$-C$_7$) alkyl(optionally substituted with one to three halogens), or R1 and R2 and the nitrogen to which they are attached form an azetidinyl ring, a pyrrolidinyl ring, or a piperidinyl ring, wherein further the azetidinyl, pyrrolidinyl, or piperidinyl ring so formed may be optionally substituted one to three times with R5;

R3 is independently
  —H, -halogen, —(C$_1$-C$_4$) alkyl(optionally substituted with one to three halogens), or —O—(C$_1$-C$_3$) alkyl(optionally substituted with one to three halogens);

R4 is independently
  -halogen, —(C$_1$-C$_7$) alkyl(optionally substituted with one to three halogens), —CN, —C(O)R7, —C(O)(C$_3$-C$_7$) cycloalkyl(optionally substituted with one to three halogens), —C(O)NR7R8, —OR7, —O-phenyl(R10)(R11), —NO$_2$, —NR7R8, —NR7SO$_2$R7, —NR7C(O)R7, —NR7CO$_2$R7, —NR7C(O)NR7R8, —SR7, —SO$_2$R7, —SO$_2$NR7R8, —S(O)R7, —O(CH$_2$)mNR7R8, -heteroaryl-R9, —O—CH$_2$-heteroaryl-R9, or

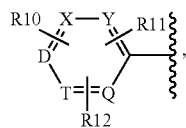

wherein the zig-zag lines represent the point of attachment, and wherein Q, T, D, X, and Y independently represent carbon (substituted with hydrogen or the optional substituents indicated herein) or nitrogen, provided that no more than two of Q, T, D, X, and Y are nitrogen; and provided however that wherein D is nitrogen, then R10, R11, and R12 are not attached to D, and provided that wherein X is nitrogen, then R10, R11, and R12 are not attached to X, and provided that wherein T is nitrogen, then R10, R11, and R12 are not attached to T, and provided that wherein Q is nitrogen, then R10, R11, and R12 are not attached to Q, and provided that wherein Y is nitrogen, then R10, R11, and R12 are not attached to Y; or

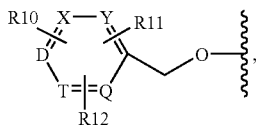

wherein the zig-zag lines represent the point of attachment, and wherein Q, T, D, X, and Y independently represent carbon (substituted with hydrogen or the optional substituents indicated herein) or nitrogen, provided that no more than two of Q, T, D, X, and Y are nitrogen; provided however that wherein D is nitrogen, then R10, R11, and R12 are not attached to D, and provided that wherein X is nitrogen, then R10, R11, and R12 are not attached to X, and provided that wherein T is nitrogen, then R10, R11, and R12 are not attached to T, and provided that wherein Q is nitrogen, then R10, R11, and R12 are not attached to Q, and provided that wherein Y is nitrogen, then R10, R11, and R12 are not attached to Y;

R5 is independently
—H, —OH, -halogen, —($C_1$—$C_4$) alkyl(optionally substituted with one to three halogens), —O—($C_1$-$C_3$) alkyl (optionally substituted with one to three halogens), or —($C_1$-$C_3$) alkyl-O—($C_1$-$C_3$)alkyl(optionally substituted with one to three halogens);

R6 is independently at each occurrence
—H, -halogen, or —$CH_3$;

R7 and R8 are independently at each occurrence
—H, or —($C_1$-$C_7$) alkyl(optionally substituted with one to three halogens), or NR7R8 combine to form a four to seven membered ring;

R9 is independently at each occurrence
—H; —CN, or —($C_1$-$C_3$) alkyl(optionally substituted with one to three halogens);

R10, R11, and R12 are independently at each occurrence
—H, -halogen, —($C_1$-$C_7$) alkyl(optionally substituted with one to three halogens), —($C_1$-$C_7$) alkyl-OH(optionally substituted with one to three halogens), —CN, —C(O)—($C_1$-$C_7$) alkyl(optionally substituted with one to three halogens), —C(O)OR7, —C(O)($C_3$—$C_7$)cycloalkyl(optionally substituted with one to three halogens), —C(O)NR7R8, —OR7, —NR7R8, —NR9$SO_2$R7, —NR9C(O)R7, —NR9$CO_2$R7, —NR9C(O)NR7R8, —SR7, —$SO_2$R7, —$SO_2$NR7R8, —S(O)R7, -heteroaryl-R9, or when R10 and R11 are adjacent to each other they may combine along with the respective atoms to which they are attached to form a five membered or six membered heterocarbon ring containing at least one but not more than two atoms selected from O, S, or N, provided the heteroatoms are not adjacent to each other, and wherein optionally said five membered or six membered heterocarbon ring may contain one to three double bonds.

The present invention provides compounds that show a selective and high affinity binding for the histamine H3 receptor, and thus the compounds are useful as histamine H3 receptor antagonists or inverse agonists. In another aspect, the present invention provides compounds that are useful as selective antagonists or inverse agonists of the histamine H3 receptor but have little or no binding affinity of GPRv53. In addition, the present invention provides a method for the treatment of a nervous system disorder, which comprises administering to a patient in need thereof an effective amount of a compound of formula I. The present invention further provides a method for the treatment of obesity or cognitive disorders, which comprises administering to a patient in need thereof an effective amount of a compound of formula I. In yet another aspect, the present invention provides pharmaceutical compositions comprising antagonists or inverse agonists of the histamine H3 receptor.

DETAILED DESCRIPTION OF THE INVENTION

General terms used in the description of compounds, compositions, and methods herein described, bear their usual meanings. Throughout the instant application, the following terms have the indicated meanings:

The term "GPRv53" means a recently identified novel histamine receptor as described in Oda, et al., supra. Alternative names for this receptor are PORT3 or H4R.

The term "H3R" means the histamine H3 receptor that inhibits the release of a number of monoamines, including histamine.

The term "H1R" means the histamine H1 receptor subtype.
The term "H2R" means the histamine H2 receptor subtype.
The term "H3R antagonists" is defined as a compound with the ability to block forskolin-stimulated cAMP production in response to agonist R-(–)α methylhistamine. The term "H3R inverse agonist" is defined as a compound with the ability to inhibit the constitutive activity of H3R. "Selective H3R antagonists or inverse agonists" means a compound of the present invention having a greater affinity for H3 histamine receptor than for GPRv53 histamine receptor.

In the general formulae of the present document, the general chemical terms have their usual meanings. For example; "($C_1$-$C_3$) Alkyl" are one to three carbon atoms such as methyl, ethyl, propyl, and the like, optionally substituted with one to three halogens, and "($C_1$-$C_4$) alkyl" are one to four carbon atoms such as methyl, ethyl, propyl, butyl and the like, optionally substituted with one to three halogens, and "($C_1$-$C_7$) Alkyl" are one to seven carbon atoms such as methyl, ethyl, propyl, butyl, pentyl, hexyl, heptyl, and the like, optionally substituted with one to three halogens, and as defined herein "alkyl" includes branched or isomeric forms.

"Cycloalkyl" means a ring with three to seven carbon atoms such as cyclopropyl, cyclobutyl, cyclopentyl and cyclohexyl, cycloheptyl, and the like.

"Heteroaryl" means a monocyclic aromatic ring containing five atoms, and containing at least one ring heteroatom selected from N, O and S (including SO and $SO_2$). Examples of heteroaryl include pyrrolyl, isoxazolyl, isothiazolyl, pyrazolyl, oxazolyl, oxadiazolyl, thiadiazolyl, thiazolyl, imidazolyl, triazolyl, tetrazolyl, furanyl, thienyl, thiophenyl, and the like.

"Halogen" or "halo" means fluoro, chloro, bromo and iodo.

The term "optionally substituted" as used herein means that the groups in question are either unsubstituted or substituted with one or more of the substituents specified. When the groups in question are substituted with more than one substituent, the substituents may be the same or different.

Furthermore, when using the terms "independently", "independently are", and "independently selected from" it should be understood that the groups in question may be the same or different.

The term "patient" includes human and non-human animals such as companion animals (dogs and cats and the like) and livestock animals. Livestock animals are animals raised for food production. Ruminants or "cud-chewing" animals such as cows, bulls, heifers, steers, sheep, buffalo, bison, goats and antelopes are examples of livestock. Other examples of livestock include pigs and avians (poultry) such as chickens, ducks, turkeys and geese. Yet other examples of livestock include fish, shellfish and crustaceans raised in aquaculture. Also included are exotic animals used in food production such as alligators, water buffalo and ratites (e.g., emu, rheas or ostriches). The patient to be treated is preferably a mammal, in particular a human being.

The terms "treatment", "treating" and "treat", as used herein, include their generally accepted meanings, i.e., the management and care of a patient for the purpose of preventing, prohibiting, restraining, alleviating, ameliorating, slowing, stopping, delaying, or reversing the progression or severity of a disease, disorder, or pathological condition, described herein, including the alleviation or relief of symptoms or complications, or the cure or elimination of the disease, disorder, or condition.

"Composition" means a pharmaceutical composition and is intended to encompass a pharmaceutical product comprising the active ingredient(s) including compound(s) of Formula I and the inert ingredient(s) that make up the carrier. Accordingly, the pharmaceutical compositions of the present invention encompass any composition made by admixing a compound of the present invention and a pharmaceutically acceptable carrier.

The term "suitable solvent" refers to any solvent, or mixture of solvents, inert to the ongoing reaction that sufficiently solubilizes the reactants to afford a medium within which to effect the desired reaction.

The term "unit dosage form" means physically discrete units suitable as unitary dosages for human subjects and other non-human animals, each unit containing a predetermined quantity of active material calculated to produce the desired therapeutic effect, in association with a suitable pharmaceutical carrier.

Certain of the above defined terms may occur more than once in the structural formulae, and upon such occurrence each term shall be defined independently of the other.

In one embodiment, the present invention provides compounds of Formula I as described in detail above. While all of the compounds of the present invention are useful, certain of the compounds are particularly interesting and are preferred. The following listings set out several groups of preferred compounds. It will be understood that each of the listings may be combined with other listings to create additional groups of preferred embodiments.

In a preferred embodiment the invention provides a compound structurally represented by Formula I, or a pharmaceutically acceptable salt thereof wherein:

m is independently at each occurrence 1 or 2, wherein optionally one or two of the hydrogens of the —$CH_2$—, or —$CH_2$—$CH_2$— so formed may independently be replaced by halogen, or optionally on the carbon not adjacent to nitrogen one of the hydrogens of the —$CH_2$—$CH_2$— so formed may independently be replaced by —OH, —O—($C_1$-$C_4$) alkyl(optionally substituted with one to three halogens), or —($C_1$-$C_3$)alkyl(optionally substituted with one to three halogens);

Z independently represents carbon (substituted with hydrogen or the optional substituents indicated herein);

R1 and R2 are independently
—($C_1$-$C_7$) alkyl(optionally substituted with one to three halogens), or R1 and R2 and the nitrogen to which they are attached form an azetidinyl ring, a pyrrolidinyl ring, or a piperidinyl ring, wherein further the azetidinyl, pyrrolidinyl, or piperidinyl ring so formed may be optionally substituted once with R5;

R3 is independently —H, or —$CH_3$ (optionally substituted with one to three halogens);

R5 is independently —H, —$CH_3$ (optionally substituted with one to three halogens);

R6 is independently at each occurrence —H, -halogen, or —$CH_3$;

R7 and R8 are independently at each occurrence
—H, or —($C_1$-$C_7$) alkyl(optionally substituted with one to three halogens), or NR7R8 combine to form a four to seven membered ring;

R9 is independently at each occurrence
—H, —CN, or —($C_1$-$C_3$) alkyl(optionally substituted with one to three halogens);

R10, R11, and R12 are independently at each occurrence
—H, -halogen, —($C_1$-$C_7$) alkyl(optionally substituted with one to three halogens), —($C_1$-$C_7$) alkyl-OH(optionally substituted with one to three halogens), —CN, —C(O)—($C_1$-$C_7$) alkyl(optionally substituted with one to three halogens), —CO(O)R7, —C(O)($C_3$—$C_7$)cycloalkyl(optionally substituted with one to three halogens), —C(O)NR7R8, —OR7, —NR7R8, —NR9$SO_2$R7, —NR9C(O)R7, —NR9$CO_2$R7, —NR9C(O)NR7R8, —SR7, —$SO_2$R7, —$SO_2$NR7R8, —S(O)R7, -heteroaryl-R9, or when R10 and R11 are adjacent to each other they may combine along with the respective atoms to which they are attached to form a five membered or six membered heterocarbon ring containing at least one but not more than two atoms selected from O, S, or N, provided the heteroatoms are not adjacent to each other, and wherein optionally said five membered or six membered heterocarbon ring may contain one to three double bonds.

In another preferred embodiment the invention provides a compound structurally represented by Formula I, or a pharmaceutically acceptable salt thereof wherein:

m is independently at each occurrence 2, wherein optionally one or two of the hydrogens of the —$CH_2$—$CH_2$— so formed may independently be replaced by halogen, or optionally on the carbon not adjacent to nitrogen one of the hydrogens of the —$CH_2$—$CH_2$— so formed may independently be replaced by —OH, —O—($C_1$-$C_4$) alkyl(optionally substituted with one to three halogens), or —($C_1$-$C_3$) alkyl(optionally substituted with one to three halogens);

Z independently represents carbon (substituted with hydrogen);

R1 and R2 and the nitrogen to which they are attached form a pyrrolidinyl ring, or a piperidinyl ring, wherein further the pyrrolidinyl or piperidinyl ring so formed may be optionally substituted once with R5;

R3 is independently —H, or —CH$_3$ (optionally substituted with one to three halogens);

R5 is independently —H, or —CH$_3$ (optionally substituted with one to three halogens);

R6 is independently at each occurrence —H, or -halogen, provided that at least one of R6 is —H;

R7 and R8 are independently at each occurrence
—H, or —(C$_1$-C$_7$) alkyl(optionally substituted with one to three halogens), or NR7R8 combine to form a four to seven membered ring;

R9 is independently at each occurrence —H, —CN, or —(C$_1$-C$_3$) alkyl(optionally substituted with one to three halogens);

R10, R11, and R12 are independently at each occurrence
—H, -halogen, —(C$_1$-C$_7$) alkyl(optionally substituted with one to three halogens), —(C$_1$-C$_7$) alkyl-OH(optionally substituted with one to three halogens), —CN, —C(O)—(C$_1$-C$_7$) alkyl(optionally substituted with one to three halogens), —C(O)OR7, —C(O)(C$_3$—C$_7$)cycloalkyl(optionally substituted with one to three halogens), —C(O)NR7R8, —OR7, —NR7R8, —NR9SO$_2$R7, —NR9C(O)R7, —NR9CO$_2$R7, —NR9C(O)NR7R8, —SR7, —SO$_2$R7, —SO$_2$NR7R8, —S(O)R7, -heteroaryl-R9, provided that not more than one of R10, R11, and R12 are -heteroaryl-R9.

In another preferred embodiment the invention provides a compound structurally represented by Formula I, or a pharmaceutically acceptable salt thereof wherein:

m is independently at each occurrence 2; Z independently represents carbon (substituted with hydrogen); R1 and R2 and the nitrogen to which they are attached form a pyrrolidinyl ring, wherein further the pyrrolidinyl ring so formed may be optionally substituted once with R5; R3 is independently —CH$_3$ (optionally substituted with one to three halogens); R5 is independently —H, or —CH$_3$ (optionally substituted with one to three halogens); R6 is independently at each occurrence —H; R7 and R8 are independently at each occurrence —H, or —(C$_1$-C$_7$) alkyl(optionally substituted with one to three halogens);

R9 is independently at each occurrence —H, —CN, or —(C$_1$-C$_3$) alkyl(optionally substituted with one to three halogens); R10, R11, and R12 are independently at each occurrence —H, -halogen, —(C$_1$-C$_7$) alkyl(optionally substituted with one to three halogens), —(C$_1$-C$_7$)alkyl-OH(optionally substituted with one to three halogens), —CN, —C(O)—(C$_1$-C$_7$)alkyl(optionally substituted with one to three halogens), —C(O)OR7, —C(O)(C$_3$—C$_7$)cycloalkyl(optionally substituted with one to three halogens), —C(O)NR7R8, —OR7, —NR7R8, —NR9SO$_2$R7, —NR9C(O)R7, —NR9CO$_2$R7, —NR9C(O)NR7R8, —SR7, —SO$_2$R7, —SO$_2$NR7R8, —S(O)R7, -heteroaryl-R9, provided that not more than one of R10, R11, and R12 are -heteroaryl-R9.

In another preferred embodiment the invention provides a compound structurally represented by Formula I, or a pharmaceutically acceptable salt thereof wherein:

R4 is independently
—O-phenyl(R10)(R11), -heteroaryl-R9, —O—CH$_2$-heteroaryl-R9, or

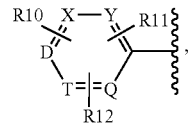

wherein the zig-zag lines represent the point of attachment, and wherein Q, T, D, X, and Y independently represent carbon (substituted with hydrogen or the optional substituents indicated herein) or nitrogen, provided that no more than two of Q, T, D, X, and Y are nitrogen; and provided however that wherein D is nitrogen, then R10, R11, and R12 are not attached to D, and provided that wherein X is nitrogen, then R10, R11, and R12 are not attached to X, and provided that wherein T is nitrogen, then R10, R11, and R12 are not attached to T, and provided that wherein Q is nitrogen, then R10, R11, and R12 are not attached to Q, and provided that wherein Y is nitrogen, then R10, R11, and R12 are not attached to Y; or

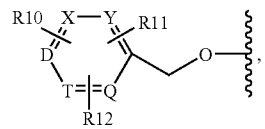

wherein the zig-zag lines represent the point of attachment, and wherein Q, T, D, X, and Y independently represent carbon (substituted with hydrogen or the optional substituents indicated herein) or nitrogen, provided that no more than two of Q, T, D, X, and Y are nitrogen; provided however that wherein D is nitrogen, then R10, R11, and R12 are not attached to D, and provided that wherein X is nitrogen, then R10, R11, and R12 are not attached to X, and provided that wherein T is nitrogen, then R10, R11, and R12 are not attached to T, and provided that wherein Q is nitrogen, then R10, R11, and R12 are not attached to Q, and provided that wherein Y is nitrogen, then R10, R11, and R12 are not attached to Y.

In another embodiment the invention provides a compound structurally represented by Formula I, or a pharmaceutically acceptable salt thereof wherein: —(CH2)$_m$— is —CH$_2$—, —CH$_2$CH$_2$—, or —CH$_2$—CH$_2$—CH$_2$—, wherein one of the hydrogens on a carbon not adjacent to a nitrogen may be replaced by —OH or —OCH$_3$; Z is carbon (substituted with hydrogen or optionally substituted with fluorine) or nitrogen, provided that when Z is nitrogen then R6 is not attached to Z; R1 and R2 are independently —CH$_3$, —CH$_2$CH$_3$, or —CH(CH$_3$)$_2$, wherein Ri and R2 and the nitrogen to which they are attached may optionally from an azetidinyl ring, a piperidinyl ring, or a pyrrolidinyl ring, wherein further the azetidinyl, piperidinyl, or pyrrolidinyl ring so formed may, independently, be optionally substituted once with —F, —OH, —OCH$_3$, —CH$_3$, —CH$_2$—CH$_3$, —CH$_2$—F, or —CH$_2$—O—CH$_3$; R3 is hydrogen or —CH$_3$; R4 is —Br, —OH, —OCH$_2$CH$_2$CH$_3$, —O-phenyl, -2-pyridinyl, -3-pyridinyl, -4-pyridinyl, -pyrimidinyl, —OCH$_2$—R14, -pyridazinyl, -1H-indolyl, -phenyl, -2-thiophenyl, or -benzo[1,3]dioxolyl, wherein further the -2-pyridinyl, -3-pyridinyl, -4-pyridinyl, -pyrimidinyl, -pyridazinyl, -1H-indolyl, -phenyl, or -2-thiophenyl, may be optionally substituted one to two times with R7 provided that R7 is not directly attached to the nitrogen of -2-pyridinyl, -3-pyridinyl, -4-pyridinyl, -pyrimidinyl, -pyridazinyl, -1H-indolyl, or the sulfur of -2-thiophenyl; R6 is hydrogen or —F; R7 is —S(O)₂—R9, —N—S(O)₂—CH₃, —S(O)CH₃, 2-methyl-[1,3,4]oxadiazolyl, —CN, —C(O)N (CH₃)₂, —F, —CH₃, —CH₂—OH, —OCH₃, —CF₃, —OCF₃, —C(O)—CH₃, —C(O)-pyrrolidinyl, or —C(O) NH₂; R14 is -2-pyridinyl, -3-pyridinyl, -4-pyridinyl, -Phenyl, -thiazolyl, 4-methanesulfonyl-phenyl, -5-thiophenyl-2—Carbonitrile, -2-methylthiazol-4-yl, -2-methoxy-pyridin-5-yl, 2-methyl-pyridin-6-yl; and R9 is —CH₃, —CH₂CH₃, —CH₂—CH₂ $_{CH3}$, —CF₃, —CH₂—CH₂—CH₂—F, or -N(CH₃)₂.

In another preferred embodiment R4 is —Br, —OH, —OCH₂CH₂CH₂CH₃, -O-phenyl, -2-pyridinyl, -3-pyridinyl, -4-pyridinyl, -pyrimidinyl,-2-oxymethylpyridinyl, -3-oxymethylpyridinyl, -4-oxymethylpyridinyl, -oxymethylbenzene, -4-oxymethyl-2-methylthiazolyl, -4-oxymethylthiazolyl, -benzyloxy-4-methanesulfonyl, -5-oxymethyl-thiophene-2-carbonitrile, -5-oxymethyl-2-methoxy-pyridyl, -2-oxymethyl-6-methyl-pyridinyl -pyridazinyl, -1H-indolyl, -phenyl, -2-thiophenyl, or -benzo[1,3]dioxolyl, wherein further the -2-pyridinyl, -3-pyridinyl, -4-pyridinyl, -pyrimidinyl, -pyridazinyl, -1H-indolyl, -phenyl, -2-thiophenyl, may be optionally substituted one to two times with R7 provided that R7 is not directly attached to the nitrogen of -2-pyridinyl, -3-pyridinyl, -4-pyridinyl, -pyrimidinyl, -pyridazinyl, -1H-indolyl, or the sulfur of -2-thiophenyl.

In another preferred embodiment the invention provides a compound of formula I or a pharmaceutically acceptable salt wherein Z is nitrogen and R6 is not attached to Z. Other preferred embodiments of the invention include;

1. wherein m is 1,
2. wherein m is 2,
3. wherein m is 3,
4. wherein R1 and R2 and the nitrogen to which they are attached form an azetidinyl ring, and wherein the azetidinyl ring so formed may be optionally substituted once with R5,
5. wherein R1 and R2 and the nitrogen to which they are attached form a pyrrolidinyl ring, and wherein the pyrrolidinyl ring so formed may be optionally substituted once with R5,
6. wherein R1 and R2 and the nitrogen to which they are attached form a piperidinyl ring, and wherein further the piperidinyl ring so formed may be optionally substituted once with R5,
7. wherein R5 is H,
8. wherein R5 is —(C₁-C₄) alkyl (optionally substituted with one to three halogens),
9. wherein R5 is —CH₃,
10. wherein R5 is halogen,
11. wherein R3 is —(C₁-C₄) alkyl(optionally substituted with one to three halogens),
12. wherein R3 is —CH₃,
13. wherein R3 is halogen,
14. wherein Z is carbon(substituted with hydrogen or the optional substituents indicated herein),
15. wherein Z is nitrogen,
16. wherein R6 is halogen,
17. wherein R6 is hydrogen,
18. wherein R6 is —CH₃.
19. wherein R4 is -halogen, —(C₁-C₇) alkyl(optionally substituted with one to three halogens), —CN, —C(O) R7, —C(O)(C₃—C₇)cycloalkyl(optionally substituted with one to three halogens), —C(O)NR7R8, —OR7, —NO₂, —NR7R8, —NR7SO₂R7, —NR7C(O)R7, —NR7CO₂R7, —NR7C(O)NR7R8, —SR7, —SO₂R7, —SO₂ NR7R8, —S(O)R7, or —O(CH₂)mNR7R8,
20. wherein R4 is —O-phenyl(R10)(R11),
21. wherein R4 is -heteroaryl-R9,
22. wherein R4 is —O—CH₂-heteroaryl-R9,
23. wherein R4 is

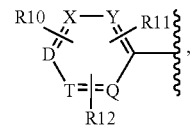

wherein the zig-zag lines represent the point of attachment, and wherein Q, T, D, X, and Y independently represent carbon (substituted with hydrogen or the optional substituents indicated herein), or nitrogen, provided that no more than two of Q, T, D, X, and Y are nitrogen;

and provided however that wherein D is nitrogen, then R10 or R11 or R12 are not attached to D, and provided that wherein X is nitrogen, then R10 or R11, or R12 are not attached to X, and provided that wherein T is nitrogen, then R10 or R11 or R12 are not attached to T, and provided that wherein Q is nitrogen, then R10 or R11 or R12 are not attached to Q, and provided that wherein Y is nitrogen, then R10 or R11, or R12 are not attached to Y;

24. wherein R4 is

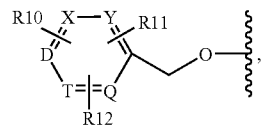

wherein the zig-zag lines represent the point of attachment, and wherein Q, T, D, X, and Y independently represent carbon (substituted with hydrogen or the optional substituents indicated herein), or nitrogen, provided that no more than two of Q, T, D, X, and Y are nitrogen; provided however that wherein D is nitrogen, then R10 or R11 or R12 are not attached to D, and provided that wherein X is nitrogen, then R10 or R11 or R12 are not attached to X, and provided that wherein T is nitrogen, then R10 or R11 or R12 are not attached to T, and provided that wherein Q is nitrogen; then R10 or R11 or R12 are not attached to Q, and provided that wherein Y is nitrogen, then R10 or R11 or R12 are not attached to Y;

25. wherein Q, T, D, X, and Y are carbon (substituted with hydrogen or the optional substituents indicated herein),
26. wherein X is carbon and R10 is attached to X,
27. wherein D is carbon and R10 is attached to D,
28. wherein T is carbon and RIO is attached to T,
29. wherein D is carbon and R10 is attached to D and R10 is selected from the group consisting of —NR9SO₂R7, —SO₂R7, —SO₂ NR7R8, and —S(O)R7,
30. wherein one of Q, T, D, X, or Y is nitrogen,
31. wherein Q is nitrogen,
32. wherein T is nitrogen,
33. wherein D is nitrogen,
34. wherein X is nitrogen,
35. wherein Y is nitrogen,
36. wherein two of Q, T, D, X, or Y is nitrogen,
37. wherein D and Q are nitrogen,
38. wherein T and X are nitrogen,
39. wherein D and Y are nitrogen, 40. wherein D and Q are nitrogen,
41. wherein Q and Y are nitrogen,
42. wherein R10 is selected from the group consisting of -halogen, —($C_1$-$C_7$) alkyl optionally substituted with one to three halogens), —($C_1$-$C_7$) alkyl-OH optionally substituted with one to three halogens), —CN, —C(O)—($C_3$—$C_7$)cycloalkyl (optionally substituted with one to three halogens), —C(O)OR7, —C(O)($C_3$—$C_7$)cycloalkyl, —C(O)NR7R8, —OR7, —NR7R8, —NR9$SO_2$R7, —NR9C(O)R7, —NR9$CO_2$R7, —NR9C(O)NR7R8, —SR7, —$SO_2$R7, —$SO_2CF_3$, —$SO_2$NR7R8, and —S(O)R7,
43. wherein R10 is -heteroaryl-R9,
44. wherein when R10 and R11 are adjacent to each other they may combine along with the respective atoms to which they are attached to form a saturated or unsaturated five membered or six membered ring containing at least one but not more than two atoms selected from O, S, and N, In another embodiment according to the invention there is provided a compound structurally represented by Formula I, or pharmaceutically acceptable salts thereof wherein:

m is 1, 2, or 3, wherein one or two of the hydrogens of the —$CH_2$—, —$CH_2$—$CH_2$—, or —$CH_2$—$CH_2$—$CH_2$— so formed may be replaced by halogen, or —OH, or —($C_1$-$C_3$)alkyl;

Z independently represents carbon or nitrogen, provided that when Z is nitrogen then R6 is not attached to Z;

R1 and R2 are independently
—($C_1$-$C_7$) alkyl,
wherein R1 and R2 and the nitrogen to which they are attached may optionally form an azetidinyl ring, a pyrrolidinyl ring, or a piperidinyl ring, provided the combination of R1 and R2 represent a sufficient number of carbon atoms to form the azetidinyl, pyrrolidinyl, or piperidinyl ring, wherein further the azetidinyl, pyrrolidinyl, or piperidinyl ring so formed may be optionally substituted one to three times with R5;

R3 is independently
—H, -halogen, —$CF_3$, —($C_1$-$C_4$) alkyl, or —O—($C_1$-$C_3$) alkyl;

R4 is independently
—H, -halogen, —($C_1$-$C_7$) alkyl, —CN, —C(O)R7, —C(O)($C_3$—$C_7$)cycloalkyl, —C(O)NR7R8, —$OCF_3$, —OR7, —$NO_2$, —NR7R8, —NR7$SO_2$R7, —NR7C(O)R7, —NR7$CO_2$R7, —NR7C(O)NR7R8, —SR7, —$SO_2$R7, —$SO_2CF_3$, —$SO_2$ NR7R8, —S(O)R7, —O($CH_2$)mNR7R8, -heteroaryl-R9,

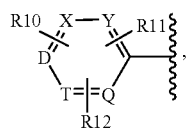

wherein the zig-zag lines represent the point of attachment, and wherein Q, T, D, X, and Y independently represent carbon or nitrogen, provided that no more than two of Q, T, D, X, and Y are nitrogen; and provided however that wherein D is nitrogen, then R10 or R11 or R12 are not attached to D, and provided that wherein X is nitrogen, then R10 or R11 or R12 are not attached to X, and provided that wherein T is nitrogen, then R10 or R11 or R12 are not attached to T, and provided that wherein Q is nitrogen, then R10 or R11 or R12 are not attached to Q, and provided that wherein Y is nitrogen, then R10 or R11 or R12 are not attached to Y; or

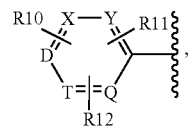

wherein the zig-zag lines represent the point of attachment, and wherein Q, T, D, X, and Y independently represent carbon or nitrogen, provided that no more than two of Q, T, D, X, and Y are nitrogen; provided however that wherein D is nitrogen, then R10 or R11 or R12 are not attached to D, and provided that wherein X is nitrogen, then R10 or R11 or R12 are not attached to X, and provided that wherein T is nitrogen, then R10 or R11, or R12 are not attached to T, and provided that wherein Q is nitrogen, then R10 or R11 or R12 are not attached to Q, and provided that wherein Y is nitrogen, then R10 or R11 or R12 are not attached to Y;

R5 is independently
—H, —OH, -halogen, —($C_1$-$C_4$) alkyl, —O—($C_1$-$C_3$) alkyl, or —($C_1$-$C_3$) alkyl-O—($C_1$-$C_3$)alkyl;

R6 is independently at each occurrence
-halogen or —$CH_3$;

R7 and R8 are independently at each occurrence
—H, or —($C_1$-$C_7$) alkyl, wherein R7 and R8 can combine with the atom to which they are attached to form a three to seven membered ring, provided that R7 and R8 are attached to the same atom;

R9 is independently at each occurrence
—H, —CN, or —($C_1$-$C_3$) alkyl;

R10, R11, and R12 are independently at each occurrence
—H, -halogen, —($C_1$-$C_7$) alkyl, —($C_1$-$C_7$) alkyl-OH, —$CF_3$, —CN, —C(O)R14, —CO(O)R7, —CO(O)Li, —C(O)($C_3$—$C_7$)cycloalkyl, —C(O)NR7R8, —$OCF_3$, —OR7, —NR7R8, —$NH_2SO_2$R7, —NR9$SO_2$R7, —NR9C(O)R7, —NR9$CO_2$R7, —NR9C(O)NR7R8, —SR7, —$SO_2$R7, —$SO_2CF_3$, —$SO_2$NR7R8, —S(O) R7, —$CH_2SO_2$R14, -heteroaryl-R9, -pyridyl, or -pyrimidyl,
wherein R and R11 may combine along with the respective atoms to which they are attached to form a saturated or unsaturated five membered or six membered ring containing at least one but not more than two atoms selected from O, S, or N;

R14 is
—H, —($C_1$-$C_7$) alkyl, or -phenyl.

In another embodiment, the invention provides a compound of Formula (II),

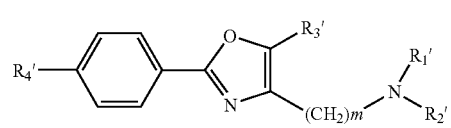

(II)

or a pharmaceutically acceptable salt thereof, wherein:
m is 1 or 2,
wherein one or two of the hydrogens of the —$CH_2$— or —$CH_2$—$CH_2$— so formed may be replaced by halogen;

R1' and R2' are independently
—(C$_1$-C$_7$) alkyl,
wherein R1' and R2' and the nitrogen to which they are attached may optionally form an azetidinyl ring, a pyrrolidinyl ring, or a piperidinyl ring, provided the combination of R1' and R2' represent a sufficient number of carbon atoms to form the azetidinyl, pyrrolidinyl, or piperidinyl ring, wherein further the azetidinyl, pyrrolidinyl, or piperidinyl ring so formed may be optionally substituted one to three times with R5';

R3' is independently
—H, or —(C$_1$-C$_4$) alkyl;

R4' is independently
—H, -halogen, —(C$_1$-C$_7$) alkyl, —CN, —C(O)R7', —C(O)(C$_3$—C$_7$)cycloalkyl, —C(O)NR7'R8', —OCF$_3$, —OR7', —NO$_2$, —NR7'R8', —NR7'SO$_2$R7', —NR7°C(O)R7', —NR7° CO$_2$R7', —NR7'C(O)NR7'R8', —SR7', —SO$_2$R7', —SO$_2$CF$_3$, —SO$_2$NR7'R8', —S(O)R7', —O(CH$_2$)mNR7'R8', -heteroaryl-R9',

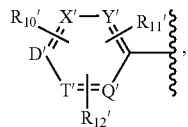

wherein the zig-zag lines represent the point of attachment, and wherein Q', T', D', X', and Y' independently represent carbon or nitrogen, provided that no more than two of Q', T', D', X', and Y' are nitrogen; and provided however that wherein D' is nitrogen, then R10' or R11' or R12' are not attached to D', and provided that wherein X' is nitrogen, then R10' or R11' or R12' are not attached to X', and provided that wherein T' is nitrogen, then R10' or R11' or R12' are not attached to T', and provided that wherein Q' is nitrogen, then R10' or R11' or R12' are not attached to Q', and provided that wherein Y' is nitrogen, then R10' or R11' or R12' are not attached to Y'; or

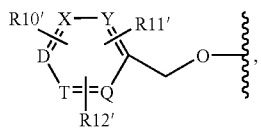

wherein the zig-zag lines represent the point of attachment, and wherein Q', T', D', X', and Y' independently represent carbon or nitrogen, provided that no more than two of Q', T', D', X', and Y' are nitrogen; provided however that wherein D' is nitrogen, then R10' or R11' or R12' are not attached to D', and provided that wherein X' is nitrogen, then R10' or R11' or R12' are not attached to X', and provided that wherein T' is nitrogen, then R10' or R11' or R12' are not attached to T', and provided that wherein Q' is nitrogen, then R10' or R11' or R12' are not attached to Q', and provided that wherein Y' is nitrogen, then R10' or R11' or R12' are not attached to Y';

R5' is independently
—H, —OH, -halogen, —(C$_1$-C$_4$) alkyl, —O—(C$_1$-C$_3$) alkyl, or —(C$_1$-C$_3$) alkyl-O—(C$_1$-C$_3$) alkyl, R7' and R8' are independently at each occurrence
—H, or —(C$_1$-C$_7$) alkyl,
wherein R7' and R8' can combine with the atom to which they are attached to form a three to seven membered ring, provided that R7' and R8' are attached to the same atom;

R9' is independently at each occurrence
—H, —CN, or —(C$_1$-C$_3$) alkyl;

R10', R11', and R12' are independently at each occurrence
—H, -halogen, —(C$_1$-C$_7$) alkyl, —(C$_1$-C$_7$) alkyl-OH, —CF$_3$, —CN, —C(O)R14', —CO(O)R7', —CO(O)Li, —C(O)(C$_3$-C$_7$)cycloalkyl, —C(O)NR7'R8', —OCF$_3$, —OR7', —NR7'R8', —NH$_2$SO$_2$R7', —NR9'SO$_2$R7', —NR9'C(O)R7', —NR9'CO$_2$R7', —NR9'C(O)NR7'R8', —SR7', —SO$_2$R7', —SO$_2$CF$_3$, —SO$_2$NR7'R8', —S(O)R7', —CH$_2$SO$_2$R14', -heteroaryl-R9', -pyridinyl, -pyrimidinyl,
wherein R10' and R11' may combine along with the respective atoms to which they are attached to form a saturated or unsaturated five membered or six membered ring containing at least one but not more than two atoms selected from O, S, or N;

R14' is
—H, —(C$_1$-C$_7$) alkyl, or -phenyl.

Due to their interaction with the histamine H3 receptor, the present compounds are useful in the treatment of a wide range of conditions and disorders in which an interaction with the histamine H3 receptor is beneficial. Thus, the compounds may find use for example to prevent, treat and/or alleviate diseases or conditions of the central nervous system, the peripheral nervous system, the cardiovascular system, the pulmonary system, the gastrointestinal system and the endocrinological system, while reducing and or eliminating one or more of the unwanted side effects associated with the current treatments. Such diseases or conditions include those responsive to the modulation of histamine H3 receptors, such as nervous system disorders which include but are not limited to obesity, cognitive disorders, attention deficit disorders, memory processes, dementia and cognition disorders such as Alzheimer's disease and attention-deficit hyperactivity disorder; bipolar disorder, cognitive enhancement, cognitive deficits in psychiatric disorders, deficits of memory, deficits of learning, dementia, mild cognitive impairment, migraine, mood and attention alteration, motion sickness, narcolepsy, neurogenic inflammation, obsessive compulsive disorder, Parkinson's disease, schizophrenia, depression, epilepsy, and seizures or convulsions; sleep disorders such as narcolepsy; vestibular dysfunction such as Meniere's disease, migraine, motion sickness, pain, drug abuse, depression, epilepsy, jet lag, wakefulness, Tourette's syndrome, vertigo, and the like, as well as cardiovascular disorders such as acute myocardial infarction; cancer such as cutaneous carcinoma, medullary thyroid carcinoma and melanoma; respiratory disorders such as asthma; gastrointestinal disorders, inflammation, and septic shock, diabetes, type II diabetes, insulin resistance syndrome, metabolic syndrome, polycystic ovary syndrome, Syndrome X, and the like.

The present invention also provides a pharmaceutical composition which comprises a compound of Formula I or Formula II and a pharmaceutically acceptable carrier. Pharmaceutical formulations of Formula I or Formula II can provide a method of selectively increasing histamine levels in cells, or increasing histamine release by cells, by contacting the cells with an antagonist or inverse agonist of the histamine H3 receptor, the antagonist or inverse agonist being a compound of Formula I or Formula II. Thus, the methods of this invention encompass a prophylactic and therapeutic administration of a compound of Formula I or Formula II.

The present invention further provides an antagonist or inverse agonist of Formula I or Formula II which is characterized by having little or no binding affinity for the histamine receptor GPRv53.

Thus, a pharmaceutical preparation of Formula I or Formula II can be useful in the treatment or prevention of obesity, cognitive disorders, attention deficit disorders, memory processes, dementia and cognition disorders such as Alzheimer's disease and attention-deficit hyperactivity disorder; bipolar disorder, cognitive enhancement, cognitive deficits in psychiatric disorders, deficits of memory, deficits of learning, dementia, mild cognitive impairment, migraine, mood and attention alteration, motion sickness, narcolepsy, neurogenic inflammation, obsessive compulsive disorder, Parkinson's disease, schizophrenia, depression, epilepsy, and seizures or convulsions; sleep disorders such as narcolepsy; vestibular dysfunction such as Meniere's disease, migraine, motion sickness, pain, drug abuse, depression, epilepsy, jet lag, wakefulness, Tourette's syndrome, vertigo, and the like, which comprises administering to a subject in need of such treatment or prevention an effective amount of a compound of Formula I or Formula II. In addition, a pharmaceutical preparation of Formula I or Formula II can be useful in the treatment or prevention of a disorder or disease in which modulation of histamine H3 receptor activity has a beneficial effect or the treatment or prevention of eating disorders which comprises administering to a subject in need of such treatment or prevention an effective amount of a compound of Formula I or Formula II. In yet another aspect, the present invention provides compounds, pharmaceutical compositions, and methods useful in the treatment of nervous system and other disorders associated with histamine H3 receptor.

In addition, the present invention relates to a compound of Formula I or II, or a pharmaceutical salt thereof, or a pharmaceutical composition which comprises a compound of Formula I or II, or a pharmaceutical salt thereof, and a pharmaceutically acceptable carrier, diluent, or excipient; for use in inhibiting the histamine H3 receptor; for use in inhibiting a histamine H3 receptor mediated cellular response in a mammal; for use to increase the release of H3 receptor-regulated neurotransmitters in a mammal; for use in treating a disease arising from excessive histamine H3 receptor activity; and for use in treating nervous system disorders in a mammal including but not limited to obesity, cognitive disorders, attention deficit disorders, memory processes, dementia and cognition disorders such as Alzheimer's disease and attention-deficit hyperactivity disorder; bipolar disorder, cognitive enhancement, cognitive deficits in psychiatric disorders, deficits of memory, deficits of learning, dementia, mild cognitive impairment, migraine, mood and attention alteration, motion sickness, narcolepsy, neurogenic inflammation, obsessive compulsive disorder, Parkinson's disease, schizophrenia, depression, epilepsy, and seizures or convulsions; sleep disorders such as narcolepsy; vestibular dysfunction such as Meniere's disease, migraine, motion sickness, pain, drug abuse, depression, epilepsy, jet lag, wakefulness, Tourette's syndrome, and vertigo. Thus, the uses and methods of this invention encompass a prophylactic and therapeutic administration of a compound of Formula I or II.

The present invention is further related to the use of a compound of Formula I or II, or a pharmaceutical salt thereof, or a pharmaceutical composition which comprises a compound of Formula I or II, or a pharmaceutical salt thereof, and a pharmaceutically acceptable carrier, diluent, or excipient; for the manufacture of a medicament for inhibiting the histamine H3 receptor; for the manufacture of a medicament for inhibiting a histamine H3 receptor mediated cellular response in a mammal; for the manufacture of a medicament to increase the release of H3 receptor-regulated neurotransmitters in the brain of a mammal; for the manufacture of a medicament for treating a disease arising from excessive histamine H3 receptor activity; for the manufacture of a medicament for treating cognitive disorders in a mammal; and for the manufacture of a medicament for treating nervous system disorders in a mammal including but not limited to obesity, cognitive disorders, attention deficit disorders, memory processes, dementia and cognition disorders such as Alzheimer's disease and attention-deficit hyperactivity disorder; bipolar disorder, cognitive enhancement, cognitive deficits in psychiatric disorders, deficits of memory, deficits of learning, dementia, mild cognitive impairment, migraine, mood and attention alteration, motion sickness, narcolepsy, neurogenic inflammation, obsessive compulsive disorder, Parkinson's disease, schizophrenia, depression, epilepsy, and seizures or convulsions; sleep disorders such as narcolepsy; vestibular dysfunction such as Meniere's disease, migraine, motion sickness, pain, drug abuse, depression, epilepsy, jet lag, wakefulness, Tourette's syndrome, and vertigo.

The present invention further provides; a method of treating conditions resulting from excessive histamine H3 receptor activity in a mammal; a method of inhibiting the histamine H3 receptor activity in a mammal; a method of inhibiting a histamine H3 receptor mediated cellular response in a mammal; a method to increase the release of H3 receptor-regulated neurotransmitters in the brain of a mammal; a method of treating cognitive disorders in a mammal; a method of treating nervous system disorders in a mammal including but not limited to obesity, cognitive disorders, attention and attention deficit disorders, memory processes, learning, dementia, Alzheimer's disease, attention-deficit hyperactivity disorder, Parkinson's disease, schizophrenia, depression, epilepsy, and seizures or convulsions; comprising administering to a mammal in need of such treatment a histamine H3 receptor-inhibiting amount of a compound of Formula I or II or a pharmaceutically acceptable salt thereof, or a pharmaceutical composition which comprises a compound of Formula I or II, or a pharmaceutical salt thereof, and a pharmaceutically acceptable carrier, diluent, or excipient.

The present invention further provides a method of treating conditions resulting from excessive histamine H3 receptor activity in a mammal comprising administering to a mammal in need of such treatment a histamine H3 receptor inhibiting amount of a pharmaceutical composition which comprises a compound of Formula I or II, or a pharmaceutical salt thereof, and a pharmaceutically acceptable carrier, diluent, or excipient. In addition, a pharmaceutical composition of Formula I or II can be useful in the treatment or prevention of a disorder or disease in which modulation of histamine H3 receptor activity has a beneficial effect. The present invention further provides an antagonist or inverse agonist of Formula I or II which is characterized by having greater affinity for the histamine H3 receptor as compared to the affinity for the histamine H1R, H2R, or H4R receptors. In addition the embodiments of the present invention include the synthesis of the examples named herein by methods included herein, and supplemented by methods known in the art, to create positron emission topography (PET) ligands that bind to histamine H3 receptors and are useful for PET imaging.

The invention includes tautomers, enantiomers and other stereoisomers of the compounds also. Thus, as one skilled in the art knows, certain aryls may exist in tautomeric forms. Such variations are contemplated to be within the scope of the invention. It will be understood that, as used herein, references to the compounds of Formula I or Formula II are meant to also include the pharmaceutical salts, its enantiomers and racemic mixtures thereof.

As used herein, the term "stereoisomer" refers to a compound made up of the same atoms bonded by the same bonds but having different three-dimensional structures which are not interchangeable. The three-dimensional structures are called configurations. As used herein, the term "enantiomer" refers to two stereoisomers whose molecules are nonsuperimposable mirror images of one another. The term "chiral center" refers to a carbon atom to which four different groups are attached. As used herein, the term "diastereomers" refers to stereoisomers which are not enantiomers. In addition, two diastereomers which have a different configuration at only one chiral center are referred to herein as "epimers." The terms "racemate," "racemic mixture" or "racemic modification" refer to a mixture of equal parts of enantiomers.

The compounds of the present invention may be chiral, and it is intended that any enantiomers, as separated, pure or partially purified enantiomers or racemic mixtures thereof are included within the scope of the invention. Furthermore, when a double bond or a fully or partially saturated ring system or more than one center of asymmetry or a bond with restricted rotatability is present in the molecule diastereomers may be formed. It is intended that any diastereomers, as separated, pure or partially purified diastereomers or mixtures thereof are included within the scope of the invention. Furthermore, some of the compounds of the present invention may exist in different tautomeric forms and it is intended that any tautomeric forms, which the compounds are able to form, are included within the scope of the present invention. Thus, as one skilled in the art knows, certain aryls may exist in tautomeric forms. The invention also includes tautomers, enantiomers and other stereoisomers of the compounds of Formula I or Formula II. Such variations are contemplated to be within the scope of the invention.

The terms "R" and "S" are used herein as commonly used in organic chemistry to denote specific configuration of a chiral center. The term "R" (rectus) refers to that configuration of a chiral center with a clockwise relationship of group priorities (highest to second lowest) when viewed along the bond toward the lowest priority group. The term "S" (sinister) refers to that configuration of a chiral center with a counterclockwise relationship of group priorities (highest to second lowest) when viewed along the bond toward the lowest priority group. The priority of groups is based upon their atomic number (in order of decreasing atomic number). A partial list of priorities and a discussion of stereochemistry is contained in "Nomenclature of Organic Compounds: Principles and Practice", (J. H. Fletcher, et al., eds., 1974) at pages 103-120.

The designation "―" refers to a bond that protrudes forward out of the plane of the page. The designation "''''''" refers to a bond that protrudes backward out of the plane of the page. The designation "∼" refers to a bond wherein the stereochemistry is not defined.

The compounds of Formula I or Formula II, when existing as a diastereomeric mixture, may be separated into diastereomeric pairs of enantiomers by, for example, fractional crystallization from a suitable solvent, for example methanol or ethyl acetate or a mixture thereof. The pair of enantiomers thus obtained may be separated into individual stereoisomers by conventional means, for example by the use of an optically active acid as a resolving agent. Alternatively, any enantiomer of a compound of Formula I or Formula II may be obtained by stereospecific synthesis using optically pure starting materials or reagents of known configuration or through enantioselective synthesis.

The term "enantiomeric enrichment" as used herein refers to the increase in the amount of one enantiomer as compared to the other. A convenient method of expressing the enantiomeric enrichment achieved is the concept of enantiomeric excess, or "ee," which is found using the following equation:

$$ee = \frac{E^1 - E^2}{E^1 + E^2} \times 100$$

wherein $E^1$ is the amount of the first enantiomer and $E^2$ is the amount of the second enantiomer. Thus, if the initial ratio of the two enantiomers is 50:50, such as is present in a racemic mixture, and an enantiomeric enrichment sufficient to produce a final ratio of 70:30 is achieved, the ee with respect to the first enantiomer is 40%. However, if the final ratio is 90:10, the ee with respect to the first enantiomer is 80%. An ee of greater than 90% is preferred, an ee of greater than 95% is most preferred and an ee of greater than 99% is most especially preferred. Enantiomeric enrichment is readily determined by one of ordinary skill in the art using standard techniques and procedures, such as gas or high performance liquid chromatography with a chiral column. Choice of the appropriate chiral column, eluent and conditions necessary to effect separation of the enantiomeric pair is well within the knowledge of one of ordinary skill in the art. In addition, the specific stereoisomers and enantiomers of compounds of Formula I or Formula II can be prepared by one of ordinary skill in the art utilizing well known techniques and processes, such as those disclosed by J. Jacques, et al., "*Enantiomers, Racemates, and Resolutions,*" John Wiley and Sons, Inc., 1981, and E. L. Eliel and S. H. Wilen, "*Stereochemistry of Organic Compounds*" (Wiley-Interscience 1994), and European Patent Application No. EP-A-838448, published Apr. 29, 1998. Examples of resolutions include recrystallization techniques or chiral chromatography.

In general, the term "pharmaceutical" when used as an adjective means substantially non-toxic to living organisms. For example, the term "pharmaceutical salt" as used herein, refers to salts of the compounds of Formula I or Formula II which are substantially non-toxic to living organisms. See, e.g., Berge, S. M, Bighley, L. D., and Monkhouse, D. C., "Pharmaceutical Salts," *J. Pharm. Sci.*, 66:1, 1977. The present invention also encompasses pharmaceutically acceptable salts of the present compounds. Such salts include pharmaceutically acceptable acid addition salts, pharmaceutically acceptable metal salts, ammonium and alkylated ammonium salts. Also intended as pharmaceutically acceptable acid addition salts are any hydrates that the present compounds are able to form. Furthermore, the pharmaceutically acceptable salts comprise basic amino acid salts such as lysine, arginine and omithine. Typical pharmaceutical salts include those salts prepared by reaction of the compounds of Formula I or Formula II with an inorganic or organic acid or base. Such salts are known as acid addition or base addition salts respectively. These pharmaceutical salts frequently have enhanced solubility characteristics compared to the compound from which they are derived, and thus are often more amenable to formulation as liquids or emulsions.

The term "acid addition salt" refers to a salt of a compound of Formula I or Formula II prepared by reaction of a compound of Formula I or Formula II with a mineral or organic acid. For exemplification of pharmaceutical acid addition salts see, e.g., Berge, S. M, Bighley, L. D., and Monkhouse, D. C., *J. Pharm. Sci.*, 66:1, 1977. Since compounds of this invention can be basic in nature, they accordingly react with any of a number of inorganic and organic acids to form pharmaceutical acid addition salts.

The acid addition salts may be obtained as the direct products of compound synthesis. In the alternative, the free base may be dissolved hi a suitable solvent containing the appropriate acid, and the salt isolated by evaporating the solvent or otherwise separating the salt and solvent.

Acids commonly employed to form acid addition salts are inorganic acids such as hydrochloric acid, hydrobromic acid, hydroiodic acid, sulfuric acid, phosphoric acid, and the like, and organic acids, such as p-toluenesulfonic acid, ethanesulfonic acid, methanesulfonic acid, oxalic acid, p-bromophenylsulfonic acid, carbonic acid, succinic acid, citric acid, tartaric acid, benzoic acid, acetic acid and the like. Preferred pharmaceutical acid addition salts are those formed with mineral acids such as hydrochloric acid, hydrobromic acid, and sulfuric acid, and those formed with organic acids such as maleic acid, tartaric acid, and methanesulfonic acid. Examples of such pharmaceutically acceptable salts thus are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, β-hydroxybutyrate, glycollate, tartrate, methanesulfonate, propanesulfonate, naphthalene-1-sulfonate, naphthalene-2-sulfonate, mandelate and the like.

The skilled artisan would appreciate that some compounds of Formula I or Formula II may be acidic in nature and accordingly react with any of a number of inorganic and organic bases to form pharmaceutical base addition salts. The term "base addition salt" refers to a salt of a compound of Formula I or Formula II prepared by reaction of a compound of Formula I or Formula II with a mineral or organic base. For exemplification of pharmaceutical base addition salts see, e.g., Berge, S. M, Bighley, L. D., and Monkhouse, D. C., *J. Pharm. Sci.*, 66:1, 1977. Bases commonly employed to form pharmaceutical base addition salts are inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate, and the like. Examples of pharmaceutical base addition salts are the ammonium, lithium, potassium, sodium, calcium, magnesium, methylamino, diethylamino, ethylene diamino, cyclohexylamino, and ethanolamino salts, and the like of a compound of Formula I or Formula II. The potassium and sodium salt forms are particularly preferred. The present invention also contemplates pharmaceutical base addition salts of compounds of Formula I or Formula II.

The pharmaceutical salts of the invention are typically formed by reacting a compound of Formula I or Formula II with an equimolar or excess amount of acid or base. The reactants are generally combined in a mutual solvent such as diethylether, tetrahydrofuran, methanol, ethanol, isopropanol, benzene, and the like for acid addition salts, or water, an alcohol or a chlorinated solvent such as dichloromethane for base addition salts. The salts normally precipitate out of solution within about one hour to about ten days and can be isolated by filtration or other conventional methods.

The compounds of the present invention may form solvates with standard low molecular weight solvents using methods well known to the person skilled in the art. Such solvates are also contemplated as being within the scope of the present invention.

The invention also encompasses prodrugs of the present compounds, which on administration undergo chemical conversion by metabolic processes before becoming pharmacologically active substances. In general, such prodrugs will be functional derivatives of present compounds, which are readily convertible in vivo into a compound of the present invention. Conventional procedures for the selection and preparation of suitable prodrug derivatives are described, for example in "Design of Prodrugs", ed. H. Bundgaard, Elsevier, 1985.

Furthermore, they may be applicable as diagnostic agents for identifying patients having a defect in the histamine H3 receptor. Furthermore, the invention relates to the use of a compound of the general formula I as well as any diastereomer or enantiomer or tautomeric form thereof including mixtures of these or a pharmaceutically acceptable salt thereof for the preparation of a medicament for the treatment of disorders or diseases, wherein a histamine H3 receptor antagonistic action is beneficial.

The invention also relates to a method for the treatment of disorders or diseases, wherein a histamine H3 receptor antagonistic action is beneficial the method comprising administering to a subject in need thereof an effective amount of a compound according to the invention. In another embodiment of the invention the present compounds are used for the preparation of a medicament for the treatment of any histamine H3 receptor-mediated conditions and diseases. In still another embodiment of the invention the present compounds are used for the preparation of a pharmaceutical composition for the treatment of an appetite regulation or energy expenditure disorder. In a further embodiment of the invention, treatment of a patient with the present compounds is combined with diet and/or exercise. In another embodiment the intermediate compounds are useful for preparing final compounds of the invention, or may themselves possess H3 antagonist or inverse agonist activity.

The compounds of Formula I or Formula II can be prepared by one of ordinary skill in the art following a variety of procedures, some of which are illustrated in the procedures and schemes set forth below. The particular order of steps required to produce the compounds of Formula I or Formula II is dependent upon the particular compound to being synthesized, the starting compound, and the relative liability of the substituted moieties. The reagents or starting materials are readily available to one of skill in the art, and to the extent not commercially available, are readily synthesized by one of ordinary skill in the art following standard procedures commonly employed in the art, along with the various procedures and schemes set forth below.

The following Schemes, Procedures, Preparations and Examples are provided to better elucidate the practice of the present invention and should not be interpreted in any way as to limit the scope of the same. Those skilled in the art will recognize that various modifications may be made while not departing from the spirit and scope of the invention. All publications mentioned in the specification are indicative of the level of those skilled in the art to which this invention pertains.

The terms and abbreviations used herein have their normal meanings unless otherwise designated. For example, as used herein, the following terms have the meanings indicated:

"Boc" or "BOC" refer to t-butyl carbonyl. "HOBt" is 1-hydrobenzotriazole. "HATU" is O-(7-azabenzotriazol-1-yl)-N-N-N'-N'-tetramethyluronium hexafluorophosphate. "DCC" is dicyclohexylcarbodiimide. "EDC" is 1-(3-dimethylaminopropyl)-3-ethylcarbodiimide hydrochloride. "Red-Al®" is 65+ weight % solution of sodium bis(2-methoxyethoxy)aluminum hydride. "DMAP" is 4-dimethylaminopyridine. "DIPEA" is diisopropylethylamine. "DIBAL-H" is diisobutylaluminum hydride. "NBS" is N-bromosuccinimide. "DMEA" is dimethylethylamine. "THF" is tetrahydrofuran. "DMF" is dimethylformamide. "EtOAc" is ethyl acetate. "EtOH" is ethyl alcohol or ethanol. "MeOH" is methyl alcohol or methanol. "DMSO" is dimethylsulfoxide. "TBAF" is tetrabutylammonium fluoride. "DME" is ethylene glycol dimethyl ether.

"PS-Trisamine" is Tris-(2-aminoethyl)amine polystyrene. "PS-Carbodiimide" or "PS-CDI" is N-Cyclohexylcarbodiimide-N'-propyloxymethyl polystyrene. "PS-DIEA" is N,N-(Diisopropyl)aminomethylpolystyrene (1% inorganic antistatic agent). "PS-DMAP" is N-(methylpolystyrene)-4-(methylamino) pyridine.

"Rpm" refers to revolutions per minute; "W" refers to watts; "mmnhg" refers to millimeters of mercury; "CAS" or "CAS#" refers to Chemical Abstract Service number; "SCX" refers to strong cation exchange; "eq" refers to equivalents; "N" refers to normal or normality, "M" refers to molar or molarity, "mol" refers to moles; "mmol" refers to millimoles; "psi" refers to pounds per square inch; "min" refers to minutes; "h" or "hr" refers to hours; "° C." refers to degrees Celsius; "TLC" refers to thin layer chromatography; "$R_f$" refers to retention factor; "HPLC" refers to high performance liquid chromatography; "$R_t$" refers to retention time; "MS" refers to mass spectrometry, Observed Mass indicates (M+1) unless indicated otherwise. "m/e" refers to mass to charge ratio. "MS(FD)" refers to field desorption mass spectrometry, "MS(IS)" refers to ion spray mass spectrometry, "MS(FIA)" refers to flow injection analysis mass spectrometry, "MS(FAB)" refers to fast atom bombardment mass spectrometry, "MS(EI)" refers to electron impact mass spectrometry, "MS(ES)" refers to electron spray mass spectrometry; "UV" refers to ultraviolet spectrometry; "$^1$H NMR" refers to proton nuclear magnetic resonance spectrometry. "δ" refers to part per million down-field from tetramethylsilane. "s", "d", "t", "q", "dd", and, "m" refer to singlet, doublet, triplet, quartet, doublet of doublets, and multiplet, respectively; In addition, "IR" refers to infrared spectrometry, and the absorption maxima listed for the IR spectra are only those of interest and not all of the maxima observed. "RT" refers to room temperature.

General Schemes

Compounds of the present invention have been formed as specifically described in the examples. Further, many compounds are prepared using the general schemes described below. Unless otherwise indicated, all variables are defined as in the summary of the invention and as otherwise defined herein. Alternative synthesis methods may also be effective and known to the skilled artisan

SCHEME A

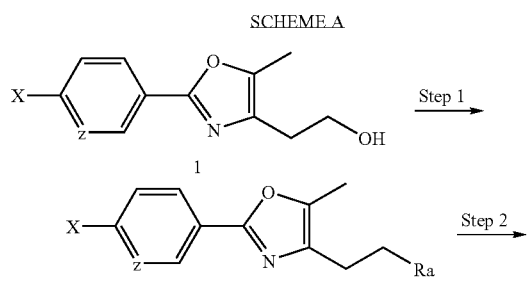

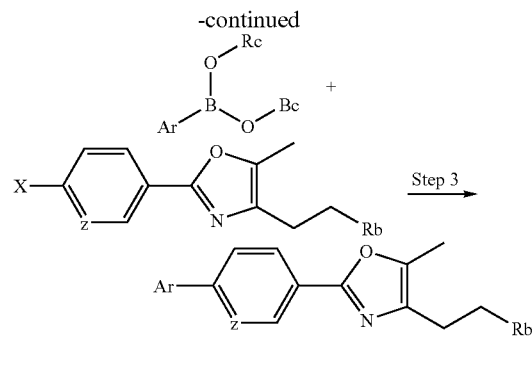

In Scheme A, Ar is any mono, di or trisubstituted six membered aromatic or heteroaromatic ring, such as those described herein in R4, for example but not limited to phenyl, pyridine, pyrimidine, pyrazine, pyridazine, and Z independently represents carbon (substituted with hydrogen or the optional substituents indicated herein), or nitrogen. In (step 1) the hydroxyl group of compound 1 [obtained by the method of D. Brooks, J. Med. Chem., 2001, 44, 2061-2064 or the patent WO 0116120] is converted to a suitable leaving group i.e. mesylate, tosylate, iodide (Ra=OMs, OTs, I) etc. using standard literature procedures. For example, a mixture of 2-[2-(4-Bromo-phenyl)-5-methyl-oxazol-4-yl]-ethanol and a suitable base in this case triethylamine in an aprotic solvent such as dichloromethane is cooled to 0° C. and treated with methanesulfonyl chloride. The mixture is allowed to stir at room temperature for 1-4 h. The reaction is concentrated and purified according to techniques well known in the art or used crude in the next reaction.

In Scheme A (step 2), this activated alcohol is treated with excess amine (Rb=pyrrolidine, 2-methylpyrrolidine, piperidine, 2-methylpiperidine, etc.) in a suitable solvent to provide the desired amines. For example, the crude methanesulfonic acid Methanesulfonic acid 2-[2-(4-bromo-phenyl)-5-methyl-oxazol-4-yl]-ethyl ester is dissolved in a suitable solvent such as THF and 2-10 equivalents of 2-methylpyrrolidine is added. The mixture is stirred at room temperature or heated for a period of 8-48 h at 70° C. The reaction is concentrated and purified according to techniques well known in the art. In step 3, the amine from step 2 substituted with halogen X, where X can be Cl, Br, I combined with an aryl boronic acid ($R_c$=H) or ester ($R_c$=pinacol) are converted to the corresponding triaryls. The triaryls can be achieved by a variety of palladium catalyzed Suzuki reaction methods as described in Section IV-14 of the following review (Hassan, Jwanro; Sevignon, Marc; Gozzi, Christel; Schulz, Emmanuelle; Lemaire, Marc. Aryl-Aryl Bond Formation One Century after the Discovery of the Ullmann Reaction. Chemical Reviews (Washington, D.C.) (2002), 102(5), 1359-1469). For example, 2-(4-Bromo-phenyl)-5-methyl-4-(2-pyrrolidin-1-yl-ethyl)-oxazole and 4-methylsulfonylphenylboronic acid are dissolved in a suitable organic solvent such as dioxane, acetonitrile, DME, THF, EtOH, or mixtures thereof. A suitable palladium catalyst such as tetrakis-(triphenylphosphine) palladium (0), palladium(II) dichloride (dppf) complex with dichloromethane, dichloropalladium di-triphenylphosphine etc. is added followed by a suitable base such as aqueous sodium or potassium carbonate, anhydrous cesium or potassium fluoride, anhydrous potassium or cesium carbonate etc. The reaction is heated within a temperature range of 70 to 100° C. for a period of 4-24 hours. The reaction is concentrated and purified according to techniques well known in the art.

Alternatively, the triaryl formation (step 3) can also be performed using microwave assisted Suzuki couplings. For example, 2-(4-Bromo-phenyl)-5-methyl-4-(2-pyrrolidin-1-yl-ethyl)-oxazole and pyridine 3-boronic acid are dissolved in a suitable organic solvent such as dioxane, acetonitrile, DME, THF, EtOH, or mixtures thereof. A suitable palladium catalyst such as tetrakis-(triphenylphosphine) palladium (0), palladium(II) dichloride (dppf) complex with dichloromethane, dichloropalladium di-triphenylphosphine etc. is added followed by a suitable base such as aqueous sodium or potassium-carbonate, anhydrous cesium or potassium fluoride, anhydrous potassium or cesium carbonate etc. The reaction is run in a CEM or MARS microwave reactor for 10-40 minutes, at 90-120° C., with 75 W power and cooling control on to maintain temperature range. The reaction is concentrated and purified according to techniques well known in the art.

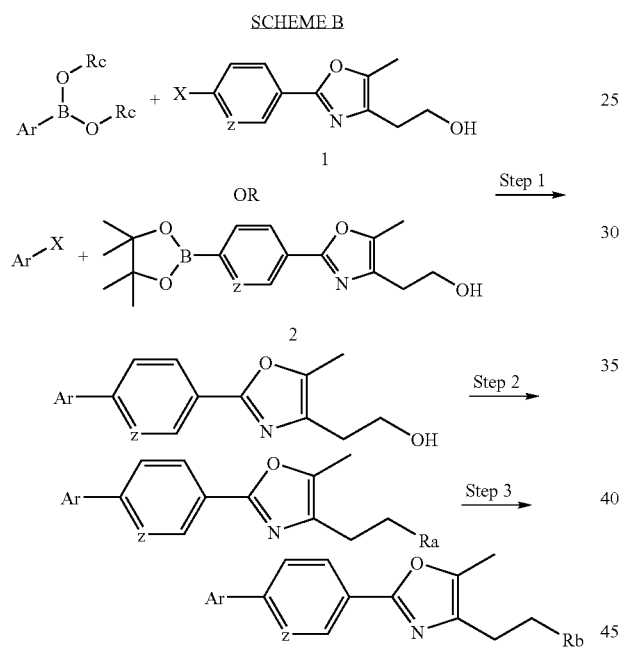

SCHEME B

In Scheme B, compound 1, Ra, Rb, Rc, X and Ar are previously defined. In Scheme B (step 1), compound 1 is combined with an aryl boronic acid ($R_c$=H) or ester ($R_c$=pinacol) is converted to the corresponding triaryl alcohols. The triaryl alcohols can be achieved by the methods of tie Review previously described for Scheme A (step 3). For example, 2-[2-(4-Bromo-phenyl)-5-methyl-oxazol-4-yl]-ethanol and 4-methylsulfonylphenylboronic acid are dissolved in a suitable organic solvent such as dioxane, acetonitrile, DME, THF, EtOH, or mixtures thereof. A suitable palladium catalyst such as tetrakis-(triphenylphosphine) palladium (0), palladium(II) dichloride (dppf) complex with dichloromethane, dichloropalladium di-triphenylphosphine etc. is added followed by a suitable base such as aqueous sodium or potassium carbonate, anhydrous cesium or potassium fluoride, anhydrous potassium or cesium carbonate etc. The reaction is heated within a temperature range of 70 to 100° C. for a period of 4-24 hours. The reaction is concentrated and purified according to techniques well known in the art.

Alternatively in Scheme B (step 1), aryl chlorides, bromides, or iodides can be combined with compound 2 [which is obtained by the methods of T. Ishiyama, Tetrahedron, 57, 9813-9816, 2001 using compound 1] to give the corresponding triaryl alcohols. For example, 2-{5-Methyl-2-[4-(4,4,5,5-tetramethyl-[1,3,2]dioxaborolan-2-yl)-phenyl]-oxazol-4-yl}-ethanol and 2-(4-Chloro-phenyl)-5-methyl-[1,3,4]oxadiazole are dissolved in a suitable organic solvent such as dioxane, acetonitrile, DME, THF, EtOH, or mixtures thereof. A suitable palladium catalyst such as tetrakis-(triphenylphosphine) palladium (0), palladium(II) dichloride (dppf) complex with dichloromethane, dichloropalladium di-triphenylphosphine etc. is added followed by a suitable base such as aqueous sodium or potassium carbonate, anhydrous cesium or potassium fluoride, anhydrous potassium or cesium carbonate etc. The reaction is run in a CEM or MARS microwave reactor for 2-4 hours, at 90-120° C., with 75 W power and cooling control on to maintain temperature range. The reaction is concentrated and purified according to techniques well known in the art.

In Scheme B (step 2), the resulting triaryl alcohol can be converted to a leaving group i.e. mesylate, tosylate, iodide (Ra=OMs, OTs, I) etc. using standard literature procedures. For example, a mixture of 2-[2-(4'-Methanesulfonyl-biphenyl-4-yl)-5-methyl-oxazol-4-yl]-ethanol and a suitable base in this case triethylamine in an aprotic solvent such as dichloromethane is cooled to 0° C. and treated with methanesulfonyl chloride. The mixture is allowed to stir at room temperature for 1-4 h. The reaction is concentrated and purified according to techniques well known in the art or used crude in the next reaction.

In Scheme B (step 3), this activated alcohol is treated with excess amine in a suitable solvent to provide the desired triaryl amine.

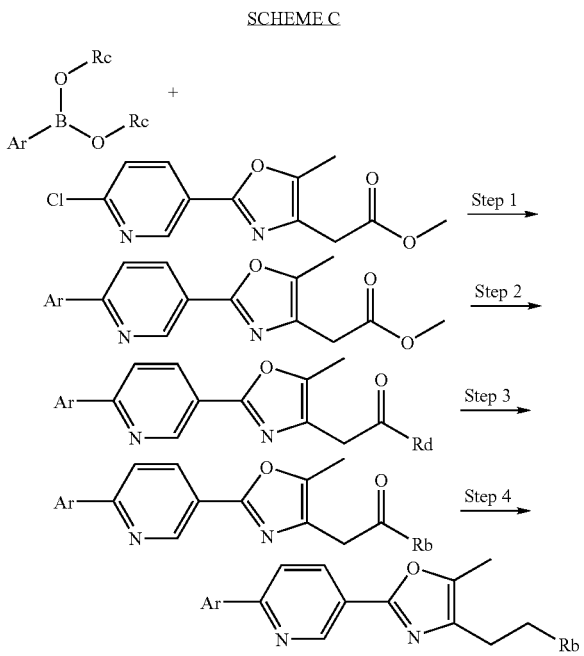

SCHEME C

In Scheme C, Rb, Rc, X and Ar are previously defined. In Scheme C (step 1), compound 3 [CAS# 478540-95-3] is combined with an aryl boronic acid ($R_c$=H) or ester ($R_c$=pinacol) under the previously described Suzuki conditions to provide the corresponding triaryl carboxylate. For example, [2-(6-Chloro-pyridin-3-yl)-5-methyl-oxazol-4-yl]-acetic acid methyl ester and 4-methylsulfonylphenylboronic acid are dissolved in a suitable organic solvent such as dioxane, acetonitrile, DME, THF, EtOH, or mixtures thereof. A suitable palladium catalyst such as tetrakis-(triphenylphosphine) palladium (0), palladium(II) dichloride (dppf) complex with dichloromethane, dichloropalladium di-triphenylphosphine etc. is added followed by a suitable base such as aqueous sodium or potassium carbonate, anhydrous cesium or potassium fluoride, anhydrous potassium or cesium carbonate etc. The reaction is heated within a temperature range of 70 to 100° C. for a period of 4-24 hours. The reaction is concentrated and purified according to techniques well known in the art.

In Scheme C (step 2), the ester can be saponified using standard conditions to yield the corresponding triaryl carboxylic acid or the lithium, sodium or potassium salt of the acid where $R_d$ can be H, Li, Na or K. For example, [2-(6-Chloro-pyridin-3-yl)-5-methyl-oxazol-4-yl]-acetic acid methyl ester and NaOH are combined in methanol/tetrahydrofuran and heated to reflux for 1 hour. The reaction is concentrated and the resulting sodium salt is washed with dichloromethane and dried to purify.

In Scheme C (step 3) the triaryl carboxylic acid or the lithium, sodium or potassium salt of the acid where $R_d$ can be H, Li, Na or K are converted to the corresponding amides using a number of different methods known in the literature. Some of these methods can be found described in a review of coupling reagents in peptide synthesis by Klausner & Bodansky, Synthesis, 1972, 9, 453-463. For example, Sodium {2-[6-(4-methanesulfonyl-phenyl)-pyridin-3-yl]-5-methyl-oxazol-4-yl}-acetate, oxalyl chloride, and catalytic dimethylformamide are dissolved in a suitable solvent such as dioxane or acetonitrile and heated to reflux for or a period of 0.5-1.0 hours. After solvent exchange to dichloromethane the resulting acid chloride is combined with a suitable acid scavenger such as n-methylmorpholine, triethylamine, pyridine etc. and a cyclic or dialkylated amine such as pyrrolidine, 2-methylpyrrolidine, piperidine, etc. and the mixture is stirred for a period of 1-4 hours. The reaction is concentrated and purified according to techniques well known in the art.

In Scheme C (step 4) the resulting triaryl carboxamides are converted to the corresponding amines using standard literature reduction methods. For example, 2-{2-[6-(4-Methanesulfonyl-phenyl)-pyridin-3-yl]-5-methyl-oxazol-4-yl}-1-(2-(R)-methyl-pyrrolidin-1-yl)-ethanone is combined with a suitable reducing agent such as LAH or Red-Al® in a suitable solvent such as tetrahydrofuran or diethyl ether at a temperature of −78-0° C. and warming to room temperature for a period of 4-8 hours. The reaction is quenched according to standard literature procedures (Fieser and Fieser) and after concentration is purified according to techniques well known in the art.

SCHEME D

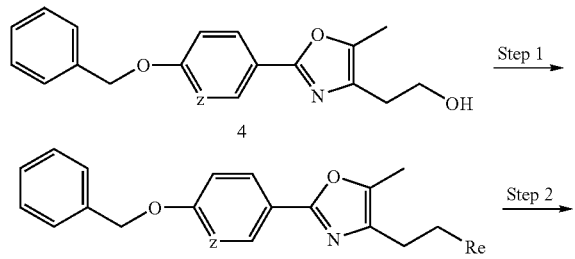

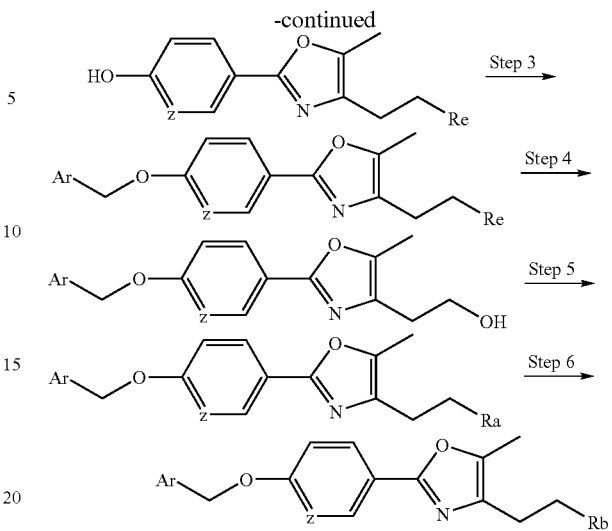

In Scheme D, Ra, Rb, and Ar are previously defined. In Scheme D (step 1), the hydroxyl group of compound 4 [CAS# 403611-91-6, 2-[2-(4-Benzyloxy-phenyl)-5-methyl-oxazol-4-yl]-ethanol] is protected by a silyl group using standard literature procedures. For example, 2-[2-(4-Benzyloxy-phenyl)-5-methyl-oxazol-4-yl]-ethanol is combined with a suitable base such as triethylamine, imidazole, dimethylaminopyridine etc., in a suitable solvent such as dichloromethane or dimethylformamide and treated with a silylating reagent such as tert-butylchlorodiphenylsilane or tert-butylchlorodimethylsilane at 0° C. to room temperature for a period of 6-18 hours. The crude material extracted from an acidic aqueous work up is purified according to techniques well known in the art.

In Scheme D (step 2), the benzyl protecting is removed by catalytic hydrogenation using standard literature procedures. For example, 2-(4-Benzyloxy-phenyl)-4-[2-(tert-butyl-diphenyl-silanyloxy)-ethyl]-5-methyl-oxazole is combined with 5-10% palladium on carbon and dissolved in a suitable solvent such as ethyl acetate, tetrahydrofuran, ethanol or a mixture thereof under an atmosphere of 1-60 mmHg of hydrogen for 24-48 hours. After filtration, the reaction is concentrated and purified according to techniques well known in the art.

In Scheme D (step 3), the resulting phenol is alkylated with a variety of aryl chlorides, bromides and iodides under standard literature conditions. For example, 4-{4-[2-(tert-Butyl-diphenyl-silanyloxy)-ethyl]-5-methyl-oxazol-2-yl}-phenol and 2-bromomethylpyridine hydrobromide is combined with a suitable base such as potassium carbonate, cesium carbonate, sodium carbonate etc., in a suitable solvent such as acetone, dimethylformamide, acetonitrile or a mixture thereof at a temperature of 20-100° C. for a period of 12-24 hours. The crude material extracted from an aqueous work up is purified according to techniques well known in the art.

In Scheme D (step 4), the silyl protecting group of the resulting aryl ether is removed using standard literature procedures. For example, 2-(4-{4-[2-(tert-Butyl-diphenyl-silanyloxy)-ethyl]-5-methyl-oxazol-2-yl}-phenoxymethyl)-pyridine and tetrabutylammonium fluoride are combined in a suitable solvent such as tetrahydrofuran, dioxane or a mixture thereof at a temperature of -10-40° C. for a period of 2-8 hours. The crude material extracted from an aqueous work up is purified according to techniques well known in the art.

In Scheme D (step 5), the resulting alcohol can be converted to a leaving group i.e. mesylate, tosylate, iodide (Ra=OMs, OTs, I) etc. using standard literature procedures. For example, a mixture of 2-{5-Methyl-2-[4-(pyridin-2-yl-methoxy)-phenyl]-oxazol-4-yl}-ethanol and a suitable base in this case triethylamine in an aprotic solvent such as dichloromethane is cooled to 0° C. and treated with methanesulfonyl chloride. The mixture is allowed to stir at room temperature for 1-4 h. The reaction is concentrated and purified according to techniques well known in the art or used crude in the next reaction. In Scheme D (step 6), this activated alcohol is treated with excess amine in a suitable solvent to provide the desired triaryl amine.

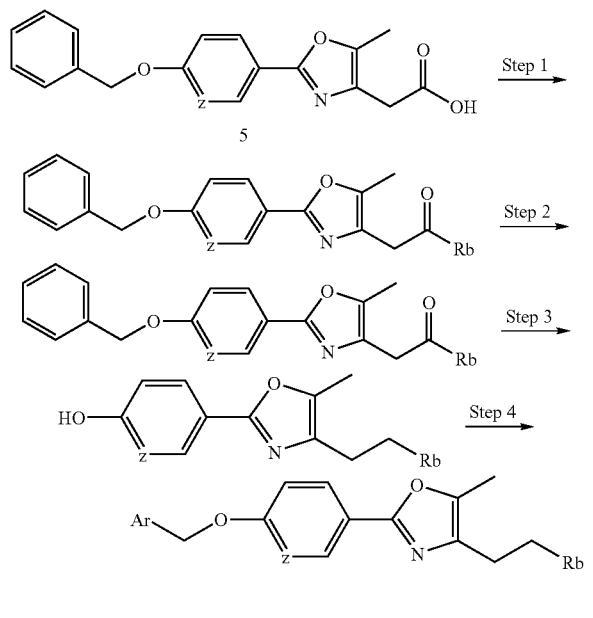

In Scheme E, Rb and Ar are previously defined. In Scheme E (step 1), the carboxylic acid of compound 5 [CAS 403611-89-2, [2-(4-Benzyloxy-phenyl)-5-methyl-oxazol-4-yl]-acetic acid] is converted to the corresponding amides using a number of different methods known in the literature. Some of these methods can be found described in a review of coupling reagents in peptide synthesis by Klausner & Bodansky, Synthesis, 1972, 9, 453-463. For example, [2-(4-Benzyloxy-phenyl)-5-methyl-oxazol-4-yl]-acetic acid is suspended in a suitable organic solvent such as dichloromethane, DMF or mixtures thereof. A suitable amide coupling agent i.e EDC, DCC, etc. is added followed by HOBt, HATU, etc. at room temperature. Diisopropylethyl amine and suitable amine in this case, pyrrolidine or (2R)-methylpyrrolidine for example are added to the mixture. The mixture is stirred at room temperature for a period of 8-48 hours. The reaction is quenched by addition of water. The resulting mixture may be extracted, concentrated and purified according to techniques well known in the art.

In Scheme E (step 2), the amide is reduced to the corresponding amine using procedures analogous to Scheme C (step 4). For example, 2-[2-(4-Benzyloxy-phenyl)-5-methyl-oxazol-4-yl]-1-(2-(R)-methyl-pyrrolidin-1-yl)-ethanone is combined with a suitable reducing agent such as LAH or Red-Al® in a suitable solvent such as tetrahydrofuran or diethyl ether at a temperature of −78-0° C. and warming to room temperature for a period of 4-8 hours. The reaction is quenched according to standard literature procedures (Fieser and Fieser) and after concentration is purified according to techniques well known in the art.

In Scheme E (step 3), the resulting amine is deprotected to the corresponding phenol using procedures analogous to the procedure of Scheme D (step 2). For example, 2-(4-Benzyloxy-phenyl)-5-methyl-4-[2-(2-(R)-methyl-pyrrolidin-1-yl)-ethyl]-oxazole is combined with 5-10% palladium on carbon and dissolved in a suitable solvent such as ethyl acetate, tetrahydrofuran, ethanol or a mixture thereof under an atmosphere of 1-60 mm of hydrogen for 24-48 hours. After filtration, the reaction is concentrated and purified according to techniques well known in the art.

In Scheme E (step 4), the resulting phenol is alkylated using procedures analogous to the procedure of Scheme D (step 3). For example, 2-[2-(4-Hydroxy-phenyl)-5-methyl-oxazol-4-yl]-1-(2-(R)-methyl-pyrrolidin-1-yl)-ethanone and 2-bromomethylpyridine hydrobromide is combined with a suitable base such as potassium carbonate, cesium carbonate, sodium carbonate etc., in a suitable solvent such as acetone, dimethylformamide, acetonitrile or a mixture thereof at a temperature of 20-100° C. for a period of 12-24 hours. The crude material extracted from an aqueous work up is purified according to techniques well known in the art.

SCHEME F

In Scheme F, Rb, X and Ar are previously defined. In Scheme F (step 1), halo substituted phenylcarboxamides are condensed with dihalo ketones to form halo methyloxazoles. For example, 4-bromo-benzamide and 1,3 dichloro or dibromo acetone is dissolved in a suitable solvent such as isopropanol, ethanol, or a mixture thereof and heated to temperature of 60-80° C. for a period of 5-10 hours. The reaction is concentrated and used crude or purified according to techniques well known in the art. In Scheme F (step 2), the resulting halo methyloxazoles are converted to an amino methyl oxazole by procedures analogous to Scheme A (step 2). For example, 2-(4-Bromo-phenyl)-4-chloromethyl-oxazole is dissolved in a suitable solvent such as THF and 2-10 equivalents of pyrrolidine is added. The mixture is stirred at room temperature or heated for a period of 8-48 h at 70° C. The reaction is concentrated and purified according to techniques well known in the art.

In Scheme F (step 3), the resulting amino methyloxazole can be converted to the triaryl amine using procedures analogous to those of Scheme A 9 step 3). For example, 2-(4-Bromo-phenyl)-4-pyrrolidin-1-ylmethyl-oxazole and pyridine 3-boronic acid are dissolved in a suitable organic solvent such as dioxane, acetonitrile, DME, THF, EtOH, or mixtures thereof. A suitable palladium catalyst such as tetrakis-(triphenylphosphine) palladium (0), palladium(II) dichloride (dppf) complex with dichloromethane, dichloropalladium ditriphenylphosphine etc. is added followed by a suitable base such as aqueous sodium or potassium carbonate, anhydrous cesium or potassium fluoride, anhydrous potassium or cesium carbonate etc. The reaction is run in a CEM or MARS microwave reactor for 10-40 minutes, at 90-120° C., with 75 W power and cooling control on to maintain temperature range. The reaction is concentrated and purified according to techniques well known in the art.

PREPARATIONS AND EXAMPLES

Intermediate 1

2-(4-Bromo-phenyl)-4-chloromethyl-oxazole

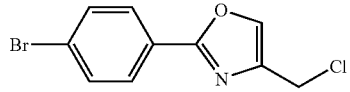

4-bromo-benzamide (4.03 g, 20.11 mmol), and 1,3-dichloro-acetone (3.83 g, 30.17 mmol) are placed in a 250 mL flask and dissolved in 150 mL of isopropyl alcohol. The mixture is heated to reflux for 5 hours and cooled to ambient temperature. The reaction is concentrated to dryness. The resulting solid is triturated with diethyl ether and filtered to remove unreacted 4-bromo-benzamide. The filtrate is concentrated to the title compound as an oily solid (3.1 g) and is used without further purification. MS (m/e) 273.9 (M+1)

Intermediate 2

2-[5-Methyl-2-(4-pyridin-3-yl-phenyl)-oxazol-4-yl]-ethanol

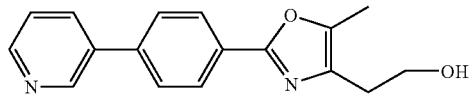

2-(4-Chlorophenyl)-5-methyl-oxazoleethanol (0.4 g, 1.68 mmol) [which is obtained by the method of D. Brooks, J. Med. Chem., 2001, 44, 2061-2064 or see WO 0116120], 3-pyridylboronic acid (0.516 g, 4.2 mmol), tricyclohexylphosphine (0.0235 g, 0.084 mmol), palladium (II) acetate (0.0094 g, 0.042 mmol), and potassium carbonate (1.16 g, 8.4 mmol) are placed in a 10 mL CEM microwave tube. To this mixture is added 8.0 mL of ethanol. The tube is capped and placed in a CEM microwave reactor for 4 hours at 90° C., 65 psi, applying 70 W of power with cooling to maintain temperature. The reaction is cooled and concentrated to a dark residue which is dissolved in 30 mL of 1N HCl and washed with ethyl acetate. The aqueous layer is adjusted to pH 9 with sodium carbonate and extracted with 15% isopropyl alcohol/85% dichloromethane. The organics are separated, dried with sodium sulfate, filtered, and concentrated to give pure title compound (0.377 g, 71.5% yield). MS (m/e) 281.1 (M+1)

Intermediate 3

2-{5-Methyl-2-[4-(4,4,5,5-tetramethyl-[1,3,2]dioxaborolan-2-yl)phenyl]-oxazol-4-yl}-ethanol

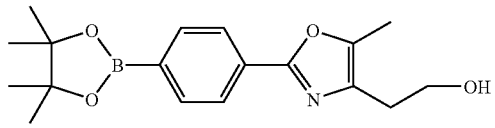

To a stirring solution of 2-(4-bromophenyl)-5-methyl-oxazoleethanol (CAS# 328918-84-9) (1.0 mmol), potassium acetate (1.5 mmol), and bis(pinacolato)diboron (1.1 mmol) in dioxane (0.15 M), add [1,1 bis(diphenylphosphino)ferrocene]di-chloropalladium(II) complex with CH$_2$Cl$_2$ (1:1) (0.03 mmol) and heat to reflux for 1.5 hours. After this time, cool the reaction to room temperature and concentrate in vacuo. Wash the crude mixture with water while extracting with dichloromethane. Dry the organics with sodium sulfate, filter and concentrate in vacuo. Purify on an Isco Combi-Flash® chromatography system eluting with ethyl acetate and hexane. MS (m/e) 330.2 (M+1)

Intermediate 4

2-{5-Methyl-2-[4'-(5-methyl-[1,3,4]oxadiazol-2-yl)-biphenyl-4-yl]-oxazol-4-yl}ethanol

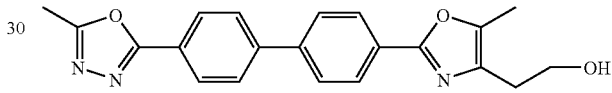

To a 10 mL CEM microwave tube is placed 2-{5-Methyl-2-[4-(4,4,5,5-tetramethyl-[1,3,2]dioxaborolan-2-yl)phenyl]-oxazol-4-yl }-ethanol (See Intermediate 3) (0.125 g, 0.38 mmol), 2-(4-Chloro-phenyl)-5-methyl-[1,3,4]oxadiazole (0.061 g, 0.317 mmol) [obtained by the method B. Rigo, Synthetic Comm., 19, 2321-2335, 1989, CAS#22815-98-1], tricyclohexylphosphine (0.0044 g, 0.016 mmol), palladium acetate (0.0018 g, 0.008 mmol), and potassium carbonate (0.105 g, 0.76 mmol) and 8.0 mL of ethanol. The mixture is placed in a CEM microwave reactor for 4 hours at 90° C., 65 psi, applying 70 W of power with cooling to maintain temperature. Reaction is cooled and all solids are collected by filtration. The solids are washed with 15% methanol/dichloromethane and the washes are concentrated to provide 49 mg of pure titled compound. MS (m/e) 362.2 (M+1)

Intermediate 5

2S-Methanesulfonyloxymethyl-pyrrolidine-1-carboxylic acid tert-butyl ester

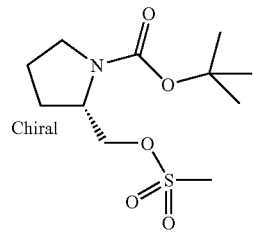

(S)-(−)-1-(tert-Butoxycarbonyl)-2-pyrrolidinemethanol (Aldrich) (11.49 g, 57.09 mmol), and triethylamine (8.64 mL, 62 mmol) is placed in a 1 L flask and dissolved in 150 mL of dichloromethane. Methanesulfonyl chloride (4.8 mL, 62 mmol) is added and the mixture is stirred for 2 hours. The reaction mixture is diluted with ethyl acetate and water and the organics are separated. The organics are washed with 0.1 N HCl, saturated sodium bicarbonate solution, separated and dried over sodium sulfate, filtered and concentrated to pure title compound (15.95 g, 100% yield). MS (m/e) 224.1 (M+1, -t-butyl)

Intermediate 6

2R-Methyl-pyrrolidine-1-carboxylic acid tert-butyl ester

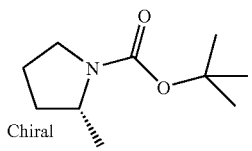

To a 1000 mL flask is placed 2S-Methanesulfonyloxymethyl-pyrrolidine-1-carboxylic acid tert-butyl ester (see Intermediate 5) (8.13 g, 29.1 mmol) in 15 mL of tetrahydrofuran and cooled to 0° C. Lithium triethylborohydride (1M, 90 mL) is added to the flask over 20 minutes. The mixture is warmed to ambient temperature and allowed to stir for 16 hours. The mixture is diluted with ethyl acetate and washed successively with 0.1N HCl, saturated sodium bicarbonate solution, and brine. The organics phase is separated, dried over sodium sulfate, filtered and concentrated to an oil. The oil is dissolved in diethyl ether and any particulate is removed by filtration. The filtrate is concentrated to give 5.4 g of pure title compound. MS (m/e) 130.1 (M+1 -t-butyl). 400 MHz NMR (CDCl$_3$) δ 3.83 (m, 1H), 3.38 (m, 2H), 1.92 (m, 3H), 1.58 (m, 1H), 1.48 (s, 9H), and 1.2 (d, J=8 Hz, 3H)

Intermediate 7

2R-Methyl-pyrrolidine; hydrochloride

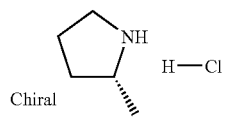

To a 500 mL flask is placed 2R-Methyl-pyrrolidine-1-carboxylic acid tert-butyl ester (see Intermediate 6) (5.4 g, 29.1 mmol) and HCl/acetic acid (1M, 45 mL) at ambient temperature. The mixture is stirred for 1 hour and then concentrated to an oily solid. The solid is triturated with 2:1 diethyl ether/hexane and dried to give 3.02 g of pure titled compound. 400 MHz NMR (Methanol-d$_4$) δ 3.67 (m, 1H), 3.35 (m, 2H), 2.25 (m, 1H) 2.1 (m, 2H), 1.66 (m, 1H), and 1.43 (d, J=8 Hz, 3H)

Intermediate 8

5-Methyl-4-(2-pyrrolidin-1-yl-ethyl)-2-[4-(4,4,5,5-tetramethyl-[1,3,2]dioxaborolan-2-yl)-phenyl]-oxazole

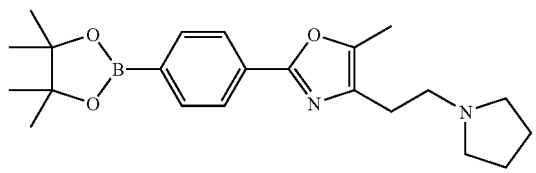

The titled compound is prepared substantially in accordance with the procedure of 2-{5-Methyl-2-[4-(4,4,5,5-tetramethyl-[1,3,2]dioxaborolan-2-yl)phenyl]-oxazol-4-yl}-ethanol (see Intermediate 3) using 2-(4-Bromo-phenyl)-5-methyl-4-(2-pyrrolidin-1-yl-ethyl)-oxazole (See Example 8). MS (m/e) 383.3 (M+1)

Intermediate 9

2-[2-(4'-Methanesulfonyl-biphenyl-4-yl)-5-methyl-oxazol-4-yl]-ethanol

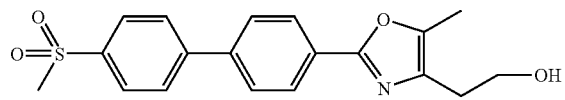

2-(4-Bromophenyl)-5-methyl-oxazoleethanol (4.0 g, 14.18 mmol) [which is obtained by the method of D. Brooks, J. Med. Chem., 2001, 44, 2061-2064 or see WO 0116120], 4-methylsulfonylphenylboronic acid (3.97 g, 19.85 mmol), [1,1 bis(diphenylphosphino)ferrocene]dichloropalladium(II) complex with CH$_2$Cl$_2$ (1:1) (0.347 g, 0.425 mmol), and aqueous sodium carbonate (2M, 22.15 mL) is placed in a 500 mL flask with 150 mL dioxane and heated to reflux for 2 hours. The reaction is concentrated to about 100 mL and cooled in an ice bath. The solids are filtered and the filtrate is set aside. The solids are then stirred with 200 mL of 15% methanol/dichloromethane. This slurry is filtered and the filtrate is concentrated to give 4.0 g of pure titled compound. MS (m/e) 358.1 (M+1)

Intermediate 10

(1-{2-[2-(4-Bromo-phenyl)-5-methyl-oxazol-4-yl]-ethyl}-pyrrolidin-3-yl)-methyl-carbamic acid tert-butyl ester

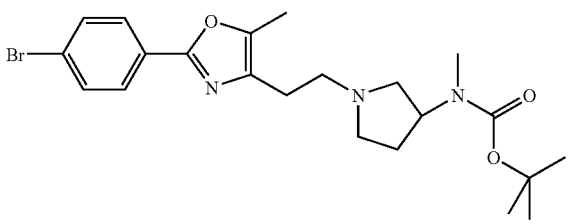

The titled compound is prepared significantly in accordance with the procedure of Example 8 using 2-(4-Bromophenyl)-5-methyl-oxazoleethanol [which is obtained by the method of D. Brooks, J. Med. Chem., 2001, 44, 2061-2064 or see WO 0116120], and 3-(Boc-methylamino)pyrrolidine. Purification via radial chromatography eluting with methanol and dichloromethane gives the titled compound. MS (m/e) ($^{79}$Br/$^{81}$Br): 464.1/466.0 (M+1)

Intermediate 11

(1-{2-[2-(4-Bromo-phenyl)-5-methyl-oxazol-4-yl]-ethyl}-pyrrolidin-3-yl)-methyl-amine

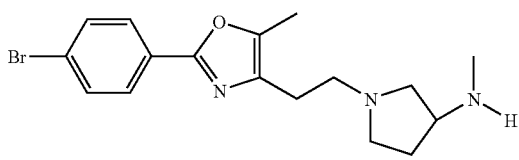

Stir (1-{2-[2-(4-Bromo-phenyl)-5-methyl-oxazol-4-yl]-ethyl}-pyrrolidin-3-yl)-methyl-carbamic acid tert-butyl ester (see Intermediate 10) with a 1:1 solution of trifluoroacetic acid and dichloromethane (0.30M) for 30 minutes at room temperature. After this time, quench the reaction with 1N sodium hydroxide and extract with dichloromethane. Extract from the organic layer with 1N hydrochloric acid. Basify the aqueous layer with 1N sodium hydroxide and extract with dichloromethane. Dry the organics with sodium sulfate, decant and concentrate in vacuo to yield the pure title compound, MS (m/e) ($^{79}$Br/$^{81}$Br): 364.1/366.0 (M+1)

(The present case does not have an intermediate 12)

Intermediate 13

Methanesulfonic acid 2-[2-(4-bromo-phenyl)-5-methyl-oxazol-4-yl]-ethyl ester

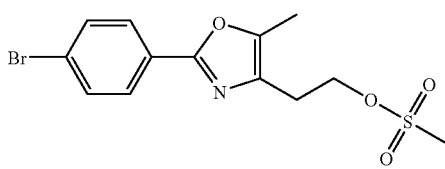

To a stirring solution of 2-[2-(4-Bromo-phenyl)-5-methyl-oxazol-4-yl]-ethanol (1.0 mmol) [which is obtained by the method of D. Brooks, J. Med. Chem., 2001, 44, 2061-2064 or see WO 0116120], and triethylamine (1.25 mmol) in dichloromethane (0.25M) in a 0° C. ice bath, add methylsulfonyl chloride (1.05 mmol) and remove the ice bath. Stir at room temperature for 1 hour and then concentrate in vacuo to yield the title compound. MS (m/e) ($^{81}$Br): 362.3 (M+1)

Intermediate 14

2-(4-Benzyloxy-phenyl)-4-[2-(tert-butyl-diphenyl-silanyloxy)-ethyl]-5-methyl-oxazole

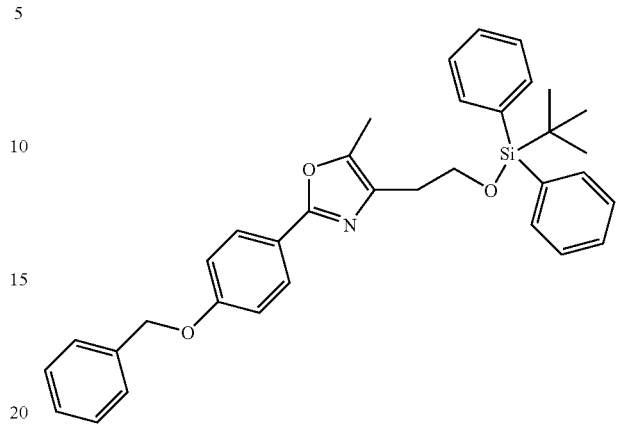

To a mixture of 2-[2-(4-Benzyloxy-phenyl)-5-methyl-oxazol-4-yl]-ethanol [CAS 403611-91-6] (4.04 g, 13.0 mmol), triethylamine (3.6 mL, 25 mmol, and DMAP (0.16 g, 1.3 mmol) in CH$_2$Cl$_2$ (80 mL) at 0° C. is added a solution of tert-butylchlorodiphenylsilane (3.95 g, 14.4 mmol) in CH$_2$Cl$_2$ (10 mL) drop wise. The mixture is warmed to room temperature and stirred for 6 h. The mixture is washed with 0.5 N HCl (80 mL), and the organic phase is dried (MgSO$_4$). After the solvent is removed in vacuo, the residue is purified by flash chromatography (elute 2:1 hexanes:EtOAc) to yield 7.09 g of the title compound as a white solid. MS (ES+) 548

Intermediate 15

4-{4-[2-(tert-Butyl-diphenyl-silanyloxy)-ethyl]-5-methyl-oxazol-2-yl}4-phenol

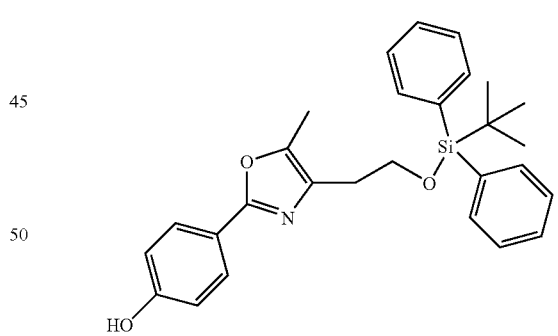

A mixture of 2-(4-Benzyloxy-phenyl)-4-[2-(tert-butyl-diphenyl-silanyloxy)-ethyl]-5-methyl-oxazole (7.0 g, 12.8 mmol) and 5% Pd/C (1.75 g) in EtOAc (105 mL) is stirred under a hydrogen atmosphere (balloon) for 18 h. The mixture is filtered and concentrated. The residue is resubjected to the reaction conditions of 5% Pd/C (1.75 g) in a mixture of THF and EtOH for an additional 24 h. The mixture is filtered and concentrated. After the solvent is removed, the residue is purified by flash chromatography (elute 4:1 hexanes:EtOAc) to obtain 3.25 g of the title compound. $^1$H NMR (400 MHz, CDCl$_3$) δ 7.8 (d, 2H), 7.6 (m, 4H), 7.3 (m, 6H), 6.8 (d, 2H), 3.9 (t, 2H), 2.7 (t, 2H), 2.2 (s, 3H), 1.0 (s, 9H)

Intermediate 16

2-(4-{4-[2-(tert-Butyl-diphenyl-silanyloxy)-ethyl]-5-methyl-oxazol-2-yl}-phenoxymethyl)-pyridine

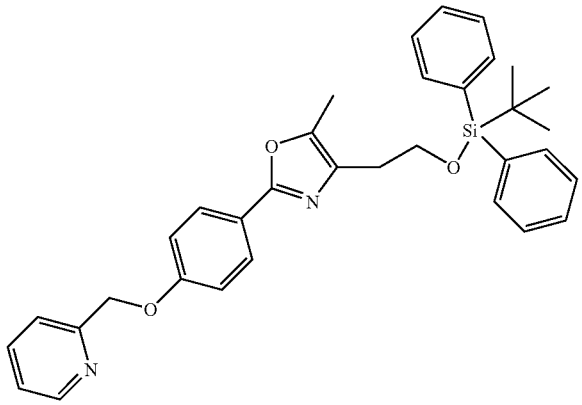

A mixture of 4-{4-[2-(tert-Butyl-diphenyl-silanyloxy)-ethyl]-5-methyl-oxazol-2-yl}-phenol (1.0 g, 2.25 mmol), 2-bromomethylpyridine hydrobromide (0.85 g, 3.4 mmol), and $K_2CO_3$ (1.1 g, 7.9 mmol) in acetone (20 mL) is heated at reflux for 12 h. The mixture is filtered, and the solvent is removed in vacuo. The residue is partitioned between EtOAc and water. The organic phase is washed with water and brine, dried ($Na_2SO_4$), and concentrated. The residue is purified by flash chromatography (90 g $SiO_2$, elute 10% to 50% EtOAc/hexane) to yield 0.97 g of the title compound. MS (ES+) 549.3

Intermediate 17

2-{5-Methyl-2-[4-(pyridin-2-ylmethoxy)-phenyl]-oxazol-4-yl}-ethanol

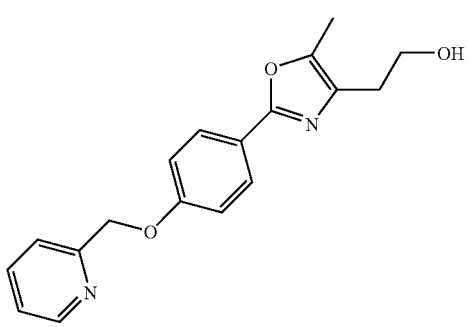

To a mixture of 2-(4-{4-[2-(tert-Butyl-diphenyl-silanyloxy)-ethyl]-5-methyl-oxazol-2-yl}-phenoxymethyl)-pyridine (0.97 g, 1.76 mmol) in THF (20 mL) at 0° C. is added a solution of TBAF in THF (1.0 M, 1.76 mL). The mixture is warmed to room temperature and stirred for 2 h. The mixture is partitioned between EtOAc and water. The aqueous phase is extracted with EtOAc (3×). The combined organic phase is washed with brine (2×), dried ($Na_2SO_4$), and concentrated. The residue is purified by flash chromatography ($SiO_2$, elute 0% to 10% MeOH/$CH_2Cl_2$) to yield 0.53 g of the title compound. $^1$H NMR (400 MHz, DMSO-$d_6$) δ 8.6 (dd, 1H), 7.8 (m, 3H), 7.6 (d, 1H), 7.4 (dd, 1H), 7.2 (d, 2H), 5.2 (s, 2H), 3.6 (t, 2H), 2.6 (t, 2H), 2.2 (s, 3H). MS (m/e) 311.1 (M+1)

Intermediate 18

2-[2-(4-Benzyloxy-phenyl)-5-methyl-oxazol-4-yl]-1-(2-(R)-methyl-pyrrolidin-1-yl)-ethanone

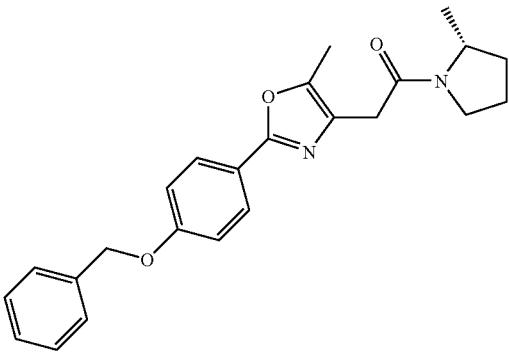

To a mixture of [2-(4-Benzyloxy-phenyl)-5-methyl-oxazol-4-yl]-acetic acid [CAS 403611-89-2] (2.2 g, 6.8 mmol) in $CH_2Cl_2$ (40 mL) is added EDC (1.57 g, 8.2 mmol) and HOBT (1.11 g, 8.2 mmol). After a few minutes, (R)-2-methylpyrrolidine hydrochloride [CAS 41720-98-3] (1.0 g, 8.2 mmol) and DIPEA (2.5 mL, 13.6 mmol) are added. The mixture is stirred at room temperature overnight. The mixture is partitioned between EtOAc and water. The aqueous phase is extracted with EtOAc (2×), and the combined organic phase is washed with brine, dried ($Na_2SO_4$), and concentrated. The residue is purified by flash chromatography [120 g $SiO_2$, elute gradient 30% EtOAc/hexane to 80% EtOAc/hexane) to yield 1.25 g of the title compound as a yellow oil. MS (m/e): 391.2 (M+1)

Intermediate 19

{2-[6-(4-Methanesulfonyl-phenyl)-pyridin-3-yl]-5-methyl-oxazol-4-yl}-acetic acid methyl ester

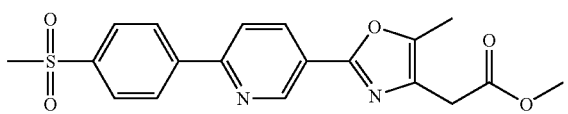

The titled compound is prepared substantially in accordance with the procedure of Example 4 using 4-(methanesulfonyl)benzene boronic acid and [2-(6-Chloro-pyridin-3-yl)-5-methyl-oxazol-4-yl]-acetic acid methyl ester [CAS 478540-95-3].
MS (m/e): 387.3 (M+1)

Intermediate 20

Sodium {2-[6-(4-methanesulfonyl-phenyl)-pyridin-3-yl]-5-methyl-oxazol-4-yl}-acetate

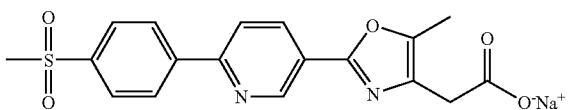

To a stirring solution of {2-[6-(4-Methanesulfonyl-phenyl)-pyridin-3-yl]-5-methyl-oxazol-4-yl}-acetic acid methyl ester (See Intermediate 19) (1.0 mmol) in 1:1 methanol/tetrahydrofuran (0.10M), add 2N sodium hydroxide (1.2 mmol) and heat to reflux for 1 hour. After this time, concentrate the reaction in vacuo. Wash the resulting solid twice with dichloromethane to rinse away any impurities. MS (nme): 373.3 (M+1)

Intermediate 21

2-{2-[6-(4-Methanesulfonyl-phenyl)-pyridin-3-yl]-5-methyl-oxazol-4-yl}-1-(2-(R)-methyl-pyrrolidin-1-yl)-ethanone

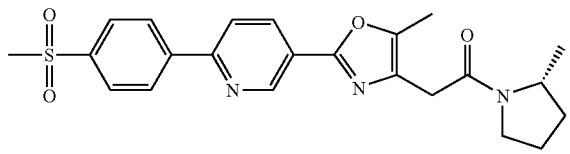

To a stirring solution of Sodium {2-[6-(4-methanesulfonyl-phenyl)-pyridin-3-yl]-5-methyl-oxazol-4-yl}-acetate (See Intermediate 20) (1.0 mmol) and oxalyl chloride (3.0 mmol) in dioxane (0.10M), add a catalytic amount of dimethylformamide and heat to reflux for 30 minutes. After this time, remove the heat and concentrate in vacuo. Take the resulting solid into dichloromethane (0.10M) and slowly add a solution of (R)-methyl-pyrrolidine hydrochloride (1.0 mmol) and n-methylmorpholine (2.0 mmol) in dichloromethane. Stir at room temperature for 1 hour. After this time, the reaction appears complete. Wash the reaction with 1N hydrochloric acid while extracting with dichloromethane. Concentrate the organic layer in vacuo and purify via radial chromatography eluting with methanol and dichloromethane. MS (m/e): 440.2(M+1)

Intermediate 22

2-Ethanesulfonyl-5-iodo-pyridine

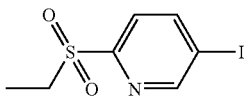

To a solution of 2-chloro-5-iodopyridine (1.0 mmol) in ethanol (0.33M), add sodium ethanethiolate (0.95 mmol) and heat reaction to reflux for 24 hours. After this time, remove the heat and concentrate in vacuo. Wash with water and saturated aqueous sodium bicarbonate while extracting with dichloromethane. Dry the organic layer with sodium sulfate, filter and concentrate in vacuo to a crude residue. To a portion of this crude material (1.0 mmol) in ethanol (0.2M), add m-chloroperoxybenzoic acid (2.95 mmol) and stir at room temperature for 18 hours. After this time, concentrate the reaction in vacuo. Dilute in ethyl acetate and wash with 1N sodium hydroxide. Concentrate the organic layer in vacuo and purify on a silica column eluting with ethyl acetate and hexane. 400 MHz NMR (CDCl$_3$) δ 8.98 (d, J=2.2 Hz, 1H), 8.34 (q, J=3.4 Hz, 1H), 7.89 (d, J=7.9 Hz, 1H), 3.43 (q, J=7.5 Hz, 2H), 1.34 (t, J=7.5 Hz, 3H)

Intermediate 23

2-{2-[4-(6-Ethanesulfonyl-pyridin-3-yl)-phenyl]-5-methyl-oxazol-4-yl}-ethanol

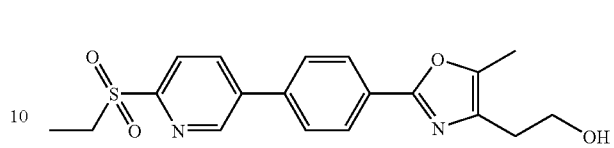

The titled compound is prepared substantially in accordance with the procedure of Intermediate 9 using 2-{5-Methyl-2-[4-(4,4,5,5-tetramethyl-[1,3,2]dioxaborolan-2-yl)phenyl]-oxazol-4-yl}-ethanol (See Intermediate 3) and 2-Ethanesulfonyl-5-iodo-pyridine (See Intermediate 22). MS (m/e) 373.3 (M+1)

Intermediate 24

2S-Fluoromethyl-pyrrolidine hydrochloride

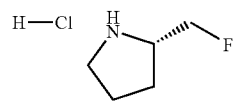

2S-Fluoromethyl-pyrrolidine hydrochloride is prepared by the method of M. Cowart (See WO 2002074758).

Intermediate 25

2R-Ethyl-pyrrolidine-1-carboxylic acid tert-butyl ester

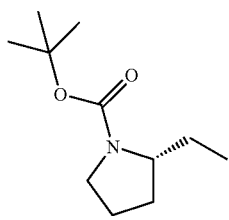

Add methanesulfonyl chloride (2.30 mL, 29.7 mmol) over five minutes to a cold (0° C.) stirred solution of 2S-hydroxymethyl-pyrrolidine-1-carboxylic acid tert-butyl ester (5.04 g, 25.0 mmol) and triethylamine (4.60 mL, 32.8 mmol) in dry dichloromethane (100 mL) and stir at 0° C. for 90 minutes before adding saturated aqueous sodium bicarbonate. Separate the layers, wash the organic layer one time with water, dry over anhydrous magnesium sulfate, and concentrate under reduced pressure to afford the crude mesylate which is used in the next step without further purification.

In a separate flask, add enough methyllithium (1.4-1.6 M in diethyl ether, ~250 mmol) to a cold (−20° C.) stirred suspension of copper(I)iodide (23.84 g, 125.2 mmol) in dry diethyl ether and until the bright yellow suspension gives way to a pale yellow homogeneous mixture. Add to this mixture the crude mesylate prepared as described above as a solution using dry diethyl ether (45 mL). Store the reaction mixture in a freezer at −15° C. overnight, and then add saturated aqueous ammonium chloride (adjusted to pH 8 with ammonium hydroxide) and warm to room temperature with vigorous stirring until the aqueous layer is deep blue. Filter the mixture through Celite® and wash the filter cake with diethyl ether and water. Separate the layers, extract the aqueous layer with diethyl ether, wash the combined organic extracts successively with brine, and 20% aqueous sodium thiosulfate, dry over anhydrous magnesium sulfate, and concentrate under reduced pressure. The residue is purified by flash chromatography (SiO$_2$, elute 0% to 20% EtOAc/hexanes) to yield 2.445 g of the title compound as a colorless oil. $^1$H NMR (400 MHz, CDCl$_3$) δ 3.65-3.75 (m, 1H), 3.29-3.45 (m, 2H), 1.62-1.98 (m, 5H), 1.49 (s, 9H), 1.28-1.41 (m, 1H), 0.89 (dd, J=7.6, 7.6 Hz, 3H).

Intermediate 26

2R-Ethyl-pyrrolidine hydrochloride

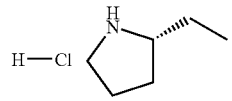

Add HCl (23 mL, 4N in 1,4-dioxane, 92 mmol) to a stirred solution of 2R-ethyl-pyrrolidine-1-carboxylic acid tert-butyl ester (2.4 g, 12 mmol) and stir at room temperature for 3 days. Concentrate under reduced pressure to afford the title compound as a colorless solid (1.6 g). $^1$H NMR (CDCl$_3$) δ 9.81 (br s, 1H), 9.18 (br s, 1H), 3.25-3.53 (m, 3H), 1.90-2.21 (m, 6H), 1.03-1.10 (m, 3H).

Intermediate 27

1-Bromo-4-propylsulfanyl-benzene

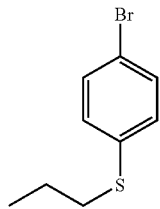

Add sodium hydride (625 mg, 60% in oil, 15.6 mmol) to a stirred solution of 4-bromo-benzenethiol (2.305 g, 12.2 mmol) in dry DMF (40 mL) and then rinse the sides of the flask down with DMF (5 mL). Stir at room temperature for 1 hr and then add 1-iodopropane and stir at room temperature for 2.5 h. Add water, 1N sodium hydroxide, and ethyl acetate, and separate the layers. Extract the aqueous layer twice with ethyl acetate, wash the organic layer successively, once with 1N sodium hydroxide, and three times with brine, dry over anhydrous magnesium sulfate, and concentrate under reduced pressure. The residue is purified by flash chromatography (SiO$_2$, elute 0% to 5% EtOAc/hexanes) to yield 2.53 g of the title compound as a colorless oil. $^1$H NMR (400 MHz, CDCl$_3$) δ 7.42 (d, J=6.8 Hz, 2H), 7.21 (d, J=6.4 Hz, 2H), 2.91 (dd, J=6.8, 6.8 Hz, 2H), 1.70 (ddddd, J=7.2, 7.2, 7.2, 6.8, 6.8 Hz, 2H), 1.05 (dd, J=7.2, 7.2 Hz, 3H).

Intermediate 28

1-Bromo-4-(propane-1-sulfonyl)-benzene

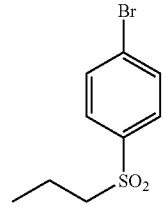

Add oxone (potassium mono persulfate, 15.03 g, 24.4 mmol) in one portion to a cold (0° C.) stirred solution of 1-bromo-4-propylsulfanyl-benzene (1.881 g, 8.14 mmol) in THF (20 mL), methanol (10 mL), and water (10 mL) and slowly warm to room temperature overnight. Remove the solvents under reduced pressure and add dichloromethane and water to the residue. Separate the layers, extract the aqueous layer twice with dichloromethane, wash the organic layer with saturated aqueous sodium bicarbonate, dry over anhydrous magnesium sulfate, and concentrate under reduced pressure. Purify the residue by flash chromatography (SiO$_2$, elute 0% to 30% EtOAc/hexanes) to yield 1.96 g of the title compound as a colorless oil. $^1$H NMR (400 MHz, CDCl$_3$) δ 7.80 (d, J=9.2 Hz, 2H), 7.74 (d, J=8.8 Hz, 2H), 3.06-3.11 (m, 2H), 1.72-1.83 (m, 2H), 1.04 (dd, J=7.2, 7.2 Hz, 3H).

Intermediate 29

4,4,5,5-Tetramethyl-2-[4-(propane-1-sulfonyl)-phenyl]-[1,3,2]dioxaborolane

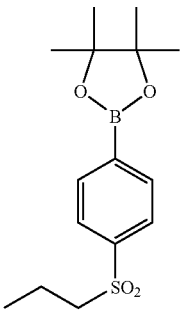

Add dichloro [1,1'-bis(diphenylphosphino)ferrocene]palladium (II) dichloromethane adduct (37 mg, 0.045 mmol) to a solution of 1-bromo-4-(propane-1-sulfonyl)-benzene (238 mg, 0.904 mmol), potassium acetate (270 mg, 2.15 mmol) and bis(pinacolato)diboron(II) (355 mg, 1.40 mmol) in DMSO (5 mL) and heat at 100° C. overnight. Cool to room temperature and add ethyl acetate, water, and saturate aqueous sodium bicarbonate and separate the layers. Extract the aqueous layer twice with ethyl acetate, wash the organic layer four times with water, dry over anhydrous magnesium sulfate, and concentrate under reduced pressure. Heat the residue under vacuum to approximately 240° C. to remove some of the unreacted bis(pinacolato)diboron(II) via sublimation.

Dissolve the residue in ethyl acetate and dichloromethane, add decolorizing charcoal, filter through Celite®, and concentrate the filtrate under reduced pressure to afford 256 mg of the title compound as a brown solid. ¹H NMR (400 MHz, CDCl₃) δ 8.02 (d, J=8.4 Hz, 2H), 7.92 (d, J=8.4 Hz, 2H), 3.06-3.11 (m, 2H), 1.70-1.80 (m, 2H), 1.39 (s, 12H), 1.01 (dd, J=6.8, 6.8 Hz, 3H).

Intermediate 30

2-(4-Bromo-phenyl)-4-(2-iodo-ethyl)-5-methyl-oxazole

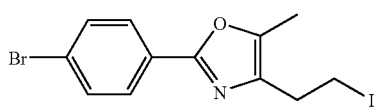

Add iodine (1.90 g, 7.49 mmol) to a stirred mixture of 2-[2-(4-bromo-phenyl)-5-methyl-oxazol-4-yl]-ethanol (1.503 g, 5.33 mmol), triphenylphosphine (2.101 g, 8.01 mmol), and pyridine (1.4 mL, 17 mmol) in toluene (48 mL) and heat at 100° C. for 45 min. Cool to room temperature, add ethyl acetate and water, and separate the layers. Extract the aqueous layer twice with ethyl acetate, wash the organic layer with 0.1N HCl, dry over anhydrous magnesium sulfate, and concentrate under reduced pressure. Purify the residue by flash chromatography (SiO₂, elute 0% to 10% EtOAc/hexanes) to-yield 1.804 g of the title compound as a colorless solid. ¹H NMR (400 MHz, CDCl₃) δ 7.89 (d, J=8.4 Hz, 2H), 7.60 (d, J=8.8 Hz, 2H), 3.49 (dd, J=7.2, 7.2 Hz, 2H), 3.11 (dd, J=7.2, 7.2 Hz, 2H), 2.39 (s, 3H).

Intermediate 31

2-{2-[6-(4-Methanesulfonyl-phenyl)-pyridin-3-yl]-5-methyl-oxazol-4-yl}-N,N-dimethyl-acetamide

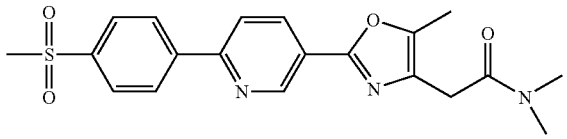

The reaction which produces Intermediate 21 also produces Intermediate 31. MS (m/e): 400.3 (M+1)

Intermediate 32

Methanesulfonic acid 2-{2-[4-(6-methoxy-pyridazin-3-yl)-phenyl]-5-methyl-oxazol-4-yl}-ethyl ester

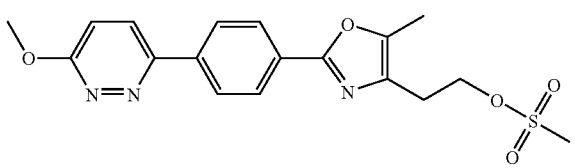

The titled compound is prepared substantially in accordance with the procedures of Example 4 and Intermediate 13 using 2-{5-Methyl-2-[4-(4,4,5,5-tetramethyl-[1,3,2]dioxaborolan-2-yl)phenyl]-oxazol-4-yl}-ethanol (see Intermediate 3) and 3-Chloro-6-methoxy-pyridazine [CAS: 1722-10-7]. MS (m/e): 390.3 (M+1)

Intermediate 33

2-Methanesulfonyl-5-iodo-pyridine

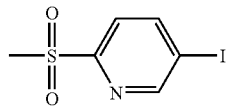

The titled compound is prepared substantially in accordance with the procedure of Intermediate 22 using sodium methanethiolate in place of sodium ethanethiolate.
MS (m/e): 284.0 (M+1)

Intermediate 34

2-Amino-4-benzyloxy-butyric acid hydrochloride salt

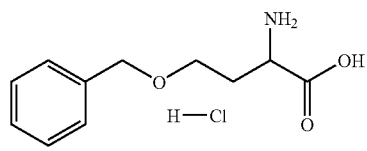

In a round bottom flask containing 4-benzyloxy-2-tert-butoxycarbonylamino-butyric acid (1.0 mmol), add 1M hydrochloric acid in ether (1.7 mmol) and stir at room temperature for two days. The product precipitates out as the hydrochloride salt. Collect by centrifugation in which the mother liquor is decanted off of the product. Rinse two times with ether, transfer solid to a flask and concentrate in vacuo.
MS (m/e): 210.2 (M+1)

Intermediate 35

4-Benzyloxy-2-(4-bromo-2-fluoro-benzoylamino)-butyric acid

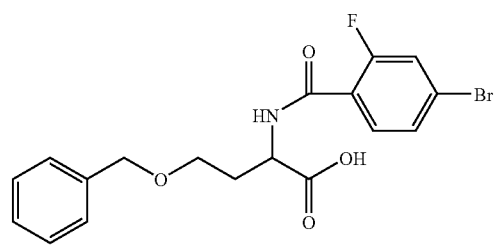

To a stirring solution of 2-amino-4-benzyloxy-butyric acid hydrochloride salt (1.0 mmol) (See Intermediate 34) and sodium carbonate (3.0 mmol) in 1:1 acetone/water (0.5M) in a 0° C. ice bath, slowly add 4-bromo-2-fluoro-benzoyl chloride (1.2 mmol) diluted in acetone (prepared from 4-bromo-2-fluoro-benzoic acid (1.0 mmol) and oxalyl chloride (1.0 mmol) in dichloromethane using catalytic dimethylformamide). Stir for 30 minutes at 0° C. After this time, wash the reaction with 1N hydrochloric acid while extracting with ethyl acetate. Concentrate the organics in vacuo. Purify on an Isco CombiFlash® chromatography system eluting with 1% acetic acid in ethyl acetate and hexane. MS (m/e) ($^{79}$Br/$^{81}$Br): 410.3/412.3 (M+1)

Intermediate 36

N-[1-(2-Benzyloxy-ethyl)-2-oxo-propyl]-4-bromo-2-fluoro-benzamide

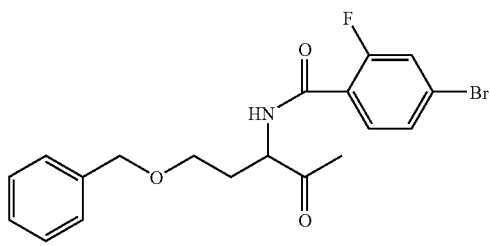

Add acetic anhydride (0.97 mmol) and pyridine (0.58 mmol) to a round bottom flask containing 4-benzyloxy-2-(4-bromo-2-fluoro-benzoylamino)-butyric acid (1.0 mmol) (See Intermediate 35) and heat to 90° C. for two hours. After this time, remove the heat and concentrate in vacuo. Wash crude with 1N hydrochloric acid and water while extracting with diethyl ether. Concentrate the organics in vacuo and purify on an Isco CombiFlash® chromatography system eluting with ethyl acetate and hexane. MS (m/e) ($^{79}$Br/$^{81}$Br): 408.3/410.3 (M+1)

Intermediate 37

4-(2-Benzyloxy-ethyl)-2-(4-bromo-2-fluoro-phenyl)-5-methyl-oxazole

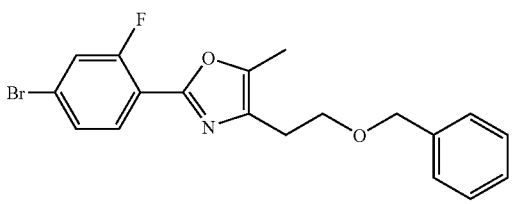

To a stirring solution of N-[1-(2-benzyloxy-ethyl)-2-oxo-propyl]-4-bromo-2-fluoro-benzamide (1.0 mmol) (See Intermediate 36) in dimethylformamide (0.25M), slowly add phosphorus oxychloride (3.0 mmol) and heat to 90° C. for 2.5 hours. After this time, remove the heat and carefully add water (same amount as DMF) and allow the reaction to cool to room temperature before extracting with ether. Wash organics with water and brine. Dry the organics with sodium sulfate, filter and concentrate in vacuo. Purify via radial chromatography eluting with ethyl acetate and hexane. MS (m/e) ($^{79}$Br/$^{81}$Br): 390.2/392.2 (M+1)

Intermediate 38

2-[2-(3-Fluoro-4'-methanesulfonyl-biphenyl-4-yl)-5-methyl-oxazol-4-yl]-ethanol

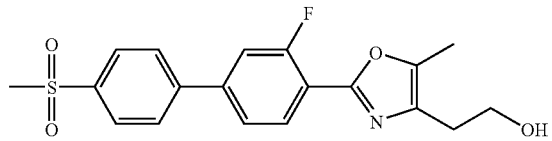

Using 4-(2-benzyloxy-ethyl)-2-(4-bromo-2-fluoro-phenyl)-5-methyl-oxazole (see Intermediate 37) and 4-methylsulfonylphenylboronic acid, follow a procedure in substantial accordance with that found in Example 4. Take this product and hydrogenate using 20% palladium hydroxide on carbon in tetrahydrofuran for 36 hours at 40° C. and 60 psi. After this time, filter the reaction and concentrate in vacuo. Purify via radial chromatography eluting with methanol and dichloromethane. MS (m/e): 376.2 (M+1)

Intermediate 39

2-[4-(3-Fluoro-propane-1-sulfonyl)-phenyl]-4,4,5,5-tetramethyl-[1,3,2]dioxaborolane

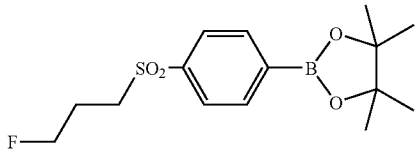

Charge a flame dried round bottom flask with 1-bromo-4-(3-fluoro-propane-1-sulfonyl)-benzene (0.330 g, 1.17 mmol), bis(pinocolato)diboron (0.318 g, 1.25 mmol), Pd(dppf)$_2$Cl$_2$.CH$_2$Cl$_2$ (0.045 g, 0.054 mmol), potassium acetate (0.346 g, 3.53 mmol), and dry DMSO (6 mL). Heat at 80-100° C. overnight. Cool, add ethyl acetate and water, and separate the layers. Wash the crude organic extracts with water, dry over MgSO$_4$, add decolorizing charcoal, filter through Celite® and concentrate the filtrate to give the title compound. $^1$H NMR (400 Hz): (CDCl$_3$) δ 8.03 (d, 2H, J=8 Hz), 7.93 (d, 2H, J=8 Hz), 4.51 (ddd, 2H, J=47, 5, 5 Hz), 3.26 (dd, 2H, J=8, 8 Hz), 2.04-2.22 (m, 2H), 1.40 (s, 6H), 1.30 (s, 6H).

Intermediate 40

4,4,5,5-Tetramethyl-2-(4-trifluoromethanesulfonyl-phenyl)-[1,3,2]dioxaborolane

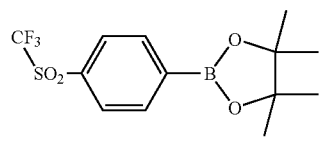

Charge a flame dried round bottom flask with 1-bromo-4-trifluoromethanesulfonyl-benzene (1.01 g, 3.50 mmol), bis (pinocolato)diboron (1.33 g, 5.23 mmol), Pd(dppf)$_2$Cl$_2$.CH$_2$Cl$_2$ (0.147 g, 0.180 mmol), potassium acetate (1.08 g, 11.0 mmol), and dry DMSO (18 mL). Heat at 80-100° C. overnight. Cool, add ethyl acetate and water, and separate the layers. Wash the crude organic material with water, dry over MgSO₄, add decolorizing charcoal, and filter through Celite®. Concentrate the filtrate and purify on silica gel (0-100% EtOAc/Hexanes, then 0-20% EtOAc/Hexanes) to give the title compound (0.416 g, 35%). ¹H NMR (400 Hz): (CDCl₃) δ 8.11 (d, 2H, J=8 Hz), 8.05 (d, 2H, J=8 Hz), 1.40 (s, 12H).

Intermediate 41

3-[2-(4-bromo-phenyl)-5-methyl-oxazol-4-yl]-propan-1-ol

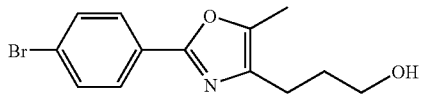

a) Add a cold (−78° C.) solution of 2-(4-bromo-phenyl)-4-(2-iodo-ethyl)-5-methyl-oxazole (See Intermediate 30) (1.05 g, 2.67 mmol) in 15 mL THF to a cold (−78° C.) solution of dithiane anion [Preparation: Add n-BuLi (7.5 mL, 12 mmol, 1.6M in hexanes) to a −20° C. solution of 1,3-dithiane (1.92 g, 15.9 mmol) in 25 mL THF. Stir 20 min at −78° C. and add 1,3-dimethyl-3,4,5,6-tetrahydro-2(1H)-pyrimidinone (DMPU, 4.03 g, 31.4 mmol).] Stir the reaction mixture at −78° C. for 15 min. Add water and warm to room temperature. Add dichloromethane, and separate the layers. Dry the crude organic extracts over MgSO₄, filter and concentrate. Purify on silica gel 0-10% EtOAc/Hexanes to give 2-(4-bromo-phenyl)-4-(2-[1,3]dithian-2-yl-ethyl)-5-methyl-oxazole (0.672 g, 66%). MS (m/e): 384 (M+1).

b) Add HgClO₄.4H₂O (1.49 g, 4.00 mmol) to a solution of 2-(4-bromo-phenyl)-4-(2-[1,3]dithian-2-yl-ethyl)-5-methyl-oxazole (0.672 g, 1.75 mmol) in 1:1 THF:CH₂Cl₂ (16 mL) and water (1.6 mL). After 6 hours, filter and wash the solids with dichloromethane. Concentrate to give 3-[2-(4-bromo-phenyl)-5-methyl-oxazol-4-yl]-propionaldehyde (0.445 g, 86%). MS (m/e): 294 (M+1).

d) Add DIBAL-H (1M in THF, 2.0 mL, 2.0 mmol) to a 0° C. solution of 3-[2-(4-bromo-phenyl)-5-methyl-oxazol-4-yl]-propionaldehyde (0.395 g, 1.39 mmol) in dichloromethane. After 15 min add 1N HCl and warm to room temperature. Add 5N HCl and stir until two clear, homogeneous layers are formed. Separate the layers and extract the aqueous layer with dichloromethane. Dry the crude organic extracts over MgSO₄, filter, and concentrate. Purify on silica gel (0-70% EtOAc/Hexanes) to give the title compound (0.315 g, 79%): MS (m/e): 296 (M+1).

Intermediate 42

2-Bromo-1-[2-(4-bromo-phenyl)-5-methyl-oxazol-4-yl]-ethanol

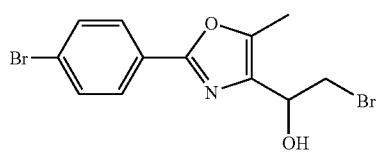

a) Add 2,8,9-trimethyl-2,5,8,9-tetraaza-1-phosphabicyclo [3.3.3]undecane (3.17 g, 14.7 mmol) as a solution using acetonitrile (10 mL) to a solution of 2-(4-bromo-phenyl)-4-(2-iodo-ethyl)-5-methyl-oxazole (See Intermediate 30) (4.38 g, 11.1 mmol) in 2.8:1 acetonitrile:THF (190 mL). After 4 hrs, concentrate under reduced pressure and add EtOAc and water to the residue. Separate the layers and extract the aqueous material with EtOAc. Wash the crude organic extract with water, dry over MgSO₄, filter and concentrate. Purify on silica gel eluting with 7% EtOAc to give 2-(4-bromo-phenyl)-5-methyl-4-vinyl-oxazole (2.31 g, 83%): ¹H NMR (400 Hz): (CDCl₃) δ 7.89 (d, 2H, J=8 Hz), 7.57 (d, 2H, J=8 Hz), 6.54 (dd, 1H, J=17, 11 Hz), 5.93 (dd, 1H, J=17, 2 Hz), 5.29 (dd, 1H, J=11, 2 Hz), 2.40 (s, 3H).

b) Add NBS (1.44 g, 8.08 mmol) to a solution of 2-(4-bromo-phenyl)-5-methyl-4-vinyl-oxazole (1.01 g, 4.02 mmol) in water (0.180 mL) and DMSO (30 mL). After 10 min add water and EtOAc. Separate the layers, extract aqueous material with EtOAc, and wash the crude organic extracts with water. Dry over MgSO₄, filter and concentrate. Purify on silica gel eluting with 20% EtOAc/Hexanes to give the title compound (1.08 g, 74%): MS (m/e): 362 (M+1).

Intermediate 43

(R)-(+)-2-Hydroxymethyl-pyrrolidine-1-carboxylic acid tert-butyl ester

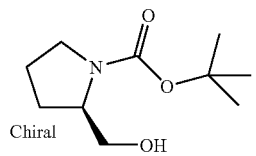

Add di-tert-butyldicarbonate (5.2 g, 24 mmol) to a 10% triethylamine:methanol (15 mL) solution containing pyrrolidin-2-yl-methanol (1.20 g, 11.9 mmol). Heat the reaction mixture for 30 min at reflux, then remove the solvent under reduced pressure to give the title compound (2.96 g, quant.): MS (m/e): 146 (M+2,-tert-butyl).

Intermediate 44

2R-Methanesulfonyloxymethyl-pyrrolidine-1-carboxylic acid tert-butylester

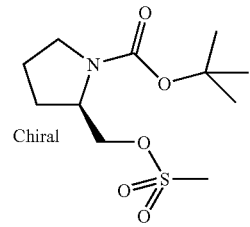

Add methanesulfonyl chloride (0.937 g, 6.46 mmol) to a cold (0° C.) solution of (R)-(+)-2-hydroxymethyl-pyrrolidine-1-carboxylic acid tert-butyl ester (1.0 g, 5.0 mmol) and triethylamine (1.0 mL, 7.5 mmol) in dichloromethane (10 mL). Warm the reaction mixture slowly to room temperature and stir overnight. The reaction mixture is diluted with dichloromethane and saturated aqueous sodium chloride and the layers are separated. Dry the crude organic extracts over MgSO₄, filter, and concentrated to give crude title compound (1.55 g, quantitative): MS (m/e): 224.1 (M+2-tert-butyl).

Intermediate 45

2S-Methyl-pyrrolidine-1-carboxylic acid tert-butyl ester

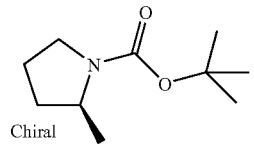

Slowly add lithium triethylborohydride (1M in THF, 17 mL, 17. mmol) to a 0° C. solution of 2R-methanesulfonyloxymethyl-pyrrolidine-1-carboxylic acid tert-butyl ester (1.6 g, 5.73 mmol) in 10 mL of tetrahydrofuran. Warm the reaction mixture to ambient temperature and stir for 16 hours. Dilute the reaction mixture with ethyl acetate and water and wash successively with 0.1N HCl and brine. Dry the crude organic extracts over $MgSO_4$, filter and concentrate to afford the title compound as a clear oil (0.930 g, 88%). 400 MHz NMR ($CDCl_3$) δ 3.83 (m, 1H), 3.38 (m, 2H), 1.92 (m, 3H), 1.58 (m, 1H), 1.48 (s, 9H), and 1.2 (d, J=8 Hz, 3H).

Intermediate 46

2S-Methyl-pyrrolidine; hydrochloride

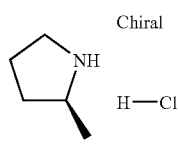

Add 1N HCl in ether to neat 2S-methyl-pyrrolidine-1-carboxylic acid tert-butyl ester (0.930 g, 5.02 mmol) at ambient temperature. The mixture is stirred for 1 hour and then concentrated to afford an oily solid. The solid is triturated with diethyl ether and dried to give (0.109 g, 18%) of the title compound. 400 MHz NMR (Methanol-$d_4$) δ 3.67 (m, 1H), 3.35 (m, 2H), 2.25 (m, 1H) 2.1 (m, 2H), 1.66 (m, 1H), and 1.43 (d, J=8Hz, 3H).

Intermediate 47

2-{5-Methyl-2-[4-(6-methyl-pyridazin-3-yl)-phenyl]-oxazol-4-yl}-ethanol

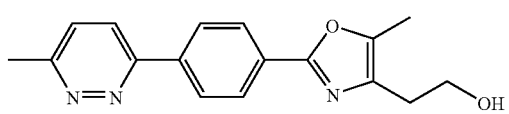

To a stirring solution of 2-{5-Methyl-2-[4-(4,4,5,5-tetramethyl-[1,3,2]dioxaborolan-2-yl)phenyl]-oxazol-4-yl}-ethanol (0.314 g, 0.952 mmol) (See Intermediate 3), 3-Iodo-6-methyl-pyridazine (0.178 g, 0.810 mmol) [CAS# 1618-47-9] and [1,1 bis(diphenylphosphino)ferrocene]dichloropalladium(II) complex with $CH_2Cl_2$ (1:1) (0.02 g, 0.024 mmol) in 10 mL dioxane is added aqueous sodium carbonate (2M, 1.22 mL) and the reaction is carried out substantially in accordance with the procedure of Example 9 to provide after purification by radial chromatography pure titled compound (0.208 g, 87%). MS (m/e): 296.3 (M+1).

Intermediate 48 tert-Butyl (3S)-3-fluoropyrrolidine-1-carboxylate

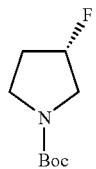

Slowly add [bis(2-methoxyethyl)amino]sulfur trifluoride (2.40 mL, 13.03 mmol) to a solution of N-Boc-(R)-(−)-3-pyrrolidinol (2.00 g, 10.86 mmol) in anhydrous dichloromethane (10 mL), at −78° C. and under nitrogen. Allow the reaction mixture to warm to room temperature and stir overnight. Carefully add an aqueous solution of sodium hydrogen carbonate (saturated, 20 mL) and extract with dichloromethane. Concentrate the combined organic extracts under vacuum then purify using automated flash chromatography (ISCO® System, 120 g Redisep® $SiO_2$ column; 0-40% ethyl acetate in cyclohexane gradient elution over 30 minutes at 85 mL/min) to give the title compound as a pale yellow liquid (1.67 g): MS (m/e): 212 (M+23).

Intermediate 49

(3S)-3-Fluoropyrrolidine 4-methylbenzenesulfonate (salt)

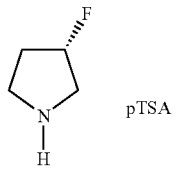

Add p-toluenesulfonic acid monohydrate (0.50 g, 2.64 mmol) to tert-butyl (3S)-3-fluoropyrrolidine-1-carboxylate (See Intermediate 48) (0.50 g, 2.64 mmol) in ethanol (5 mL) at room temperature. Stir the resulting solution overnight. Concentrate the reaction mixture in vacuo to remove solvent and bi-products to give the title compound as an off-white solid (0.65 g): MS (m/e): 90 (M+1).

Intermediate 50 tert-Butyl (3R)-3-fluoropyrrolidine-1-carboxylate

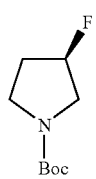

Prepare using the method of Intermediate 48 with N-Boc-(S)-(+)-3-pyrrolidinol (0.50 g, 2.67 mmol), [bis(2-methoxyethyl)amino]sulfur trifluoride (0.59 mL, 3.20 mmol) and anhydrous dichloromethane (4 mL) to give the title compound as a colourless oil (0.36 g): MS (m/e): 212 (M+23).

Intermediate 51

(3R)-3-Fluoropyrrolidine 4-methylbenzenesulfonate (salt)

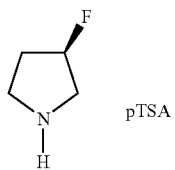

Prepare using the method of Intermediate 49 with p-toluenesulfonic acid monohydrate (0.356 g, 1.87 mmol), tert-butyl (3R)-3-fluoropyrrolidine-1-carboxylate (See Intermediate50) (0.353 g, 1.87 mmol) and ethanol (2 mL) to give the title compound as a white solid (0.478 g): MS (m/e): 90 (M+1).

Intermediate 52

(3R)-Pyrrolidin-3-ol 4-methylbenzenesulfonate (salt)

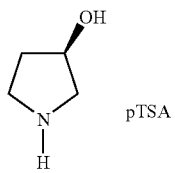

Prepare using the method of Intermediate 49 with p-toluenesulfonic acid monohydrate (0.255 g, 1.34 mmol), N-Boc-(R)-(−)-3-pyrrolidinol (0.251 g, 1.34 mmol) and ethanol (5 mL) to give the title compound as a pale yellow oil (0.34 g): MS (m/e): 88 (M+1).

Intermediate 53

(3S)-Pyrrolidin-3-ol 4-methylbenzenesulfonate (salt)

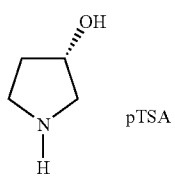

Prepare using the method of Intermediate 49 with p-toluenesulfonic acid monohydrate (0.254 g, 1.34 mmol), N-Boc-(S)-(+)-3-pyrrolidinol (0.250 g, 1.34 mmol) and ethanol (2 mL) to give the title compound as a white solid (0.35 g): MS (m/e): 88 (M+1).

Intermediate 54 tert-Butyl (3S)-3-(fluoromethyl)pyrrolidine-1-carboxylate

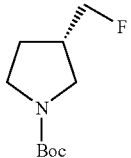

Prepare using the method of Intermediate 48 with (S)-N-Boc-(S)-pyrrolidine-3-methanol (0.50 g, 2.48 mmol), [bis(2-methoxyethyl)amino]sulfur trifluoride (0.55 mL, 2.98 mmol) and anhydrous dichloromethane (2.5 mL) to give the title compound as a colourless oil (0.17 g): MS (m/e): 226 (M+23).

Intermediate 55

(3S)-3-(Fluoromethyl)pyrrolidine 4-methylbenzenesulfonate (salt)

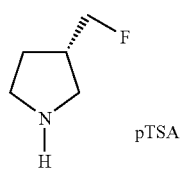

Prepare using the method of Intermediate 49 with p-toluenesulfonic acid monohydrate (0.14 g, 0.74 mmol), tert-butyl (3S)-3-(fluoromethyl)pyrrolidine-1-carboxylate (See Intermediate 54) (0.15 g, 0.74 mmol) and ethanol (2 mL) to give the title compound as a white solid (0.20 g): MS (m/e): 104 (M+1).

Intermediate 56 tert-Butyl (3R)-3-(fluoromethyl)pyrrolidine-1-carboxylate

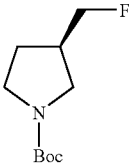

Prepare using the method of Intermediate 48 with (R)-N-Boc-pyrrolidine-3-methanol (0.50 g, 2.48 mmol), [bis(2-methoxyethyl)amino]sulfur trifluoride (0.55 mL, 2.98 mmol) and anhydrous dichloromethane (2.5 mL) to give the title compound as a colourless oil (0.34 g): MS (m/e): 226 (M+23).

Intermediate 57

(3R)-3-(Fluoromethyl)pyrrolidine 4-methylbenzenesulfonate (salt)

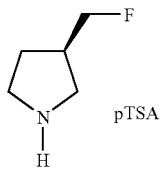

Prepare using the method of Intermediate 49 with p-toluenesulfonic acid monohydrate (0.304 g, 1.87 mmol), tert-butyl (3R)-3-(fluoromethyl)pyrrolidine-1-carboxylate (See Intermediate 56) (0.325 g, 1.87 mmol) and ethanol (2 mL) to give the title compound as a white solid (0.421 g): MS (m/e): 104 (M+1).

Intermediate 58 tert-Butyl (3R)-3-methoxypyrrolidine-1-carboxylate and (3R)-3-Methoxypyrrolidine

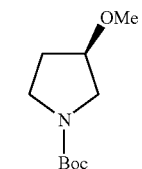

Add sodium hydride (60% dispersion in oil, 0.048 g, 1.20 mmol) to a solution of N-Boc-(R)-(−)-3-pyrrolidinol (0.20 g, 1.09 mmol), under nitrogen. Leave to stir at room temperature for 10 minutes then add methyl iodide (0.10 mL, 1.64 mmol). Stir the mixture for 2 days then add methanol (10 mL). Load the methanol solution onto an Isolute® SCX-2 (5 g) column. Wash the column with methanol then concentrate this methanol fraction in vacuo to give an orange/red oil (0.42 g) containing oil from the sodium hydride dispersion and the title compounds: MS (m/e): 102 (M+1).

Intermediate 59

(3R)-3-Methoxypyrrolidine 4-methylbenzenesulfonate (salt)

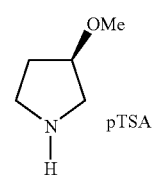

Prepare using the method of Intermediate 49 with p-toluenesulfonic acid monohydrate (0.207 g, 1.09 mmol), crude tert-butyl (3R)-3-methoxypyrrolidine-1-carboxylate and (3R)-3-methoxypyrrolidine (See Intermediate 58) (0.42 g, 1.09 mmol) and ethanol (2 mL) to give the title compound as a red solid (0.42 g): MS (m/e): 102(M+1).

Intermediate 60 tert-Butyl (3S)-3-methoxypyrrolidine-1-carboxylate and (3S)-3-Methoxypyrrolidine

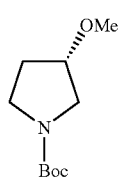

Prepare using the method of Intermediate 58 using sodium hydride (60% dispersion in oil, 0.048 g, 1.20 mmol), N-Boc-(S)-3-pyrrolidinol (0.20 g, 1.09 mmol) and methyl iodide (0.10 mL, 1.64 mmol) to give an dark orange oil (0.50 g) containing oil from the sodium hydride dispersion and the title compounds: MS (m/e): 102 (M+1).

Intermediate 61

(3S)-3-Methoxypyrrolidine 4-methylbenzenesulfonate (salt)

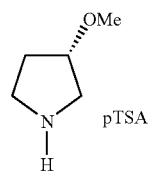

Prepare using the method of Intermediate 49 with p-toluenesulfonic acid monohydrate (0.207 g, 1.09 mmol), crude tert-butyl (3S)-3-methoxypyrrolidine-1-carboxylate (See Intermediate 60) (0.50 g, 1.09 mmol) and ethanol (2 mL) to give the title compound as a dark orange coloured oil (0.42 g): MS (m/e): 102 (M+1).

Intermediate 62

2-[2-(4-Hydroxy-phenyl)-5-methyl-oxazol-4-yl]-1-(2-(R)-methyl-pyrrolidin-1-yl)-ethanone

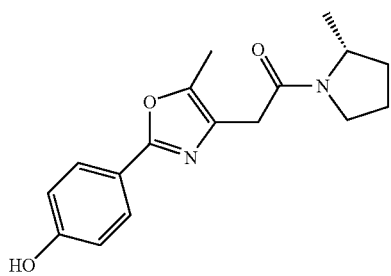

The title compound is prepared in a manner substantially similar to Example 56 from 2-[2-(4-Benzyloxy-phenyl)-5-

53 methyl-oxazol-4-yl]-1-(2-(R)-methyl-pyrrolidin-1-yl)-ethanone (See Intermediate 18). MS (ES+) 301.2

Intermediate 63

1-(2-(R)-Methyl-pyrrolidin-1-yl)-2-{5-methyl-2-[4-(thiazol-4-ylmethoxy)-phenyl]-oxazol-4-yl}-ethanone

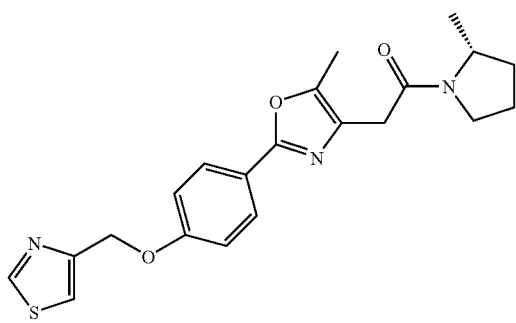

The title compound is prepared in a manner substantially similar to Intermediate 16 from 2-[2-(4-Hydroxy-phenyl)-5-methyl-oxazol-4-yl]-1-(2-(R)-methyl-pyrrolidin-1-yl)-ethanone (See Intermediate 62) and 4-(chloromethyl)thiazole hydrochloride except KI (1.5 eq.) is also added. MS (ES+) 398.3

Intermediate 64

[2-(4-Hydroxy-phenyl)-oxazol-4-yl]-acetic acid ethyl ester

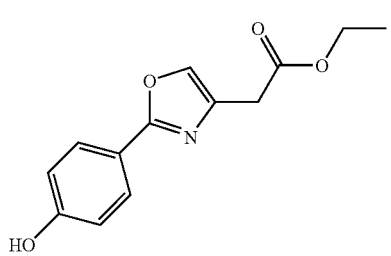

A mixture of 4-hydroxybenzamide (25.2 g, 0.18 mol) and ethyl chloroacetoacetate (90 mL) is heated to 110° C. After 1 h, more ethyl chloroacetoacetate (30 mL) is added, and continue to heat for 3 h more. The mixture is cooled to approximately 60° C., and MeOH is added. The mixture is filtered and dried to yield the title compound (36.6 g, 80%) as an off-white solid. MS (m/e): 248.3 (M+1)

54

Intermediate 65

{2-[4-(Pyridin-2-ylmethoxy)-phenyl]-oxazol-4-yl}-acetic acid ethyl ester

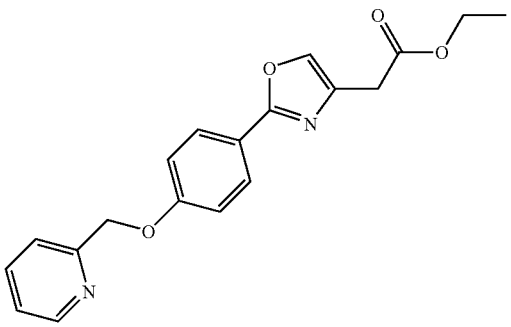

The title compound is prepared in a manner substantially similar to Intermediate 16 from [2-(4-Hydroxy-phenyl)-oxazol-4-yl]-acetic acid ethyl ester (See Intermediate 64) and 2-(bromomethyl)pyridine hydrobromide. MS (m/e): 339.2 (M+1)

Intermediate 66

2-{2-[4-(Pyridin-2-ylmethoxy)-phenyl]-oxazol-4-yl}-ethanol

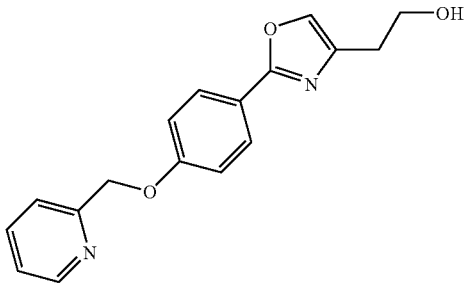

The title compound is prepared in a manner substantially similar to Example 55 from {2-[4-(Pyridin-2-ylmethoxy)-phenyl]-oxazol-4-yl}-acetic acid ethyl ester (See Intermediate 65). The crude material was purified by flash chromatography (40 g SiO$_2$, elute 1% to 10% MeOH/CH$_2$Cl$_2$). MS (m/e): 297.2 (M+1)

Intermediate 67

{2-[4-(Thiazol-4-ylmethoxy)-phenyl]-oxazol-4-yl}-acetic acid ethyl ester

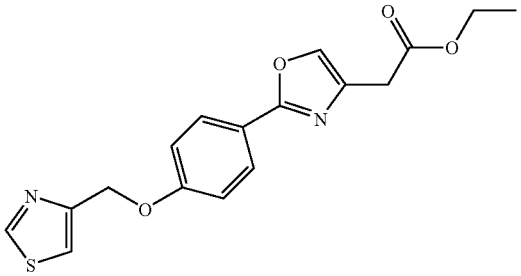

The title compound is prepared in a manner substantially similar to Intermediate 16 from [2-(4-Hydroxy-phenyl)-oxazol-4-yl]-acetic acid ethyl ester (See Intermediate 64) and 4-(chloromethyl)thiazole hydrochloride except KI (2 eq.) is also added. MS (m/e): 345.2 (M+1)

Intermediate 68

2-{2-[4-(Thiazol-4-ylmethoxy)-phenyl]-oxazol-4-yl}-ethanol

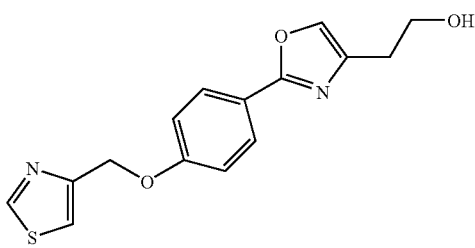

The title compound is prepared in a manner substantially similar to Example 55 from {2-[4-(Thiazol-4-ylmethoxy)-phenyl]-oxazol-4-yl}-acetic acid ethyl ester (See Intermediate 67). The crude material was purified by flash chromatography (12 g SiO₂, elute 1% to 10% MeOH/CH₂Cl₂). MS (m/e): 303.2 (M+1)

Intermediate 69

[2-(4-Trifluoromethanesulfonyloxy-phenyl)-oxazol-4-yl]-acetic acid ethyl ester

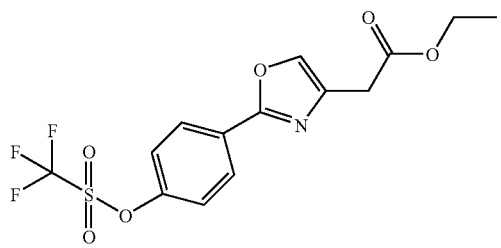

To a mixture of [2-(4-Hydroxy-phenyl)-oxazol-4-yl]-acetic acid ethyl ester (See Intermediate 64) (1.0 g, 4 mmol) and triethylamine (0.61 mL, 4.4 mmol) in CH₂Cl₂ (20 mL) at 0° C. is added trifluoromethanesulfonic anhydride (0.71 mL, 4.2 mmol). The cooling bath is removed, and the mixture is stirred at room temperature overnight. The mixture is partitioned between EtOAc and Sat. NaHCO₃. The aqueous phase is extracted with EtOAc, and the combined organic phase is washed with brine, dried (Na₂SO₄), and concentrated. The residue is purified by flash chromatography (40 g SiO₂, elute 5% to 50% EtOAc/hexane to yield 0.83 g (55%) of the title compound. MS (m/e): 380.2 (M+1)

Intermediate 70

[2-(4'-Methanesulfonyl-biphenyl-4-yl)-oxazol-4-yl]-acetic acid ethyl ester

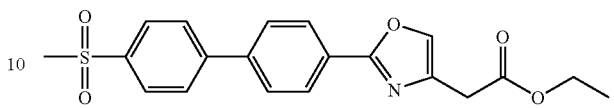

A suspension of [2-(4-Trifluoromethanesulfonyloxy-phenyl)-oxazol-4-yl]-acetic acid ethyl ester (See Intermediate 69) (0.83 g, 2.2 mmol), 4-(methanesulfonyl)phenyl boronic acid (0.48 g, 2.4 mmol), triphenylphosphine (69 mg, 0.26 mmol), cesium fluoride (0.67 g, 4.4 mmol) and palladium acetate (15 mg, 0.066 mmol) in DMF (10 mL) is heated at 110° C. for 24 h. The suspension is cooled to room temperature and filtered. The filtrate is partitioned between EtOAc and water. The aqueous phase is extracted with EtOAc. The combined organic phase is washed with brine, dried (Na₂SO₄), and concentrated. The residue is purified by flash chromatography (40 g SiO₂, elute 20% to 80% EtOAC/hexane) to yield the title compound (0.10 g, 12%). MS (m/e): 386.2 (M+1)

Intermediate 71

2-[2-(4'-Methanesulfonyl-biphenyl-4-yl)-oxazol-4-yl]-ethanol

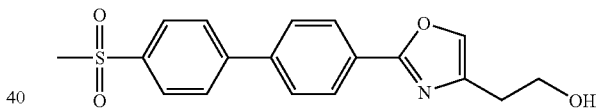

The title compound is prepared in a manner substantially similar to Example 55 from [2-(4'-Methanesulfonyl-biphenyl-4-yl)-oxazol-4-yl]-acetic acid ethyl ester (See Intermediate 70). MS (m/e): 344.3 (M+1)

Example 1

2-(4-Bromo-phenyl)-4-pyrrolidin-1-ylmethyl-oxazole

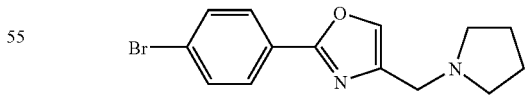

2-(4-Bromo-phenyl)-4-chloromethyl-oxazole (See Intermediate 1) (0.321 g, 1.18 mmol), and pyrrolidine (0.639 g, 9.0 mmol) are dissolved in 20 mL tetrahydrofuran and stirred at ambient temperature for 1.5 hours. The reaction is concentrated to an oil and redissolved in diethyl ether which is washed with aqueous sodium bicarbonate, water, separated and dried over sodium sulfate, filtered and concentrated to a dark oil. The oil is purified by flash silica gel chromatography (2% 2M NH₃ in MeOH/dichloromethane) to give 0.185 g of the titled compound. MS (m/e) ($^{81}$Br): 309.1 (M+1)

Example 2

2-(4-Bromo-phenyl-4-pyrrolidin-1-ylmethyl-oxazole; hydrochloride

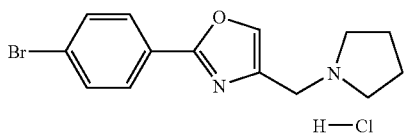

The free base of the titled compound is prepared substantially in accordance the procedure of Example 1 without chromatography. The crude free base is treated with 1M HCl in diethyl ether and the resulting solids are dissolved a minimum amount of dichloromethane. Diethyl ether is added and the brown precipitate is removed by filtration. To the filtrate is added 1:1 diethyl ether/hexane to precipitate the titled compound as a light tan solid. MS (m/e) ($^{81}$Br): 309.1 (M+1)

Example 3

3-[4-(4-Pyrrolidin-1-ylmethyl-oxazol-2-yl)-phenyl]-pyridine; dihydrochloride

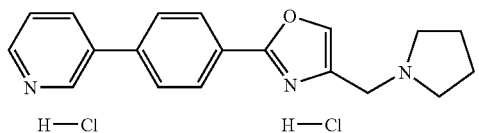

Step A: 2-(4-Bromo-phenyl)-4-pyrrolidin-1-ylmethyl-oxazole (See Example 1) (0.174 g, 0.57 mmol), 3-pyridylboronic acid (0.184 g, 1.5 mmol), dichloropalladium di-triphenylphosphine (0.060 g, 0.086 mmol), cesium fluoride (0.866 g, 5.7 mmol) and 6 mL acetonitrile are placed in a 10 mL CEM microwave tube. The tube is placed in a CEM microwave reactor for 30 minutes at 140° C., 125 psi, and 75 watts of power. The mixture is cooled and concentrated to a dark residue which is purified by radial silica gel chromatography (1% 2M NH₃ in MeOH/dichloromethane) to give 0.015 g of the free base of the titled compound.
Step B: The free base is dissolved in 1 mL of dichloromethane and 0.20 mL of a 1M HCl in diethyl ether solution is added to precipitate 0.018 g of the pure titled compound. MS (m/e): 306.1 (M+1)

Example 4

2-(4'-Methanesulfonyl-biphenyl-4-yl)-4-pyrrolidin-1-ylmethyl-oxazole

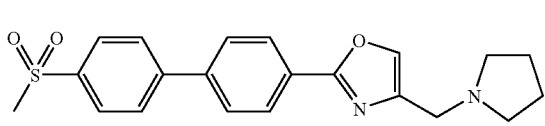

2-(4-Bromo-phenyl-4-pyrrolidin-1-ylmethyl-oxazole hydrochloride (See Example 2) (0.151 g, 0.439 mmol), 4-methylsulfonylphenylboronic acid (0.132 g, 0.66 mmol), tetrakis-(triphenylphosphine) palladium (0.010 g, 0.009 mmol), aqueous sodium carbonate (2M, 0.88 mL, 1.76 mmol) and 7 mL of dioxane is placed in a 10 mL CEM microwave tube. The tube is placed in a CEM microwave reactor for 30 minutes at 90° C., 25 psi, and 45 watts of power. The mixture is cooled and concentrated to a dark residue which is purified by radial silica gel chromatography (1% 2M NH₃ in MeOH/dichloromethane) to give 0.125 g of the titled compound. MS (m/e): 383.1 (M+1)

Example 5

(+/-)-2-(4-Bromo-phenyl)-4-(2-methyl-pyrrolidin-1-ylmethyl)-oxazole; hydrochloride

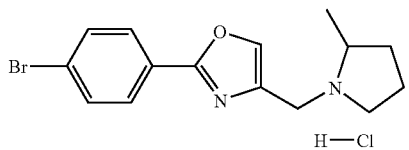

The titled compound is prepared substantially in accordance with the procedures of Examples 1 and 2 using 2-(4-Bromo-phenyl)-4-chloromethyl-oxazole (See
Intermediate 1) and racemic 2-methylpyrrolidine [CAS# 765-38-8]. MS (m/e) ($^{81}$Br): 323.1 (M+1)

Example 6

(+/-)-2-(4'-Methanesulfonyl-biphenyl-4-yl)-4-(2-methyl-pyrrolidin-1-ylmethyl)-oxazole

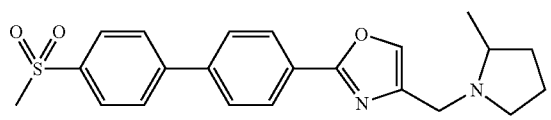

The titled compound is prepared substantially in accordance with the procedure of Example 4 using 4-methylsulfonylphenylboronic acid and (+/-)-2-(4-Bromo-phenyl)-4-(2-methyl-pyrrolidin-1-ylmethyl)-oxazole; hydrochloride (See Example 5). MS (m/e) 397.1 (M+1)

Example 7

N-[4'-(4-Pyrrolidin-1-ylmethyl-oxazol-2-yl)-biphenyl-4-yl]-methanesulfonamide

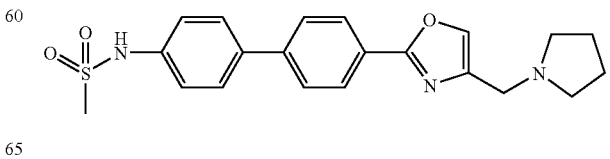

The titled compound is prepared substantially in accordance with the procedure of Example 4 using 4-(methylsulfonylamino)phenylboronic acid and 2-(4-Bromo-phenyl-4-pyrrolidin-1-ylmethyl-oxazole; hydrochloride (See Example 2). MS (m/e) 398.2 (M+1)

Example 8

2-(4-Bromo-phenyl)-5-methyl-4-(2-pyrrolidin-1-yl-ethyl)-oxazole

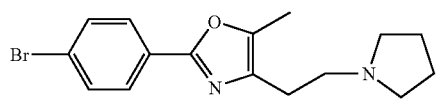

2-(4-Bromophenyl)-5-methyl-oxazoleethanol (10.0 g, 35.44 mmol) [which is obtained by the method of D. Brooks, J. Med. Chem., 2001, 44, 2061-2064 or see WO 0116120], triethylamine (5.4 mL, 38.6 mmol), and methanesulfonyl chloride (3.0 mL, 38.6 mmol) is dissolved in 200 mL of dichloromethane and stirred at ambient temperature for 1 hour. The mixture is then concentrated to an tan residue and redissolved in 100 mL of tetrahydrofuran. Pyrrolidine (32.2 mL, 386 mmol) is added and the mixture is heated to reflux for 4 hours. The reaction is concentrated and redissolved in ethyl acetate and washed successively with water and aqueous sodium bicarbonate. The organics phase is separated, dried over sodium sulfate, filtered and concentrated to provide the titled compound (11.87 g, 99.9% yield). MS (m/e) ($^{81}$Br): 337.0 (M+1)

Example 9

4-{4-[5-Methyl-4-(2-pyrrolidin-1-yl-ethyl)-oxazol-2-yl]-phenyl}-pyridine

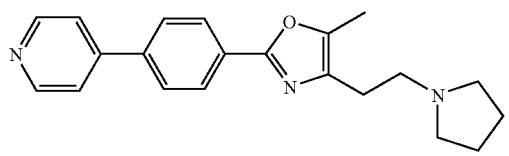

2-(4-Bromo-phenyl)-5-methyl-4-(2-pyrrolidin-1-yl-ethyl)-oxazole (See Example 8) (7.23 g, 21.57 mmol), 4-pyridylboronic acid (3.98 g, 32.35 mmol), [1,1 bis(diphenylphosphino)ferrocene]dichloropalladium(II) complex with CH$_2$Cl$_2$ (1:1) (0.616 g, 0.755 mmol), and aqueous sodium carbonate (2M, 40 mL) are dissolved in 200 mL of dioxane and heated to reflux for 1.5 hours. The mixture is concentrated to a dark residue and purified by flash silica gel chromatography (gradient: 3-6% 2M NH$_3$ in MeOH/dichloromethane) to provide the titled compound (5.94 g, 82.5% yield). MS (m/e): 334.2 (M+1)

Example 10

4-{4-[5-Methyl-4-(2-pyrrolidin-1-yl-ethyl)-oxazol-2-yl]-phenyl}-pyridine: dihydrochloride

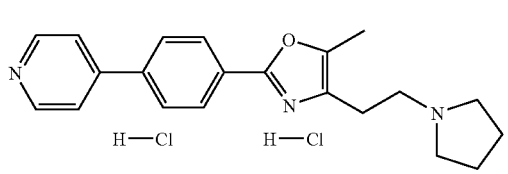

The titled compound is prepared substantially in accordance with the procedure of Example 3, Step B using 4-{4-[5-Methyl-4-(2-pyrrolidin-1-yl-ethyl)-oxazol-2-yl]-phenyl}-pyridine (See Example 9). MS (m/e): 334.2 (M+1)

Example 11

3-{4-[5-Methyl-4-(2-pyrrolidin-1-yl-ethyl)-oxazol-2-yl]-phenyl}-pyridine

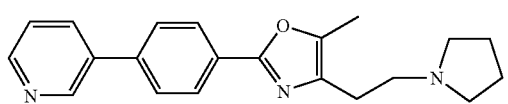

The titled compound is prepared by either of the following methods:

Method A: Using 2-[5-Methyl-2-(4-pyridin-3-yl-phenyl)-oxazol-4-yl}-ethanol (See Intermediate 2), the titled compound is prepared substantially in accordance with the procedure of Example 8. MS (m/e): 334.2 (M+1)

Method B: The titled compound is prepared substantially in accordance with the procedure of Example 9 using 2-(4-Bromo-phenyl)-5-methyl-4-(2-pyrrolidin-1-yl-ethyl)-oxazole (See Example 8) and 3-pyridylboronic acid. MS (m/e): 334.2 (M+1)

Example 12

3-{4-[5-Methyl-4-(2-pyrrolidin-1-yl-ethyl)-oxazol-2-yl]-phenyl}-pyridine: dihyrdochloride

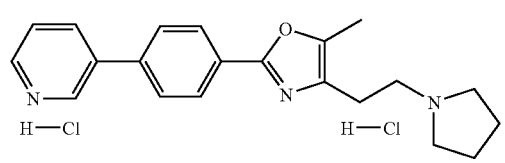

The titled compound is prepared substantially in accordance with the procedure of Example 3, Step B using 3-{4-[5-Methyl-4-(2-pyrrolidin-1-yl-ethyl)-oxazol-2-yl]-phenyl}-pyridine (See Example 11). MS (m/e): 334.2 (M+1)

Example 13

(+/−)-2-(4-Bromo-phenyl)-5-methyl-4-[2-(2-methyl-pyrrolidin-1-yl)-ethyl]-oxazole

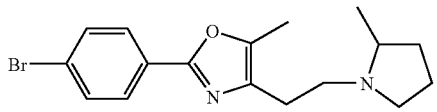

The titled compound is prepared substantially in accordance with the procedure of Example 8 using racemic 2-methylpyrrolidine. MS (m/e): 334.2 (M+1)

Example 14

(+/−)-4-(4-{5-Methyl-4-[2-(2-methyl-pyrrolidin-1-yl)-ethyl]-oxazol-2-yl}-phenyl)-pyridine: dihydrochloride

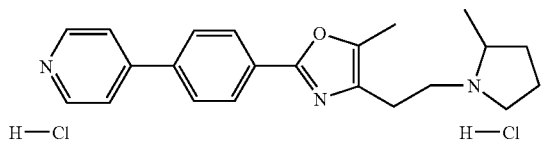

The free base of the titled compound is prepared substantially in accordance with the procedure of Example 4 using (+/−)-2-(4-Bromo-phenyl)-5-methyl-4-[2-(2-methyl-pyrrolidin-1-yl)-ethyl]-oxazole (See Example 13) and 4-pyridylboronic acid. The free base is converted to the dihydrochloride salt according to the procedure of Example 3, Step B to provide the titled compound. MS (m/e): 348.3 (M+1)

Example 15

2-Methyl-5-{4'-[5-methyl-4-(2-pyrrolidin-1-yl-ethyl)-oxazol-2-yl]-biphenyl-4-yl}-[1,3,4]oxadiazole

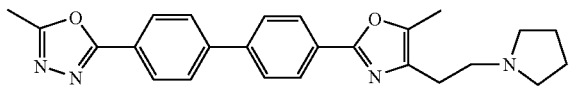

The titled compound is prepared substantially in accordance with the procedure of Example 8 using 2-{5-Methyl-2-[4-(5-methyl-[1,3,4]oxadiazol-2-yl)-phenyl]-oxazol-4-yl}-ethanol (See Intermediate 4). MS (m/e): 415.3 (M+1)

Example 16

2-(4-Bromo-phenyl)-5-methyl-4-[2-(2R-methyl-pyrrolidin-1-yl)-ethyl]-oxazole; hydrochloride

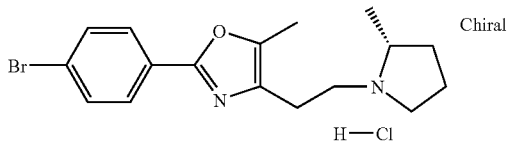

2-(4-Bromophenyl)-5-methyl-oxazoleethanol (0.592 g, 2.1 mmol) [which is obtained by the method of D. Brooks, J. Med. Chem., 2001, 44, 2061-2064 or see WO 0116120], triethylamine (0.316 mL, 2.27 mmol), and methanesulfonyl chloride (0.176 mL, 2.27 mmol) are dissolved in 12 mL of dichloromethane and stirred at ambient temperature for 1 hour. The mixture is concentrated to a tan residue and redissolved in 4 mL of tetrahydrofuran. Triethylamine (0.585 mL, 4.2 mmol), and 2R-Methyl-pyrrolidine; hydrochloride (See Intermediate 7) (0.510 g, 4.2 mmol) are added and the mixture is heated to reflux for 40 hours. The reaction is concentrated and redissolved in dichloromethane and washed successively with water and aqueous sodium bicarbonate. The organics phase is separated, dried over sodium sulfate, filtered and concentrated to provide the free base of the titled compound (0.586 g) which is converted to the titled compound substantially in accordance with the procedure of Example 2. MS (m/e): 349.1 (M+1)

Example 17

4-(4-{5-Methyl-4-[2-(2R-methyl-pyrrolidin-1-yl)-ethyl]-oxazol-2-yl}-phenyl)-pyridine: dihydrochloride

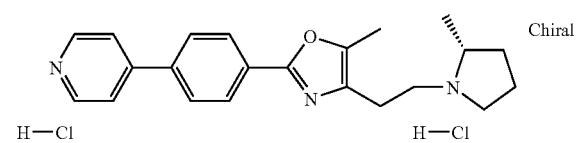

The free base of the titled compound is prepared substantially in accordance with the procedure of Example 4 using 2-(4-Bromo-phenyl)-5-methyl-4-[2-(2R-methyl-pyrrolidin-1-yl)-ethyl]-oxazole; hydrochloride (See Example 16) and 4-pyridylboronic acid. The free base is converted to the dihydrochloride salt according to the procedure of Example 3, Step B to provide the titled compound. MS (m/e): 348.3 (M+1)

Example 18

6-{4-[5-Methyl-4-(2-pyrrolidin-1-yl-ethyl)-oxazol-2-yl]-phenyl}-nicotinontrile: dihydrochloride

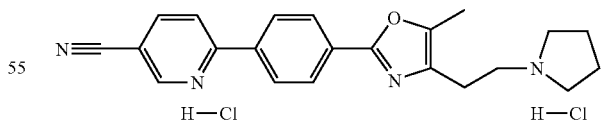

The free base of the titled compound is prepared substantially in accordance with the procedure of Example 4 using 5-Methyl-4-(2-pyrrolidin-1-yl-ethyl)-2-[4-(4,4,5,5-tetramethyl-[1,3,2]dioxaborolan-2-yl)-phenyl]-oxazole (See Intermediate 8) and 6-chloronicotinonitrile (Alfa Aesar, CAS# 33252-28-7). The free base is converted to the dihydrochloride salt according to the procedure of Example 3, Step B to provide the titled compound. MS (m/e): 359.2 (M+1)

Example 19

2-(4'-Methanesulfonyl-biphenyl-4-yl)-5-methyl-4-[2-(2R-methyl-pyrrolidin-1-yl)-ethyl]-oxazole

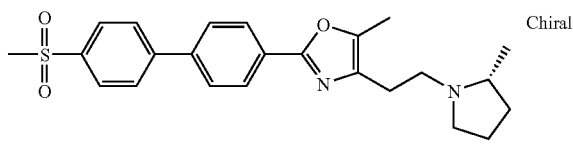

The titled compound is prepared by either of the following methods:

Method A: Using 2-[2-(4'-Methanesulfonyl-biphenyl-4-yl)-5-methyl-oxazol-4-yl]-ethanol (See Intermediate 9) the titled compound is prepared substantially in accordance with the procedure of Example 16. MS (m/e) 425.2 (M+1)

Method B: The titled compound is prepared substantially in accordance with the procedure from Example 4 using 2-(4-Bromo-phenyl)-5-methyl-4-[2-(2R-methyl-pyrrolidin-1-yl)-ethyl]-oxazole; hydrochloride (see Example 16) and 4-methylsulfonylphenylboronic acid. MS (m/e): 425.2 (M+1)

Example 20

3-(4-{5-Methyl-4-[2-(2R-methyl-pyrrolidin-1-yl)-ethyl]-oxazol-2-yl}-phenyl)-pyridine: dihydrochloride

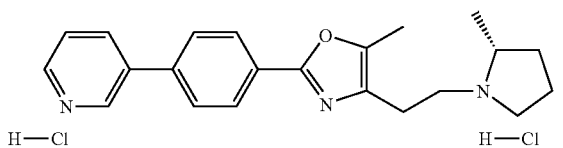

The free base of the titled compound is prepared substantially in accordance with the procedure of Example 9 using (+/−)-2-(4-Bromo-phenyl)-5-methyl-4-[2-(2-methyl -pyrrolidin-1-yl)-ethyl]-oxazole (See Example 13) and 3-pyridyl-boronic acid. The free base is converted to the dihydrochloride salt according to the procedure of Example 3, Step B to provide the titled compound. MS (m/e): 348.3 (M+1)

Example 21

(+/−)-1-[2-(4-Bromo-phenyl)-oxazol-4-ylmethyl]-2-methyl-piperidine

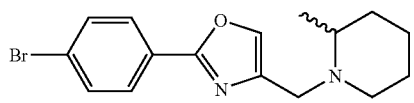

The titled compound is prepared substantially in accordance with the procedure of Example 16 using 2-(4-Bromo-phenyl)-4-chloromethyl-oxazole (See Intermediate 1) and 2-methylpiperidine. MS (m/e): 336.2 (M+1)

Example 22

(+/−)-3-{4-[4-(2-Methyl-piperidin-1-ylmethyl)-oxazol-2-yl]-phenyl}-pyridine

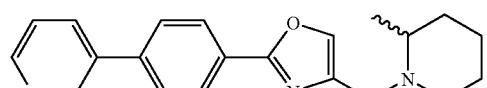

1-[2-(4-Bromo-phenyl)-oxazol-4-ylmethyl]-2-methyl-piperidine (See Example 21) (1.0 mmol; N96-A03858-154), 3-pyridyl boronic acid (1.2 mmol), tetrakis-(triphenylphosphine)palladium (0.044 mmol), 2M aqueous sodium carbonate (3 mmol) and dioxane (0.1M) is placed in a microwave reactor vessel with a stirbar. Run the reaction in a CEM microwave reactor at 90° C. with 30 W power and cooling for 30 minutes. After this time, perform an aqueous workup and purify via radial chromatography eluting with 2M ammonia in methanol and dichloromethane to provide the titled compound. MS (m/e): 334.2 (M+1)

Example 23

(+/−)-3-{4-[4-(2-Methyl-piperidin-1-ylmethyl)-oxazol-2-yl]-phenyl}-pyridine dihydrochloride salt

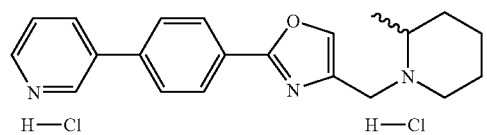

Dissolve 3-{4-[4-(2-Methyl-piperidin-1-ylmethyl)-oxazol-2-yl]-phenyl}-pyridine (See Example 22) in minimal dichloromethane and add 1M hydrochloric acid in diethyl ether until the solution is cloudy. Add hexane and concentrate in vacuo to yield the titled compound. MS (m/e): 334.1 (M+1)

Example 24

2-(4'-Methanesulfonyl-biphenyl-4-yl)-5-methyl-4-(2-pyrrolidin-1-yl-ethyl)-oxazole

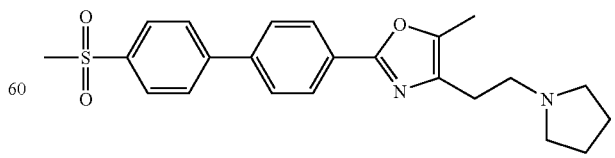

Starting with 2-(4-Bromo-phenyl)-5-methyl-4-(2-pyrrolidin-1-yl-ethyl)-oxazole (See Example 8) and 4-methylsulfonylphenylboronic acid, follow a procedure significantly analogous to that found in Example 22 to give the titled compound. MS (m/e): 411.2 (M+1)

Example 25

4'-[5-Methyl-4-(2-pyrrolidin-1-yl-ethyl)-oxazol-2-yl]-biphenyl-4-carboxylic acid dimethylamide

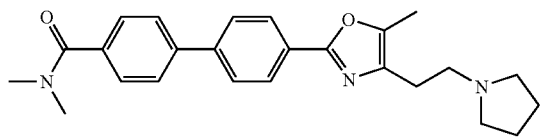

Starting with 2-(4-Bromo-phenyl)-5-methyl-4-(2-pyrrolidin-1-yl-ethyl)-oxazole (See Example 8) and 4-(N,N-dimethylcarbamoyl)phenylboronic acid, follow a procedure significantly analogous to that found in Example 22 to give the titled compound. MS (m/e): 404.3 (M+1)

Example 26

5-{4-[5-Methyl-4-(2-pyrrolidin-1-yl-ethyl)-oxazol-2-yl]-phenyl}-thiophene-2-carbonitrile

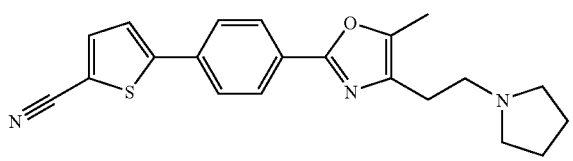

Starting with 2-(4-Bromo-phenyl)-5-methyl-4-(2-pyrrolidin-1-yl-ethyl)-oxazole (See Example 8) and 4-cyanothiophene boronic acid, follow a procedure significantly analogous to that found in Example 22 to give the titled compound. MS (m/e): 364.2 (M+1)

Example 27

2-(4-Bromo-phenyl)-4-[2-(S)-(+)-(2-methoxymethyl-pyrrolidin-1-yl)-ethyl]-5-methyl-oxazole

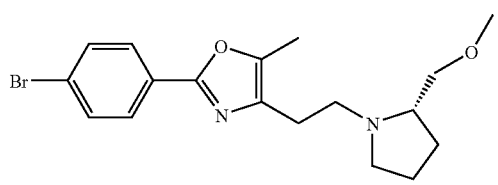

The titled compound is prepared significantly in accordance with the procedure of Example 8 using 2-(4-Bromophenyl)-5-methyl-oxazoleethanol [which is obtained by the method of D. Brooks, J. Med. Chem., 2001, 44, 2061-2064 or the see WO 0116120] and (S)-(+)-2-methoxymethylpyrrolidine. MS (m/e) ($^{79}$Br/$^{81}$Br): 379.2/381.2 (M+1)

Example 28

2-(4'-Methanesulfonyl-biphenyl-4-yl)-4-[2-(S)-(+)-(2-methoxymethyl-pyrrolidin-1-yl)-ethyl]-5-methyl-oxazole

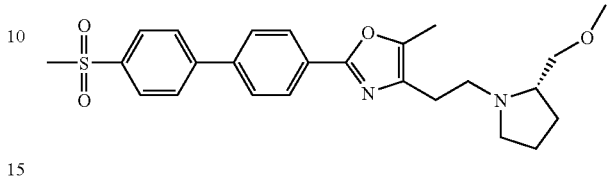

Starting with 2-(4-Bromo-phenyl)-4-[2-(S)-(+)-(2-methoxymethyl-pyrrolidin-1-yl)-ethyl]-5-methyl-oxazole (See Example 27) and 4-methylsulfonylphenylboronic acid, follow a procedure significantly analogous to Example 22 to give the titled compound. MS (m/e): 455.2 (M+1)

Example 29

3-(4-{4-[2-(S)-(+)-(2-Methoxymethyl-pyrrolidin-1-yl)-ethyl]-5-methyl-oxazol-2-yl}-phenyl)-pyridine dihydrochloride salt

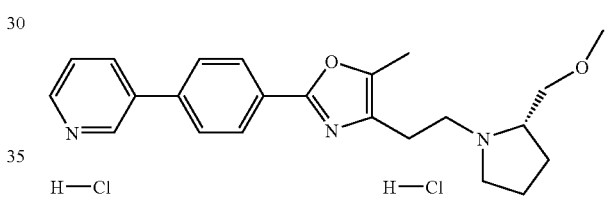

Starting with 2-(4-Bromo-phenyl)-4-[2-(S)-(+)-(2-methoxymethyl-pyrrolidin-1-yl)-ethyl]-5-methyl-oxazole (See Example 27) and 3-pyridylboronic acid, follow procedures significantly analogous to those found in Example 22 to give the free base of the titled compound. The free base is converted to the titled compound significantly in accordance with the procedure of Example 23. MS (m/e): 378.3 (M+1)

Example 30

4-(4-{4-[2-(S)-(+)-(2-Methoxymethyl-pyrrolidin-1-yl)-ethyl]-5-methyl-oxazol-2-yl}-phenyl)-pyridine dihydrochloride salt

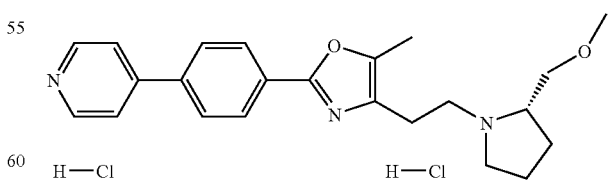

Starting with 2-(4-Bromo-phenyl)-4-[2-(S)-(+)-(2-methoxymethyl-pyrrolidin-1-yl)-ethyl]-5-methyl-oxazole (See Example 27) and 4-pyridylboronic acid, follow procedures significantly analogous to Example 22 to give the free base of the titled compound. The free base is converted to the titled compound significantly in accordance with the procedure of Example 23. MS (m/e): 378.3 (M+1)

Example 31

2-(4-Bromo-phenyl)-4-[2-(R)-(+)-(2-methoxymethyl-pyrrolidin-1-yl)-ethyl]-5-methyl-oxazole

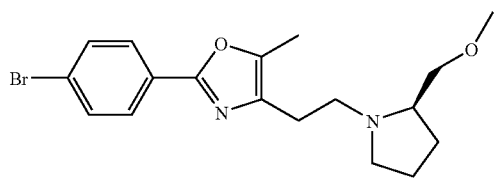

The titled compound is prepared significantly in accordance with the procedure of Example 8 using 2-(4-Bromophenyl)-5-methyl-oxazoleethanol [which is obtained by the method of D. Brooks, J. Med. Chem., 2001, 44, 2061-2064 or see WO 0116120] and (R)-(−)-2-methoxymethylpyrrolidine. MS (m/e) ($^{79}$Br/$^{81}$Br): 379.2/381.2 (M+1)

Example 32

2-(4'-Methanesulfonyl-biphenyl-4-yl)-4-[2-(R)-(+)-(2-methoxymethyl-pyrrolidin-1-yl)-ethyl]-5-methyl-oxazole

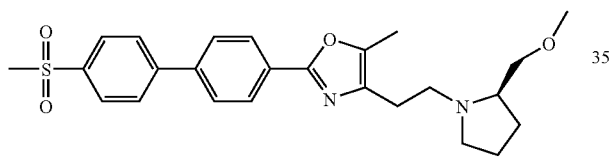

Starting with 2-(4-Bromo-phenyl)-4-[2-(R)-(+)-(2-methoxymethyl-pyrrolidin-1-yl)-ethyl]-5-methyl-oxazole (See Example 31) and 4-methylsulfonylphenylboronic acid, follow a procedure significantly analogous to that found in Example 22 to give the titled compound. MS (m/e): 455.2 (M+1)

Example 33

(+/−)-2-(4-Butoxy-phenyl)-5-methyl-4-[2-(2-methyl-pyrrolidin-1-yl)-ethyl]-oxazole hydrocholoride salt

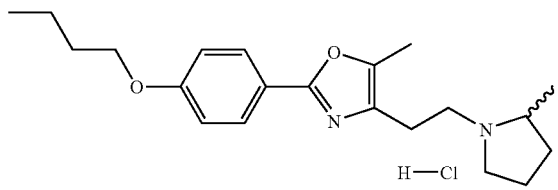

Starting with Toluene-4-sulfonic acid 2-[2-(4-butoxy-phenyl)-5-methyl-oxazol-4-yl]-ethyl ester [CAS 478540-91-9] and racemic 2-methylpyrrolidine, follow procedures significantly analogous to Example 8 to provide the free base of the titled compound. The free base is converted to the titled compound significantly in accordance with the procedure of Example 23. MS (m/e): 343.3 (M+1)

Example 34

1-{2-[2-(4-bromo-phenyl)-5-methyl-oxazol-4-yl]-ethyl}-piperidine

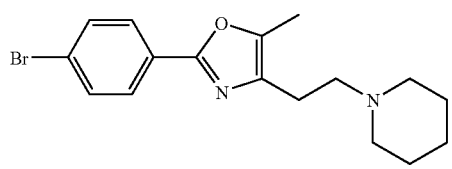

a) Add piperidine (3.04 g, 36.11 mmol) to a solution of Methanesulfonic acid 2-[2-(4-bromo-phenyl)-5-methyl-oxazol-4-yl]-ethyl ester (See Intermediate 13) (1.3 g, 3.61 mmol) in anhydrous THF (15 mL). Reflux the reaction overnight and cool. Wash organic material with 1N HCl (50 mL) and extract aqueous layer with diethyl ether (2×50 mL). Add 5N NaOH to aqueous layer (pH>10) and extract with dichloromethane (2×50 mL). Dry organics over $Na_2SO_4$, filter and concentrate. Purify crude on silica gel, eluting with 5% 2N $NH_3$ in methanol/dichloromethane to give 1-{2-[2-(4-bromo-phenyl)-5-methyl-oxazol-4-yl]-ethyl}-piperidine (0.944 g, 75%).

Example 35

5-Methyl-4-(2-pyrrolidin-1-yl-ethyl)-2-(3'-trifluoromethyl-biphenyl-4-yl)-oxazole

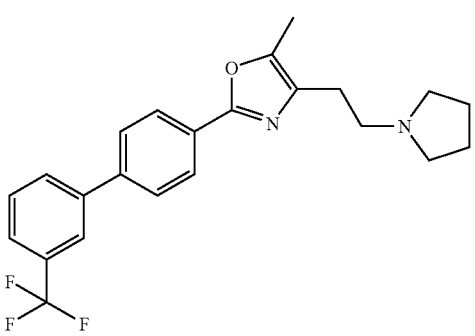

To a stirred solution of 2-(4-Bromo-phenyl)-5-methyl-4-(2-pyrrolidin-1-yl-ethyl)-oxazole (100 mg, 0.299 mmol), sodium carbonate (94.9 mg, 0.895 mmol) and 3-Trifluoromethylbenzene boronic acid (284 mg, 1.49 mmol) in toluene (5 mL), water (1 mL) and ethanol (1.5 mL) under nitrogen was added Tetrakis(triphenylphosphine) palladium (0) (34.5 mg, 0.030 mmol). The reaction was then heated to reflux for 48 h. The reaction was allowed to cool and bound to a SCX-2 cartridge (5 g). The cartridge was washed with one cartridge volume of dimethylformamide and two volumes of methanol. The product was eluted using 2M ammonia in methanol. The ammonia/methanol solution was evaporated on a Genevac® HT4. The sample was further purified by prep-LCMS. The resulting acetonitrile/water fractions were combined and evaporated using a Genevac® HT4 to give 77.7 mg of a colourless oil (65%). MS (m/e): 401.2 (M+1)

Example 36

2-(3',4'-Dimethoxy-biphenyl-4-yl)-5-methyl-4-(2-pyrrolidin-1-yl-ethyl)-oxazole

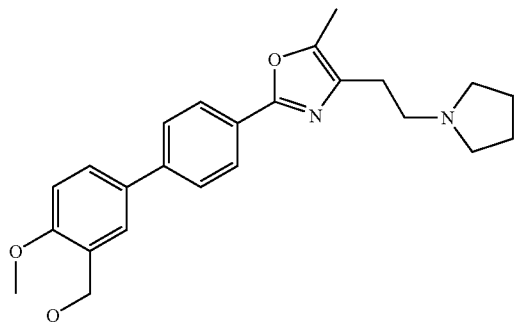

The title compound is prepared in a manner substantially analogous to Example 35 starting from 3,4-Dimethoxybenzene boronic acid and 2-(4-Bromo-phenyl)-5-methyl-4-(2-pyrrolidin-1-yl-ethyl)-oxazole. MS (m/e): 393.2 (M+1)

Example 37

5-Methyl-4-(2-pyrrolidin-1-yl-ethyl)-2-(3'-trifluoromethoxy-biphenyl-4-yl)-oxazole

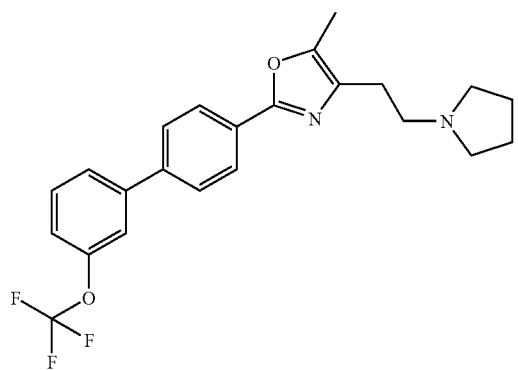

The title compound is prepared in a manner substantially analogous to Example 35 starting from 3-Trifluoromethoxy-benzene boronic acid and 2-(4-Bromo-phenyl)-5-methyl-4-(2-pyrrolidin-1-yl-ethyl)-oxazole. MS (m/e): 417.1 (M+1)

Example 38

5-Methyl-4-(2-pyrrolidin-1-yl-ethyl)-2-(4'-trifluoromethoxy-biphenyl-4-yl)-oxazole

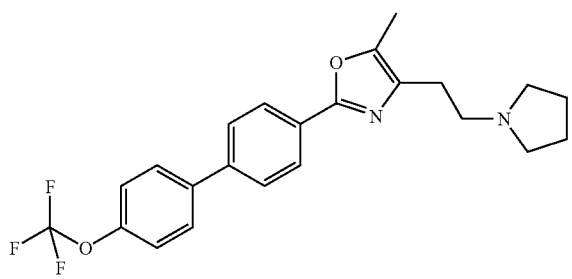

The title compound is prepared in a manner substantially analogous to Example 35 starting from 4-Trifluoromethoxy-benzene boronic acid and 2-(4-Bromo-phenyl)-5-methyl-4-(2-pyrrolidin-1-yl-ethyl)-oxazole. MS (m/e): 417.1 (M+1)

Example 39

2-(4'-Methoxy-biphenyl-4-yl)-5-methyl-4-(2-pyrrolidin-1-yl-ethyl)-oxazole

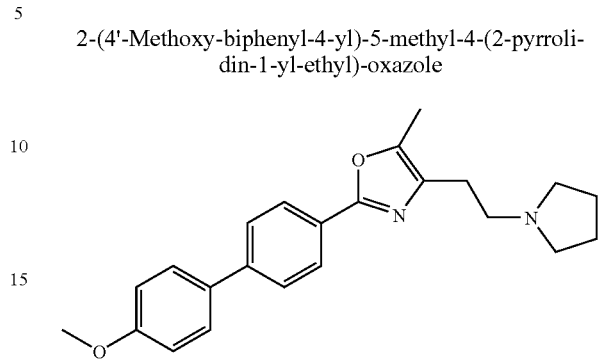

The title compound is prepared in a manner substantially analogous to Example 35 starting from 4-Methoxybenzene boronic acid and 2-(4-Bromo-phenyl)-5-methyl-4-(2-pyrrolidin-1-yl-ethyl)-oxazole. MS (m/e): 363.2 (M+1)

Example 40

2-(4-Benzo[1,3]dioxol-5-yl-phenyl)-5-methyl-4-(2-pyrrolidin-1-yl-ethyl)-oxazole

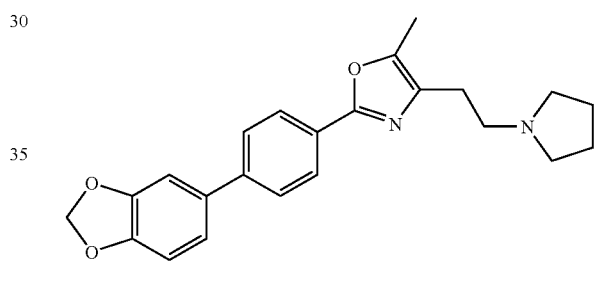

The title compound is prepared in a manner substantially analogous to Example 35 starting from 3,4-Methylenedioxy-benzene boronic acid and 2-(4-Bromo-phenyl)-5-methyl-4-(2-pyrrolidin-1-yl-ethyl)-oxazole. MS (m/e): 377.1 (M+1)

Example 41

2-(2',4'-Dimethoxy-biphenyl-4-yl)-5-methyl-4-(2-pyrrolidin-1-yl-ethyl)-oxazole

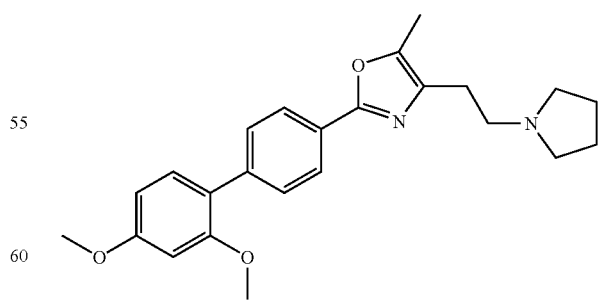

The title compound is prepared in a manner substantially analogous to Example 35 starting from 2,4-Dimethoxybenzene boronic acid and 2-(4-Bromo-phenyl)-5-methyl-4-(2-pyrrolidin-1-yl-ethyl)-oxazole. MS (m/e): 393.2 (M+1)

Example 42

3-Methoxy-5-{4-[5-methyl-4-(2-pyrrolidin-1-yl-ethyl)-oxazol-2-yl]-phenyl}-pyridine

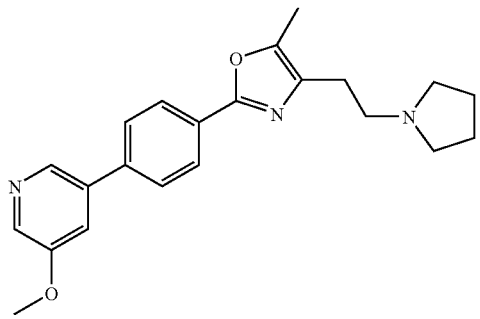

The title compound is prepared in a manner substantially analogous to Example 35 starting from 3-Methoxypyridine-5-boronic acid and 2-(4-Bromo-phenyl)-5-methyl-4-(2-pyrrolidin-1-yl-ethyl)-oxazole. MS (m/e): 364.2 (M+1)

Example 43

2-(3'-Methanesulfonyl-biphenyl-4-yl)-5-methyl-4-(2-pyrrolidin-1-yl-ethyl)-oxazole

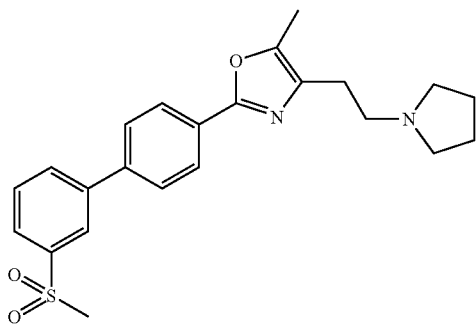

The title compound is prepared in a manner substantially analogous to Example 35 starting from 3-Methylsulfonylbenzene boronic acid and 2-(4-Bromo-phenyl)-5-methyl-4-(2-pyrrolidin-1-yl-ethyl)-oxazole. MS (m/e): 411.1 (M+1)

Example 44

2-(4'-Ethanesulfonyl-biphenyl-4-yl)-5-methyl-4-(2-pyrrolidin-1-yl-ethyl)-oxazole

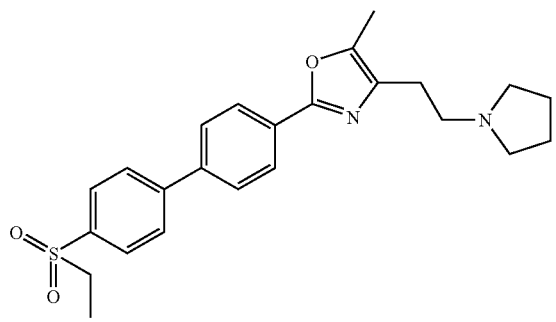

The title compound is prepared in a mamler substantially analogous to Example 35 starting from 4-Ethylsulfonylbenzene boronic acid and 2-(4-Bromo-phenyl)-5-methyl-4-(2-pyrrolidin-1-yl-ethyl)-oxazole. MS (m/e): 425.1 (M+1)

Example 45

2-(4'-Methanesulfinyl-biphenyl-4-yl)-5-methyl-4-(2-pyrrolidin-1-yl-ethyl)-oxazole

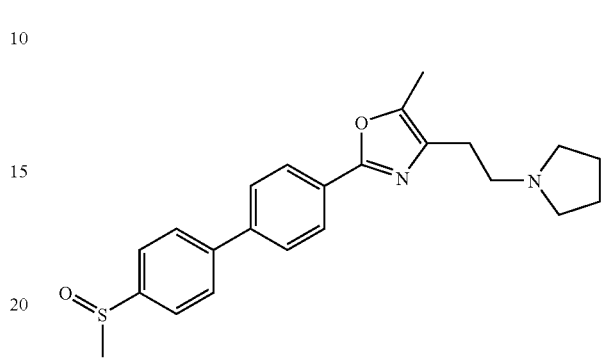

To a stirred solution of 2-(4-Bromo-phenyl)-5-methyl-4-(2-pyrrolidin-1-yl-ethyl)-oxazole (50 mg, 0.149 mmol), sodium carbonate (47.5 mg, 0.448 mmol) and 4-Methylsulfinylbenzene boronic acid (137.3 mg, 0.75 mmol) in toluene (2.5 mL), water (0.75 mL) and ethanol (1 mL) under nitrogen was added Tetrakis(triphenylphosphine) palladium (0) (17. 2 mg, 0.015 mmol). The reaction was then heated to reflux for 48 h. The reaction was allowed to cool and bound to a SCX-2 cartridge (5 g). The cartridge was washed with one cartridge volume of dimethylformamide and two volumes of methanol. The product was eluted using 2M ammonia in methanol. The ammonia/methanol solution was evaporated on a Genevac® HT4. The sample was further purified by prep-LCMS. The resulting acetonitrile/water fractions were combined and evaporated using a Genevac® HT4 to give 17.8 mg of a colourless oil (30%). MS (m/e): 395.2 (M+1)

Example 46

5-{4-[5-Methyl-4-(2-pyrrolidin-1-yl-ethyl)-oxazol-2-yl]-phenyl}-pyrimidine

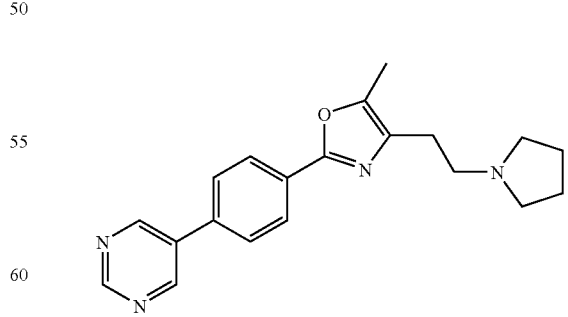

The title compound is prepared in a manner substantially analogous to Example 45 starting from 5-Pyrimidine boronic acid and 2-(4-Bromo-phenyl)-5-methyl-4-(2-pyrrolidin-1-yl-ethyl)-oxazole. MS (m/e): 335.2 (M+1)

Example 47

2-Methoxy-5-{4-[5-methyl-4-(2-pyrrolidin-1-yl-ethyl)-oxazol-2-yl]-phenyl}-pyrimidine

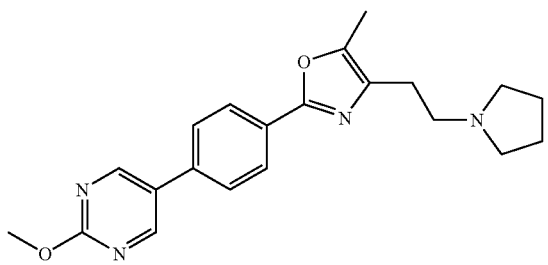

The title compound is prepared in a manner substantially analogous to Example 45 starting from 2-Methoxy-5-pyrimidine boronic acid and 2-(4-Bromo-phenyl)-5-methyl-4-(2-pyrrolidin-1-yl-ethyl)-oxazole. MS (m/e): 365.2 (M+1)

Example 48

5-{4-[5-Methyl-4-(2-pyrrolidin-1-yl-ethyl)-oxazol-2-yl]-phenyl}-1H-indole

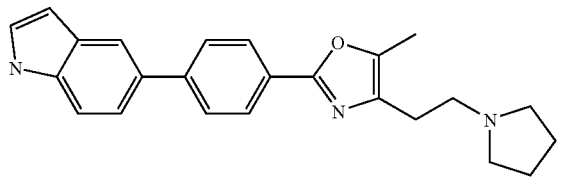

The title compound is prepared in a manner substantially analogous to Example 45 starting from 5-Indole boronic acid and 2-(4-Bromo-phenyl)-5-methyl-4-(2-pyrrolidin-1-yl-ethyl)-oxazole. MS (m/e): 372.2 (M+1)

Example 49

5-Methyl-4-(2-pyrrolidin-1-yl-ethyl)-2-(4-thiophen-2-yl-phenyl)-oxazole

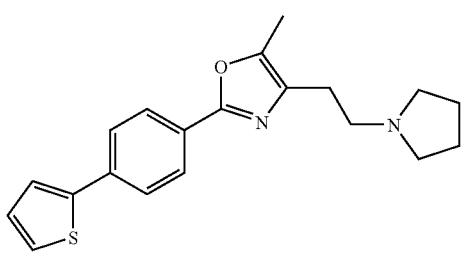

The title compound is prepared in a manner substantially analogous to Example 45 starting from 2-Thiophene boronic acid and 2-(4-Bromo-phenyl)-5-methyl-4-(2-pyrrolidin-1-yl-ethyl)-oxazole. MS (m/e): 339.1 (M+1)

Example 50

1-{2-[2-(4'-Methanesulfonyl-biphenyl-4-yl)-5-methyl-oxazol-4-yl]-ethyl}-piperidine hydrochloride

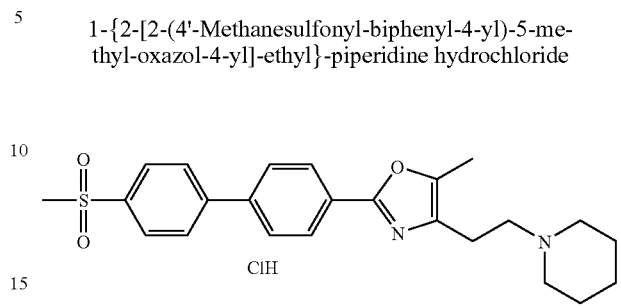

b) Add 1-{2-[2-(4-bromo-phenyl)-5-methyl-oxazol-4-yl]-ethyl}-piperidine (See Example 34) (0.290 g, 0.830 mmol), Pd(Ph$_3$)$_4$ (0.043 g, 0.037 mmol), 4-methanesulfonylphenylboronic acid (0.249 g, 1.25 mmol), 2N Na$_2$CO$_3$ (2.1 mL), and 1,4-dioxane (1 mL) to a microwave vessel. Microwave at 30 W, 90° C. for 30-45 minutes. Concentrate and purify on silica gel eluting with 10% 2N NH$_3$ in methanol/dichloromethane to give 1-{2-[2-(4'-methanesulfonyl-biphenyl-4-yl)-5-methyl-oxazol-4-yl]-ethyl}-piperidine (0.323 g, 92%).

c) Treat the recovered material (0.211 g, 0.499 mmol) with 1N HCl (523 μL, 0.523 mmol) in ether and lyophilize to give the title compound: MS (m/e): 351 (M+2).

Example 51

(+/−)-1-{2-[2-(4'-Methanesulfonyl-biphenyl-4-yl)-5-methyl-oxazol-4-yl]-ethyl}-2-methyl-piperidine hydrochloride

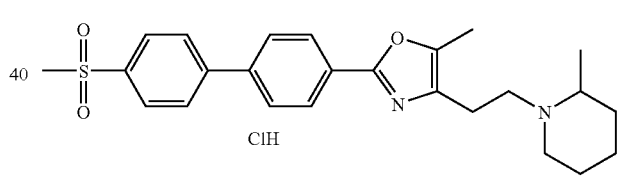

a) Add 2-methylpiperidine (3.55 g, 36.1 mmol) to a solution of Methanesulfonic acid 2-[2-(4-bromo-phenyl)-5-methyl-oxazol-4-yl]-ethyl ester (See Intermediate 13) (1.3 g, 3.61 mmol) in anhydrous THF (15 mL). Reflux the reaction overnight and cool. Wash organic material with 1N HCl (50 mL) and extract aqueous layer with diethyl ether (2×50 mL). Add 5N NaOH to aqueous layer (pH>10) and extract with dichloromethane (2×50 mL). Dry organics over Na$_2$SO$_4$, filter and concentrate to give 1-{2-[2-(4-bromo-phenyl)-5-methyl-oxazol-4-yl]-ethyl}-2-methylpiperidine (1.32 g, quant).

b) Add 1-{2-[2-(4-bromo-phenyl)-5-methyl-oxazol-4-yl]-ethyl}-2-methylpiperidine (0.290 g, 0.798 mmol), Pd(Ph$_3$)$_4$ (0.041 g, 0.035 mmol), 4-methanesulfonylphenylboronic acid (0.240 g, 1.20 mmol), 2N Na$_2$CO$_3$ (1.98 mL), and 1,4-dioxane (1 mL) to a microwave vessel. Microwave at 30 W, 90° C. for 30-45 minutes. Concentrate and purify on silica gel eluting with 10% 2N NH$_3$ in methanol/dichloromethane to give 1-{2-[2-(4'-methanesulfonyl-biphenyl-4-yl)-5-methyl-oxazol-4-yl]-ethyl}-2-methylpiperidine (0.120 g, 34%).

c) Treat the recovered material (0.095 g, 0.218 mmol) with 1N HCl (228 μL, 0.288 mmol) in ether and lyophilize to give the title compound: MS (m/e): 365(M+2).

Example 52

1-{2-[2-(4'-Methanesulfonyl-biphenyl-4-yl)-5-methyl-oxazol-4-yl]-ethyl}-2S-methyl-piperidine hydrochloride

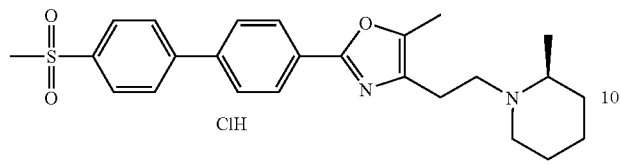

a) Add S-2-methylpiperidine (1.0 g, 10.19 mmol) to a solution of Methanesulfonic acid 2-[2-(4-bromo-phenyl)-5-methyl-oxazol-4-yl]-ethyl ester (See Intermediate 13) (1.28 g, 3.55 mmol) in anhydrous THF (15 mL). Reflux the reaction overnight and cool. Wash organic material with 1N HCl (50 mL) and extract aqueous layer with diethyl ether (2×50 mL). Add 5N NaOH to aqueous layer (pH>10) and extract with dichloromethane (2×50 mL). Dry organics over $Na_2SO_4$, filter and concentrate to give 1-{2-[2-(4-bromo-phenyl)-5-methyl-oxazol-4-yl]-ethyl}-S-2-methylpiperidine (0.315 g, 25%).

b) Add 1-{2-[2-(4-bromo-phenyl)-5-methyl-oxazol-4-yl]-ethyl}-S-2-methylpiperidine (0.315 g, 0.867 mmol), $Pd(Ph_3)_4$ (0.044 g, 0.038 mmol), 4-methanesulfonylphenylboronic acid (0.260 g, 1.30 mmol), 2N $Na_2CO_3$ (2.20 mL), and 1,4-dioxane (1.5 mL) to a microwave vessel. Microwave at 30 W, 90° C. for 30-45 minutes. Add dichloromethane (10 mL) and water (5 mL). Extract aqueous with dichloromethane (15 mL). Wash organics with saturated sodium chloride. Dry over $Na_2SO_4$, filter and concentrate. Precipitate from ethyl acetate/hexanes to give 1-{2-[2-(4'-methanesulfonyl-biphenyl-4-yl)-5-methyl-oxazol-4-yl]-ethyl}-S-2-methylpiperidine (0.264 g, 69%).

c) Treat the recovered material (0.264 g, 0.605 mmol) with 1N HCl (635 μL, 0.635 mmol) in ether and lyophilize to give the title compound: MS (m/e): 365 (M+2).

Example 53

2-{4-[5-Methyl-4-(2-pyrrolidin-1-yl-ethyl)-oxazol-2-yl]-phenoxymethyl}-pyridine

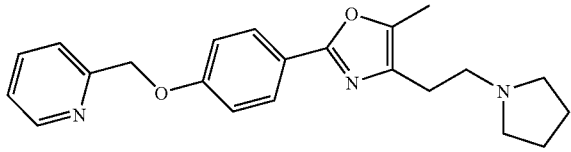

To a mixture of 2-{5-Methyl-2-[4-(pyridin-2-ylmethoxy)-phenyl]-oxazol-4-yl}-ethanol (0.264 g, 0.85 mmol) and triethylamine (0.154 mL, 1.1 mmol) in $CH_2Cl_2$ (4 mL) at 0° C. is added methanesulfonyl chloride (0.077 mL, 1.0 mmol). The mixture is warmed to room temperature and stirred for 2 h. The mixture is concentrated to provide methanesulfonic acid 2-{5-methyl-2-[4-(pyridin-2-ylmethoxy)-phenyl]-oxazol-4-yl}-ethyl ester, which is used without purification. MS (m/e): 389 (M+1)

A mixture of methanesulfonic acid 2-{5-methyl-2-[4-(pyridin-2-ylmethoxy)-phenyl]-oxazol-4-yl}-ethyl ester (0.85 mmol) and pyrrolidine (0.71 mL, 8.5 mmol) in THF (4 mL) is heated at reflux overnight. The mixture is partitioned between EtOAc and water. The aqueous phase is extracted with EtOAc (2×), and the combined organic phase is washed with brine and dried ($NaSO_4$). After the solvent is removed, the residue is purified by flash chromatography chromatography [40 g $SiO_2$, elute 20% (10% 2 M $NH_3$ in MeOH/90% $CH_2Cl_2$): 80% $CH_2Cl_2$ to 70% (10% 2 M $NH_3$ in MeOH/90% $CH_2Cl_2$): 30% $CH_2Cl_2$] to yield the title compound. MS (m/e): 364.2 (M+1)

Example 54

(+/−)-2-(4-{5-Methyl-4-[2-(2-methyl-pyrrolidin-1-yl)-ethyl]-oxazol-2-yl}-phenoxymethyl)-pyridine

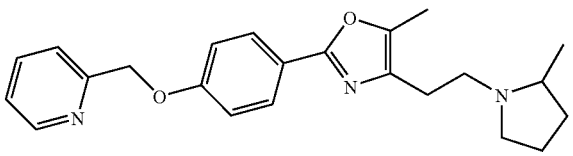

2-(4-{5-Methyl-4-[2-(2-methyl-pyrrolidin-1-yl)-ethyl]-oxazol-2-yl}-phenoxymethyl)-pyridine is prepared in a manner substantially similar to Example 53 from 2-{5-Methyl-2-[4-(pyridin-2-ylmethoxy)-phenyl]-oxazol-4-yl}-ethanol and 2-methylpyrrolidine. MS (m/e): 378.3 (M+1)

Example 55

2-(4-Benzyloxy-phenyl)-5-methyl-4-[2-(2-(R)-methyl-pyrrolidin-1-yl)-ethyl]-oxazole

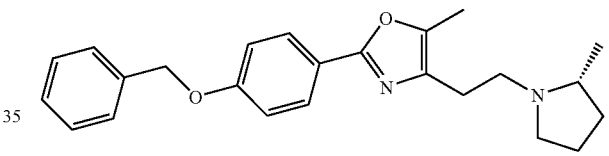

To a solution of 2-[2-(4-Benzyloxy-phenyl)-5-methyl-oxazol-4-yl]-1-(2-(R)-methyl-pyrrolidin-1-yl)-ethanone (See Intermediate 18) (0.62 g, 1.6 mmol) in THF (5 mL) at 0° C. is added a solution of lithium aluminum hydride in THF (1 M, 1.6 mL, 1.6 mmol). The cooling bath is removed, and the reaction mixture is allowed to warm to room temperature and stirred for 3.5 h. The reaction is quenched by the sequential addition of water (0.06 mL), 5 N NaOH (0.06 mL), and water (0.18 mL). The mixture is stirred at room temperature overnight and filtered. The solvent is removed in vacuo, and the crude product is obtained (0.49 g, 81%) and used without purification. MS (m/e): 377.2 (M+1)

Example 56

2-[2-(4-Hydroxy-phenyl)-5-methyl-oxazol-4-yl]-1-(2-(R)-methyl-pyrrolidin-1-yl)-ethanone

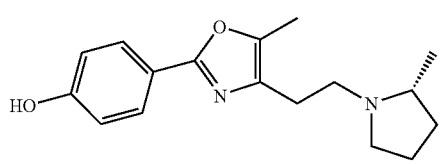

A mixture of 2-(4-Benzyloxy-phenyl)-5-methyl-4-[2-(2-(R)-methyl-pyrrolidin-1-yl)-ethyl]-oxazole (See Example 55) (0.48 g, 1.3 mmol) and 5% Pd/C (0.046 g) in absolute ethanol (25 mL) is shaken under a hydrogen atmosphere (65 psi) for 18 h. The mixture is filtered and concentrated to provide the title compound (0.35 g, 94%) as a yellow oil, which was used without purification. MS (m/e): 287.3 (M+1)

Example 57

2-(4-{5-Methyl-4-[2-(2-(R)-methyl-pyrrolidin-1-yl)-ethyl]-oxazol-2-yl}-phenoxymethyl)-pyridine

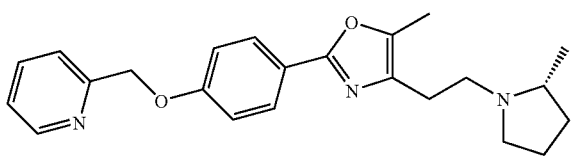

A mixture of 2-[2-(4-Hydroxy-phenyl)-5-methyl-oxazol-4-yl]-1-(2-(R)-methyl-pyrrolidin-1-yl)-ethanone (See Example 56) (0.35 g, 1.2 mmol), 2-bromomethylpyridine hydrobromide (0.40 g, 1.6 mmol), and $Cs_2CO_3$ (1.4 g, 4.3 mmol) in DMF (5 mL) is stirred at room temperature overnight. The mixture is partitioned between EtOAc and water. The aqueous phase is extracted with EtOAc (2×), and the combined organic phase is washed with brine, dried ($Na_2SO_4$), and concentrated. The residue is purified by flash chromatography [40 g $SiO_2$, elute 20% (10% 2 M $NH_3$ in MeOH/90% $CH_2Cl_2$): 80% $CH_2Cl_2$ to 70% (10% 2 M $NH_3$ in MeOH/90% $CH_2Cl_2$): 30% $CH_2Cl_2$] to yield the title compound. MS (m/e): 378.3 (M+1)

Example 58

2-[4-(4-Methanesulfonyl-benzyloxy)-phenyl]-5-methyl-4-[2-(2-(R)-methyl-pyrrolidin-1-yl)-ethyl]-oxazole

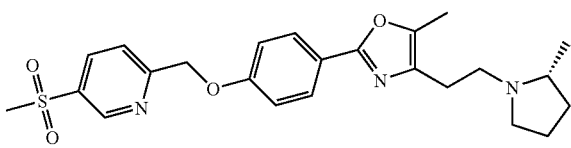

A mixture of 2-[2-(4-Hydroxy-phenyl)-5-methyl-oxazol-4-yl]-1-(2-(R)-methyl-pyrrolidin-1-yl)-ethanone (See Example 56) (0.32 g, 1.1 mmol), 4-methylsulfonylbenzyl chloride (0.29 g, 1.4 mmol), $Cs_2CO_3$ (0.9 g, 2.75 mmol), and potassium iodide (0.24 g, 1.4 mmol) in DMF (5 mL) is stirred at room temperature overnight. The mixture is partitioned between EtOAc and water. The aqueous phase is extracted with EtOAc (2×), and the combined organic phase is washed with brine, dried ($Na_2SO_4$), and concentrated. The residue is purified by flash chromatography [40 g $SiO_2$, elute 20% (10% 2 M $NH_3$ in MeOH/90% $CH_2Cl_2$): 80% $CH_2Cl_2$ to 70% (10% 2 M $NH_3$ in MeOH/90% $CH_2Cl_2$): 30% $CH_2Cl_2$] to yield the title compound. MS (m/e): 455.3 (M+1)

Example 59

2-(4-Methanesulfonyl-phenyl)-5-{5-methyl-4-[2-(2-(R)-methyl-pyrrolidin-1-yl)-ethyl]-oxazol-2-yl}-pyridine

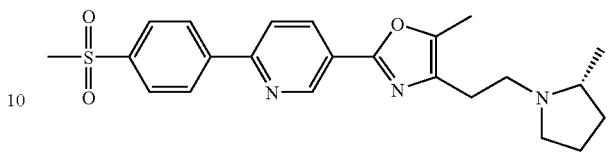

To a stirring solution of 2-{2-[6-(4-Methanesulfonyl-phenyl)-pyridin-3-yl]-5-methyl-oxazol-4-yl}-1-(2-(R)-methyl-pyrrolidin-1-yl)-ethanone (See Intermediate 21) (1.0 mmol) in tetrahydrofuran (0.10M) in a 0° C. ice bath, slowly add 1M lithium aluminum hydride in tetrahydrofuran (2.0 mmol). Remove the ice bath and stir for four hours. After this time, perform a Fieser and Fieser work up by adding water (1 mL per gram of LAH used) followed by 5N sodium hydroxide (1 mL per gram of LAH used) and then water again (3 mL per gram of LAH used). Stir this for 18 hours and then filter the reaction through Celite®. Wash the filtrate with dichloromethane while extracting with 1N hydrochloric acid. Basify the aqueous layer with 2N sodium hydroxide and extract with dichloromethane. Concentrate the organic layer and purify via radial chromatography eluting with 2M ammonia in methanol and dichloromethane. MS (m/e): 426.2 (M+1)

Example 60

2-Ethanesulfonyl-5-(4-{5-methyl-4-[2-(2-(R)-methyl-pyrrolidin-1-yl)-ethyl]-oxazol-2-yl}-phenyl)-pyridine

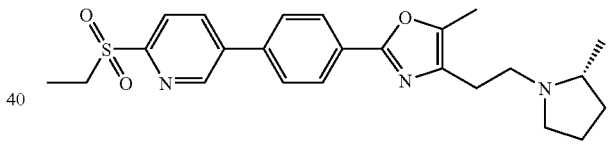

The titled compound is prepared substantially in accordance with the procedure of Example 16 using 2-{2-[4-(6-Ethanesulfonyl-pyridin-3-yl)-phenyl]-5-methyl-oxazol-4-yl}-ethanol (See Intermediate 23). MS (m/e) 440.2 (M+1)

Example 61

4-(2-Azetidin-1-yl-ethyl)-2-(4-bromo-phenyl)-5-methyl-oxazole

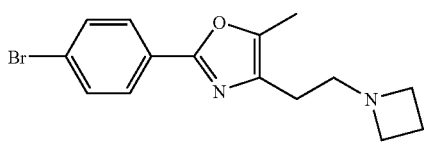

Add methanesulfonyl chloride (0.745 g, 6.50 mmol) to a cool (0° C.) solution of 2-[2-(4-bromo-phenyl)-5-methyl-oxazol-4-yl]-ethanol (1.4 g, 5.0 mmol) and triethylamine (1.26 g, 12.5 mmol) in dichloromethane (20 mL). Warm to room temperature and stir for 1 hour. Remove solvents, transfer crude of methanesulfonic acid 2-[2-(4-bromo-phenyl)-5-methyl-oxazol-4-yl]-ethyl ester residue to a sealed tube, add tetrahydrofuran (30 mL), azetidine (2.0 g, 35.5 mmol), and heat at 60° C. overnight. Wash the crude organic material with 1N HCl. Separate layers and add 5N NaOH to the aqueous layer until it is basic. Extract the aqueous layer with diethyl ether (2×50 mL), dry the organic extracts over Na$_2$SO$_4$, filter, and concentrate. Purify on silica gel eluting with 10% ammoniated methanol in dichloromethane to give 4-(2-azetidin-1-yl-ethyl)-2-(4-bromo-phenyl)-5-methyl-oxazole (1.22 g, 72%): mass spectrum (m/e): 323 (M+1).

Example 62

1-{2-[2-(4-Bromo-phenyl)-5-methyl-oxazol-4-yl]-ethyl}-piperidine

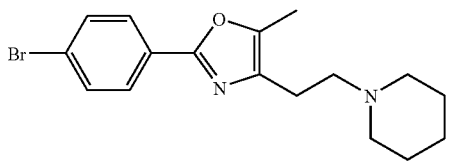

Add piperidine (1.3 g, 15 mmol) to a solution of methanesulfonic acid 2-[2-(4-bromo-phenyl)-5-methyl-oxazol-4-yl]-ethyl ester (0.531 g, 1.47 mmol) in tetrahydrofuran (5 mL) in a sealed tube, and heat at 60° C. overnight. Cool to room temperature and add dichloromethane. Wash the crude organic material with saturated sodium chloride solution. Dry the organic layer over Na$_2$SO$_4$, filter, and concentrate. Purify on silica gel eluting with 10% ammoniated methanol in dichloromethane to give 1-{2-[2-(4-bromo-phenyl)-5-methyl-oxazol-4-yl]-ethyl}-piperidine (0.421 g, 82%): MS (m/e): 349 (M+1).

Example 63

(+/−)-1-{2-[2-(4-Bromo-phenyl)-5-methyl-oxazol-4-yl]-ethyl}-2-methyl-piperidine

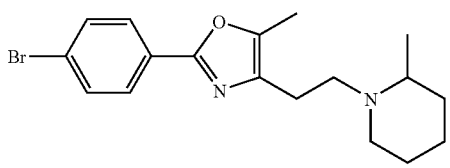

Add 2-methyl piperidine (0.871 g, 8.77 mmol) to a solution of methanesulfonic acid 2-[2-(4-bromo-phenyl)-5-methyl-oxazol-4-yl]-ethyl ester (0.316 g, 0.877 mmol) in tetrahydrofuran (5 mL) in a sealed tube, and heat at 60° C. overnight. Cool to room temperature and add dichloromethane. Wash the crude organic material with saturated sodium chloride solution. Dry the organic layer over Na$_2$SO$_4$, filter, and concentrate. Purify on silica gel eluting with 10% ammoniated methanol in dichloromethane to give (+/−)-1-{2-[2-(4-bromo-phenyl)-5-methyl-oxazol-4-yl]-ethyl}-piperidine (0.215 g, 67%): MS (m/e): 363 (M+1).

Example 64

1-{2-[2-(4-Bromo-phenyl)-5-methyl-oxazol-4-yl]-ethyl}-2S-methyl-piperidine

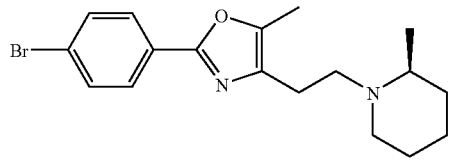

Add 2-S-methyl piperidine (0.734 g, 7.4 mmol) to a solution of methanesulfonic acid 2-[2-(4-bromo-phenyl)-5-methyl-oxazol-4-yl]-ethyl ester (0.261 g, 0.74 mmol) in tetrahydrofuran (5 mL) in a sealed tube, and heat at 60° C. overnight. Cool and add dichloromethane. Wash crude organic material with saturated sodium chloride solution. Dry organic layer over Na$_2$SO$_4$, filter, and concentrate. Purify on silica gel eluting with 10% ammoniated methanol in dichloromethane to give 1-{2-[2-(4-bromo-phenyl)-5-methyl-oxazol-4-yl]-ethyl}-2S-methyl-piperidine (0.166 g, 62%): MS (m/e): 363 (M+1).

Example 65

4-(2-Azetidin-1-yl-ethyl)-2-(4'-methanesulfonyl-biphenyl-4-yl)-5-methyl-oxazole hydrochloride

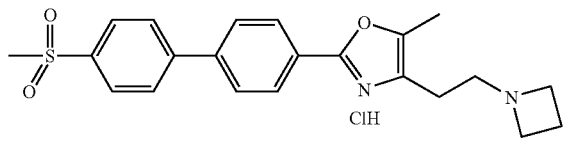

Add 4-(2-azetidin-1-yl-ethyl)-2-(4-bromo-phenyl)-5-methyl-oxazole (0.606 g, 1.88 mmol), Pd(Ph$_3$P)$_4$ (0.083 g, 0.096 mmol), 4-methanesulfonyl boronic acid (0.566 g, 2.83 mmol), 2N Na$_2$CO$_3$ (4.7 mL), and 1,4-dioxane (3 mL) to a microwave vessel. Microwave at 30 W, 90° C. for 60 minutes. Add dichloromethane and water. Wash the organic layer with saturated sodium chloride solution. Dry the organic layer over Na$_2$SO$_4$, filter, and concentrate. Purify on silica gel eluting with 10% ammoniated methanol in dichloromethane to give 4-(2-azetidin-1-yl-ethyl)-2-(4'-methanesulfonyl-biphenyl-4-yl)-5-methyl-oxazole (0.350 g, 47%): MS (m/e): 397 (M+1). Treat the recovered material (0.350 g, 0.883 mmol) with 1N HCl (971 μL, 0.971 mmol) in ether, concentrate, and lyophilize to give the title compound: MS (m/e): 397 (M+1).

Example 66

2-(4'-Ethanesulfonyl-biphenyl-4-yl)-5-methyl-4-[2-(2R-methyl-pyrrolidin-1-yl)-ethyl]-oxazole hydrochloride

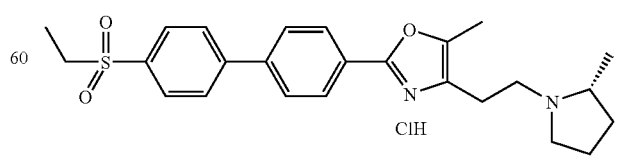

Add 2-(4-bromo-phenyl)-5-methyl-4-[2-(2R-methyl-pyrrolidin-1-yl)-ethyl]-oxazole (0.221 g, 0.634 mmol), Pd(Ph₃P)₄ (0.032 g, 0.029 mmol), 4-ethanesulfonyl boronic acid (0.203 g, 0.950 mmol), 2N Na₂CO₃ (1.6 mL), and 1,4-dioxane (2 mL) to a microwave vessel. Microwave at 30 W, 90° C. for 60 minutes. Add dichloromethane and water. Wash the organic layer with saturated sodium chloride solution. Dry the organic layer over Na₂SO₄, filter, and concentrate. Purify on silica gel eluting with 10% ammoniated methanol in dichloromethane to give 2-(4'-ethanesulfonyl-biphenyl-4-yl)-5-methyl-4-[2-(2R-methyl-pyrrolidin-1-yl)-ethyl]-oxazole (0.235 g, 85%): MS (m/e): 439 (M+1).

Treat the recovered material (0.235 g, 0.536 mmol) with 1N HCl (589 μL, 0.589 mmol) in ether, concentrate, and lyophilize to give the title compound (221 mg): MS (m/e): 439 (M+1).

Example 67

4-[2-(2R-Ethyl-pyrrolidin-1-yl)-ethyl]-2-(4'-methanesulfonyl-biphenyl-4-yl)-5-methyl-oxazole hydrochloride

Charge a sealed tube with 2-(4-bromo-phenyl)-4-(2-iodo-ethyl)-5-methyl-oxazole (0.385 g, 0.983 mmol) (see intermediate 30), 2R-ethyl-pyrrolidine hydrochloride (0.400 g, 2.95 mmol) (see intermediate 26), triethylamine (0.329 g, 3.24 mmol), and tetrahydrofuran (5 mL). Seal and heat at 60° C. overnight. Wash the crude organic material with 1N HCl. Separate layers and add 5N NaOH to the aqueous layer until basic. Extract the aqueous layer with diethyl ether (2×50 mL), dry the organic extracts over Na₂SO₄, filter, and concentrate. Purify on silica gel eluting with 5% ammoniated methanol in dichloromethane to give 2-(4-bromo-phenyl)-4-[2-(2R-ethyl-pyrrolidin-1-yl)-ethyl]-5-methyl-oxazole (0.249 g, 70%): MS (m/e): 365 (M+2).

Add 2-(4-bromo-phenyl)-4-[2-(2R-ethyl-pyrrolidin-1-yl)-ethyl]-5-methyl-oxazole (0.249 g, 0.685 mmol), Pd(Ph₃P)₄ (0.030 g, 0.035 mmol), 4-methanesulfonyl boronic acid (0.206 g, 1.03 mmol), 2N Na₂CO₃ (1.7 mL), and 1,4-dioxane (2 mL) to a microwave vessel. Microwave at 30 W, 90° C. for 60 minutes. Add dichloromethane and water. Wash the organic layer with saturated sodium chloride solution. Dry the organic layer over Na₂SO₄, filter, and concentrate. Purify on silica gel eluting with 10% ammoniated methanol in dichloromethane to give 4-[2-(2R-ethyl-pyrrolidin-1-yl)-ethyl]-2-(4'-methanesulfonyl-biphenyl-4-yl)-5-methyl-oxazole (0.170 g, 55%): MS (m/e): 439 (M+1).

Treat the recovered material (0.170 g, 0.387 mmol) with 1N HCl (426 μL, 0.426 mmol) in ether, concentrate, and lyophilize to give the title compound (174 mg): MS (m/e): 439 (M+1).

Example 68

(4'-{5-Methyl-4-[2-(2R-methyl-pyrrolidin-1-yl)-ethyl]-oxazol-2-yl}-biphenyl-4-yl)-methanol hydrochloride

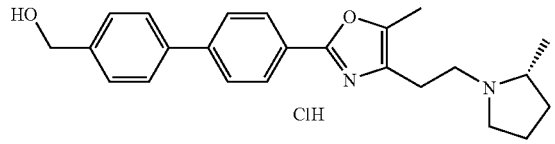

Add methanesulfonyl chloride (0.742 g, 5.14 mmol) to a cool (0° C.) solution of 2-[2-(4-bromo-phenyl)-5-methyl-oxazol-4-yl]-ethanol (1.1 g, 3.95 mmol) and triethylamine (0.999 g, 9.88 mmol) in dichloromethane (10 mL). Warm to room temperature and stir for 1 hour. Remove solvents, transfer residue to a sealed tube, add tetrahydrofuran (30 mL) and 2R-methyl pyrrolidine hydrochloride (2.4 g, 20 mmol), triethylamine (2.2 g, 22 mmol), and heat at 60° C. overnight. Add dichloromethane and wash the crude organic material with saturated sodium chloride solution. Dry the organic layer over Na₂SO₄, filter, and concentrate. Purify on silica gel eluting with 2% ammoniated methanol in dichloromethane to give 2-(4-bromo-phenyl)-5-methyl-4-[2-(2R-methyl-pyrrolidin-1-yl)-ethyl]-oxazole (0.471 g, 34%): MS (m/e): 349 (M+1).

Add 2-(4-bromo-phenyl)-5-methyl-4-[2-(2R-methyl-pyrrolidin-1-yl)-ethyl]-oxazole (0.200 g, 0.573 mmol), Pd(Ph₃P)₄ (0.025 g, 0.029 mmol), 4-hydroxymethyl boronic acid (0.131 g, 0.859 mmol), 2N Na₂CO₃ (1.4 mL), and 1,4-dioxane (2 mL) to a microwave vessel. Microwave at 30 W, 90° C. for 60 minutes. Add dichloromethane and water. Wash the organic layer with saturated sodium chloride solution. Dry the organic layer over Na₂SO₄, filter, and concentrate. Purify on silica gel eluting with 10% ammoniated methanol in dichloromethane to give (4'-{5-methyl-4-[2-(2R-methyl-pyrrolidin-1-yl)-ethyl]-oxazol-2-yl}-biphenyl-4-yl)-methanol (0.181 g, 84%): MS (m/e): 377 (M+1).

Treat the recovered material (0.170 g, 0.387 mmol) with 1N HCl (426 μL, 0.426 mmol) in ether, concentrate, and lyophilize to give the title compound (173 mg): MS (mle): 377 (M+1).

Example 69

(4'-{5-Methyl-4-[2-(2R-methyl-pyrrolidin-1-yl)-ethyl]-oxazol-2-yl}-biphenyl-3-yl)-methanol hydrochloride

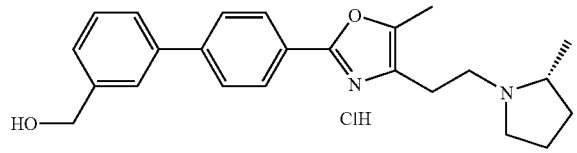

Add 2-(4-bromo-phenyl)-5-methyl-4-[2-(2R-methyl-pyrrolidin-1-yl)-ethyl]-oxazole (0.200 g, 0.573 mmol), Pd(Ph₃P)₄ (0.025 g, 0.029 mimol), 3-hydroxymethyl boronic acid (0.131 g, 0.859 mmol), 2N Na₂CO₃ (1.4 mL), and 1,4-dioxane (2 mL) to a microwave vessel. Microwave at 30 W, 90° C. for 60 minutes. Add dichloromethane and water. Wash the organic layer with saturated sodium chloride solution. Dry the organic layer over Na₂SO₄, filter, and concentrate. Purify on silica gel eluting with 10% ammoniated methanol in dichloromethane to give (4'-{5-methyl-4-[2-(2R-methyl-pyrrolidin-1-yl)-ethyl]-oxazol-2-yl}-biphenyl-3-yl)-methanol (0.131 g, 61%): MS (m/e): 377 (M+1).

Treat the recovered material (0.131 g, 0.348 mmol) with 1N HCl (383 µL, 0.383 mmol) in ether, concentrate, and lyophilize to give the title compound (143 mg): MS (m/e): 377 (M+1).

Example 70

5-Methyl-4-[2-(2R-methyl-pyrrolidin-1-yl)-ethyl]-2-[4'-(propane-1-sulfonyl)-biphenyl-4-yl]-oxazole hydrochloride

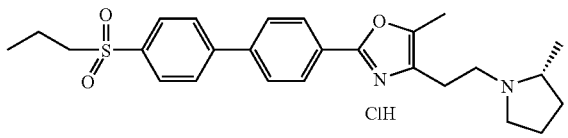

Add 2-(4-bromo-phenyl)-5-methyl-4-[2-(2R-methyl-pyrrolidin-1-yl)-ethyl]-oxazole (0.070 g, 0.20 mmol), Pd(Ph$_3$P)$_4$ (0.008 g, 0.005 mmol), 4,4,5,5-tetramethyl-2-[4-(propane-1-sulfonyl)-phenyl]-[1,3,2]dioxaborolane (0.093 g, 0.30 mmol) (see intermediate 29), 2N Na$_2$CO$_3$ (0.50 mL), and 1,4-dioxane (2 mL) to a microwave vessel. Microwave at 30 W, 90° C. for 60 minutes. Add dichloromethane and water. Wash the organic layer with saturated sodium chloride solution. Dry the organic layer over Na$_2$SO$_4$, filter, and concentrate. Purify on silica gel eluting with 10% ammoniated methanol in dichloromethane to give 5-methyl-4-[2-(2R-methyl-pyrrolidin-1-yl)-ethyl]-2-[4'-(propane-1-sulfonyl)-biphenyl-4-yl]-oxazole (0.075 g, 83%): MS (m/e): 453 (M+1).

Treat the recovered material (0.036 g, 0.078 mmol) with 1N HCl (86 µL, 0.086 mmol) in ether, concentrate, and lyophilize to give the title compound (35 mg): MS (m/e): 453 (M+1).

Example 71

4-[2-(2S-Fluoromethyl-pyrrolidin-1-yl)-ethyl]-2-(4'-methanesulfonyl-biphenyl-4-yl)-5-methyl-oxazole hydrochloride

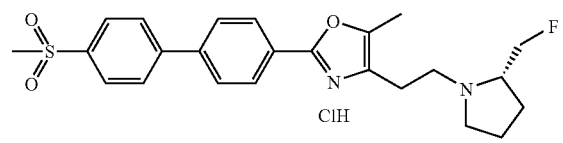

Add 2-[2-(4-bromo-phenyl)-5-methyl-oxazol-4-yl]-ethanol (0.200 g, 0.709 mmol), Pd(Ph$_3$P)$_4$ (0.031 g, 0.036 mmol), 4-methanesulfonyl boronic acid (0.213 g, 1.06 mmol), 2N Na$_2$CO$_3$ (0.251 mL), and 1,4-dioxane (1 mL) to a microwave vessel. Microwave at 30 W, 90° C. for 60 minutes. Add dichloromethane and water. Wash the organic layer with saturated sodium chloride solution. Dry the organic layer over Na$_2$SO$_4$, filter, and concentrate. Purify on silica gel eluting with 10% ammoniated methanol in dichloromethane to give 2-[2-(4'-methanesulfonyl-biphenyl-4-yl)-5-methyl-oxazol-4-yl]-ethanol (0.167 g, 66%).

Add methanesulfonyl chloride (0.088 g, 0.607 mmol) to a cool (0° C.) solution of 2-[2-(4'-methanesulfonyl-biphenyl-4-yl)-5-methyl-oxazol-4-yl]-ethanol (0.167 g, 0.467 mmol) and triethylamine (0.118 g, 1.17 mmol) in dichloromethane (5 mL). Warm to room temperature and stir for 1 hour. Remove the solvents, transfer the residue to a sealed tube, add tetrahydrofuran (5 mL) and 2S-fluoromethyl-pyrrolidine hydrochloride (lit. prep. M. Cowart, WO 2002074758) (0.326 g, 2.34 mmol), triethylamine (0.280 g, 2.57 mmol), and heat at 60° C. overnight. Add dichloromethane and wash the crude organic material with saturated sodium chloride solution. Dry the organics over Na$_2$SO$_4$, filter, and concentrate. Purify on silica gel eluting with 5% ammoniated methanol in dichloromethane to give 4-[2-(2S-fluoromethyl-pyrrolidin-1-yl)-ethyl]-2-(4'-methanesulfonyl-biphenyl-4-yl)-5-methyl-oxazole (0.077 g, 37%): MS (m/e): 443 (M+1).

Treat the recovered material (0.077 g, 0.174 mmol) with 1N HCl (192 µL, 0.192 mmol) in ether, concentrate, and lyophilize to give the title compound (79 mg): MS (m/e): 443 (M+1).

Example 72

Isopropyl-{2-[2-(4'-methanesulfonyl-biphenyl-4-yl)-5-methyl-oxazol-4-yl]-ethyl}-methyl-amine hydrochloride

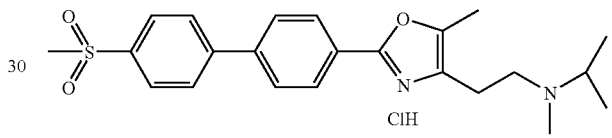

Add methanesulfonyl chloride (0.135 g, 0.935 mmol) to a cool (0° C.) solution of 2-[2-(4'-methanesulfonyl-biphenyl-4-yl)-5-methyl-oxazol-4-yl]-ethanol (0.257 g, 0.719 mmol) and triethylamine (0.182 g, 1.80 mmol) in dichloromethane (5 mL). Warm to room temperature and stir for 1 hour. Remove the solvents, transfer the residue to a sealed tube, add tetrahydrofuran (5 mL) and N-methyl-isopropylamine (0.526 g, 7.19 mmol), and heat at 60° C. overnight. Add dichloromethane and wash the crude organic material with saturated sodium chloride solution. Dry the organic layer over Na$_2$SO$_4$, filter, and concentrate. Purify on silica gel eluting with 5% ammoniated methanol in dichloromethane to give isopropyl-{2-[2-(4'-methanesulfonyl-biphenyl-4-yl)-5-methyl-oxazol-4-yl]-ethyl}-methyl-amine (0.056 g, 18%): mass spectrum (m/e): 413 (M+1). Treat the recovered material (0.056 g, 0.131 mmol) with 1N HCl (144 µL, 0.144 mmol) in ether, concentrate, and lyophilize to give the title compound (12.8 mg): MS (m/e): 413 (M+1).

Example 73

4'-{5-Methyl-4-[2-(2-(R)-methyl-pyrrolidin-1-yl)-ethyl]-oxazol-2-yl}-biphenyl-4-carbonitrile

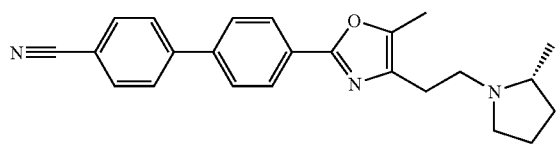

The titled compound is prepared substantially in accordance with the procedure of Example 4 using 2-(4-Bromophenyl)-5-methyl-4-[2-(2R-methyl-pyrrolidin-1-yl)-ethyl]-oxazole; hydrochloride (See Example 16) and 4-cyanobenzeneboronic acid. MS (m/e): 472.4 (M+1)

Example 74

(2-{2-[6-(4-Methanesulfonyl-phenyl)-pyridin-3-yl]-5-methyl-oxazol-4-yl}-ethyl)-dimethyl-amine

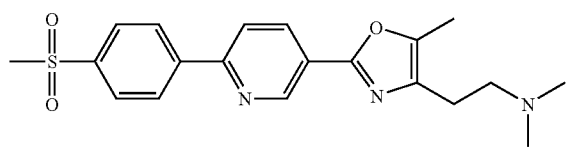

The titled compound is prepared substantially in accordance with the procedure of Example 59 using 2-{2-[6-(4-Methanesulfonyl-phenyl)-pyridin-3-yl]-5-methyl-oxazol-4-yl}-N,N-dimethyl-acetamide (See Intermediate 31). MS (m/e): 386.2 (M+1)

Example 75

3-Methoxy-6-(4-{5-methyl-4-[2-(2-methyl-pyrrolidin-1-yl)-ethyl]-oxazol-2-yl}-phenyl)-pyridazine

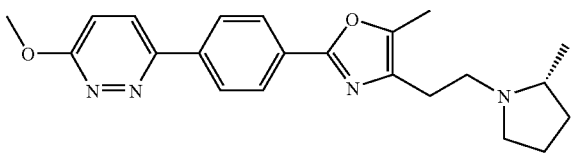

To a stirring solution of methanesulfonic acid 2-{2-[4-(6-methoxy-pyridazin-3-yl)-phenyl]-5-methyl-oxazol-4-yl}-ethyl ester (1.0 mmol) (see Intermediate 32), potassium carbonate (3.5 mmol), potassium iodide (0.1nmol) in acetonitrile (01M), add 2R-methylpyrrolidine hydrochloride (1.8 mmol) (see Intermediate 7). The reaction is heated to a light reflux for 18 hours. After this time, the heat is removed and the product is extracted into 1N HCl while washing with dichloromethane. The aqueous layer is then made basic with 2N NaOH and extracted with dichloromethane. The organic layer is concentrated in vacuo and purified via radial chromatography eluting with 2M ammonia in methanol and dichloromethane. MS (m/e): 379.2 (M+1)

Example 76

3-Ethanesulfonyl-6-(4-{5-methyl-4-[2-(2-methyl-pyrrolidin-1-yl)-ethyl]-oxazol-2-yl}-phenyl)-pyridazine

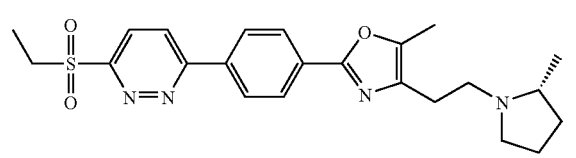

The titled compound is prepared in substantial accordance with the procedures found in Example 4, Intermediate 22, Intermediate 13, and Example 75 using 2-{5-Methyl-2-[4-(4,4,5,5-tetramethyl-[1,3,2]dioxaborolan-2-yl)phenyl]-oxazol-4-yl}-ethanol (see Intermediate 3) and 3,6-Dichloropyridazine. MS (m/e): 441.3 (M+1)

Example 77

2-(4-{5-Methyl-4-[2-(2-methyl-pyrrolidin-1-yl)-ethyl]-oxazol-2-yl}-phenyl)-pyridine

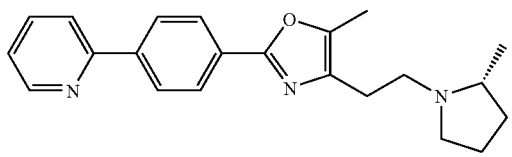

The titled compound is prepared in substantial accordance with the procedures found in Example 4, Intermediate 13, and Example 75 using 2-{5-Methyl-2-[4-(4,4,5,5-tetramethyl-[1,3,2]dioxaborolan-2-yl)phenyl]-oxazol-4-yl}-ethanol (see Intermediate 3) and 2-bromopyridine. MS (m/e): 348.3 (M+1)

Example 78

3-Methanesulfonyl-6-(4-{5-methyl-4-[2-(2-methyl-pyrrolidin-1-yl)-ethyl]-oxazol-2-yl}-phenyl)-pyridazine

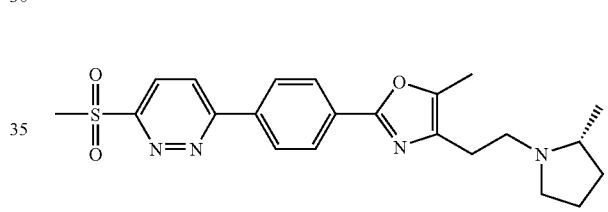

The titled compound is prepared in substantial accordance with the procedures found in Example 4, Intermediate 33, Intermediate 13, and Example 75 using 2-{5-Methyl-2-[4-(4,4,5,5-tetramethyl-[1,3,2]dioxaborolan-2-yl)phenyl]-oxazol-4-yl}-ethanol (see Intermediate 3) and 3,6-Dichloro-pyridazine. MS (m/e): 427.3 (M+1)

Example 79

2-Ethanesulfonyl-5-(4-{5-methyl-4-[2-(2-(R)-methyl-pyrrolidin-1-yl)-ethyl]-oxazol-2-yl}-phenyl)-pyridine dihydrochloride salt

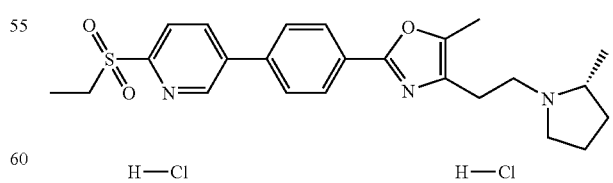

The titled compound is prepared substantially in accordance with the procedure of Example 23 using 2-ethanesulfonyl-5-(4-{5-methyl-4-[2-(2-(R)-methyl-pyrrolidin-1yl)-ethyl]-oxazol-2-yl}-phenyl)-pyridine (see Example 60). MS (m/e): 440.4 (M+1)

Example 80

2-Methanesulfonyl-5-(4-{5-methyl-4-[2-(2-(R)-methyl-pyrrolidin-1-yl)-ethyl]-oxazol-2-yl}-phenyl)-pyridine

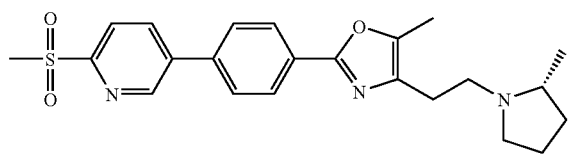

The titled compound is prepared substantially in accordance with the procedures of Example 4, Intermediate 13, and Example 75 using 2-{5-methyl-2-[4-(4,4,5,5-tetramethyl-[1,3,2]dioxaborolan-2-yl)phenyl]-oxazol-4-yl}-ethanol (see Intermediate 3) and 2-methanesulfonyl-5-iodo-pyridine (see Intermediate 33). MS (m/e): 426.3 (M+1)

Example 81

2-Methanesulfonyl-5-(4-{5-methyl-4-[2-(2-(R)-methyl-pyrrolidin-1-yl)-ethyl]-oxazol-2-yl}-phenyl)-pyridine dihydrochloride salt

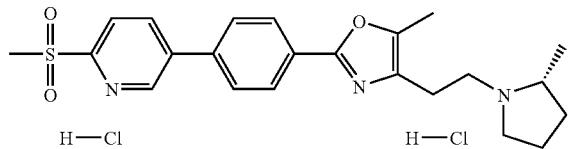

The titled compound is prepared substantially in accordance with the procedure of Example 23 using 2-methanesulfonyl-5-(4-{5-methyl-4-[2-(2-(R)-methyl-pyrrolidin-1-yl)-ethyl]-oxazol-2-yl}-phenyl)-pyridine (see Example 80). MS (m/e): 426.3 (M+1)

Example 82

2-(3-Fluoro-4'-methanesulfonyl-biphenyl-4-yl)-5-methyl-4-[2-(2-methyl-pyrrolidin-1-yl)-ethyl]-oxazole

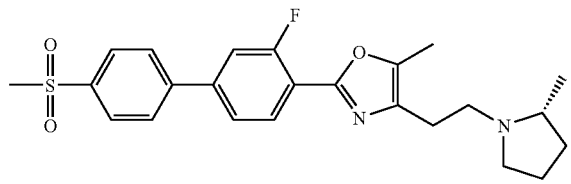

The titled compound is prepared in substantial accordance with the procedures found in Intermediate 13 and Example 75 using 2-[2-(3-Fluoro-4'-methanesulfonyl-biphenyl-4-yl)-5-methyl-oxazol-4-yl]-ethanol (see Intermediate 38). MS (m/e): 443.3 (M+1)

Example 83

2-(3-Fluoro-4'-methanesulfonyl-biphenyl-4-yl)-5-methyl-4-[2-(2-methyl-pyrrolidin-1-yl)-ethyl]-oxazole hydrochloride salt

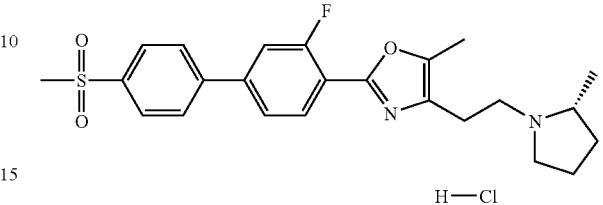

The titled compound is prepared substantially in accordance with the procedure of Example 23 using 2-(3-Fluoro-4'-methanesulfonyl-biphenyl-4-yl)-5-methyl-4-[2-(2-methyl-pyrrolidin-1-yl)-ethyl]-oxazole (see Example 82). MS (m/e): 443.3 (M+1)

Example 84

5-Methanesulfonyl-2-(4-{5-methyl-4-[2-(2-methyl-pyrrolidin-1-yl)-ethyl]-oxazol-2-yl}-phenyl)-pyrimidine

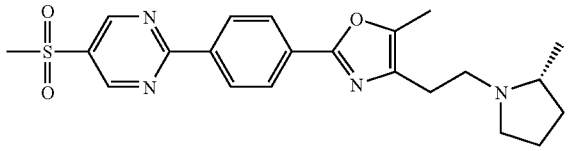

The titled compound is prepared in substantial accordance with the procedures found in Example 4, Intermediate 33, Intermediate 13, and Example 75 using 2-{5-Methyl-2-[4-(4,4,5,5-tetramethyl-[1,3,2]dioxaborolan-2-yl)phenyl]-oxazol-4-yl}-ethanol (see Intermediate 3) and 5-bromo-2-iodo-pyrimidine. MS (m/e): 427.3 (M+1)

Example 85

5-Methanesulfonyl-2-(4-{5-methyl-4-[2-(2-methyl-pyrrolidin-1-yl)-ethyl]-oxazol-2-yl}-phenyl)-pyrimidine hydrochloride salt

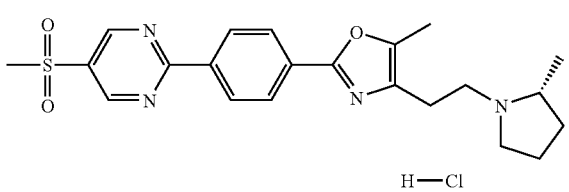

The titled compound is prepared substantially in accordance with the procedure of Example 23 using 5-methanesulfonyl-2-(4-{5-methyl-4-[2-(2-methyl-pyrrolidin-1-yl)-ethyl]-oxazol-2-yl}-phenyl)-pyrimidine (See Example 84). MS (m/e): 427.3 (M+1)

Example 86

N,N-Dimethyl-6-(4-{5-methyl-4-[2-(2-methyl-pyrrolidin-1-yl)-ethyl]-oxazol-2-yl}-phenyl)-nicotinamide

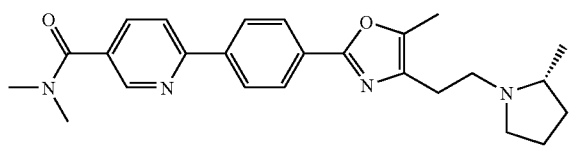

The titled compound is prepared substantially in accordance with the procedures of Example 4, Intermediate 13, and Example 75 using 2-{5-methyl-2-[4-(4,4,5,5-tetramethyl-[1,3,2]dioxaborolan-2-yl)phenyl]-oxazol-4-yl}-ethanol (see Intermediate 3) and 6-chloro-N,N-dimethyl-nicotinamide [CAS: 54864-83-4].

MS (m/e): 419.3 (M+1)

Example 87

4-(4-{5-Methyl-4-[2-(2-methyl-piperidin-1-yl)-ethyl]-oxazol-2-yl}-phenyl)-pyridine hydrochloride

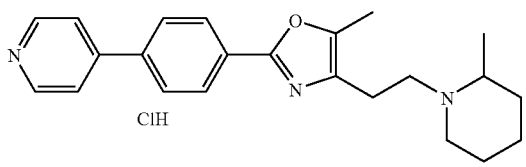

a) Add 2-methylpiperidine (3.55 g, 36.1 mmol) to a solution of methanesulfonic acid 2-[2-(4-bromo-phenyl)-5-methyl-oxazol-4-yl]-ethyl ester (See Intermediate 13)(1.3 g, 3.6 mmol) in anhydrous THF (15 mL). Heat the reaction mixture at reflux overnight and cool to room temperature. Wash the organic material with 1N HCl (50 mL) and extract the aqueous layer with diethyl ether (2×50 mL). Add 5N NaOH to the aqueous layer (pH >10) and extract with dichoromethane (2×50 mL). Dry the organic extracts over Na$_2$SO$_4$, filter and concentrate to give 1-{2-[2-(4-bromo-phenyl)-5-methyl-oxazol-4-yl]-ethyl}-2-methylpiperidine (1.32 g, quantitative).

b) Add 1-{2-[2-(4-bromo-phenyl)-5-methyl-oxazol-4-yl]-ethyl }-2-methylpiperidine (0.724 g, 1.99 mmol), Pd(Ph$_3$)$_4$ (0.101 g, 0.088 mmol), 4-pyridylboronic acid (0.367 g, 2.99 mmol), 2N Na$_2$CO$_3$ (5 mL), and 1,4-dioxane (1.5 mL) to a microwave vessel. Subject the reaction mixture to microwave irradiation at 30 W, 90° C. for 30-45 minutes. Concentrate and purify on silica gel eluting with 10% 2N NH$_3$ in methanol/dichloromethane to give 4-(4-{5-methyl-$^4$-[2-(2-methyl-piperidin-1 -yl)-ethyl]-oxazol-2-yl}-phenyl)-pyridine (0.059 g, 10%).

c) Treat the recovered material (0.059 g, 0.164 mmol) with 1N HCl (173 μL, 0.173 mmol) in ether and freeze dry to give the title compound (0.070 g, quantitative):

MS (mn/e): 362(M+1).

Example 88

Diethyl-{2-[2-(4'-methanesulfonyl-biphenyl-4-yl)-5-methyl-oxazol-4-yl]-ethyl}-amine trifluoroacetate

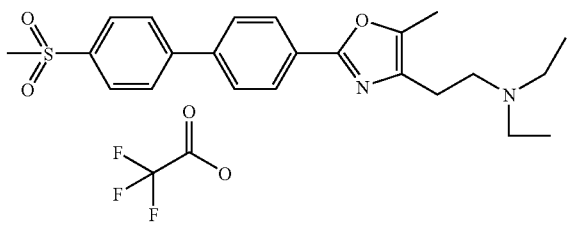

a) Add diethyl amine (0.488 g, 6.68 mmol) to a solution of methanesulfonic acid 2-[2-(4-bromo-phenyl)-5-methyl-oxazol-4-yl]-ethyl ester (See Intermediate 13) (0.240 g, 0.668 mmol) in anhydrous THF (5 mL) in a sealed tube, and heat at 60° C. overnight. Add dichloromethane and wash the crude organic layer with saturated sodium chloride solution. Dry the organic extracts over Na$_2$SO$_4$, filter, and concentrate. Purify on silica gel eluting with 5% anmioniated methanol in dichloromethane to give {2-[2-(4-bromo-phenyl)-5-methyl-oxazol-4-yl]-ethyl}-diethyl-amine (0.150 g, 67%): MS (nme): 337 (M+1).

b) Add {2-[2-(4-bromo-phenyl)-5-methyl-oxazol-4-yl]-ethyl}-diethyl-amine (0.150 g, 0.445 mmol), Pd(Ph$_3$)$_4$ (0.023 g, 0.020 mmol), 4-methylsulfonylphenylboronic acid (0.133 g, 0.667 mmol), 2N Na$_2$CO$_3$ (2.0 mL), and 1,4-dioxane (1.1 mL) to a microwave vessel. Microwave at 30 W, 90° C. for 30-45 minutes, Concentrate and purify on reversed phase HPLC (20-70% MeCN, 0.1% TFA; 100 mL/min, 30 min, 50×250 Symmetry C18, 7 μm) to give the title compound (0.092 g, 50%): MS (mle): 413 (M+1).

Example 89

1-(4'-{5-Methyl-4-[2-(2R-methyl-pyrrolidin-1-yl)-ethyl]-oxazol-2-yl}-biphenyl-3-yl)-ethanone hydrochloride

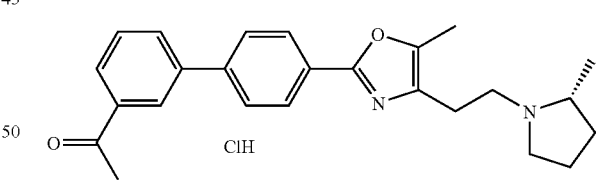

a) Add 2-[2-(4-bromo-phenyl)-5-methyl-oxazol-4-yl]-ethanol (0.200 g, 709 mmol) [which is obtained by the method of D. Brooks, J. Med. Chem., 2001, 44, 2061-2064 or see WO 0116120], Pd(Ph$_3$)$_4$ (0.036 g, 0.031 mmol), 3-acetylphenylboronic acid (0.174 g, 1.06 mmol), 2N Na$_2$CO$_3$ (1.8 mL), and 1,4-dioxane (1.5 mL) to a microwave vessel. Subject the reaction mixture to microwave irradiation at 30 W, 90° C. for 30-45 minutes. Concentrate and purify on silica gel eluting with 10% 2N NH$_3$ in methanol/dichloromethane to give 1-{4'-[4-(2-hydroxy-ethyl)-5-methyl-oxazol-2-yl]-biphenyl-3-yl}-ethanone (0.188 g, 83%).

b) Add methanesulfonyl chloride (0.110 g, 0.760 mmol) to a cool (0° C.) solution of 1-{4'-[4-(2-hydroxy-ethyl)-5-methyl-oxazol-2-yl]-biphenyl-3-yl}-ethanone (0.188 g, 0.584 mmol) and triethylamine (0.089 g, 0.88 mmol) in dichloromethane (5 mL). Warm the reaction mixture to room temperature and stir for 1 hour. Add dichloromethane and wash the crude organic layer with saturated sodium chloride solution. Dry the organic extracts over Na₂SO₄, filter, and concentrate to give crude methanesulfonic acid 2-[2-(3'-acetyl-biphenyl-4-yl)-5-methyl-oxazol-4-yl]-ethyl ester (0.256 g, >100%).

c) Add a solution of methanesulfonic acid 2-[2-(3'-acetyl-biphenyl-4-yl)-5-methyl-oxazol-4-yl]-ethyl ester (0.233 g, 0.583 mmol) in 3 mnL acetonitrile to a sealed tube containing 2R-methylpyrrolidine hydrochloride (See Intermediate 7) (0.142 g, 1.17 mmol), K₂CO₃ (0.282 g, 2.04 mmol), and KI (0.010 g, 0.058 mmol), and heat at 60° C. overnight. Add dichloromethane and wash the crude organic layer with saturated sodium chloride solution. Dry the organic extracts over Na₂SO₄, filter, and concentrate. Purify on silica gel eluting with 8% ammoniated methanol in dichloromethane to give to give 1-(4'-{5-methyl-4-[2-(2R-methyl-pyrrolidin-1-yl)-ethyl]-oxazol-2-yl}-biphenyl-3-yl)-ethanone (0.201 g, 89%).

d) Treat the recovered material (0.201 g, 0.517 mmol) with 1N HCl (569 µL, 0.569 mmol) in ether and freeze dry to give the title compound (0.207 g, 94%): MS (m/e): 389(M+1).

Example 90

2-[4'-(3-Fluoro-propane-1-sulfonyl)-biphenyl-4-yl]-5-methyl-4-[2-(2R-methyl-pyrrolidin-1-yl)-ethyl]-oxazole hydrochloride

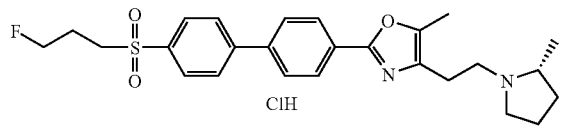

The free base of the title compound is prepared in a manner similar to that described in Example 89 using 2-[2-(4-bromo-phenyl)-5-methyl-oxazol-4-yl]-ethanol and 2-[4-(3-fluoro-propane-1-sulfonyl)-phenyl]-4,4,5,5-tetramethyl-[1,3,2]dioxaborolane (See Intermediate 39). The free base is converted to the hydrochloride salt according to the procedure of example 89 to provide the title compound: MS (m/e): 471(M+1).

Example 91

5-Methyl-4-[2-(2R-methyl-pyrrolidin-1-yl)-ethyl]-2-(4'-trifluoromethanesulfonyl-biphenyl-4-yl)-oxazole hydrochloride

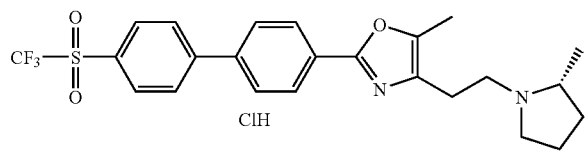

The free base of the title compound is prepared in a manner similar to that described in Example 89 using 2-[2-(4-bromo-phenyl)-5-methyl-oxazol-4-yl]-ethanol (See Example 13) and 4,4,5,5-tetramethyl-2-(4-trifluoromethanesulfonyl-phenyl)-[1,3,2]dioxaborolane (See Intermediate 40). The free base is converted to the hydrochloride salt according to the procedure of Example 89 to provide the title compound. MS (m/e): 479(M+1).

Example 92

2-(4'-Methanesulfonyl-biphenyl-4-yl)-5-methyl-4-[3-(2R-methyl-pyrrolidin-1-yl)-propyl]-oxazole hydrochloride

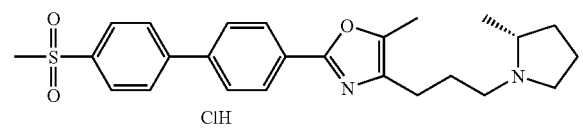

a) Add 3-[2-(4-bromo-phenyl)-5-methyl-oxazol-4-yl]-propan-1-ol (See Intermediate 41) (0.189 g, 0.638 nimol), Pd(Ph₃)₄ (0.038 g, 0.032 nmnol), 4-methylsulfoniylphenyl-boronic acid (0.192 g, 0.957 mmol), 2N Na₂CO₃ (1.6 mL), and 1,4-dioxane (2.0 mL) to a microwave vessel. Subject the reaction mixture to microwave irradiation at 30 W, 90° C. for 30-45 minutes. Concentrate and purify on silica gel eluting with 8% 2N NH3 in methanol/dichloromethane to give 3-[2-(4'-methanesulfonyl-biphenyl-4-yl)-5-methyl-oxazol-4-yl]-propan-1-ol (0.170 g, 72%): MS (m/e): 372(M+1).

b) Add methanesulfonyl chloride (0.086 g, 0.60 mmol) to a cool (0° C.) solution of 3-[2-(4'-methanesulfonyl-biphenyl-4-yl)-5-methyl-oxazol-4-yl]-propan-1-ol (0.170 g, 0.458 mmol) and triethylamine (0.070 g, 0.69 mmol) in dichloromethane (3 mL). Warm the reaction mixture to room temperature and stir for 1 hour. Add dichloromethane and wash the crude organic material with saturated sodium chloride solution. Dry the organic extracts over Na₂SO₄, filter, and concentrate to give crude methanesulfonic acid 3-[2-(4'-methanesulfonyl-biphenyl-4-yl)-5-methyl-oxazol-4-yl]-propyl ester (0.206 g, 100%): MS (m/e): 450(M+1).

c) Add a solution of methanesulfonic acid 3-[2-(4'-methanesulfonyl-biphenyl-4-yl)-5-methyl-oxazol-4-yl]-propyl ester (0.206 g, 0.458 mmol) in 3 mL acetonitrile to a sealed tube containing 2R-methyl-pyrrolidine hydrochloride (See Intermediate 7) (0.111 g, 0.916 mmol), K₂CO₃ (0.221 g, 1.60 mmol), and KI (0.008 g, 0.05 mmol), and heat at 60° C. overnight. Add dichloromethane and wash the crude organic layer with saturated sodium chloride solution. Dry the organic extracts over Na₂SO₄, filter, and concentrate. Purify on silica gel eluting with 8% ammoniated methanol in dichloromethane to give to give 2-(4'-methanesulfonyl-biphenyl-4-yl)-5-methyl-4-[3-(2R-methyl-pyrrolidin-1-yl)-propyl]-oxazole (0.130 g, 65%): MS (m/e): 439(M+1).

d) Treat the recovered material (0.130 g, 0.296 mmol) with 1N HCl (326 µL, 0.326 mmol) in ether and freeze dry to give the title compound (0.144 g, 100%): MS (m/e): 439(M+1).

Example 93

1-{2-[2-(4'-Methanesulfonyl-biphenyl-4-yl)-5-methyl-oxazol-4-yl]-ethyl}-2R-methyl-piperidine hydrochloride

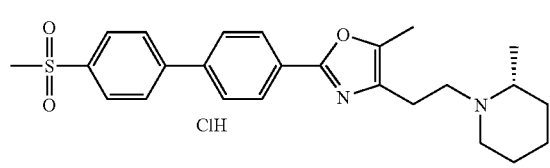

a) 1-{2-[2-(4-bromo-phenyl)-5-methyl-oxazol-4-yl]-ethyl}-2-methylpiperidine was separated into its isomers on 0.46×15 cm Chiralpak® AD-H column with MeOH w/0.2% DMEA (Flow: 0.6 mL/min, UV: 290 nm). The isomers were assigned by comparison to a standard 1-{2-[2-(4-bromo-phenyl)-5-methyl-oxazol-4-yl]-ethyl}-2S-methylpiperidine prepared from enantiomerically pure commercially available 2S-methylpiperidine.

b) Add 1-{2-[2-(4-bromo-phenyl)-5-methyl-oxazol-4-yl]-ethyl}-2R-methylpiperidine (0.094 g, 0.26 mmol), Pd(Ph$_3$)$_4$ (0.013 g, 0.011 mmol), 4-methylsulfonylphenylboronic acid (0.072 g, 0.36 mmol), 2N Na$_2$CO$_3$ (0.64 mL), and 1,4-dioxane (1 mL) to a microwave vessel. Subject the reaction mixture to microwave irradiation at 30 W, 90° C. for 30-45 minutes. Add dichloromethane and wash the crude organic layer with saturated sodium chloride solution. Dry the organic extracts over Na$_2$SO$_4$, filter, and concentrate. Purify on silica gel eluting with 8% ammoniated methanol in dichloromethane to give 1-{2-[2-(4'-methanesulfonyl-biphenyl-4-yl)-5-methyl-oxazol-4-yl]-ethyl}-2R-methyl-piperidine (0.094 g, 84%): MS (m/e): 439(M+1).

c) Treat the recovered material (0.094 g, 0.22 mmol) with 1N HCl (237 µL, 0.237 mmol) in ether and freeze dry to give the title compound (79 mg, 77%): MS (m/e): 439 (M+1).

Example 94

2-(4'-Methanesulfonyl-biphenyl-4-yl)-5-methyl-4-(3-pyrrolidin-1-yl-propyl)-oxazole hydrochloride

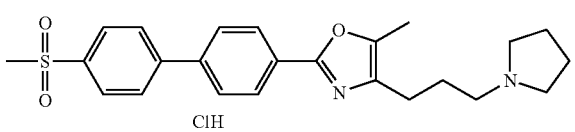

The free base of the title compound is prepared in a manner similar to that described in Example 92 using 3-[2-(4-bromo-phenyl)-5-methyl-oxazol-4-yl]-propan-1-ol and pyrrolidine. The free base is converted to the hydrochloride salt according to the procedure described for Example 92 to provide the title compound: MS (m/e): 425 (M+1).

Example 95

1-[2-(4'-Methanesulfonyl-biphenyl-4-yl)-5-methyl-oxazol-4-yl]-2-(2R-methyl-pyrrolidin-1-yl)-ethanol hydrochloride

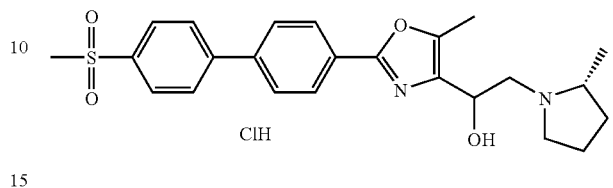

a) Add a solution of 2-bromo-1-[2-(4-bromo-phenyl)-5-methyl-oxazol-4-yl]-ethanol (0.500 g, 0.139 mmol) in 8 mL acetonitrile to a sealed tube containing 2R-methyl-pyrrolidine hydrochloride (See Intermediate 7) (0.507 g, 4.16 mmol), K$_2$CO$_3$ (0.959 g, 6.95 mmol), and KI (0.002 g, 0.01 mmol), and heat at 60° C. overnight. Add dichloromethane and wash the crude organic layer with saturated sodium chloride solution. Dry the organic extracts over Na$_2$SO$_4$, filter, and concentrate. Purify on silica gel eluting with 5% ammoniated methanol in dichloromethane to give 1-[2-(4-bromo-phenyl)-5-methyl-oxazol-4-yl]-2-(2R-methyl-pyrrolidin-1-yl)-ethanol (0.221 g, 44%): mass spectrum (m/e): 365 (M+1).

b) Add 1-[2-(4-bromo-phenyl)-5-methyl-oxazol-4-yl]-2-(2R-methyl-pyrrolidin-1-yl)-ethanol (0.220 g, 0.580 mmol) to a solution of Pd(Ph$_3$)$_4$ (0.034 g, 0.029 mmol), 4-methylsulfonylphenylboronic acid (0.104 g, 0.522 mmol), Na$_2$CO$_3$ (0.123 g, 1.16 mL) in acetonitrile (5 mL) and water (5 mL). Heat the reaction mixture at reflux for 3 hrs. Add dichloromethane and wash the crude organic material with saturated sodium chloride solution. Dry the organic extracts over Na$_2$SO$_4$, filter, and concentrate. Purify on silica gel eluting with 8% ammoniated methanol in dichloromethane to give 1-[2-(4'-methanesulfonyl-biphenyl-4-yl)-5-methyl-oxazol-4-yl]-2-(2R-methyl-pyrrolidin-1-yl)-ethanol (0.189 g, 72%): mass spectrum (m/e): 441(M+1).

c) Treat the recovered material (0.100 g, 0.227 mmol) with 1N HCl (250 µL, 0.250 mmol) in ether and freeze dry to give the title compound (0.101 g): mass spectrum (m/e): 441(M+1).

Example 96

2-(4'-Methanesulfonyl-biphenyl-4-yl)-4-[(-methoxy-2-(2R-methyl-pyrrolidin-1-yl)-ethyl]-5-methyl-oxazole hydrochloride

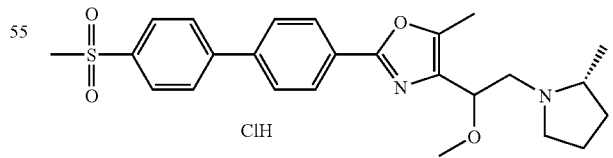

a) Add MeI (0.035 g, 0.25 mmol) and NaH (60%, 0.006 g, 0.2 mmol) to a cold (0° C.) solution of 1-[2-(4'-methanesulfonyl-biphenyl-4-yl)-5-methyl-oxazol-4-yl]-2-(2R-methyl-pyrrolidin-1-yl)-ethanol (See Example 95) (0.078 g, 0.18 mmol) in THF and stir at this temperature for 2 hr. Add several drops of saturated NH$_4$Cl and dichloromethane. Wash the crude organic extracts with saturated NaCl, dry over MgSO$_4$, filter, and concentrate. Purify on silica gel eluting with 7% ammoniated methanol in dichloromethane to give 2-(4'-methanesulfonyl-biphenyl-4-yl)-4-[1-methoxy-2-(2R-methyl-pyrrolidin-1-yl)-ethyl]-5-methyl-oxazole (0.010 g, 13%): mass spectrum (m/e): 455(M+1).

b) Treat the recovered material (0.010 g, 0.023 mmol) with 1N HCl (24 µL, 0.024 mmol) in ether and freeze dry to give the title compound (11.2 mg): mass spectrum (m/e): 455(M+1).

Example 97

2-(4'-Methanesulfonyl-biphenyl-4-yl)-5-methyl-4-[2-(2S-methyl-pyrrolidin-1-yl)-ethyl]-oxazole hydrochloride

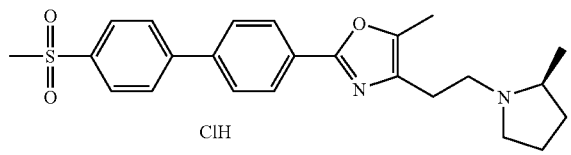

a) Add methanesulfonic acid 2-[2-(4'-methanesulfonyl-biphenyl-4-yl)-5-methyl-oxazol-4-yl]-ethyl ester (TPl-A07475-04) (0.139 g, 0.299 mmol) to a solution of 2S-methyl-pyrrolidine hydrochloride (See Intermediate 46) (0.109 g, 0.896 mmol), K$_2$CO$_3$ (0.206 g, 1.49 mmol), and KI (0.0005 g, 0.003 mmol), and heat the reaction mixture at reflux for 6 hrs. Add dichloromethane and wash the crude organic layer with saturated sodium chloride solution. Dry the organic extracts over Na$_2$SO$_4$, filter, and concentrate. Purify on silica gel eluting with 5% ammoniated methanol in dichloromethane to give 2-(4'-methanesulfonyl-biphenyl-4-yl)-5-methyl-4-[2-(2S-methyl-pyrrolidin-1-yl)-ethyl]-oxazole (0.140 g, quantatative): mass spectrum (m/e): 425 (M+1).

b) Treat the recovered material (0.100 g, 0.227 mmol) with 1N HCl (250 µL, 0.250 mmol) in ether and freeze dry to give the title compound (115 mg): mass spectrum (m/e): 425 (M+1).

Example 98

3-Methyl-6-(4-{5-methyl-4-[2-(2-methyl-pyrrolidin-1-yl)-ethyl]-oxazol-2-yl}-pheny-pyridazine

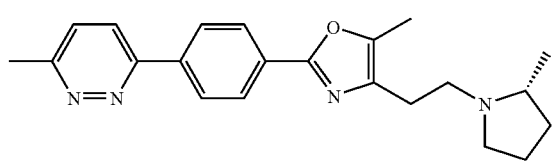

The titled compound is prepared substantially in accordance with the procedures of Intermediate 13 and Example 75 using 2-{5-Methyl-2-[4-(6-methyl-pyridazin-3-yl)-phenyl]-oxazol-4-yl}-ethanol (See Intermediate 47) and 2R-methylpyrrolidine hydrochloride (see Intermediate 7). MS (m/e) 363.3 (M+1).

Example 99

2-(4-Bromo-phenyl)-5-methyl-4-(2-methyl-pyrrolidin-1-ylmethyl)-oxazole

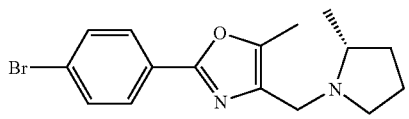

The titled compound is prepared substantially in accordance with the procedure of Example 75 using the 2-(4-Bromo-phenyl)-4-chloromethyl-oxazole (See Intermediate 1) and 2R-methylpyrrolidine hydrochloride (see Intermediate 7). MS (m/e) 337.0 (M+1).

Example 100

2-(4'-Methanesulfonyl-biphenyl-4-yl)-5-methyl-4-(2-methyl-pyrrolidin-1-ylmethyl)-oxazole

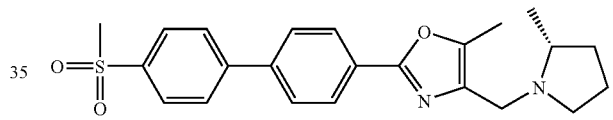

The titled compound is prepared substantially in accordance with the procedure of Example 9 using 2-(4-Bromo-phenyl)-5-methyl-4-(2-methyl-pyrrolidin-1-ylmethyl)-oxazole (See Example 99) and 4-methylsulfonylphenylboronic acid. MS (m/e) 411.2 (M+1).

Example 101

5-{5-Methyl-4-[2-(2-methyl-pyrrolidin-1-yl)-ethyl]-oxazol-2-yl}-2-phenoxy-pyridine

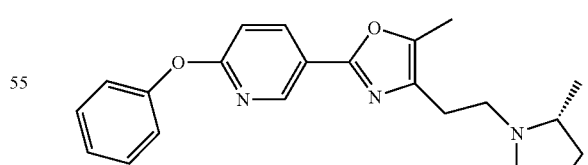

The titled compound is prepared substantially in accordance with the procedure of Example 75 using Toluene-4-sulfonic acid 2-[5-methyl-2-(6-phenoxy-pyridin-3-yl)-oxazol-4-yl]-ethyl ester [prepared by the method of S.E.Connor, WO 2003072102] and 2R-methylpyrrolidine hydrochloride (see Intermediate 7). MS (m/e) 364.2 (M+1).

Example 102

2-(4-Bromophenyl)-4-{2-[(3S)-3-fluoropyrrolidin-1-yl]ethyl}-5-methyl-1,3-oxazo

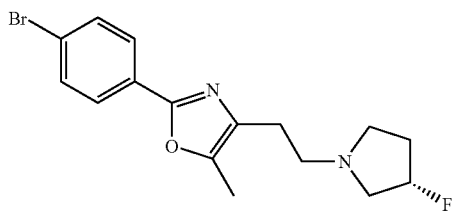

To a solution of 2-[2-(4-bromophenyl)-5-methyl-1,3-oxazol-4-yl]ethyl methanesulfonate (See Intermediate 13) (0.16 g, 0.44 mmole) in anhydrous acetonitrile (2 mL) add potassium carbonate (0.21 g, 1.54 mmol) and potassium iodide (0.007 g, 0.04 mmol), followed by (3S)-3-fluoropyrrolidine 4-methylbenzenesulfonate (salt) (See Intermediate 49) (0.21 g, 0.79 mmol). Heat the reaction mixture to 60° C. (oil bath temperature) overnight. Add water and extract with dichloromethane. Dry the combined extracts over sodium sulfate then concentrate in vacuo to give an orange oil (0.15 g). Load the oil onto a 5 g Isolute® SCX-2 column (preconditioned with methanol). Wash the SCX-2 with methanol then elute the target compound with 2N ammonia in methanol solution. Concentrate of the ammonia solution in vacuo to give the title compound as an orange oil (0.14 g): MS (nm/e) ($^{79}$Br/$^{81}$Br): 353, 355 (M+1)

Example 103

4-{[(3S)-3-fluoropyrrolidin-1-yl]ethyl}-2-[4'-(methylsulfonyl)biphenyl-4-yl]-5-methyl-1,3-oxazole

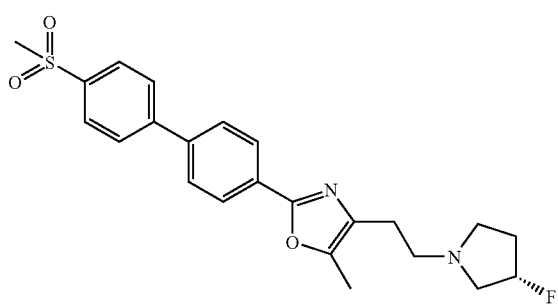

To a solution of palladium (II) acetate (0.002 g, 0.008 mmol) in anhydrous acetonitrile (4 mL), add triphenylphosphine (0.008 g, 0.032 mmol), under nitrogen and at room temperature. Stir for 15 minutes then add distilled water (1 mL), 4-(methalnesulfonyl)benzeneboronic acid (0.089 g, 0.416 mmol), 2-(4-bromophenyl)-4-{2-[(3S)-3-fluoropyrrolidin-1-yl]ethyl}-5-methyl-1,3-oxazole (0.140 g, 0.396 mmol) (see example 102) and potassium carbonate (0.164 g, 1.19 mmol). Heat the reaction mixture at 70° C. overnight.

Cool to room temperature then pour into water. Extract with dichloromethane then concentrate the combined extracts in vacuo. Load onto a 5 g Isolute® SCX-2 column (preconditioned with methanol). Wash the SCX-2 with methanol then elute the target compound with 2N ammonia in methanol solution followed by 7N ammonia in methanol. Concentrate the combined ammonia solutions in vacuo to give a pale yellow solid (0.16 g). Purify using automated flash chromatography (ISCO® System, 12 g Redisep® SiO$_2$ column; 0-30% methanol in ethyl acetate gradient elution over 20 minutes at 30 mL/min) to give the title compound as a pale yellow solid (0.133 g): MS (m/e): 429 (M+1).

Example 104

2-(4-Bromophenyl)-4-{2-[(3R)-3-fluoropyrrolidin-1-yl]ethyl}-5-methyl-1,3-oxazole

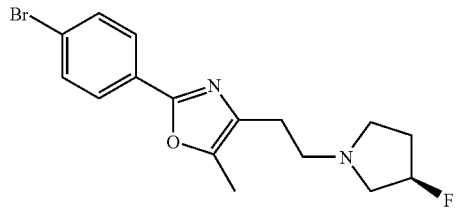

Prepare using the method of Example 102 with 2-[2-(4-bromophenyl)-5-methyl-1,3-oxazol-4-yl]ethyl methanesulfonate (See Intermediate 13) (0.16 g, 0.44 mmole), anhydrous acetonitrile (2 mL), potassium carbonate (0.21 g, 1.54 mmol), potassium iodide (0.007 g, 0.04 mmol) and (3R)-3-fluoropyrrolidine 4-methylbenzenesulfonate (salt) (See Intennediate 51) (0.21 g, 0.79 mmol) to give the title compound as a pale orange oil (0.16 g): MS (m/e) ($^{79}$Br/$^{81}$Br): 353, 355(M+1)

Example 105

4-{[(3R)-3-Fluoropyrrolidin-1-yl]ethyl}-2-[4'-(methylsulfonyl)biphenyl-4-yl]-5-methyl-1,3-oxazole

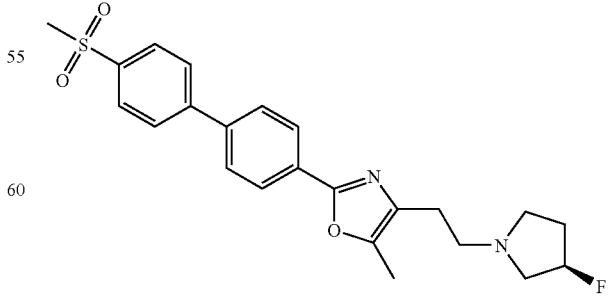

Prepare using the method of Example 103 with palladium (II) acetate (0.002 g, 0.008 mmol), anhydrous acetonitrile (4 mL), triphenylphosphine (0.009 g, 0.034 mmol), distilled water (1 mL), 4-(methanesulfonyl)benzeneboronic acid (0.096 g, 0.45 mmol), 2-(4-bromophenyl)-4-{2-[(3S)-3-fluoropyrrolidin-1-yl]ethyl}-5-methyl-1,3-oxazole (See Example 104) (0.150 g, 0.42 mmol) and potassium carbonate (0.176 g, 1.27 mmol) to give the title compound as a cream coloured solid (0.133 g): MS (m/e): 429(M+1).

Example 106

(3R)-1-{2-[2-(4-Bromophenyl)-5-methyl-1,3-oxazol-4-yl]ethyl}pyrrolidin-3-ol

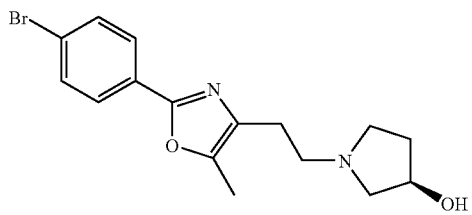

Prepare using the method of Example 102 with 2-[2-(4-bromophenyl)-5-methyl-1,3-oxazol-4-yl]ethyl methanesulfonate (See Intermediate 13) (0.16 g, 0.44 mmole), anhydrous acetonitrile (2 mL), potassium carbonate (0.21 g, 1.54 mmol), potassium iodide (0.007 g, 0.04 mmol) and (3R)-pyrrolidin-3-ol 4-methylbenzenesulfonate (salt) (See Intermediate 52) (0.13 g, 0.51 mmol) to give the title compound as a pale orange oil (0.15 g): MS (m/e) ($^{79}$Br/$^{81}$Br): 351, 353 (M+1)

Example 107

4-{[(3R)-3-Hydroxypyrrolidin-1-yl]ethyl}-2-[4'-(methylsulfonyl)biphenyl-4-yl]-5-methyl-1,3-oxazole acetate (salt)

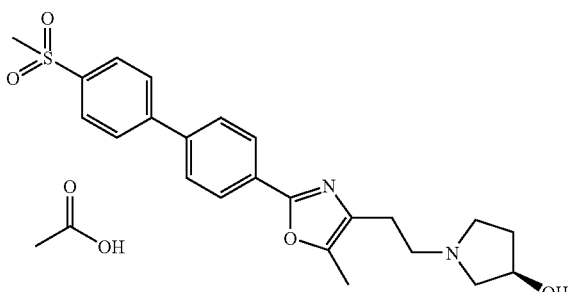

Prepare using the method of Example 103 with palladium (II) acetate (0.002 g, 0.008 mmol), anhydrous acetonitrile (4 mL), triphenylphosphine (0.009 g, 0.034 mmol), distilled water (1 mL), 4-(methanesulfonyl)benzeneboronic acid (0.096 g, 0.45 mmol), (3R)-1-{2-[2-(4-bromophenyl)-5-methyl-1,3-oxazol-4-yl]ethyl}pyrrolidin-3-ol (See Example 106) (0.150 g, 0.43 mmol) and potassium carbonate (0.177 g, 1.28 mmol). Additionally purify using mass guided HPLC to give the title compound as a cream coloured solid (0.034 g): MS (m/e): 427(M+1).

Example 108

(3S)-1-{2-[2-(4-Bromophenyl)-5-methyl-1,3-oxazol-4-yl]ethyl}pyrrolidin-3-ol

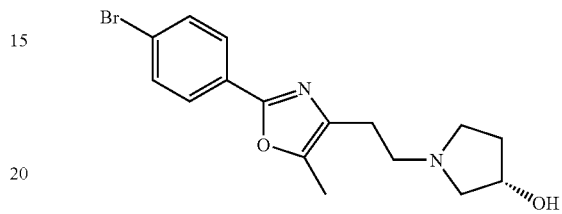

Prepare using the method of Example 102 with 2-[2-(4-bromophenyl)-5-methyl-1,3-oxazol-4-yl]ethyl methanesulfonate (See Intermediate 13) (0.16 g, 0.44 mmole), anhydrous acetonitrile (2 mL), potassium carbonate (0.21 g, 1.54 mmol), potassium iodide (0.007 g, 0.04 mmol) and (3S)-pyrrolidin-3-ol 4-methylbenzenesulfonate (salt) (See Intermediate 53) (0.21 g, 0.80 mmol) to give the title compound as a pale orange oil (0.15 g): MS (m/e) ($^{79}$Br/$^{81}$Br): 351, 353 (M+1)

Example 109

4-{[(3S)-3-Hydroxypyrrolidin-1-yl]ethyl}-2-[4'-(methylsulfonyl)biphenyl-4-yl]-5-methyl-1,3-oxazole acetate (salt)

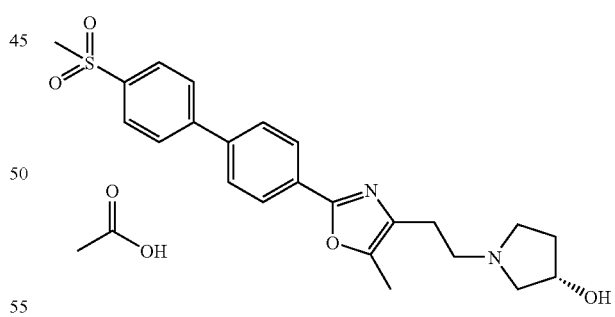

Prepare using the method of Example 103 with palladium (II) acetate (0.002 g, 0.008 mmol), anhydrous acetonitrile (4 mL), triphenylphosphine (0.009 g, 0.034 mmol), distilled water (1 mL), 4-(methanesulfonyl)benzeneboronic acid (0.096 g, 0.45 mmol), (3S)-1-{2-[2-(4-bromophenyl)-5-methyl-1,3-oxazol-4-yl]ethyl}pyrrolidin-3-ol (See Example 108) (0.150 g, 0.43 mmol) and potassium carbonate (0.177 g, 1.28 mmol). Additionally purify using mass guided HPLC to give the title compound as a cream coloured solid (0.035 g): MS (m/e): 427(M+1).

Example 110

2-(4-Bromophenyl)-4-{2-[(3S)-3-(fluoromethyl)pyrrolidin-1-yl]ethyl}-5-methyl-1,3-oxazole

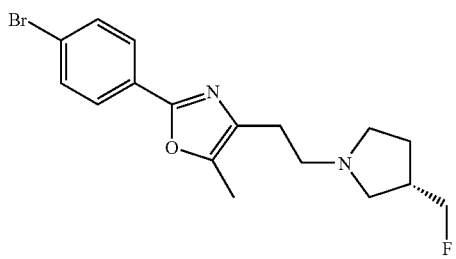

Prepare using the method of Example 102 with 2-[2-(4-bromophenyl)-5-methyl-1,3-oxazol-4-yl]ethyl methanesulfonate (See Intermediate 13) (0.17 g, 0.46 mmole), anhydrous acetonitrile (2 mL), potassium carbonate (0.25 g, 1.84 mmol), potassium iodide (0.008 g, 0.05 mmol) and (3S)-3-(fluoromethyl)pyrrolidine 4-methylbenzenesulfonate (salt) (See Intermediate 55) (0.19 g, 0.69 mmol) to give the title compound as a pale orange oil (0.17 g): MS (m/e): 367, 369(M+1)

Example 111

4-{2-[(3S)-3-(Fluoromethyl)pyrrolidin-1-yl]ethyl}-5-methyl-2-[4'-(methylsulfonyl)biphenyl-4-yl]-1,3-oxazole

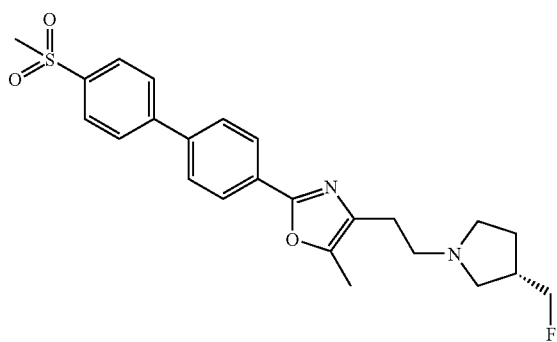

Prepare using the method of Example 103 with palladium (II) acetate (0.002 g, 0.01 mmol), anhydrous acetonitrile (4 mL), triphenylphosphine (0.010 g, 0.04 mmol), distilled water (1 mL), 4-(methanesulfonyl)benzeneboronic acid (0.10 g, 0.49 mmol), 2-(4-bromophenyl)-4-{2-[(3S)-3-(fluoromethyl)pyrrolidin-1-yl]ethyl}-5-methyl-1,3-oxazole (See Example 110) (0.17 g, 0.46 mmol) and potassium carbonate (0.19 g, 1.39 mmol). Additionally triturate the resulting solid with 2:1 diethyl ether:ethyl acetate to give the title compound as a yellow coloured solid (0.07 g): MS (m/e): 443(M+1).

Example 112

2-(4-Bromophenyl)-4-{2-[(3R)-3-(fluoromethyl)pyrrolidin-1-yl]ethyl}-5-methyl-1,3-oxazole

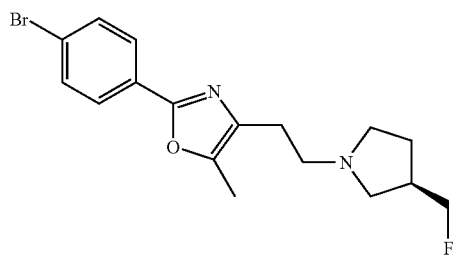

Prepare using the method of Example 102 with 2-[2-(4-bromophenyl)-5-methyl-1,3-oxazol-4-yl]ethyl methanesulfonate (See Intermediate 13) (0.36 g, 0.99 mmole), anhydrous acetonitrile (2 mL), potassium carbonate (0.55 g, 3.98 mmol), potassium iodide (0.016 g, 0.10 mmol) and (3R)-3-(fluoromethyl)pyrrolidine 4-methylbenzenesulfonate (salt) (See Intermediate 57) (0.41 g, 1.49 mmol) to give the title compound as a pale orange oil (0.34 g): MS (m/e) ($^{79}$Br/$^{81}$Br): 367, 369(M+1)

Example 113

4-{2-[(3R)-3-(Fluoromethyl)pyrrolidin-1-yl]ethyl}-5-methyl-2-[4'-(methylsulfonyl)biphenyl-4-yl]-1,3-oxazole

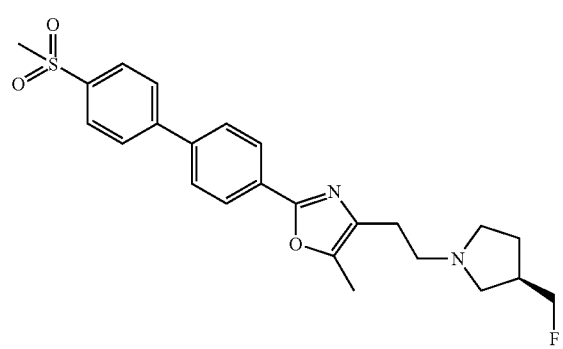

Prepare using the method of Example 103 with palladium (II) acetate (0.003 g, 0.01 mmol), anhydrous acetonitrile (4 mL), triphenylphosphine (0.014 g, 0.05 mmol), distilled water (1 mL), 4-(methanesulfonyl)benzeneboronic acid (0.15 g, 0.71 mmol), 2-(4-bromophenyl)-4-{2-[(3R)-3-(fluoromethyl)pyrrolidin-1-yl]ethyl}-5-methyl-1,3-oxazole (See Example 112) (0.25 g, 0.68 mmol) and potassium carbonate (0.28 g, 2.04 mmol). Additionally triturate the resulting solid with 2:1 diethyl ether:ethyl acetate to give the title compound as a pale yellow coloured solid (0.11 g): MS (m/e): 443 (M+1).

Example 114

3-[4-(5-{2-[(3R)-3-(Fluoromethyl)pyrrolidin-1-yl]ethyl}-4-methyl-1,3-oxazol-2-yl)phenyl]pyridine L-tartrate

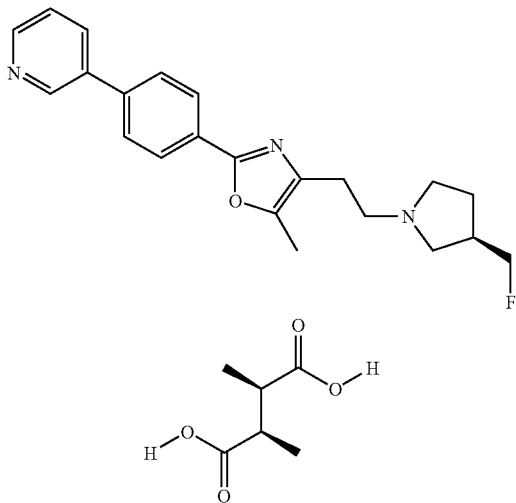

Prepare using the method of Example 103 with palladium (II) acetate (0.001 g, 0.005 mmol), anhydrous acetonitrile (4 mL), triphenylphosphine (0.006 g, 0.02 mmol), distilled water (1 mL), 3-pyridylboronic acid (0.035 g, 0.29 mmol), 2-(4-bromophenyl)-4-{2-[(3R)-3-fluoropyrrolidin-1-yl]ethyl}-5-methyl-1,3-oxazole (See Example 112) (0.09 0.25 mmol) and potassium carbonate (0.11 g, 0.82 mmol) to give a pale orange oil (0.061 g). Dissolve the oil in ethyl acetate. Add L-tartaric acid (0.025 g, 0.17 mmole) as a solution in ethanol. Remove the solvent under vacuum. Add dichloromethane and concentrate under vacuum to give the title compound as a pale yellow coloured foam (0.086 g): MS (m/e): 366(M+1).

Example 115

2-(4-Bromophenyl)-4-{2-[(3R)-3-methoxypyrrolidin-1-yl]ethyl}-5-methyl-1,3-oxazole

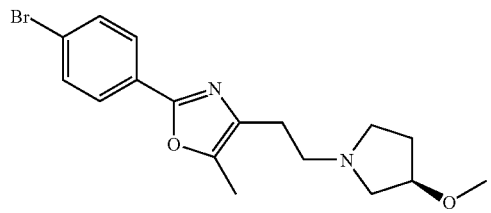

Prepare using the method of Example 102 with 2-[2-(4-bromophenyl)-5-methyl-1,3-oxazol-4-yl]ethyl methanesulfonate (See Intermediate 13) (0.32 g, 0.89 mmole), anhydrous acetonitrile (4 mL), potassium carbonate (0.43 g, 3.11 mmol), potassium iodide (0.015 g, 0.09 mmol) and (3R)-3-methoxypyrrolidine 4-methylbenzenesulfonate (salt) (See Intermediate 59) (0.25 g, 0.91 mmol) to give the title compound as a pale orange oil (0.25 g): MS (m/e) ($^{79}$Br/$^{81}$Br): 365, 367(M+1)

Example 116

4-{2-[(3R)-3-methoxypyrrolidin-1-yl]ethyl}-5-methyl-2-[4'-(methylsulfonyl)biphenyl-4-yl]-1,3-oxazole

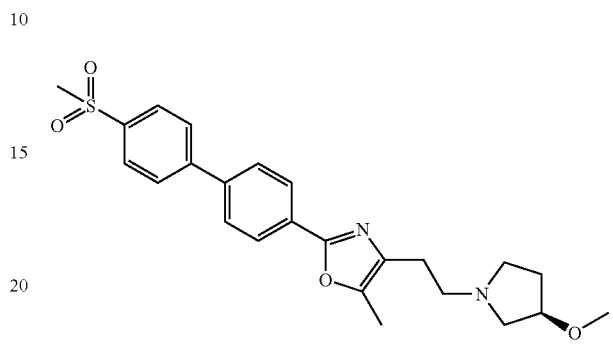

Prepare using the method of Example 103 with palladium (II) acetate (0.003 g, 0.014 mmol), anhydrous acetonitrile (4 mL), triphenylphosphine (0.014 g, 0.055 mmol), distilled water (1 mL), 4-(methanesulfonyl)benzeneboronic acid (0.22 g, 1.03 mmol), 2-(4-bromophenyl)-4-{2-[(3R)-3-methoxypyrrolidin-1-yl]ethyl}-5-methyl-1,3-oxazole (See Example 115) (0.25 g, 0.68 mmol) and potassium carbonate (0.28 g, 2.05 mmol) to give the title compound as a white solid (0.17 g): MS (m/e): 441(M+1).

Example 117

2-(4-Bromophenyl)-4-{2-[(3S)-3-methoxypyrrolidin-1-yl]ethyl}-5-methyl-1,3-oxazole

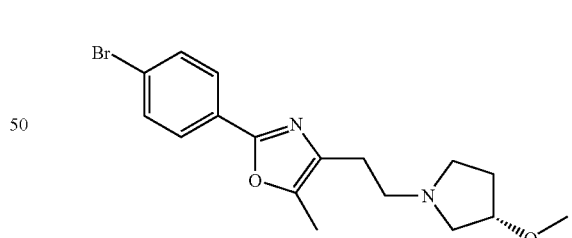

Prepare using the method of Example 102 with 2-[2-(4-bromophenyl)-5-methyl-1,3-oxazol-4-yl]ethyl methanesulfonate (See Intermediate 13) (0.16 g, 0.44 mmole), anhydrous acetonitrile (2 mL), potassium carbonate (0.21 g, 1.54 mmol), potassium iodide (0.007 g, 0.04 mmol) and (3S)-3-methoxypyrrolidine 4-methylbenzenesulfonate (salt) (See Intermediate 61) (0.22 g, 0.79 mmol) to give the title compound as a pale orange oil (0.10 g): MS (m/e) ($^{79}$Br/$^{81}$Br): 371, 373(M+1)

Example 118

4-{2-[(3S)-3-Methoxypyrrolidin-1-yl]ethyl}-5-methyl-2-[4'-(methylsulfonyl)biphenyl-4-yl]-1,3-oxazole

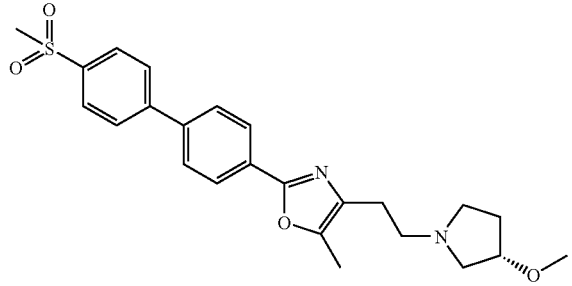

Prepare using the method of Example 103 with palladium (II) acetate (0.003 g, 0.015 mmol), anhydrous acetonitrile (4 mL), triphenylphosphine (0.016 g, 0.059 mmol), distilled water (1 mL), 4-(methanesulfonyl)benzeneboronic acid (0.24 g, 1.11 mmol), 2-(4-bromophenyl)-4-{2-[(3S)-3-methoxy-pyrrolidin-1-yl]ethyl}-5-methyl-1,3-oxazole (See Example 117) (0.27 g, 0.74 mmol) and potassium carbonate (0.31 g, 2.22 mmol) to give the title compound as a white solid (0.12 g): MS (m/e): 441(M+1).

Example 119

2-(4-Bromophenyl)-4-{2-[(2R)-2-methylpyrrolidin-1-yl]ethyl}-5-methyl-1,3-oxazole

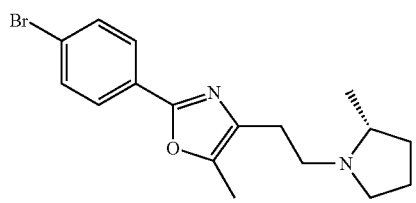

Prepare using the method of Example 102 with 2-[2-(4-bromophenyl)-5-methyl-1,3-oxazol-4-yl]ethyl methanesulfonate (See Intermediate 13) (0.65 g, 1.80 mmole), anhydrous acetonitrile (6 mL), potassium carbonate (0.87 g, 6.32 mmol), potassium iodide (0.03 g, 0.18 mmol) and (2R)-2-methylpyrrolidine hydrochloride (salt) (See Intermediate 7) (0.25 g, 2.08 mmol) to give the title compound as a pale orange oil (0.65 g): MS (m/e) ($^{79}$Br/$^{81}$Br): 349, 351(M+1)

Example 120

3-Methoxy-5-[4-(5-methyl-4-{2-[(2R)-2-methylpyrrolidin-1-yl]ethyl}-1,3-oxazol-2-yl)phenyl]pyridine

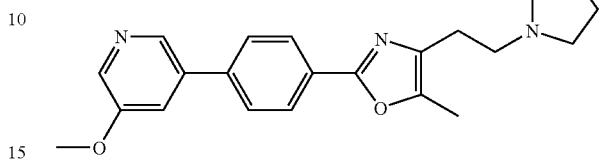

To a solution of palladium (II) acetate (0.004 g, 0.02 mmol) in anhydrous toluene (5 mL), add triphenylphosphine (0.019 g, 0.07 mmol), under nitrogen and at room temperature. Stir for 15 minutes then add distilled water (1.5 mL), ethanol (1 mL), 3-methoxypyridine-5-boronic acid pinacol ester (0.26 g, 1.10 mmol), 2-(4-bromophenyl)-4-{2-[(2R)-2-methylpyrrolidin-1-yl]ethyl}-5-methyl-1,3-oxazole (See Intermediate 73(0.32 g, 0.92 mmol) and potassium carbonate (0.38 g, 2.75 mmol). Heat the reaction mixture at 110° C. overnight. Cool to room temperature then pour into water. Extract with dichloromethane then concentrate the combined extracts in vacuo. Load onto a 10 g Isolute® SCX-2 column (preconditioned with methanol). Wash the SCX-2 with methanol then elute the target compound with 2N ammonia in methanol solution followed by 7N ammonia in methanol. Concentrate the combined ammonia solutions in vacuo to give a pale yellow solid (0.16 g). Purify using automated flash chromatography (ISCO® System, 12 g Redisep® SiO$_2$ column; 0-30% methanol in ethyl acetate gradient elution over 20 minutes at 30 mL/min) to give the title compound as a pale yellow solid (0.23 g): MS (m/e): 378(M+1).

Example 121

5-[4-(5-Methyl-4-{2-[(2R)-2-methylpyrrolidin-1-yl]ethyl}-1,3-oxazol-2-yl)phenyl]thiophene-2-carbonitrile

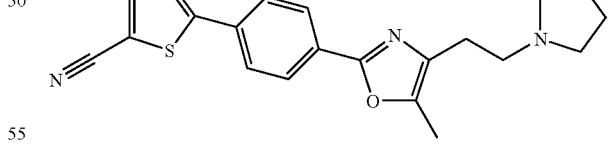

Prepare using the method of Example 120 with palladium (II) acetate (0.008 g, 0.04 mmol), anhydrous toluene (5 mL), triphenylphosphine (0.038 g, 0.15 mmol), distilled water (1.5 mL), ethanol (1 mL), 5-cyanothiophene-2-boronic acid (0.21 g, 1.37 mmol), 2-(4-bromophenyl)-4-{2-[(2R)-2-methylpyrrolidin-1-yl]ethyl}-5-methyl-1,3-oxazole (See Intermediate 73) (0.32 g, 0.92 mmol) and potassium carbonate (0.38 g, 2.75 mmol). Additionally purify by trituration with ethyl acetate to give the title compound as a cream coloured solid (0.03 g): MS (m/e): 378(M+1).

Example 122

2-Methoxy-5-[4-(5-methyl-4-{2-[(2R)-2-methylpyr-rolidin-1-yl]ethyl}-1,3-oxazol-2-yl)phenyl]pyrimi-dine

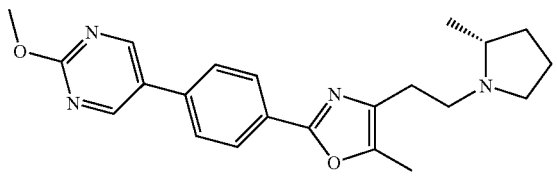

Prepare using the method of Example 103 with palladium (II) acetate (0.011 g, 0.05 mmol), anhydrous acetonitrile (8 mL), triphenylphosphine (0.051 g, 0.19 mmol), distilled water (2 mL), 2-methoxy-5-pyrimidineboronic acid (0.75 g, 4.87 mmol), 2-(4-bromophenyl)-4-{2-[(2R)-2-methylpyrrolidin-1-yl]ethyl}-5-methyl-1,3-oxazole (See Intermediate 73) (0.85 g, 2.43 mmol) and potassium carbonate (0.1.01 g, 7.30 mmol). Additionally recrystallise from acetonitrile/ethyl acetate to give the title compound as a cream coloured solid (0.016 g): MS (m/e): 379(M+1).

Example 123

5-(4-{5-Methyl-4-[2-(2-(R)-methyl-pyrrolidin-1-yl)-ethyl]-oxazol-2-yl}-phenoxymethyl)-thiophene-2-carbonitrile

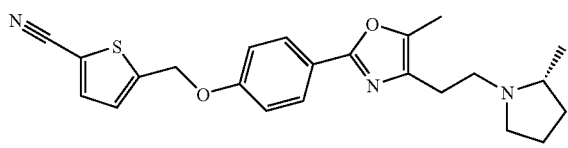

The title compound is prepared in a manner substantially similar to Example 57 from 2-[2-(4-Hydroxy-phenyl)-5-methyl-oxazol-4-yl]-1-(2-(R)-methyl-pyrrolidin-1 -yl)-ethanone (See Example 56) and 5-bromomethyl-thiophene-2-carbonitrile [CAS 134135-41-4]. MS (m/e): 408.3 (M+1)

Example 124

5-Methyl-4-[2-(2-(R)-methyl-pyrrolidin-1-yl)-ethyl]-2-[4-(2-methyl-thiazol-4-ylmethoxy)-phenyl]-oxazole

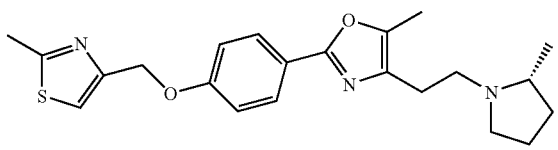

The title compound is prepared in a manner substantially similar to Example 58 from 2-[2-(4-Hydroxy-phenyl)-5-methyl-oxazol-4-yl]-1-(2-(R)-methyl-pyrrolidin-1-yl)-ethanone (See Example 56) and 4-(chloromethyl)-2-methylthiazole hydrochloride. MS (m/e): 398.3 (M+1)

Example 125

3-(4-{5-Methyl-4-[2-(2-(R)-methyl-pyrrolidin-1-yl)-ethyl]-oxazol-2-yl}-phenoxymethyl)-pyridine

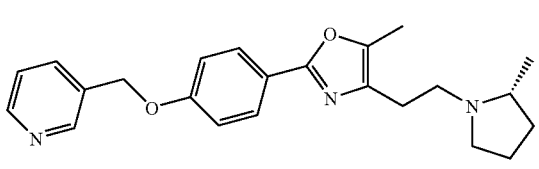

The title compound is prepared in a manner substantially similar to Example 57 from 2-[2-(4-Hydroxy-phenyl)-5-methyl-oxazol-4-yl]-1-(2-(R)-methyl-pyrrolidin-1-yl)-ethanone (See Example 56) and 3-(bromomethyl)pyridine hydrobromide. MS (m/e): 378.3 (M+1)

Example 126

4-(4-{5-Methyl-4-[2-(2-(R)-methyl-pyrrolidin-1-yl)-ethyl]-oxazol-2-yl}-phenoxymethyl)-pyridine

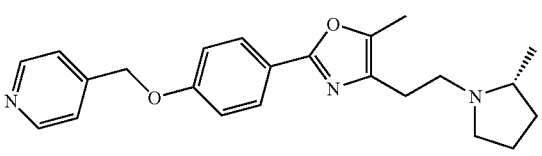

The title compound is prepared in a manner substantially similar to Example 57 from 2-[2-(4-Hydroxy-phenyl)-5-methyl-oxazol-4-yl]-1-(2-(R)-methyl-pyrrolidin-1-yl)-ethanone (See Example 56) and 4-(bromomethyl)pyridine hydrobromide. MS (m/e): 378.3 (M+1)

Example 127

2-Methoxy-5-(4-{5-methyl-4-[2-(2-(R)-methyl-pyrrolidin-1-yl)-ethyl]-oxazol-2-yl}-phenoxymethyl)-pyridine

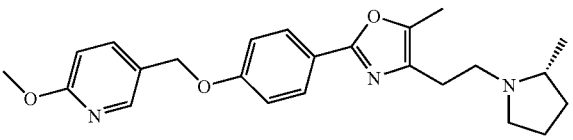

The title compound is prepared in a manner substantially similar to Example 58 from 2-[2-(4-Hydroxy-phenyl)-5-methyl-oxazol-4-yl]-1-(2-(R)-methyl-pyrrolidin-1-yl)-ethanone (See Example 56) and 5-chloro-2-methoxypyridine hydrochloride [CAS 120276-36-0]. MS (m/e): 408.3 (M+1)

Example 128

2-Methyl-6-(4-{5-methyl-4-[2-(2-(R)-methyl-pyrrolidin-1-yl)-ethyl]-oxazol-2-yl}-phenoxymethyl)-pyridine

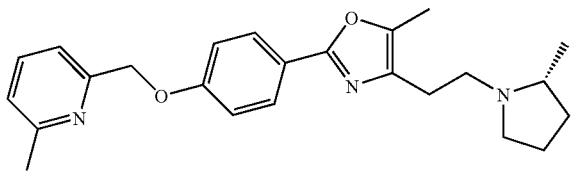

The title compound is prepared in a manner substantially similar to Example 58 from 2-[2-(4-Hydroxy-phenyl)-5-methyl-oxazol-4-yl]-1-(2-(R)-methyl-pyrrolidin-1-yl)-ethanone (See Example 56) and 2-chloromethyl-6-methyl-pyridine hydrochloride [CAS 3099-30-7]. MS (m/e): 392.3 (M+1)

Example 129

5-Methyl-4-[2-(2-(R)-methyl-pyrrolidin-1-yl)-ethyl]-2-[4-(thiazol-4-ylmethoxy)-phenyl]-oxazole

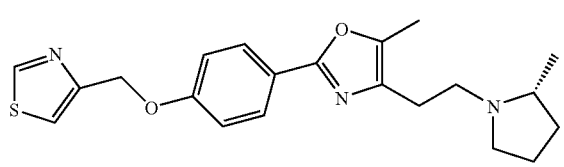

The title compound is prepared in a manner substantially similar to Example 55 from 1-(2-(R)-Methyl-pyrrolidin-1-yl)-2-{5-methyl-2-[4-(thiazol-4-ylmethoxy)-phenyl]-oxazol-4-yl}-ethanone (See Intermediate 63). The crude material is purified by flash chromatography (12 g SiO$_2$, elute 20% (10% 2 M NH$_3$ in MeOH/90% CH$_2$Cl$_2$)/80% CH$_2$Cl$_2$ to 80% (10% 2 M NH$_3$ in MeOH/90% CH$_2$Cl$_2$)/20% CH$_2$Cl$_2$). MS (m/e): 384.2 (M+1)

Example 130

2-(4-{4-[2-(2-(R)-Methyl-pyrrolidin-1-yl)-ethyl]-oxazol-2-yl}-phenoxymethyl)-pyridine

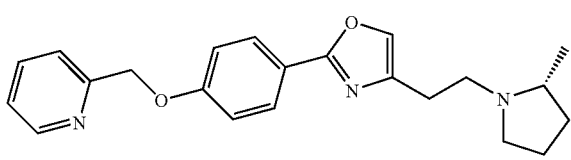

The title compound is prepared in a manner substantially similar to Example 53 from 2-{2-[4-(Pyridin-2-ylmethoxy)-phenyl]-oxazol-4-yl}-ethanol (See Intermediate 66) and (R)-2-methylpyrrolidine hydrochloride [CAS 41720-98-3]. MS (m/e): 364.2 (M+1)

Example 131

4-[2-(2-(R)-Methyl-pyrrolidin-1-yl)-ethyl]-2-[4-(thiazol-4-ylmethoxy)-phenyl]-oxazole

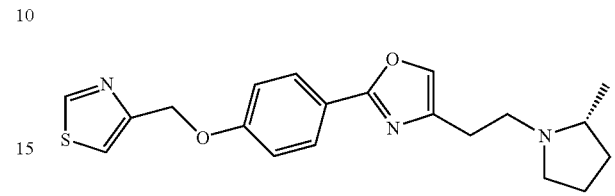

The title compound is prepared in a manner substantially similar to Example 53 from 2-{2-[4-(Thiazol-4-ylmethoxy)-phenyl]-oxazol-4-yl}-ethanol (See Intermediate 68) and (R)-2-methylpyrrolidine hydrochloride [CAS 41720-98-3]. MS (m/e): 370.2 (M+1)

Example 132

2-(4'-Methanesulfonyl-biphenyl-4-yl)-4-[2-(2-(R)-methyl-pyrrolidin-1-yl)-ethyl]-oxazole

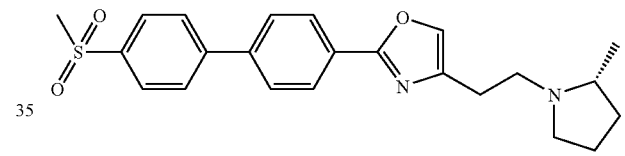

The title compound is prepared in a manner substantially similar to Example 53 from 2-[2-(4'-Methanesulfonyl-biphenyl-4-yl)-oxazol-4-yl]-ethanol (See Intermediate 71) and (R)-2-methylpyrrolidine hydrochloride [CAS 41720-98-3]. MS (m/e): 411.2 (M+1)

Example 133

1-(4'-{5-Methyl-4-[2-((R)-2-methyl-pyrrolidin-1-yl)-ethyl]-oxazol-2-yl}-biphenyl-4-yl)-ethanone

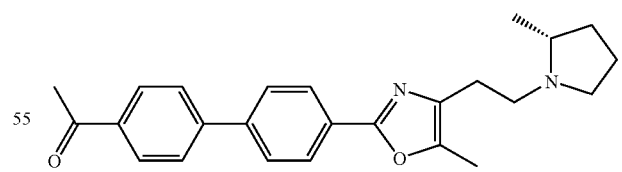

To a stirred solution of 2-(4-Bromo-phenyl)-5-methyl-4-[2-((R)-2-methyl-pyrrolidin-1-yl)-ethyl]-oxazole (100 mg, 0.287 munol), sodium carbonate (91 mg, 0.860 mmol) and 4-acetylphenyl boronic acid (235 mg, 1.43 mmol) in toluene (5 mL), water (1 mL) and ethanol (1.5 mL) under nitrogen is added Tetrakis (triphenylphosphine) palladium (0) (33.1 mg, 0.029 mmol). The reaction is heated at reflux for 48 h. The reaction is allowed to cool and bound to a SCX-2 cartridge (10 g). The cartridge is washed with one cartridge volumes of dimethylformamide and two volume of methanol. The product is eluted using 2M ammonia in methanol. The ammonia/methanol solution is evaporated on a Genevac® HT4. The sample is further purified by prep-LCMS. The resulting acetonitrile/water fractions are combined and evaporated using a Genevac® HT4 to give 62 mg of a colourless oil (56%). MS (m/e) 389.2 (M+1)

Example 134

1-(4'-{5-Methyl-4-[2-((R)-2-methyl-pyrrolidin-1-yl)-ethyl]-oxazol-2-yl}-biphenyl-2-yl)-ethanone

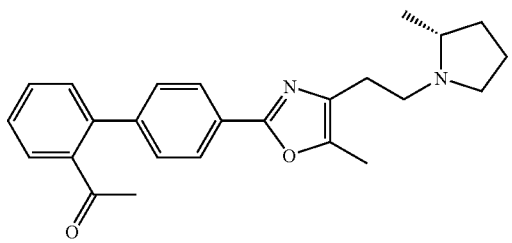

The title compound is prepared in a manner substantially analogous to example 133 starting from 2-acetylphenyl boronic acid (235 mg, 1.43 mmol) and 2-(4-Bromo-phenyl)-5-methyl-4-[2-((R)-2-methyl-pyrrolidin-1-yl)-ethyl]-oxazole (100 mg, 0.287 mmol) to give 94 mg (85%). MS (m/e) 389.2 (M+1)

Example 135

4'-{5-Methyl-4-[2-((R)-2-methyl-pyrrolidin-1-yl)-ethyl]-oxazol-2-yl}-biphenyl-3-carbonitrile

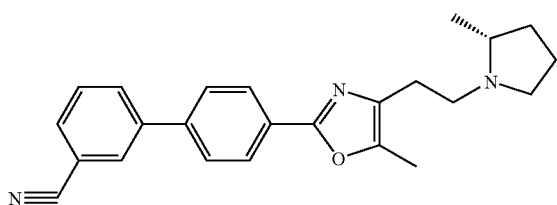

The title compound is prepared in a manner substantially analogous to example 133 starting from 3-Cyanobenzene boronic acid (211 mg, 1.43 mmol) and 2-(4-Bromo-phenyl)-5-methyl-4-[2-((R)-2-methyl-pyrrolidin-1-yl)-ethyl]-oxazole (100 mg, 0.287 mmol) to give 50 mg (47%). MS (m/e) 372.2 (M+1)

Example 136

4'-{5-Methyl-4-[2-((R)-2-methyl-pyrrolidin-1-yl)-ethyl]-oxazol-2-yl}-biphenyl-2-carbonitrile

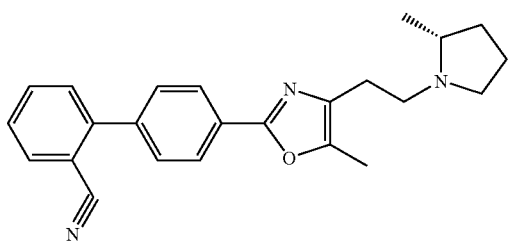

The title compound is prepared in a manner substantially analogous to example 133 starting from 2-Cyanobenzene boronic acid (211 mg, 1.43 mmol) and 2-(4-Bromo-phenyl)-5-methyl-4-[2-((R)-2-methyl-pyrrolidin-1-yl)-ethyl]-oxazole (100 mg, 0.287 mmol) to give 70 mg (66%). MS (m/e) 372.2 (M+1)

Example 137

2-(4'-Fluoro-biphenyl-4-yl)-5-methyl-4-[2-((R)-2-methyl-pyrrolidin-1-yl)-ethyl]-oxazole

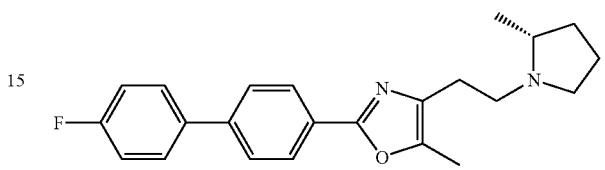

The title compound is prepared in a manner substantially analogous to example 133 starting from 4-fluorobenzene boronic acid (201 mg, 1.43 mmol) and 2-(4-Bromo-phenyl)-5-methyl-4-[2-((R)-2-methyl-pyrrolidin-1-yl)-ethyl]-oxazole (100 mg, 0.287 mmol) to give 10 mg (10%). MS (m/e) 365.2 (M+1)

Example 138

2-(3'-Fluoro-biphenyl-4-yl)-5-methyl-4-[2-((R)-2-methyl-pyrrolidin-1-yl)-ethyl]-oxazole

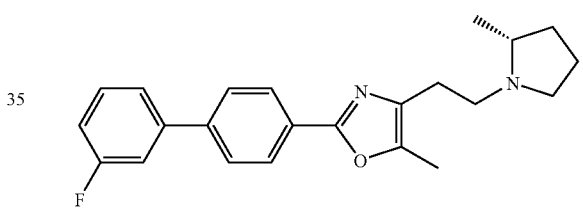

The title compound is prepared in a manner substantially analogous to example 133 starting from 3-fluorobenzene boronic acid (201 mg, 1.43 mmol) and 2-(4-Bromo-phenyl)-5-methyl-4-[2-((R)-2-methyl-pyrrolidin-1-yl)-ethyl]-oxazole (100 mg, 0.287 mmol) to give 70 mg (67%). MS (m/e) 365.2 (M+1)

Example 139

2-(2'-Fluoro-biphenyl-4-yl)-5-methyl-4-[2-((R)-2-methyl-pyrrolidin-1-yl)-ethyl]-oxazole

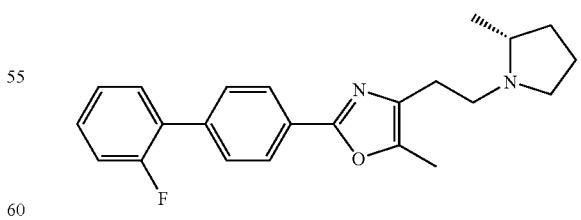

The title compound is prepared in a manner substantially analogous to example 133 starting from 2-fluorobenzene boronic acid (201 mg, 1.43 mmol) and 2-(4-Bromo-phenyl)-5-methyl-4-[2-((R)-2-methyl-pyrrolidin-1-yl)-ethyl]-oxazole (100 mg, 0.287 mmol) to give 61 mg (59%). MS (m/e) 365.2 (M+1)

Example 140

2-(4'-Methoxy-biphenyl-4-yl)-5-methyl-4-[2-((R)-2-methyl-pyrrolidin-1-yl)-ethyl]-oxazole

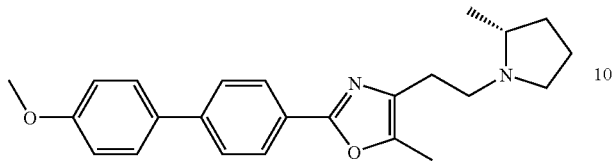

The title compound is prepared in a manner substantially analogous to example 133 starting from 4-methoxybenzene boronic acid (218 mg, 1.43 mmol) and 2-(4-Bromo-phenyl)-5-methyl-4-[2-((R)-2-methyl-pyrrolidin-1-yl)-ethyl]-oxazole (100 mg, 0.287 mmol) to give 61 mg (56%). MS (m/e) 377.2 (M+1)

Example 141

2-(3'-Methoxy-biphenyl-4-yl)-5-methyl-4-[2-((R)-2-methyl-pyrrolidin-1-yl)-ethyl]-oxazole

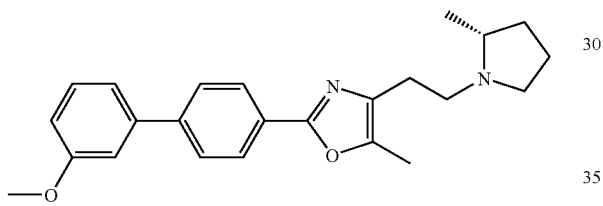

The title compound is prepared in a manner substantially analogous to example 133 starting from 3-methoxybenzene boronic acid (218 mg, 1.43 mmol) and 2-(4-Bromo-phenyl)-5-methyl-4-[2-((R)-2-methyl-pyrrolidin-1-yl)-ethyl]-oxazole (100 mg, 0.287 mmol) to give 21 mg (19%). MS (m/e) 377.2 (M+1)

Example 142

2-(2'-Methoxy-biphenyl-4-yl)-5-methyl-4-[2-((R)-2-methyl-pyrrolidin-1-yl)-ethyl]-oxazole

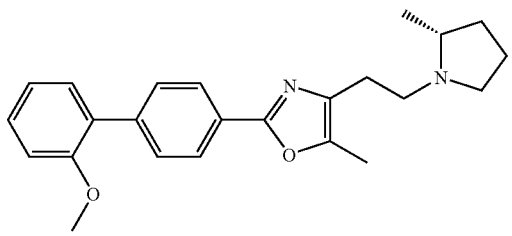

The title compound is prepared in a manner substantially analogous to example 133 starting from 2-methoxybenzene boronic acid (218 mg, 1.43 mmol) and 2-(4-Bromo-phenyl)-5-methyl-4-[2-((R)-2-methyl-pyrrolidin-1-yl)-ethyl]-oxazole (100 mg, 0.287 mmol) to give 67 mg (62%). MS (m/e) 377.2 (M+1)

Example 143

4'-[5-Methyl-4-(2-pyrrolidin-1-yl-ethyl)-oxazol-2-yl]-biphenyl-3-carbonitrile

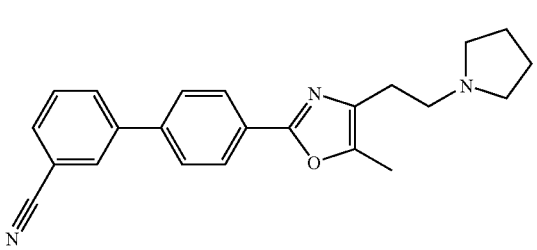

The title compound is prepared in a manner substantially analogous to example 133 starting from 3-cyanobenzene boronic acid (219 mg, 1.49 mmol) and 2-(4-Bromo-phenyl)-5-methyl-4-(2-pyrrolidin-1-yl-ethyl)-oxazole (100 mg, 0.30 mmol) to give 21 mg (20%). MS (m/e) 358.2 (M+1)

Example 144

2-Biphenyl-4-yl-5-methyl-4-[2-((R)-2-methyl-pyrrolidin-1-yl)-ethyl]-oxazole

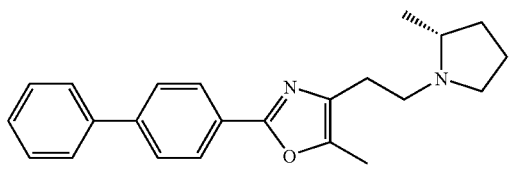

The title compound is prepared in a manner substantially analogous to example 133 starting from phenyl boronic acid (174 mg, 1.43 mmol) and 2-(4-Bromo-phenyl)-5-methyl-4-[2-((R)-2-methyl-pyrrolidin-1-yl)-ethyl]-oxazole (100 mg, 0.287 mmol) to give 16 mg (16%). MS (m/e) 347.3 (M+1)

Example 145

5-Methyl-2-(4'-methyl-biphenyl-4-yl)-4-[2-((R)-2-methyl-pyrrolidin-1-yl)-ethyl]oxazole

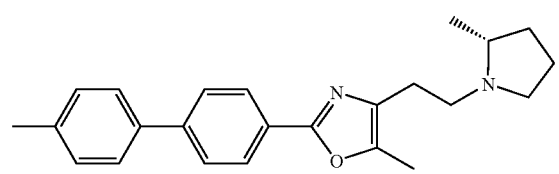

The title compound is prepared in a manner substantially analogous to example 133 starting from tolyl boronic acid (195 mg, 1.43 mmol) and 2-(4-Bromo-phenyl)-5-methyl-4-[2-((R)-2-methyl-pyrrolidin-1-yl)-ethyl]-oxazole (100 mg, 0.287 mmol) to give 33 mg (32%). MS (m/e) 361.3 (M+1)

Example 146

3-(4-{5-Methyl-4-[2-((R)-2-methyl-pyrrolidin-1-yl)-ethyl]-oxazol-2-yl}-phenyl)-pyridine

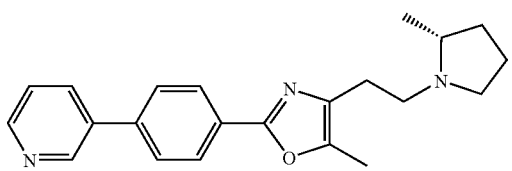

The title compound is prepared in a manner substantially analogous to example 133 starting from 3-pyridyl boronic acid (176 mg, 1.43 mmol) and 2-(4-Bromo-phenyl)-5-methyl-4-[2-((R)-2-methyl-pyrrolidin-1-yl)-ethyl]-oxazole (100 mg, 0.287 mmol) to give 49 mg (49%). MS (m/e) 348.3 (M+1)

Example 147

5-(4-{5-Methyl-4-[2-((R)-2-methyl-pyrrolidin-1-yl)-ethyl]-oxazol-2-yl}-phenyl)-pyrimidine

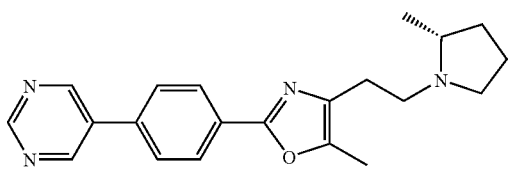

The title compound is prepared in a manner substantially analogous to example 133 starting from 5-pyrimidine boronic acid (178 mg, 1.43 mmol) and 2-(4-Bromo-phenyl)-5-methyl-4-[2-((R)-2-methyl-pyrrolidin-1-yl)-ethyl]-oxazole (100 mg, 0.287 mmol) to give 40 mg (40%). MS (m/e) 349.3 (M+1)

Example 148

4'-{5-Methyl-4-[2-((R)-2-methyl-pyrrolidin-1-yl)-ethyl]-oxazol-2-yl}-biphenyl-4-carboxylic acid dimethylamide

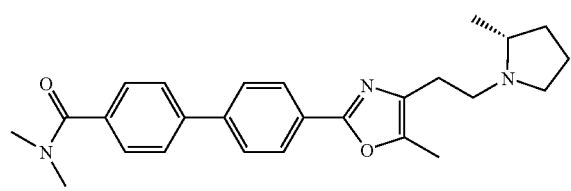

The title compound is prepared in a manner substantially analogous to example 133 starting from 4-(N,N)-dimethylaminocarbonyl phenyl boronic acid (277 mg, 1.43 mmol) and 2-(4-Bromo-phenyl)-5-methyl-4-[2-((R)-2-methyl-pyrrolidin-1-yl)-ethyl]-oxazole (100 mg, 0.287 mmol) to give 26 mg (22%). MS (m/e) 418.5 (M+1)

Example 149

(4'-{5-Methyl-4-[2-((R)-2-methyl-pyrrolidin-1-yl)-ethyl]-oxazol-2-yl}-biphenyl-4-yl)-pyrrolidin-1-yl-methanone

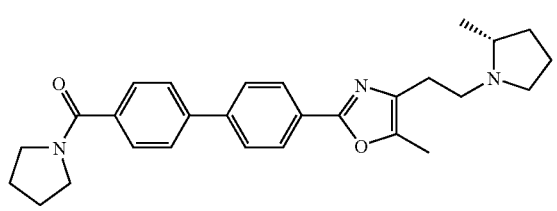

The title compound is prepared in a manner substantially analogous to example 133 starting from 4-pyrrolidine-1-carbonyl phenyl boronic acid (314 mg, 1.43 mmol) and 2-(4-Bromo-phenyl)-5-methyl-4-[2-((R)-2-methyl-pyrrolidin-1-yl)-ethyl]-oxazole (100 mg, 0.287 mmol) to give 55 mg (43%). MS (m/e) 444.4 (M+1)

Example 150

4'-{5-Methyl-4-[2-((R)-2-methyl-pyrrolidin-1-yl)-ethyl]-oxazol-2-yl}-biphenyl-4-carboxylic acid amide

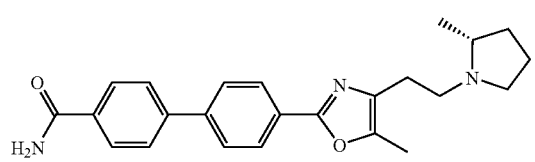

The title compound is prepared in a manner substantially analogous to example 133 starting from 4-aminocarbonyl phenyl boronic acid (236 mg, 1.43 mmol) and 2-(4-Bromo-phenyl)-5-methyl-4-[2-((R)-2-methyl-pyrrolidin-1-yl)-ethyl]-oxazole (100 mg, 0.287 mmol) to give 17 mg (15%). MS (m/e) 390.3 (M+1)

Example 151

4'-{5-Methyl-4-[2-((R)-2-methyl-pyrrolidin-1-yl)-ethyl]-oxazol-2-yl}-biphenyl-4-sulfonic acid dimethylamide

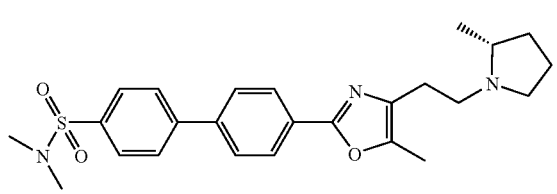

The title compound is prepared in a manner substantially analogous to example 133 starting from 4-dihydroxy borane pinocol ester dimethyl sulfonamide (446 mg, 1.43 mmol) and 2-(4-Bromo-phenyl)-5-methyl-4-[2-((R)-2-methyl-pyrrolidin-1-yl)-ethyl]-oxazole (100 mg, 0.287 mmol) to give 45 mg (35%). MS (m/e) 454.3 (M+1)

Example 152

5-Methyl-4-[2-((R)-2-methyl-pyrrolidin-1-yl)-ethyl]-2-(4'-trifluoromethoxy-biphenyl-4-yl)-oxazole

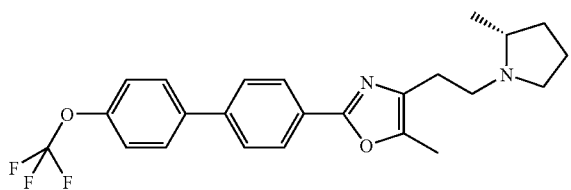

The title compound is prepared in a manner substantially analogous to example 133 starting from 4-triflouromethoxy phenyl boronic acid (295 mg, 1.43 mmol) and 2-(4-Bromo-phenyl)-5-methyl-4-[2-((R)-2-methyl-pyrrolidin-1-yl)-ethyl]-oxazole (100 mg, 0.287 mmol) to give 63 mg (51%). MS (m/e) 431.2 (M+1)

Embodiments of the invention include compounds of the following formulae, including racemates and stereoisomers, and pharmaceutically acceptable salts thereof:

2-(4-Bromo-phenyl)-4-pyrrolidin-1-ylmethyl-oxazole;
3-[4-(4-Pyrrolidin-1-ylmethyl-oxazol-2-yl)-phenyl]-pyridine;
2-(4'-Methanesulfonyl-biphenyl-4-yl)-4-pyrrolidin-1-ylmethyl-oxazole;
2-(4-Bromo-phenyl)-4-(2-methyl-pyrrolidin-1-ylmethyl)-oxazole;
2-(4'-Methanesulfonyl-biphenyl-4-yl)-4-(2-methyl-pyrrolidin-1-ylmethyl)-oxazole;
N-[4'-(4-Pyrrolidin-1-ylmethyl-oxazol-2-yl)-biphenyl-4-yl]-methanesulfonamide;
2-(4-Bromo-phenyl)-5-methyl-4-(2-pyrrolidin-1-yl-ethyl)-oxazole;
4-{4-[5-Methyl-4-(2-pyrrolidin-1-yl-ethyl)-oxazol-2-yl]-phenyl}-pyridine;
3-{4-[5-Methyl-4-(2-pyrrolidin-1-yl-ethyl)-oxazol-2-yl]-phenyl}-pyridine;
2-(4-Bromo-phenyl)-5-methyl-4-[2-(2-methyl-pyrrolidin-1-yl)-ethyl]-oxazole;
4-(4-{5-Methyl-4-[2-(2-methyl-pyrrolidin-1-yl)-ethyl]-oxazol-2-yl}-phenyl)-pyridine;
2-Methyl-5-{4'-[5-methyl-4-(2-pyrrolidin-1-yl-ethyl)-oxazol-2-yl]-biphenyl-4-yl}-[1,3,4]oxadiazole;
2-(4-Bromo-phenyl)-5-methyl-4-[2-(2-methyl-pyrrolidin-1-yl)-ethyl]-oxazole;
4-(4-{5-Methyl-4-[2-(2-methyl-pyrrolidin-1-yl)-ethyl]-oxazol-2-yl}-phenyl)-pyridine;
6-{4-[5-Methyl-4-(2-pyrrolidin-1-yl-ethyl)-oxazol-2-yl]-phenyl}-nicotinontrile;
2-(4'-Methanesulfonyl-biphenyl-4-yl)-5-methyl-4-[2-(2-methyl-pyrrolidin-1-yl)-ethyl]-oxazole;
3-(4-{5-Methyl-4-[2-(2-methyl-pyrrolidin-1-yl)-ethyl]-oxazol-2-yl}-phenyl)-pyridine;
1-[2-(4-Bromo-phenyl)-oxazol-4-ylmethyl]-2-methyl-piperidine;
3-{4-[4-(2-Methyl-piperidin-1-ylmethyl)-oxazol-2-yl]-phenyl}-pyridine;
3-{4-[4-(2-Methyl-piperidin-1-ylmethyl)-oxazol-2-yl]-phenyl}-pyridine;
2-(4'-Methanesulfonyl-biphenyl-4-yl)-5-methyl-4-(2-pyrrolidin-1-yl-ethyl)-oxazole;
4'-[5-Methyl-4-(2-pyrrolidin-1-yl-ethyl)-oxazol-2-yl]-biphenyl-4-carboxylic acid dimethylamide;
5-{4-[5-Methyl-4-(2-pyrrolidin-1-yl-ethyl)-oxazol-2-yl]-phenyl}-thiophene-2-carbonitrile;
2-(4-Bromo-phenyl)-4-[2-(2-methoxymethyl-pyrrolidin-1-yl)-ethyl]-5-methyl-oxazole;
2-(4'-Methanesulfonyl-biphenyl-4-yl)-4-[2-(2-methoxymethyl-pyrrolidin-1-yl)-ethyl]-5-methyl-oxazole;
3-(4-{4-[2-(2-Methoxymethyl-pyrrolidin-1-yl)-ethyl]-5-methyl-oxazol-2-yl}-phenyl)-pyridine;
4-(4-{4-[2-(2-Methoxymethyl-pyrrolidin-1-yl)-ethyl]-5-methyl-oxazol-2-yl}phenyl)-pyridine;
2-(4-Bromo-phenyl)-4-[2-(2-methoxymethyl-pyrrolidin-1-yl)-ethyl]-5-methyl-oxazole;
2-(4'-Methanesulfonyl-biphenyl-4-yl)-4-[2-(2-methoxymethyl-pyrrolidin-1-yl)-ethyl]-5-methyl-oxazole;
2-(4-Butoxy-phenyl)-5-methyl-4-[2-(2-methyl-pyrrolidin-1-yl)-ethyl]-oxazole;
1-{2-[2-(4-bromo-phenyl)-5-methyl-oxazol-4-yl]-ethyl}-piperidine;
5-Methyl-4-(2-pyrrolidin-1-yl-ethyl)-2-(3'-trifluoromethyl-biphenyl-4-yl)-oxazole;
2-(3',4'-Dimethoxy-biphenyl-4-yl)-5-methyl-4-(2-pyrrolidin-1-yl-ethyl)-oxazole;
5-Methyl-4-(2-pyrrolidin-1-yl-ethyl)-2-(3'-trifluoromethoxy-biphenyl-4-yl)-oxazole;
5-Methyl-4-(2-pyrrolidin-1-yl-ethyl)-2-(4'-trifluoromethoxy-biphenyl-4-yl)-oxazole;
2-(4'-Methoxy-biphenyl-4-yl)-5-methyl-4-(2-pyrrolidin-1-yl-ethyl)-oxazole;
2-(4-Benzo[1,3]dioxol-5-yl-phenyl)-5-methyl-4-(2-pyrrolidin-1-yl-ethyl)-oxazole;
2-(2',4'-Dimethoxy-biphenyl-4-yl)-5-methyl-4-(2-pyrrolidin-1-yl-ethyl)-oxazole;
3-Methoxy-5-{4-[5-methyl-4-(2-pyrrolidin-1-yl-ethyl)-oxazol-2-yl]-phenyl}-pyridine;
2-(3'-Methanesulfonyl-biphenyl-4-yl)-5-methyl-4-(2-pyrrolidin-1-yl-ethyl)-oxazole;
2-(4'-Ethanesulfonyl-biphenyl-4-yl)-5-methyl-4-(2-pyrrolidin-1-yl-ethyl)-oxazole;
2-(4'-Methanesulfinyl-biphenyl-4-yl)-5-methyl-4-(2-pyrrolidin-1-yl-ethyl)-oxazole;
5-{4-[5-Methyl-4-(2-pyrrolidin-1-yl-ethyl)-oxazol-2-yl]-phenyl}-pyrimidine;
2-Methoxy-5-{4-[5-methyl-4-(2-pyrrolidin-1-yl-ethyl)-oxazol-2-yl]-phenyl}-pyrimidine;
5-{4-[5-Methyl-4-(2-pyrrolidin-1-yl-ethyl)-oxazol-2-yl]-phenyl}-1H-indole;
5-Methyl-4-(2-pyrrolidin-1-yl-ethyl)-2-(4-thiophen-2-yl-phenyl)-oxazole;
1-{2-[2-(4'-Methanesulfonyl-biphenyl-4-yl)-5-methyl-oxazol-4-yl]-ethyl}-2-piperidine;
1-{2-[2-(4'-Methanesulfonyl-biphenyl-4-yl)-5-methyl-oxazol-4-yl]-ethyl}-2-methyl-piperidine;
1-{2-[2-(4'-Methanesulfonyl-biphenyl-4-yl)-5-methyl-oxazol-4-yl]-ethyl}-2-methyl-piperidine;
2-{4-[5-Methyl-4-(2-pyrrolidin-1-yl-ethyl)-oxazol-2-yl]-phenoxymethyl}-pyridine;
2-(4-{5-Methyl-4-[2-(2-methyl-pyrrolidin-1-yl)-ethyl]-oxazol-2-yl}-phenoxymethyl)-pyridine;
2-(4-Benzyloxy-phenyl)-5-methyl-4-[2-(2-methyl-pyrrolidin-1-yl)-ethyl]-oxazole;

2-[2-(4-Hydroxy-phenyl)-5-methyl-oxazol-4-yl]-1-(2-methyl-pyrrolidin-1-yl)-ethanone;
2-(4-{5-Methyl-4-[2-(2-methyl-pyrrolidin-1-yl)-ethyl]-oxazol-2-yl}-phenoxymethyl)-pyridine;
2-[4-(4-Methanesulfonyl-benzyloxy)-phenyl]-5-methyl-4-[2-(2-methyl-pyrrolidin-1-yl)-ethyl]-oxazole;
2-(4-Methanesulfonyl-phenyl)-5-{5-methyl-4-[2-(2-methyl-pyrrolidin-1-yl)-ethyl]-oxazol-2-yl}-pyridine;
2-Ethanesulfonyl-5-(4-{5-methyl-4-[2-(2-methyl-pyrrolidin-1-yl)-ethyl]-oxazol-2-yl-}-phenyl)-pyridine;
4-(2-Azetidin-1-yl-ethyl)-2-(4-bromo-phenyl)-5-methyl-oxazole;
1-{2-[2-(4-Bromo-phenyl)-5-methyl-oxazol-4-yl]-ethyl-}-piperidine;
1-{2-[2-(4-Bromo-phenyl)-5-methyl-oxazol-4-yl]-ethyl-}-2-methyl-piperidine;
1-{2-[2-(4-Bromo-phenyl)-5-methyl-oxazol-4-yl]-ethyl}-2S-methyl-piperidine;
4-(2-Azetidin-1-yl-ethyl)-2-(4'-methanesulfonyl-biphenyl-4-yl)-5-methyl-oxazole;
2-(4'-Ethanesulfonyl-biphenyl-4-yl)-5-methyl-4-[2-(2R-methyl-pyrrolidin-1-yl)-ethyl]-oxazole;
4-[2-(2R-Ethyl-pyrrolidin-1-yl)-ethyl]-2-(4'-methanesulfonyl-biphenyl-4-yl)-5-methyl-oxazole;
(4'-{5-Methyl-4-[2-(2-methyl-pyrrolidin-1-yl)-ethyl]-oxazol-2-yl}-biphenyl-4-yl)-methanol;
(4'-{5-Methyl-4-[2-(2-methyl-pyrrolidin-1-yl)-ethyl]-oxazol-2-yl}-biphenyl-3-yl)-methanol;
5-Methyl-4-[2-(2-methyl-pyrrolidin-1-yl)-ethyl]-2-[4'-(propane-1-sulfonyl)-biphenyl-4-yl]-oxazole;
4-[2-(2-Fluoromethyl-pyrrolidin-1-yl)-ethyl]-2-(4'-methanesulfonyl-biphenyl-4-yl)-5-methyl-oxazole;
Isopropyl-{2-[2-(4'-methanesulfonyl-biphenyl-4-yl)-5-methyl-oxazol-4-yl]-ethyl}-methyl-amine;
4'-{5-Methyl-4-[2-(2-methyl-pyrrolidin-1-yl)-ethyl]-oxazol-2-yl}-biphenyl-4-carbonitrile;
(2-{2-[6-(4-Methanesulfonyl-phenyl)-pyridin-3-yl]-5-methyl-oxazol-4-yl}-ethyl)-dimethyl-amine;
3-Methoxy-6-(4-{5-methyl-4-[2-(2-methyl-pyrrolidin-1-yl)-ethyl]-oxazol-2-yl}-phenyl)-pyridazine;
3-Ethanesulfonyl-6-(4-{5-methyl-4-[2-(2-methyl-pyrrolidin-1-yl)-ethyl]-oxazol-2-yl}-phenyl)-pyridazine;
2-(4-{5-Methyl-4-[2-(2-methyl-pyrrolidin-1-yl)-ethyl]-oxazol-2-yl}-phenyl)-pyridine;
3-Methanesulfonyl-6-(4-{5-methyl-4-[2-(2-methyl-pyrrolidin-1-yl)-ethyl]-oxazol-2-yl}-phenyl)-pyridazine;
2-Ethanesulfonyl-5-(4-{5-methyl-4-[2-(2-methyl-pyrrolidin-1-yl)-ethyl]-oxazol-2-yl}-phenyl)-pyridine;
2-Methanesulfonyl-5-(4-{5-methyl-4-[2-(2-methyl-pyrrolidin-1-yl)-ethyl]-oxazol-2-yl}-phenyl)-pyridine;
2-Methanesulfonyl-5-(4-{5-methyl-4-[2-(2-methyl-pyrrolidin-1-yl)-ethyl]-oxazol-2-yl}-phenyl)-pyridine;
2-(3-Fluoro-4'-methanesulfonyl-biphenyl-4-yl)-5-methyl-4-[2-(2-methyl-pyrrolidin-1-yl)-ethyl]-oxazole;
5-Methanesulfonyl-2-(4-{5-methyl-4-[2-(2-methyl-pyrrolidin-1-yl)-ethyl]-oxazol-2-yl}-phenyl)-pyrimidine;
N,N-Dimethyl-6-(4-{5-methyl-4-[2-(2-methyl-pyrrolidin-1-yl)-ethyl]-oxazol-2-yl}-phenyl)-nicotinamide;
4-(4-{5-Methyl-4-[2-(2-methyl-piperidin-1-yl)-ethyl]-oxazol-2-yl}-phenyl)-pyridine;
Diethyl-{2-[2-(4'-methanesulfonyl-biphenyl-4-yl)-5-methyl-oxazol-4-yl]-ethyl}-amine;
1-(4'-{5-Methyl-4-[2-(2-methyl-pyrrolidin-1-yl)-ethyl]-oxazol-2-yl}-biphenyl-3-yl)-ethanone hydrochloride;
2-[4'-(3-Fluoro-propane-1-sulfonyl)-biphenyl-4-yl]-5-methyl-4-[2-(2-methyl-pyrrolidin-1-yl)-ethyl]-oxazole;
5-Methyl-4-[2-(2-methyl-pyrrolidin-1-yl)-ethyl]-2-(4'-trifluoromethanesulfonyl-biphenyl-4-yl)-oxazole;
2-(4'-Methanesulfonyl-biphenyl-4-yl)-5-methyl-4-[3-(2-methyl-pyrrolidin-1-yl)-propyl]-oxazole;
1-{2-[2-(4'-Methanesulfonyl-biphenyl-4-yl)-5-methyl-oxazol-4-yl]-ethyl}-2-methyl-piperidine;
2-(4'-Methanesulfonyl-biphenyl-4-yl)-5-methyl-4-(3-pyrrolidin-1-yl-propyl)-oxazole;
1-[2-(4'-Methanesulfonyl-biphenyl-4-yl)-5-methyl-oxazol-4-yl]-2-(2-methyl-pyrrolidine-1-yl)-ethanol;
2-(4'-Methanesulfonyl-biphenyl-4-yl)-4-[-methoxy-2-(2-methyl-pyrrolidin-1-yl)-ethyl]-5-methyl-oxazole;
2-(4'-Methanesulfonyl-biphenyl-4-yl)-5-methyl-4-[2-(2-methyl-pyrrolidin-1-yl)-ethyl]-oxazole;
3-Methyl-6-(4-{5-methyl-4-[2-(2-methyl-pyrrolidin-1-yl)-ethyl]-oxazol-2-yl}-phenyl)-pyridazine;
2-(4-Bromo-phenyl)-5-methyl-4-(2-methyl-pyrrolidin-1-ylmethyl)-oxazole;
2-(4'-Methanesulfonyl-biphenyl-4-yl)-5-methyl-4-(2-methyl-pyrrolidin-1-ylmethyl)-oxazole;
5-{5-Methyl-4-[2-(2-methyl-pyrrolidin-1-yl)-ethyl]-oxazol-2-yl}-2-phenoxy-pyridine;
2-(4-Bromophenyl)-4-{2-[(3)-3-fluoropyrrolidin-1-yl]ethyl}-5-methyl-1,3-oxazole;
4-{[(3)-3-fluoropyrrolidin-1-yl]ethyl}-2-[4'-(methylsulfonyl)biphenyl-4-yl]-5-methyl-1,3-oxazole;
2-(4-Bromophenyl)-4-{2-[(3)-3-fluoropyrrolidin-1-yl]ethyl}-5-methyl-1,3-oxazole;
4-{[(3)-3-Fluoropyrrolidin-1-yl]ethyl}-2-[4'-(methylsulfonyl)biphenyl-4-yl]-5-methyl-1,3-oxazole;
(3)-1-{2-[2-(4-Bromophenyl)-5-methyl-1,3-oxazol-4-yl]ethyl}pyrrolidin-3-ol;
4-{[(3)-3-Hydroxypyrrolidin-1-yl]ethyl}-2-[4'-(methylsulfonyl)biphenyl-4-yl]-5-methyl-1,3-oxazole;
(3)-1-{2-[2-(4-Bromophenyl)-5-methyl-1,3-oxazol-4-yl]ethyl}pyrrolidin-3-ol;
4-{[(3)-3-Hydroxypyrrolidin-1-yl]ethyl}-2-[4'-(methylsulfonyl)biphenyl-4-yl]-5-methyl-1,3-oxazole;
2-(4-Bromophenyl)-4-{2-[(3)-3-(fluoromethyl)pyrrolidin-1-yl]ethyl}-5-methyl-1,3-oxazole;
4-{2-[(3)-3-(Fluoromethyl)pyrrolidin-1-yl]ethyl}-5-methyl-2-[4'-(methylsulfonyl)biphenyl-4-yl]-1,3-oxazole;
2-(4-Bromophenyl)-4-{2-[(3)-3-(fluoromethyl)pyrrolidin-1-yl]ethyl}-5-methyl-1,3-oxazole;
4-{2-[(3)-3-(Fluoromethyl)pyrrolidin-1-yl]ethyl}-5-methyl-2-[4'-(methylsulfonyl)biphenyl-4-yl]-1,3-oxazole;
3-[4-(5-{2-[(3)-3-(Fluoromethyl)pyrrolidin-1-yl]ethyl}-4-methyl-1,3-oxazol-2-yl)phenyl]pyridine;
2-(4-Bromophenyl)-4-{2-[(3)-3-methoxypyrrolidin-1-yl]ethyl}-5-methyl-1,3-oxazole;
4-{2-[(3)-3-methoxypyrrolidin-1-yl]ethyl}-5-methyl-2-[4'-(methylsulfonyl)biphenyl-4-yl]-1,3-oxazole;
2-(4-Bromophenyl)-4-{2-[(3)-3-methoxypyrrolidin-1-yl]ethyl}-5-methyl-1,3-oxazole;
4-{2-[(3)-3-Methoxypyrrolidin-1-yl]ethyl}-5-methyl-2-[4'-(methylsulfonyl)biphenyl-4-yl]-1,3-oxazole;
2-(4-Bromophenyl)-4-{2-[(2)-2-methylpyrrolidin-1-yl]ethyl}-5-methyl-1,3-oxazole;
3-Methoxy-5-[4-(5-methyl-4-{2-[(2)-2-methylpyrrolidin-1-yl]ethyl}-1,3-oxazol-2-yl)phenyl]pyridine;
5-[4-(5-Methyl-4-{2-[(2)-2-methylpyrrolidin-1-yl]ethyl}-1,3-oxazol-2-yl)phenyl]thiophene-2-carbonitrile;
2-Methoxy-5-[4-(5-methyl-4-{2-[(2)-2-methylpyrrolidin-1-yl]ethyl}-1,3-oxazol-2-yl)phenyl]pyrimidine;
5-(4-{5-Methyl-4-[2-(2-methyl-pyrrolidin-1-yl)-ethyl]-oxazol-2-yl}-phenoxymethyl)-thiophene-2-carbonitrile;

5-Methyl-4-[2-(2-methyl-pyrrolidin-1-yl)-ethyl]-2-[4-(2-methyl-thiazol-4-ylmethoxy)-phenyl]-oxazole;
3-(4-{5-Methyl-4-[2-(2-methyl-pyrrolidin-1-yl)-ethyl]-oxazol-2-yl}-phenoxymethyl)-pyridine;
4-(4-{5-Methyl-4-[2-(2-methyl-pyrrolidin-1-yl)-ethyl]-oxazol-2-yl}-phenoxymethyl)-pyridine;
2-Methoxy-5-(4-{5-methyl-4-[2-(2-methyl-pyrrolidin-1-yl)-ethyl]-oxazol-2-yl}-phenoxymethyl)-pyridine;
2-Methyl-6-(4-{5-methyl-4-[2-(2-methyl-pyrrolidin-1-yl)-ethyl]-oxazol-2-yl}-phenoxymethyl)-pyridine;
5-Methyl-4-[2-(2-methyl-pyrrolidin-1-yl)-ethyl]-2-[4-(thiazol-4-ylmethoxy)-phenyl]-oxazole;
2-(4-{4-[2-(2-Methyl-pyrrolidin-1-yl)-ethyl]-oxazol-2-yl}-phenoxymethyl)-pyridine;
4-[2-(2-Methyl-pyrrolidin-1-yl)-ethyl]-2-[4-(thiazol-4-ylmethoxy)-phenyl]-oxazole;
2-(4'-Methanesulfonyl-biphenyl-4-yl)-4-[2-(2-methyl-pyrrolidin-1-yl)-ethyl]-oxazole;
1-(4'-{5-Methyl-4-[2-(2-methyl-pyrrolidin-1-yl)-ethyl]-oxazol-2-yl}-biphenyl-4-yl)-ethanone;
1-(4'-{5-Methyl-4-[2-(2-methyl-pyrrolidin-1-yl)-ethyl]-oxazol-2-yl}-biphenyl-2-yl)-ethanone;
4'-{5-Methyl-4-[2-(2-methyl-pyrrolidin-1-yl)-ethyl]-oxazol-2-yl}-biphenyl-3-carbonitrile;
4'-{5-Methyl-4-[2-(2-methyl-pyrrolidin-1-yl)-ethyl]-oxazol-2-yl}-biphenyl-2-carbonitrile;
2-(4'-Fluoro-biphenyl-4-yl)-5-methyl-4-[2-(2-methyl-pyrrolidin-1-yl)-ethyl]-oxazole;
2-(3'-Fluoro-biphenyl-4-yl)-5-methyl-4-[2-(2-methyl-pyrrolidin-1-yl)-ethyl]-oxazole;
2-(2'-Fluoro-biphenyl-4-yl)-5-methyl-4-[2-(2-methyl-pyrrolidin-1-yl)-ethyl]-oxazole;
2-(4'-Methoxy-biphenyl-4-yl)-5-methyl-4-[2-(2-methyl-pyrrolidin-1-yl)-ethyl]-oxazole;
2-(3'-Methoxy-biphenyl-4-yl)-5-methyl-4-[2-(2-methyl-pyrrolidin-1-yl)-ethyl]-oxazole;
2-(2'-Methoxy-biphenyl-4-yl)-5-methyl-4-[2-(2-methyl-pyrrolidin-1-yl)-ethyl]-oxazole;
4'-[5-Methyl-4-(2-pyrrolidin-1-yl-ethyl)-oxazol-2-yl]-biphenyl-3-carbonitrile;
2-Biphenyl-4-yl-5-methyl-4-[2-(2-methyl-pyrrolidin-1-yl)-ethyl]-oxazole;
5-Methyl-2-(4'-methyl-biphenyl-4-yl)-4-[2-(2-methyl-pyrrolidin-1-yl)-ethyl]oxazole;
3-(4-{5-Methyl-4-[2-(2-methyl-pyrrolidin-1-yl)-ethyl]-oxazol-2-yl}-phenyl)-pyridine;
5-(4-{5-Methyl-4-[2-(2-methyl-pyrrolidin-1-yl)-ethyl]-oxazol-2-yl}-pheenyl)-pyrimidine;
4'-{5-Methyl-4-[2-(2-methyl-pyrrolidin-1-yl)-ethyl]-oxazol-2-yl}-biphenyl-4-carboxylic acid dimethylamide;
(4'-{5-Methyl-4-[2-(2-methyl-pyrrolidin-1-yl)-ethyl]-oxazol-2-yl}-biphenyl-4-yl)-pyrrolidin-1-yl-methanone;
4'-{5-Methyl-4-[2-(2-methyl-pyrrolidin-1-yl)-ethyl]-oxazol-2-yl}-biphenyl-4-carboxylic acid amide;
4'-{5-Methyl-4-[2-(2-methyl-pyrrolidin-1-yl)-ethyl]-oxazol-2-yl}-biphenyl-4-sulfonic acid dimethylamide; and
5-Methyl-4-[2-(2-methyl-pyrrolidin-1-yl)-ethyl]-2-(4'-trifluoromethoxy-biphenyl-4-yl)-oxazole.

The optimal time for performing the reactions of the Schemes, Preparations, and Procedures can be determined by monitoring the progress of the reaction via conventional chromatographic techniques. Furthermore, it is preferred to conduct the reactions of the invention under an inert atmosphere, such as, for example, argon, or, particularly, nitrogen. Choice of solvent is generally not critical so long as the solvent employed is inert to the ongoing reaction and sufficiently solubilizes the reactants to effect the desired reaction. The compounds are preferably isolated and purified before their use in subsequent reactions. Some compounds may crystallize out of the reaction solution during their formation and then collected by filtration, or the reaction solvent may be removed by extraction, evaporation, or decantation. The intermediates and final products of Formula I or Formula II may be further purified, if desired by common techniques such as recrystallization or chromatography over solid supports such as silica gel or alumina.

The skilled artisan will appreciate that not all substituents are compatible with all reaction conditions. These compounds may be protected or modified at a convenient point in the synthesis by methods well known in the art.

The compound of Formula I or Formula II is preferably formulated in a unit dosage form prior to administration. Therefore, yet another embodiment of the present invention is a pharmaceutical composition comprising a compound of Formula I or Formula II and one or more pharmaceutically acceptable carriers, diluents or excipients. The present pharmaceutical compositions are prepared by known procedures using well-known and readily available ingredients. Preferably the compound is administered orally. Preferably, the pharmaceutical composition is in a unit dosage form. In such form, the preparation is subdivided into suitably sized unit doses containing appropriate quantities of the active components, e.g., an effective amount to achieve the desired purpose.

The quantity of the inventive active composition in a unit dose of preparation may be generally varied or adjusted from about 0.01 milligrams to about 1,000 milligrams, preferably from about 0.01 to about 950 milligrams, more preferably from about 0.01 to about 500 milligrams, and typically from about 1 to about 250 milligrams, according to the particular application. The actual dosage employed may be varied depending upon the patient's age, sex, weight and severity of the condition being treated. Such techniques are well known to those skilled in the art. Generally, the human oral dosage form containing the active ingredients can be administered 1 or 2 times per day.

Compounds of Formula I or Formula II are effective as antagonists or inverse agonists of the histamine H3 receptor, and thus inhibit the activity of the H3 receptor. More particularly, these compounds are selective antagonists or inverse agonists of the histamine H3 receptor. As selective antagonists or inverse agonists, the compounds of Formula I or Formula II are useful in the treatment of diseases, disorders, or conditions responsive to the inactivation of the histamine H3 receptor, including but not limited to obesity and other eating-related disorders, and cognitive disorders. It is postulated that selective antagonists or inverse agonists of H3R will raise brain histamine levels and possibly that of other monoamines resulting in inhibition of food consumption while minimizing peripheral consequences. Although a number of H3R antagonists are known in the art, none have proven to be satisfactory obesity or cognitive drugs. There is increasing evidence that histamine plays an important role in energy homeostasis. Histamine, acting as a neurotransmitter in the hypothalamus, suppressed appetite. Histamine is an almost ubiquitous amine found in many cell types and it binds to a family of G protein-coupled receptors (GPCRs). This family provides a mechanism by which histamine can elicit distinct cellular responses based on receptor distribution. Both the H1R and H2R are widely distributed. H3R is primarily expressed in the brain, notably in the thalamus and caudate nucleus. High density of expression of H3R was found in feeding center of the brain. A novel histamine receptor GPRv53 has been recently identified. GPRv53 is found in high levels in peripheral white blood cells; only low levels have been identified in the brain by some investigators while others cannot detect it in the brain. However, any drug discovery effort initiated around H3R must consider GPRv53 as well as the other subtypes.

The compounds of the present invention can readily be evaluated by using a competitive inhibition Scintillation Proximity Assay (SPA) based on a H3R binding assay using R-[3H] α methylhistamine as ligand. Stable cell lines, including but not limited to HEK can be transfected with cDNA coding for H3R to prepare membranes used for the binding assay. The technique is illustrated below (*Preparation of Histamine Receptor Subtype Membranes*) for the histamine receptor subtypes.

Membranes isolated as described in (*Preparation of Histamine Receptor Subtype Membranes*) were used in a [35S] GTP$_\gamma$S functional assay. Binding of [35S]GTP$_\gamma$S to membranes indicates agonist activity. Compounds of the invention of Formula I or Formula II were tested for their ability to inhibit binding in the presence of agonists. Alternately, the same transfected cell lines were used for a cAMP assay wherein H3R agonists inhibited forskolin-activated synthesis of cAMP. Compounds of Formula I or Formula II were tested for their ability to permit forskolin—stimulated cAMP synthesis in the presence of agonist.

Preparation of Histamine Receptor Subtype Membranes

A. Preparation H1R Membranes cDNA for the human histamine 1 receptor (H1R) was cloned into a mammalian expression vector containing the CMV promoter (pcDNA3.1(+), Invitogen) and transfected into HEK293 cells using the FuGENE Tranfection Reagent (Roche Diagnostics Corporation). Transfected cells were selected using G418 (500 μ/mL). Colonies that survived selection were grown and tested for histamine binding to cells grown in 96-well dishes using a scintillation proximity assay (SPA) based radioligand binding assay. Briefly, cells, representing individual selected clones, were grown as confluent monolayers in 96-well dishes (Costar Clear Bottom Plates, #3632) by seeding wells with 25,000 cells and growing for 48 hours (37° C., 5% $CO_2$). Growth media was removed and wells were rinsed two times with PBS (minus $Ca^{2+}$ or $Mg^{2+}$). For total binding, cells were assayed in a SPA reaction containing 50 mM Tris-HCL (assay buffer), pH 7.6, 1 mg wheat germ agglutinin SPA beads (Amersham Pharmacia Biotech, #RPNQ0001), and 0.8nM $^3$H-pyrilamine (Net-594, NEN) (total volume per well=200 μl). Astemizole (10 μM, Sigma #A6424) was added to appropriate wells to determine non-specific binding. Plates were covered with FasCal and incubated at room temperature for 120 minutes. Following incubation, plates were centrifuged at 1,000 rpm (~800 g) for 10 minutes at room temperature. Plates were counted in a Wallac Trilux 1450 Microbeta scintillation counter. Several clones were selected as positive for binding, and a single clone (H1R40) was used to prepare membranes for binding studies. Cell pellets, representing ~10 grams, were resuspended in 30 mL assay buffer, mixed by vortexing, and centrifuged (40,000 g at 4° C.) for 10 minutes. The pellet resuspension, vortexing, and centrifugation was repeated 2 more times. The final cell pellet was resuspended in 30 mL and homogenized with a Polytron Tissue Homogenizer. Protein determinations were done using the Coomassie Plus Protein Assay Reagent (Pierce). Five micrograms of protein was used per well in the SPA receptor-binding assay.

B. Preparation H2R Membranes cDNA for the human histamine 2 receptor was cloned, expressed and transfected into HEK 293 cells as described above. Histamine binding to cells was assayed by SPA described above. For total binding, cells were assayed in a SPA reaction containing 50 mM Tris-HCl (assay buffer), pH 7.6, 1 mg wheat germ agglutinin SPA beads (Amersham Pharmacia Biotech, #RPNQ0001), and 6.2 nM $^3$H-tiotidine (Net-688, NEN) (total volume per well=200 μl ). Cimetidine (10 μM, Sigma #C4522) was added to appropriate wells to determine non-specific binding.

Several clones were selected as positive for binding, and a single clone (H2R10) was used to prepare membranes for binding studies. Five micrograms of protein was used per well in the SPA receptor-binding assay.

C. Preparation of H3R Membranes cDNA for the human histamine 3 receptor was cloned and expressed as described in (A. Preparation H1R membranes), above. Transfected cells were selected using G418 (500 μ/mL), grown, and tested for histamine binding by the SPA described herein. For total binding, cells were assayed in a SPA reaction described above containing 50 mM Tris-HCL (assay buffer), pH 7.6, 1 mg wheat germ agglutinin SPA beads (Amersham Pharmacia Biotech, #RPNQ0001), and 1nM ($^3$H)-n-alpha-methylhistamine (NEN, NET1027) (total volume per well=200 μl). Thioperimide was added to determine non-specific binding. Several clones were selected as positive for binding, and a single clone (H3R8) was used to prepare membranes for binding studies described herein. Five micrograms of protein was used per well in the SPA receptor-binding assay.

D. Preparation of GPRv53 Membranes cDNA for the human GPRv53 receptor was cloned and expressed as described in (A. Preparation H1R membranes), above. Transfected cells were selected, tested for histamine binding, and selected. HEK293 GPRv53 50 cells were grown to confluency in DMEM/F12 (Gibco) supplemented with 5% FBS and 500 ug/mL G418 and washed with Delbecco's PBS (Gibco) and harvested by scraping. Whole cells were homogenized with a Polytron tissuemizer in binding buffer, 50 mM Tris pH 7.5. Cell lysates, 50 ug, were incubated in 96 well dishes with 3 nM (3H) Histamine and compounds in binding buffer for 2 hours at room temperature. Lysates were filtered through glass fiber filters (Perkin Elmer) with a Tomtec cell harverster. Filters were counted with melt-on scintillator sheets (Perkin Elmer) in a Wallac Trilux 1450 Microbeta Scintillation counter for 5 minutes.

Pharmacological Assays cAMP Elisa

HEK293 H3R8 cells prepared as described above were seeded at a density of 50,000 cells/well and grown overnight in DMEM/F12 (Gibco) supplemented with 5% FBS and 500 ug/mL G418. The next day tissue culture medium was removed and replaced with 50 μl cell culture medium containing 4 mM 3-isobutyl-1-methylxanthine (Sigma) and incubated for 20 minutes at room temperature. Antagonist were added in 50 μl cell culture medium and incubated for 20 minutes at room temperature. Agonist R (−)α methylhistamine (RBI) at a dose response from $1 \times 10^{-10}$ to $1 \times 10^{-5}$ M was then added to the wells in 50 μl cell culture medium and incubated for 5 minutes at room temperature. Then 50 μl of cell culture medium containing 20 μM Forskolin (Sigma) was added to each well and incubated for 20 minutes at room temperature. Tissue culture medium was removed and cells were lysed in 0.1M HCl and cAMP was measured by ELISA (Assay Designs, Inc.).

125

[35S] GTP γ [S] Binding Assay

Antagonist activity of selected compounds was tested for inhibition of [35S] GTP γ [S] binding to H3R membranes in the presence of agonists. Assays were run at room temperature in 20 mM HEPES, 100 mM NaCl, 5 mM MgCl$_2$ and 10 uM GDP at pH 7.4 in a final volume of 200 ul in 96-well Costar plates. Membranes isolated from H3R8-expressing HEK293 cell line (20 ug/well) and GDP were added to each well in a volume of 50 μl assay buffer. Antagonist was then added to the wells in a volume of 50 μl assay buffer and incubated for 15 minutes at room temperature. Agonist R(-) alpha methylhistamine (RBI) at either a dose response from $1\times10^{-10}$ to $1\times10^{-5}$ M or fixed concentration of 100 nM were then added to the wells in a volume of 50 μl assay buffer and incubated for 5 minutes at room temperature. GTP γ [35S] was added to each well in a volume of 50 μl assay buffer at a final concentration of 200 pM, followed by the addition of 50 μl of 20 mg/mL WGA coated SPA beads (Amersham). Plates were counted in Wallac Trilux 1450 Microbeta scintillation counter for 1 minute. Compounds that inhibited more than 50% of the specific binding of radioactive ligand to the receptor were serially diluted to determine a K[i] (nM).

The compounds according to the invention preferably have a Ki value of no greater than 5 μM as determined by the Histamine H3 Receptor Binding Assay disclosed herein. More preferably, the compounds according to the invention have a Ki value of less than 1 μM, and preferably of less than 500 nM, and even more preferred of less than 100 nM as determined by the Histamine H3 Receptor Binding Assay disclosed herein. Most preferred compounds of the invention exhibit affinity for the H3 receptor greater than 20 nM. Furthermore, the compounds according to the invention preferably have a higher binding affinity to the histamine H3 receptor than to the GPRv53 receptor. All compounds set forth in the examples exhibit affinity for the H3 receptor greater than 1 μM.

The Ki's at the human H3R are given below for the indicated compound.

| Example | Ki (nM) |
|---|---|
| 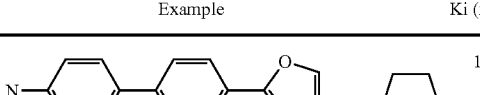 | 1.6 |
|  | 14.3 |

From the above description, one skilled in the art can ascertain the essential characteristics of the present invention, and without departing from the spirit and scope thereof, can make various changes and modifications of the invention to adapt it to various usages and conditions. Thus, other embodiments are also within the claims.

126

What is claimed:
1. A compound structurally represented by Formula I:

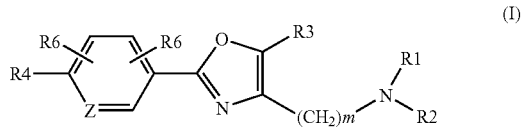

or a pharmaceutically acceptable salt thereof, wherein:
m is independently at each occurrence 1, 2, or 3,
wherein optionally one or two of the hydrogens of the —CH$_2$—, —CH$_2$—CH$_2$—, or —CH$_2$—CH$_2$—CH$_2$— so formed may independently be replaced by halogen, or optionally on a carbon not adjacent to nitrogen one of the hydrogens of the —CH$_2$—CH$_2$—, or —CH$_2$—CH$_2$—CH$_2$— so formed may independently be replaced by —OH, —O—(C$_1$-C$_4$) alkyl (optionally substituted with one to three halogens), or —(C$_1$-C$_3$)alkyl(optionally substituted with one to three halogens);
Z independently represents carbon (substituted with hydrogen or the optional substituents indicated herein) or nitrogen, provided that when Z is nitrogen then R6 is not attached to Z;
R1 and R2 are independently
—(C$_1$-C$_7$) alkyl(optionally substituted with one to three halogens), or R1 and R2 and the nitrogen to which they are attached form an azetidinyl ring, a pyrrolidinyl ring, or a piperidinyl ring, wherein further the azetidinyl, pyrrolidinyl, or piperidinyl ring so formed may be optionally substituted one to three times with R5;
R3 is independently
—H, -halogen, —(C$_1$-C$_4$) alkyl(optionally substituted with one to three halogens), or —O—(C$_1$-C$_3$) alkyl (optionally substituted with one to three halogens);
R4 is independently
-halogen, —(C$_1$-C$_7$) alkyl(optionally substituted with one to three halogens), —CN, —C(O)R7, —C(O) (C$_3$-C$_7$)cycloalkyl(optionally substituted with one to three halogens), —C(O)NR7R8, —OR7, —O-phenyl (R10)(R11), —NO$_2$, —NR7R8, —NR7SO$_2$ R7, —NR7C(O)R7, —NR7CO$_2$R7, —NR7C(O)NR7R8, —SR7, —SO$_2$R7, —SO$_2$NR7R8, —S(O)R7, —O(CH$_2$)mNR7R8, -heteroaryl-R9, —O—CH$_2$-heteroaryl-R9, or

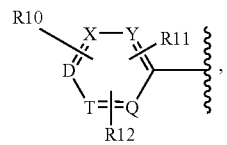

wherein the zig-zag lines represent the point of attachment, and wherein Q, T, D, X, and Y independently represent carbon (substituted with hydrogen or the optional substituents indicated herein) or nitrogen, provided that no more than two of Q, T, D, X, and Y are nitrogen; and provided however that wherein D is nitrogen, then R10, R11, and R12 are not attached to D, and provided that wherein X is nitrogen, then R10, R11, and R12 are not attached to X, and provided that wherein T is nitrogen, then R10, R11, and R12 are not attached to T, and provided that wherein Q is nitrogen, then R10, R11, and R12 are not attached to Q, and provided that wherein Y is nitrogen, then R10, R11, and R12 are not attached to Y; or

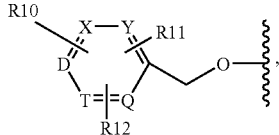

wherein the zig-zag lines represent the point of attachment, and wherein Q, T, D, X, and Y independently represent carbon (substituted with hydrogen or the optional substituents indicated herein) or nitrogen, provided that no more than two of Q, T, D, X, and Y are nitrogen; provided however that wherein D is nitrogen, then R10, R11, and R12 are not attached to D, and provided that wherein X is nitrogen, then R10, R11, and R12 are not attached to X, and provided that wherein T is nitrogen, then R10, R11, and R12 are not attached to T, and provided that wherein Q is nitrogen, then R10, R11, and R12 are not attached to Q, and provided that wherein Y is nitrogen, then R10, R11, and R12 are not attached to Y;

R5 is independently
—H, —OH, -halogen, —($C_1$-$C_4$) alkyl(optionally substituted with one to three halogens), —O—($C_1$-$C_3$) alkyl(optionally substituted with one to three halogens), or —($C_1$-$C_3$) alkyl-O—($C_1$-$C_3$)alkyl(optionally substituted with one to three halogens);

R6 is independently at each occurrence
—H, -halogen, or —$CH_3$;

R7 and R8 are independently at each occurrence
—H, or —($C_1$-$C_7$) alkyl(optionally substituted with one to three halogens), or NR7R8 combine to form a four to seven membered ring;

R9 is independently at each occurrence
—H, —CN, or —($C_1$-$C_3$) alkyl(optionally substituted with one to three halogens);

R10, R11, and R12 are independently at each occurrence
—H, -halogen, —($C_1$-$C_7$) alkyl(optionally substituted with one to three halogens), —($C_1$-$C_7$) alkyl-OH(optionally substituted with one to three halogens), —CN, —C(O)—($C_1$-$C_7$) alkyl(optionally substituted with one to three halogens), —CO(O)R7, —C(O)($C_3$-$C_7$)cycloalkyl(optionally substituted with one to three halogens), —C(O)NR7R8, —OR7, —NR7R8, —NR9$SO_2$R7, —NR9C(O)R7, —NR9$CO_2$R7, —NR9C(O)NR7R8, —SR7, —$SO_2$R7, —$SO_2$NR7R8, —S(O)R7, -heteroaryl-R9, or when R10 and R11 are adjacent to each other they may combine along with the respective atoms to which they are attached to form a five membered or six membered heterocarbon ring containing at least one but not more than two atoms selected from O, S, or N, provided the heteroatoms are not adjacent to each other, and wherein optionally said five membered or six membered heterocarbon ring may contain one to three double bonds.

2. The compound or salt of claim 1, wherein Z is nitrogen and R6 is not attached to Z.

3. The compound or salt of claim 1, wherein Z is carbon (substituted with hydrogen or the optional substituents indicated herein).

4. The compound or salt of claim 1, wherein:

m is independently at each occurrence 1 or 2, wherein optionally one or two of the hydrogens of the —$CH_2$—, or —$CH_2$—$CH_2$— so formed may independently be replaced by halogen, or optionally on the carbon not adjacent to nitrogen one of the hydrogens of the —$CH_2$—$CH_2$— so formed may independently be replaced by —OH, —O—($C_1$-$C_4$) alkyl(optionally substituted with one to three halogens), or —($C_1$-$C_3$)alkyl (optionally substituted with one to three halogens);

Z independently represents carbon (substituted with hydrogen or the optional substituents indicated herein);

R1 and R2 are independently
—($C_1$-$C_7$) alkyl(optionally substituted with one to three halogens), or R1 and R2 and the nitrogen to which they are attached form an azetidinyl ring, a pyrrolidinyl ring, or a piperidinyl ring, wherein further the azetidinyl, pyrrolidinyl, or piperidinyl ring so formed may be optionally substituted once with R5;

R3 is independently —H, or —$CH_3$ (optionally substituted with one to three halogens);

R5 is independently —H, —$CH_3$ (optionally substituted with one to three halogens);

R6 is independently at each occurrence —H, -halogen, or —$CH_3$;

R7 and R8 are independently at each occurrence
—H, or —($C_1$-$C_7$) alkyl(optionally substituted with one to three halogens), or NR7R8 combine to form a four to seven membered ring;

R9 is independently at each occurrence
—H, —CN, or —($C_1$-$C_3$) alkyl(optionally substituted with one to three halogens);

R10, R11, and R12 are independently at each occurrence
—H, -halogen, —($C_1$-$C_7$) alkyl(optionally substituted with one to three halogens), —($C_1$-$C_7$) alkyl-OH(optionally substituted with one to three halogens), —CN, —C(O)—($C_1$-$C_7$) alkyl(optionally substituted with one to three halogens), —CO(O)R7, —C(O)($C_3$-$C_7$)cycloalkyl(optionally substituted with one to three halogens), —C(O)NR7R8, —OR7, —NR7R8, —NR9$SO_2$R7, —NR9C(O)R7, —NR9$CO_2$R7, —NR9C(O)NR7R8, —SR7, —$SO_2$R7, —$SO_2$NR7R8, —S(O)R7, -heteroaryl-R9, or when R10 and R11 are adjacent to each other they may combine along with the respective atoms to which they are attached to form a five membered or six membered heterocarbon ring containing at least one but not more than two atoms selected from O, S, or N, provided the heteroatoms are not adjacent to each other, and wherein optionally said five membered or six membered heterocarbon ring may contain one to three double bonds.

5. The compound or salt of claim 1, wherein:

m is independently at each occurrence 2, wherein optionally one or two of the hydrogens of the —$CH_2$—$CH_2$— so formed may independently be replaced by halogen, or optionally on the carbon not adjacent to nitrogen one of the hydrogens of the —$CH_2$—$CH_2$— so formed may independently be replaced by —OH, —O—($C_1$-$C_4$) alkyl(optionally substituted with one to three halogens), or —($C_1$-$C_3$)alkyl(optionally substituted with one to three halogens);

Z independently represents carbon (substituted with hydrogen);

R1 and R2 and the nitrogen to which they are attached form a pyrrolidinyl ring, or a piperidinyl ring, wherein further the pyrrolidinyl or piperidinyl ring so formed may be optionally substituted once with R5;

R3 is independently —H, or —CH$_3$ (optionally substituted with one to three halogens);

R5 is independently —H, or —CH$_3$ (optionally substituted with one to three halogens);

R6 is independently at each occurrence —H, or halogen, provided that at least one of R6 is —H;

R7 and R8 are independently at each occurrence
—H, or —(C$_1$-C$_7$) alkyl(optionally substituted with one to three halogens), or NR7R8 combine to form a four to seven membered ring;

R9 is independently at each occurrence —H, —CN, or —(C$_1$-C$_3$) alkyl(optionally substituted with one to three halogens);

R10, R11, and R12 are independently at each occurrence
—H, -halogen, —(C$_1$-C$_7$) alkyl(optionally substituted with one to three halogens), —(C$_1$-C$_7$) alkyl-OH(optionally substituted with one to three halogens), —CN, —C(O) —(C$_1$-C$_7$) alkyl(optionally substituted with one to three halogens), —CO(O)R7, —C(O)(C$_3$-C$_7$)cycloalkyl(optionally substituted with one to three halogens), —C(O)NR7R8, —OR7, —NR7R8, —NR9SO$_2$R7, —NR9C(O)R7, —NR9CO$_2$R7, —NR9C(O)NR7R8, —SR7, —SO$_2$R7, —SO$_2$NR7R8, —S(O)R7, -heteroaryl-R9, provided that not more than one of R10, R11, and R12 are -heteroaryl-R9.

6. The compound or salt of claim 1 wherein:
m is independently at each occurrence 2; Z independently represents carbon (substituted with hydrogen); R1 and R2 and the nitrogen to which they are attached form a pyrrolidinyl ring, wherein further the pyrrolidinyl ring so formed may be optionally substituted once with R5; R3 is independently —CH$_3$ (optionally substituted with one to three halogens); R5 is independently —H, or —CH$_3$ (optionally substituted with one to three halogens); R6 is independently at each occurrence —H; R7 and R8 are independently at each occurrence —H, or —(C$_1$-C$_7$) alkyl(optionally substituted with one to three halogens); R9 is independently at each occurrence —H, —CN, or —(C$_1$-C$_3$) alkyl(optionally substituted with one to three halogens); R10, R11, and R12 are independently at each occurrence —H, -halogen, —(C$_1$-C$_7$) alkyl(optionally substituted with one to three halogens), —(C$_1$-C$_7$) alkyl-OH(optionally substituted with one to three halogens), —CN, —C(O)—(C$_1$-C$_7$) alkyl(optionally substituted with one to three halogens), —CO(O) R7, —C(O)(C$_3$-C$_7$)cycloalkyl(optionally substituted with one to three halogens), —C(O)NR7R8, —OR7, —NR7R8, —NR9SO$_2$R7, —NR9C(O)R7, —NR9CO$_2$R7, —NR9C(O)NR7R8, —SR7, —SO$_2$R7, —SO$_2$NR7R8, —S(O)R7, -heteroaryl-R9, provided that not more than one of R10, R11, and R12 are -heteroaryl-R9.

7. A compound or salt of claim 5 wherein R4 is independently:
—O-phenyl(R10)(R11), -heteroaryl-R9, —O—CH$_2$-heteroaryl-R9, or

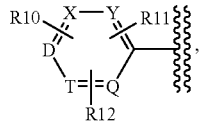

wherein the zig-zag lines represent the point of attachment, and wherein Q, T, D, X, and Y independently represent carbon (substituted with hydrogen or the optional substituents indicated herein) or nitrogen, provided that no more than two of Q, T, D, X, and Y are nitrogen; and provided however that wherein D is nitrogen, then R10, R11, and R12 are not attached to D, and provided that wherein X is nitrogen, then R10, R11, and R12 are not attached to X, and provided that wherein T is nitrogen, then R10, R11, and R12 are not attached to T, and provided that wherein Q is nitrogen, then R10, R11, and R12 are not attached to Q, and provided that wherein Y is nitrogen, then R10, R11, and R12 are not attached to Y; or

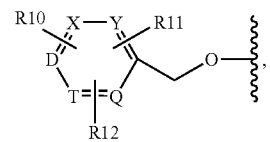

wherein the zigzag lines represent the point of attachment, and wherein Q, T, D, X, and Y independently represent carbon (substituted with hydrogen or the optional substituents indicated herein) or nitrogen, provided that no more than two of Q, T, D, X, and Y are nitrogen; provided however that wherein D is nitrogen, then R10, R11, and R12 are not attached to D, and provided that wherein X is nitrogen, then R10, R11, and R12 are not attached to X, and provided that wherein T is nitrogen, then R10, R11, and R12 are not attached to T, and provided that wherein Q is nitrogen, then R10, R11, and R12 are not attached to Q, and provided that wherein Y is nitrogen, then R10, R11, and R12 are not attached to Y.

8. A compound or salt of claim 7 wherein R3 is independently —CH$_3$ and R5 is —CH$_3$.

9. A compound or salt of claim 8 wherein T is nitrogen, and Q, D, X and Y are carbon substituted with hydrogen or the optional substituents indicated herein.

10. A compound or salt of claim 8 wherein Q and T are nitrogen and D, X and Y are carbon substituted with hydrogen or the optional substituents indicated herein.

11. A compound or salt of claim 8 wherein T and X and Q, D, and Y are carbon substituted with hydrogen or the optional substituents indicated herein.

12. The compound of claim 1, or a pharmaceutically acceptable salt thereof, wherein: —(CH$_2$)$_m$— is —CH$_2$—, —CH$_2$CH$_2$—, or —CH$_2$—CH$_2$—CH$_2$—, wherein one of the hydrogens on a carbon not adjacent to a nitrogen may be replaced by —OH or —OCH$_3$; Z is carbon (substituted with hydrogen or optionally substituted with fluorine) or nitrogen, provided that when Z is nitrogen then R6 is not attached to Z; R1 and R2 are independently —CH$_3$, —CH$_2$CH$_3$, or —CH (CH$_3$)$_2$, wherein R1 and R2 and the nitrogen to which they are attached may optionally from an azetidinyl ring, a piperidinyl ring, or a pyrrolidinyl ring, wherein further the azetidinyl, piperidinyl, or pyrrolidinyl ring so formed may, independently, be optionally substituted once with —F, —OH, —OCH$_3$, —CH$_3$, —CH$_2$—CH$_3$, —CH$_2$—F, or —CH$_2$—

O—CH₃; R3 is hydrogen or —CH₃; R4 is —Br, —OH, —OCH₂CH₂CH₂CH₃, —O-phenyl, -2-pyridinyl, -3-pyridinyl, -4-pyridinyl, -pyrimidinyl, —OCH₂—R₁₄, -pyridazinyl, -1H-indolyl, -phenyl, -2-thiophenyl, or -benzo[1,3]dioxolyl, wherein further the -2-pyridinyl, -3-pyridinyl, -4-pyridinyl, -pyrimidinyl, -pyridazinyl, -1H-indolyl, -phenyl, or -2-thiophenyl, may be optionally substituted one to two times with R7 provided that R7 is not directly attached to the nitrogen of -2-pyridinyl, -3-pyridinyl, -4-pyridinyl, -pyrimidinyl, -pyridazinyl, -1H-indolyl, or the sulfur of -2-thiophenyl; R6 is hydrogen or —F; R7 is —S(O)₂—R9, —N—S(O)₂—CH₃, —S(O)CH₃, 2-methyl-[1,3,4]oxadiazolyl, —CN, —C(O)N(CH₃)₂, —F, —CH₃, —CH₂—OH, —OCH₃, —CF₃, —OCF₃, —C(O)—CH₃, —C(O)-pyrrolidinyl, or —C(O)NH₂; R14 is -2-pyridinyl, -3-pyridinyl, -4-pyridinyl, -Phenyl, -thiazolyl, 4-methanesulfonyl-phenyl, -5-thiophenyl-2-carbonitrile, -2-methylthiazol-4-yl, -2-methoxy-pyridin-5-yl, 2-methyl-pyridin-6-yl; and R9 is —CH₃, —CH₂CH₃, —CH₂—CH₂—CH₃, —CF₃, —CH₂—CH₂—CH₂—F, or —N(CH₃)₂.

13. The compound of claim 12, or a pharmaceutically acceptable salt thereof, wherein: R4 is —Br, —OH, —OCH₂CH₂CH₂CH₃, —O-phenyl, -2-pyridinyl, -3-pyridinyl, -4-pyridinyl, -pyrimidinyl,-2-oxymethylpyridinyl, -3-oxymethylpyridinyl, -4-oxymethylpyridinyl, -oxymethyl-benzene, -4-oxymethyl-2-methylthiazolyl, -4-oxymethylthiazolyl, -benzyloxy-4-methanesulfonyl, -5-oxymethyl-thiophene-2-carbonitrile, -5-oxymethyl-2-methoxy-pyridyl, -2-oxymethyl-6-methyl-pyridinyl -pyridazinyl, -1H-indolyl, -phenyl, -2-thiophenyl, or -benzo[1,3]dioxolyl, wherein further the -2-pyridinyl, -3-pyridinyl, -4-pyridinyl, -pyrimidinyl, -pyridazinyl, -1H-indolyl, -phenyl, -2-thiophenyl, may be optionally substituted one to two times with R7 provided that R7 is not directly attached to the nitrogen of -2-pyridinyl, -3-pyridinyl, -4-pyridinyl, -pyrimidinyl, -pyridazinyl, -1H-indolyl, or the sulfur of -2-thiophenyl.

14. A compound of claim 1 further selected from the group consisting of:
2-(4-Bromo-phenyl)-4-pyrrolidin-1-ylmethyl-oxazole;
2-(4-Bromo-phenyl-4-pyrrolidin-1-ylmethyl-oxazole;
3-[4-(4-Pyrrolidin-1-ylmethyl-oxazol-2-yl)-phenyl]-pyridine;
2-(4'-Methanesulfonyl-biphenyl-4-yl)-4-pyrrolidin-1-ylmethyl-oxazole;
(+/−)-2-(4-Bromo-phenyl)-4-(2-methyl-pyrrolidin-1-ylmethyl)-oxazole;
(+/−)-2-(4'-Methanesulfonyl-biphenyl-4-yl)-4-(2-methyl-pyrrolidin-1-ylmethyl)-oxazole;
N-[4'-(4-Pyrrolidin-1-ylmethyl-oxazol-2-yl)-biphenyl-4-yl]-methanesulfonamide;
2-(4-Bromo-phenyl)-5-methyl-4-(2-pyrrolidin-1-yl-ethyl)-oxazole;
4-{4-[5-Methyl-4-(2-pyrrolidin-1-yl-ethyl)-oxazol-2-yl]-phenyl}-pyridine;
4-{4-[5-Methyl-4-(2-pyrrolidin-1-yl-ethyl)-oxazol-2-yl]-phenyl}-pyridine;
3-{4-[5-Methyl-4-(2-pyrrolidin-1-yl-ethyl)-oxazol-2-yl]-phenyl}-pyridine;
3-{4-[5-Methyl-4-(2-pyrrolidin-1-yl-ethyl)-oxazol-2-yl]-phenyl}-pyridine
(+/−)-2-(4-Bromo-phenyl)-5-methyl-4-[2-(2-methyl-pyrrolidin-1-yl)-ethyl]-oxazole;
(+/−)-4-(4-{5-Methyl-4-[2-(2-methyl-pyrrolidin-1-yl)-ethyl]-oxazol-2-yl}-pyridine;
2-Methyl-5-{4'-[5-methyl-4-(2-pyrrolidin-1-yl-ethyl)-oxazol-2-yl]-biphenyl-4-yl}-[1,3,4]oxadiazole;
2-(4-Bromo-phenyl)-5-methyl-4-[2-(2R-methyl-pyrrolidin-1-yl)-ethyl]-oxazole;
4-(4-{5-Methyl-4-[2-(2R-methyl-pyrrolidin-1-yl)-ethyl]-oxazol-2-yl}-phenyl) -pyridine;
6-{4-[5-Methyl-4-(2-pyrrolidin-1-yl-ethyl)-oxazol-2-yl]-phenyl}-nicotinontrile;
2-(4'-Methanesulfonyl-biphenyl-4-yl)-5-methyl-4-[2-(2R-methyl-pyrrolidin-1-yl)-ethyl]-oxazole;
3-(4-{5-Methyl-4-[2-(2R-methyl-pyrrolidin-1-yl)-ethyl]-oxazol-2-yl}-phenyl)-pyridine;
(+/−)-1-[2-(4-Bromo-phenyl)-oxazol-4-ylmethyl]-2-methyl-piperidine;
(+/−)-3-{4-[4-(2-Methyl-piperidin-1-ylmethyl)-oxazol-2-yl]-phenyl}-pyridine;
(+/−)-3-{4-[4-(2-Methyl-piperidin-1-ylmethyl)-oxazol-2-yl]-phenyl}-pyridine;
2-(4'-Methanesulfonyl-biphenyl-4-yl)-5-methyl-4-(2-pyrrolidin-1-yl-ethyl)-oxazole;
4'-[5-Methyl-4-(2-pyrrolidin-1-yl-ethyl)-oxazol-2-yl]-biphenyl-4-carboxylic acid dimethylamide;
5-{4-[5-Methyl-4-(2-pyrrolidin-1-yl-ethyl)-oxazol-2-yl]-phenyl}-thiophene-2-carbonitrile;
2-(4-Bromo-phenyl)-4-[2-(S)-(+)-(2-methoxymethyl-pyrrolidin-1-yl)-ethyl]-5-methyl-oxazole;
2-(4'-Methanesulfonyl-biphenyl-4-yl)-4-[2-(S)-(+)-(2-methoxymethyl-pyrrolidin-1-yl)-ethyl]-5-methyl-oxazole;
3-(4-{4-[2-(S)-(+)-(2-Methoxymethyl-pyrrolidin-1-yl)-ethyl]-5-methyl-oxazol-2-yl}-phenyl)-pyridine;
4-(4-{4-[2-(S)-(+)-(2-Methoxymethyl-pyrrolidin-1-yl)-ethyl]-5-methyl-oxazol-2-yl}-phenyl)-pyridine;
2-(4-Bromo-phenyl)-4-[2-(R)-(+)-(2-methoxymethyl-pyrrolidin-1-yl)-ethyl]-5-methyl-oxazole;
2-(4'-Methanesulfonyl-biphenyl-4-yl)-4-[2-(R)-(+)-(2-methoxymethyl-pyrrolidin-1-yl)-ethyl]-5-methyl-oxazole;
(+/−)-2-(4-Butoxy-phenyl)-5-methyl-4-[2-(2-methyl-pyrrolidin-1-yl)-ethyl]-oxazole;
1-{2-[2-(4-bromo-phenyl)-5-methyl-oxazol-4-yl]-ethyl}-piperidine;
5-Methyl-4-(2-pyrrolidin-1-yl-ethyl)-2-(3'-trifluoromethyl-biphenyl-4-yl)-oxazole;
2-(3',4'-Dimethoxy-biphenyl-4-yl)-5-methyl-4-(2-pyrrolidin-1-yl-ethyl)-oxazole;
5-Methyl-4-(2-pyrrolidin-1-yl-ethyl)-2-(3'-trifluoromethoxy-biphenyl-4-yl)-oxazole;
5-Methyl-4-(2-pyrrolidin-1-yl-ethyl)-2-(4'-trifluoromethoxy-biphenyl-4-yl)-oxazole;
2-(4'-Methoxy-biphenyl-4-yl)-5-methyl-4-(2-pyrrolidin-1-yl-ethyl)-oxazole;
2-(4-Benzo[1,3]dioxol-5-yl-phenyl)-5-methyl-4-(2-pyrrolidin-1-yl-ethyl)-oxazole;
2-(2',4'-Dimethoxy-biphenyl-4-yl)-5-methyl-4-(2-pyrrolidin-1-yl-ethyl)-oxazole;
3-Methoxy-5-{4-[5-methyl-4-(2-pyrrolidin-1-yl-ethyl)-oxazol-2-yl]-phenyl}-pyridine;
2-(3'-Methanesulfonyl-biphenyl-4-yl)-5-methyl-4-(2-pyrrolidin-1-yl-ethyl)-oxazole;
2-(4'-Ethanesulfonyl-biphenyl-4-yl)-5-methyl-4-(2-pyrrolidin-1-yl-ethyl)-oxazole;
2-(4'-Methanesulfinyl-biphenyl-4-yl)-5-methyl-4-(2-pyrrolidin-1-yl-ethyl)-oxazole;
5-{4-[5-Methyl-4-(2-pyrrolidin-1-yl-ethyl)-oxazol-2-yl]-phenyl}-pyrimidine;
2-Methoxy-5-{4-[5-methyl-4-(2-pyrrolidin-1-yl-ethyl)-oxazol-2-yl]-phenyl}-pyrimidine;

5-{4-[5-Methyl-4-(2-pyrrolidin-1-yl-ethyl)-oxazol-2-yl]-phenyl}-1H-indole;
5-Methyl-4-(2-pyrrolidin-1-yl-ethyl)-2-(4-thiophen-2-yl-phenyl)-oxazole;
1-{2-[2-(4'-Methanesulfonyl-biphenyl-4-yl)-5-methyl-oxazol-4-yl]-ethyl}-piperidine;
(+/−)-1-{2-[2-(4'-Methanesulfonyl-biphenyl-4-yl)-5-methyl-oxazol-4-yl]-ethyl}-2-methyl-piperidine;
1-{2-[2-(4'-Methanesulfonyl-biphenyl-4-yl)-5-methyl-oxazol-4-yl]-ethyl}-2S-methyl-piperidine;
2-{4-[5-Methyl-4-(2-pyrrolidin-1-yl-ethyl)-oxazol-2-yl]-phenoxymethyl}-pyridine;
(+/−)-2-(4-{5-Methyl-4-[2-(2-methyl-pyrrolidin-1-yl)-ethyl]-oxazol-2-yl}-phenoxymethyl)-pyridine;
2-(4-Benzyloxy-phenyl)-5-methyl-4-[2-(2-(R)-methyl-pyrrolidin-1-yl)-ethyl]-oxazole; 2-[2-(4-Hydroxy-phenyl)-5-methyl-oxazol-4-yl]-1-(2-(R)-methyl-pyrrolidin-1-yl)-ethanone;
2-(4-{5-Methyl-4-[2-(2-(R)-methyl-pyrrolidin-1-yl)-ethyl]-oxazol-2-yl}-phenoxymethyl)-pyridine;
2-[4-(4-Methanesulfonyl-benzyloxy)-phenyl]-5-methyl-4-[2-(2-(R)-methyl-pyrrolidin-1-yl)-ethyl]-oxazole;
2-(4-Methanesulfonyl-phenyl)-5-{5-methyl-4-[2-(2-(R)-methyl-pyrrolidin-1-yl)-ethyl]-oxazol-2-yl}-pyridine;
2-Ethanesulfonyl-5-(4-{5-methyl-4-[2-(2-(R)-methyl-pyrrolidin-1-yl)-ethyl]-oxazol-2-yl}-phenyl)-pyridine;
4-(2-Azetidin-1-yl-ethyl)-2-(4-bromo-phenyl)-5-methyl-oxazole;
1-{2-[2-(4-Bromo-phenyl)-5-methyl-oxazol-4-yl]-ethyl}-piperidine;
(+/−)-1-{2-[2-(4-Bromo-phenyl)-5-methyl-oxazol-4-yl]-ethyl}-2-methyl-piperidine;
1-{2-[2-(4-Bromo-phenyl)-5-methyl-oxazol-4-yl]-ethyl}-2S-methyl-piperidine;
4-(2-Azetidin-1-yl-ethyl)-2-(4'-methanesulfonyl-biphenyl-4-yl)-5-methyl-oxazole;
2-(4'-Ethanesulfonyl-biphenyl-4-yl)-5-methyl-4-[2-(2R-methyl-pyrrolidin-1-yl)-ethyl]-oxazole;
4-[2-(2R-Ethyl-pyrrolidin-1-yl)-ethyl]-2-(4'-methanesulfonyl-biphenyl-4-yl)-5-methyl-oxazole;
(4'-{5-Methyl-4-[2-(2R-methyl-pyrrolidin-1-yl)-ethyl]-oxazol-2-yl}-biphenyl-4-yl)-methanol;
(4'-{5-Methyl-4-[2-(2R-methyl-pyrrolidin-1-yl)-ethyl]-oxazol-2-yl}-biphenyl-3-yl)-methanol;
5-Methyl-4-[2-(2R-methyl-pyrrolidin-1-yl)-ethyl]-2-[4'-(propane-1-sulfonyl)-biphenyl-4-yl]-oxazole;
4-[2-(2S-Fluoromethyl-pyrrolidin-1-yl)-ethyl]-2-(4'-methanesulfonyl-biphenyl-4-yl)-5-methyl-oxazole;
Isopropyl-{2-[2-(4'-methanesulfonyl-biphenyl-4-yl)-5-methyl-oxazol-4-yl]-ethyl}-methyl-amine;
4'-{5-Methyl-4-[2-(2-(R)-methyl-pyrrolidin-1-yl)-ethyl]-oxazol-2-yl}-biphenyl-4-carbonitrile;
(2-{2-[6-(4-Methanesulfonyl-phenyl)-pyridin-3-yl]-5-methyl-oxazol-4-yl}-ethyl)-dimethyl-amine;
3-Methoxy-6-(4-{5-methyl-4-[2-(2-methyl-pyrrolidin-1-yl)-ethyl]-oxazol-2-yl}-phenyl)-pyridazine;
3-Ethanesulfonyl-6-(4-{5-methyl-4-[2-(2-methyl-pyrrolidin-1-yl)-ethyl]-oxazol-2-yl}-phenyl)-pyridazine;
2-(4-{5-Methyl-4-[2-(2-methyl-pyrrolidin-1-yl)-ethyl]-oxazol-2-yl}-phenyl)-pyridine;
3-Methanesulfonyl-6-(4-{5-methyl-4-[2-(2-methyl-pyrrolidin-1-yl)-ethyl]-oxazol-2-yl}-phenyl)-pyridazine;
2-Ethanesulfonyl-5-(4-{5-methyl-4-[2-(2-(R)-methyl-pyrrolidin-1-yl)-ethyl]-oxazol-2-yl}-phenyl)-pyridine;
2-Methanesulfonyl-5-(4-{5-methyl-4-[2-(2-(R)-methyl-pyrrolidin-1-yl)-ethyl]-oxazol-2-yl}-phenyl)-pyridine;
2-Methanesulfonyl-5-(4-{5-methyl-4-[2-(2-(R)-methyl-pyrrolidin-1-yl)-ethyl]-oxazol-2-yl}-phenyl)-pyridine;
2-(3-Fluoro-4'-methanesulfonyl-biphenyl-4-yl)-5-methyl-4-[2-(2-methyl-pyrrolidin-1-yl)-ethyl]-oxazole;
2-(3-Fluoro-4'-methanesulfonyl-biphenyl-4-yl)-5-methyl-4-[2-(2-methyl-pyrrolidin-1-yl)-ethyl]-oxazole;
5-Methanesulfonyl-2-(4-{5-methyl-4-[2-(2-methyl-pyrrolidin-1-yl)-ethyl]-oxazol-2-yl}-phenyl)-pyrimidine;
5-Methanesulfonyl-2-(4-{5-methyl-4-[2-(2-methyl-pyrrolidin-1-yl)-ethyl]-oxazol-2-yl}-phenyl)-pyrimidine;
N,N-Dimethyl-6-(4-{5-methyl-4-[2-(2-methyl-pyrrolidin-1-yl)-ethyl]-oxazol-2-yl}-phenyl)-nicotinamide;
4-(4-{5-Methyl-4-[2-(2-methyl-piperidin-1-yl)-ethyl]-oxazol-2-yl}-phenyl)-pyridine;
Diethyl-{2-[2-(4'-methanesulfonyl-biphenyl-4-yl)-5-methyl-oxazol-4-yl]-ethyl}-amine;
1-(4'-{5-Methyl-4-[2-(2R-methyl-pyrrolidin-1-yl)-ethyl]-oxazol-2-yl}-biphenyl-3-yl)-ethanone;
2-[4'-(3-Fluoro-propane-1-sulfonyl)-biphenyl-4-yl]-5-methyl-4-[2-(2R-methyl-pyrrolidin-1-yl)-ethyl]-oxazole;
5-Methyl-4-[2-(2R-methyl-pyrrolidin-1-yl)-ethyl]-2-(4'-trifluoromethanesulfonyl-biphenyl-4-yl)-oxazole;
2-(4'-Methanesulfonyl-biphenyl-4-yl)-5-methyl-4-[3-(2R-methyl-pyrrolidin-1-yl)-propyl]-oxazole;
1-{2-[2-(4'-Methanesulfonyl-biphenyl-4-yl)-5-methyl-oxazol-4-yl]-ethyl}-2R-methyl-piperidine;
2-(4'-Methanesulfonyl-biphenyl-4-yl)-5-methyl-4-(3-pyrrolidin-1-yl-propyl)-oxazole;
1-[2-(4'-Methanesulfonyl-biphenyl-4-yl)-5-methyl-oxazol-4-yl]-2-(2R-methyl-pyrrolidin-1-yl)-ethanol;
2-(4'-Methanesulfonyl-biphenyl-4-yl)-4-[1-methoxy-2-(2R-methyl-pyrrolidin-1-yl)-ethyl]-5-methyl-oxazole;
2-(4'-Methanesulfonyl-biphenyl-4-yl)-5-methyl-4-[2-(2S-methyl-pyrrolidin-1-yl)-ethyl]-oxazole;
3-Methyl-6-(4-{5-methyl-4-[2-(2-methyl-pyrrolidin-1-yl)-ethyl]-oxazol-2-yl}-phenyl)-pyridazine;
2-(4-Bromo-phenyl)-5-methyl-4-(2-methyl-pyrrolidin-1-ylmethyl)-oxazole;
2-(4'-Methanesulfonyl-biphenyl-4-yl)-5-methyl-4-(2-methyl-pyrrolidin-1-ylmethyl)-oxazole;
5-{5-Methyl-4-[2-(2-methyl-pyrrolidin-1-yl)-ethyl]-oxazol-2-yl}-2-phenoxy-pyridine;
2-(4-Bromophenyl)-4-{2-[(3S)-3-fluoropyrrolidin-1-yl]ethyl}-5-methyl-1,3-oxazole;
4-{[(3S)-3-fluoropyrrolidin-1-yl]ethyl}-2-[4'-(methylsulfonyl)biphenyl-4-yl]-5-methyl-1,3-oxazole;
2-(4-Bromophenyl)-4-{2-[(3R)-3-fluoropyrrolidin-1-yl]ethyl}-5-methyl-1,3-oxazole;
4-{[(3R)-3-Fluoropyrrolidin-1-yl]ethyl}-2-[4'-(methylsulfonyl)biphenyl-4-yl]-methyl-1,3-oxazole;
(3R)-1-{2-[2-(4-Bromophenyl)-5-methyl-1,3-oxazol-4-yl]ethyl}pyrrolidin-3-ol;
4-{[(3R)-3-Hydroxypyrrolidin-1-yl]ethyl}-2-[4'-(methylsulfonyl)biphenyl-4-yl]-methyl-1,3-oxazole;
(3S)-1-{2-[2-(4-Bromophenyl)-5-methyl-1,3-oxazol-4-yl]ethyl}pyrrolidin-3-ol;
4-{[(3S)-3-Hydroxypyrrolidin-1-yl]ethyl}-2-[4'-(methylsulfonyl)biphenyl-4-yl]-methyl-1,3-oxazole;
2-(4-Bromophenyl)-4-{2-[(3S)-3-(fluoromethyl)pyrrolidin-1-yl]ethyl}-5-methyl-1,3-oxazole;
4-{2-[(3S)-3-(Fluoromethyl)pyrrolidin-1-yl]ethyl}-5-methyl-2-[4'-(methylsulfonyl)biphenyl-4-yl]-1,3-oxazole;
2-(4-Bromophenyl)-4-{2-[(3R)-3-(fluoromethyl)pyrrolidin-1-yl]ethyl}-5-methyl-1,3-oxazole;

4-{2-[(3R)-3-(Fluoromethyl)pyrrolidin-1-yl]ethyl}-5-methyl-2-[4'-(methylsulfonyl)biphenyl-4-yl]-1,3-oxazole;
3-[4-(5-{2-[(3R)-3-(Fluoromethyl)pyrrolidin-1-yl]ethyl}-4-methyl-1,3-yl)phenyl]pyridine;
2-(4-Bromophenyl)-4-{2-[(3R)-3-methoxypyrrolidin-1-yl]ethyl}-5-methyl-1,3-oxazole;
4-{2-[(3R)-3-methoxypyrrolidin-1-yl]ethyl}-5-methyl-2-[4'-(methylsulfonyl)biphenyl-4-yl]-1,3-oxazole;
2-(4-Bromophenyl)-4-{2-[(3S)-3-methoxypyrrolidin-1-yl]ethyl}-5-methyl-1,3-oxazole;
4-{2-[(3S)-3-Methoxypyrrolidin-1-yl]ethyl}-5-methyl-2-[4'-(methylsulfonyl)biphenyl-4-yl]-1,3-oxazole;
2-(4-Bromophenyl)-4-{2-[(2R)-2-methylpyrrolidin-1-yl]ethyl}-5-methyl-1,3-oxazole;
3-Methoxy-5-[4-(5-methyl-4-{2-[(2R)-2-methylpyrrolidin-1-yl]ethyl}-1,3-oxazol-2-yl)phenyl]pyridine;
5-[4-(5-Methyl-4-{2-[(2R)-2-methylpyrrolidin-1-yl]ethyl}-1,3-oxazol-2-yl)phenyl]thiophene-2-carbonitrile;
2-Methoxy-5-[4-(5-methyl-4-{2-[(2R)-2-methylpyrrolidin-1-yl]ethyl}-1,3-oxazol-2-yl)phenyl]pyrimidine;
5-(4-{5-Methyl-4-[2-(2-(R)-methyl-pyrrolidin-1-yl)-ethyl]-oxazol-2-yl}-phenoxymethyl)-thiophene-2-carbonitrile;
5-Methyl-4-[2-(2-(R)-methyl-pyrrolidin-1-yl)-ethyl]-2-[4-(2-methyl-thiazol-4-ylmethoxy)-phenyl]-oxazole;
3-(4-{5-Methyl-4-[2-(2-(R)-methyl-pyrrolidin-1-yl)-ethyl]-oxazol-2-yl}-phenoxymethyl)-pyridine;
4-(4-{5-Methyl-4-[2-(2-(R)-methyl-pyrrolidin-1-yl)-ethyl]-oxazol-2-yl}-phenoxymethyl)-pyridine;
2-Methoxy-5-(4-{5-methyl-4-[2-(2-(R)-methyl-pyrrolidin-1-yl)-ethyl]-oxazol-2-yl}-phenoxymethyl)-pyridine;
2-Methyl-6-(4-{5-methyl-4-[2-(2-(R)-methyl-pyrrolidin-1-yl)-ethyl]-oxazol-2-yl}-phenoxymethyl)-pyridine;
5-Methyl-4-[2-(2-(R)-methyl-pyrrolidin-1-yl)-ethyl]-2-[4-(thiazol-4-ylmethoxy)-phenyl]-oxazole;
2-(4-{4-[2-(2-(R)-Methyl-pyrrolidin-1-yl)-ethyl]-oxazol-2-yl}-phenoxymethyl)-pyridine;
4-[2-(2-(R)-Methyl-pyrrolidin-1-yl)-ethyl]-2-[4-(thiazol-4-ylmethoxy)-phenyl]-oxazole;
2-(4'-Methanesulfonyl-biphenyl-4-yl)-4-[2-(2-(R)-methyl-pyrrolidin-1-yl)-ethyl]-oxazole;
1-(4'-{5-Methyl-4-[2-((R)-2-methyl-pyrrolidin-1-yl)-ethyl]-oxazol-2-yl}-biphenyl-4-yl)-ethanone;
1-(4'-{5-Methyl-4-[2-((R)-2-methyl-pyrrolidin-1-yl)-ethyl]-oxazol-2-yl}-biphenyl-2-yl)-ethanone;
4'-{5-Methyl-4-[2-((R)-2-methyl-pyrrolidin-1-yl)-ethyl]-oxazol-2-yl}-biphenyl-3-carbonitrile;
4'-{5-Methyl-4-[2-((R)-2-methyl-pyrrolidin-1-yl)-ethyl]-oxazol-2-yl}-biphenyl-2-carbonitrile;
2-(4'-Fluoro-biphenyl-4-yl)-5-methyl-4-[2-((R)-2-methyl-pyrrolidin-1-yl)-ethyl]-oxazole;
2-(3'-Fluoro-biphenyl-4-yl)-5-methyl-4-[2-((R)-2-methyl-pyrrolidin-1-yl)-ethyl]-oxazole;
2-(2'-Fluoro-biphenyl-4-yl)-5-methyl-4-[2-((R)-2-methyl-pyrrolidin-1-yl)-ethyl]-oxazole;
2-(4'-Methoxy-biphenyl-4-yl)-5-methyl-4-[2-((R)-2-methyl-pyrrolidin-1-yl)-ethyl]-oxazole;
2-(3'-Methoxy-biphenyl-4-yl)-5-methyl-4-[2-((R)-2-methyl-pyrrolidin-1-yl)-ethyl]-oxazole;
2-(2'-Methoxy-biphenyl-4-yl)-5-methyl-4-[2-((R)-2-methyl-pyrrolidin-1-yl)-ethyl]-oxazole;
4'-[5-Methyl-4-(2-pyrrolidin-1-yl-ethyl)-oxazol-2-yl]-biphenyl-3-carbonitrile;
2-Biphenyl-4-yl-5-methyl-4-[2-((R)-2-methyl-pyrrolidin-1-yl)-ethyl]-oxazole;
5-Methyl-2-(4'-methyl-biphenyl-4-yl)-4-[2-((R)-2-methyl-pyrrolidin-1-yl)-ethyl]oxazole;
3-(4-{5-Methyl-4-[2-((R)-2-methyl-pyrrolidin-1-yl)-ethyl]-oxazol-2-yl}-phenyl)-pyridine;
5-(4-{5-Methyl-4-[2-((R)-2-methyl-pyrrolidin-1-yl)-ethyl]-oxazol-2-yl}-phenyl)-pyrimidine;
4'-{5-Methyl-4-[2-((R)-2-methyl-pyrrolidin-1-yl)-ethyl]-oxazol-2-yl}-biphenyl-4-carboxylic acid dimethylamide;
(4'-{5-Methyl-4-[2-((R)-2-methyl-pyrrolidin-1-yl)-ethyl]-oxazol-2-yl}-biphenyl-4-yl)-pyrrolidin-1-yl-methanone;
4'-{5-Methyl-4-[2-((R)-2-methyl-pyrrolidin-1-yl)-ethyl]-oxazol-2-yl}-biphenyl-4-carboxylic acid amide;
4'-{5-Methyl-4-[2-((R)-2-methyl-pyrrolidin-1-yl)-ethyl]-oxazol-2-yl}-biphenyl-4-sulfonic acid dimethylamide; and
5-Methyl-4-[2-((R)-2-methyl-pyrrolidin-1-yl)-ethyl]-2-(4'-trifluoromethoxy-biphenyl-4-yl)-oxazole,
or a pharmaceutically acceptable salt thereof.

15. A pharmaceutical composition which comprises a compound or salt of claim 1 and a pharmaceutically acceptable carrier.

16. A method for treatment of obesity which comprises administering to a mammal in need of such treatment an effective amount of a compound of claim 1.

17. The compound 3-Methyl-6-(4-{5-methyl-4-[2-(2-methyl-pyrrolidin-1-yl)-ethyl]-oxazol-2-yl}-phenyl)-pyridazine or a pharmaceutically acceptable salt thereof.

* * * * *

UNITED STATES PATENT AND TRADEMARK OFFICE
CERTIFICATE OF CORRECTION

PATENT NO.       : 7,666,871 B2                                Page 1 of 1
APPLICATION NO. : 11/572283
DATED            : February 23, 2010
INVENTOR(S)      : Beavers et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 13 days.

Signed and Sealed this

Seventh Day of December, 2010

David J. Kappos
*Director of the United States Patent and Trademark Office*